US010300155B2

(12) United States Patent
Tu et al.

(10) Patent No.: US 10,300,155 B2
(45) Date of Patent: May 28, 2019

(54) ALPHA-SYNUCLEIN LIGANDS

(71) Applicant: Washington University, St. Louis, MO (US)

(72) Inventors: Zhude Tu, Frontenac, MO (US); Junfeng Li, Duarte, CA (US); Xuyi Yue, St. Louis, MO (US); Paul Kotzbauer, Clayton, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/393,673

(22) Filed: Dec. 29, 2016

(65) Prior Publication Data
US 2017/0189566 A1 Jul. 6, 2017

Related U.S. Application Data

(60) Provisional application No. 62/273,675, filed on Dec. 31, 2015.

(51) Int. Cl.
*A61K 51/04* (2006.01)
*C07B 59/00* (2006.01)

(52) U.S. Cl.
CPC ...... *A61K 51/0459* (2013.01); *A61K 51/0455* (2013.01); *A61K 51/0463* (2013.01); *A61K 51/0465* (2013.01); *C07B 59/002* (2013.01)

(58) Field of Classification Search
CPC .................................................... A61K 51/04
See application file for complete search history.

(56) References Cited

U.S. PATENT DOCUMENTS

| 3,580,909 | A | 5/1971 | Lehr |
| 4,883,866 | A | 11/1989 | Möckli |
| 6,083,961 | A | 7/2000 | Oku et al. |
| 7,687,052 | B2 | 3/2010 | Kung et al. |
| 8,586,585 | B2 | 11/2013 | Snow et al. |
| 2007/0249647 | A1* | 10/2007 | Vander Jagt ......... A61K 31/381 514/277 |
| 2011/0104055 | A1 | 5/2011 | Snow et al. |
| 2013/0178536 | A1 | 7/2013 | Vander Jagt et al. |
| 2013/0259805 | A1 | 10/2013 | Bacskai |
| 2013/0289066 | A1 | 10/2013 | Kennedy et al. |
| 2013/0315825 | A1 | 11/2013 | Tu et al. |

FOREIGN PATENT DOCUMENTS

| EP | 0807630 A1 | 11/1997 |
| EP | 0775138 B1 | 2/2000 |
| WO | 96/00215 | 1/1996 |
| WO | 96/00222 | 1/1996 |
| WO | 96/05200 | 2/1996 |
| WO | 96/23783 A1 | 8/1997 |
| WO | 03/000731 A1 | 1/2003 |
| WO | 03/037333 A1 | 5/2003 |
| WO | 03/062225 A1 | 7/2003 |
| WO | 03/062227 A1 | 7/2003 |
| WO | 2007/124348 A2 | 11/2007 |
| WO | 2008/030072 A1 | 3/2008 |
| WO | 2010/053732 A1 | 5/2010 |
| WO | 2010/094090 A2 | 8/2010 |
| WO | 2010/118282 A1 | 10/2010 |
| WO | 2011/128455 A1 | 10/2011 |
| WO | 2012/041292 A2 | 4/2012 |
| WO | 2012/115478 A2 | 8/2012 |
| WO | 2013/000711 A1 | 1/2013 |
| WO | 2013/179144 A2 | 12/2013 |
| WO | WO2014012889 | * 1/2014 |
| WO | 2014/037416 A2 | 3/2014 |

OTHER PUBLICATIONS

Vladimir V. Kouznetsov et al. Synthesis and antifungal activity of diverse C-2 pyridinyl and pyridinylvinyl substituted quinolones, Bioorganic & Medicinal Chemsitry, 20, 6506-6512. (Year: 2012).*
Ardah, M.T., et al., "Structure Activity Relationship of Phenolic Acid Inhibtors of α-Synuclein Fibril Formation and Toxicity," 2014, Frontiers in Aging Neuroscience, vol. 6, 17 pages.
Aulić, S., et al., "Small-Molecule Theranostic Probes: A Promising Future in Neurodegenerative Diseases," 2013, International J of Cell Biol, vol. 2013, 19 pages. HTTP://dx.doi.org/10.1155/2013/150952.
Bagchi, D.P., et al., "Binding of the Radioligand SIL23 to α-Synuclein Fibrils in Parkinson Disease Brain Tissue Establishes Feasibility and Screening Approaches for Developing a Parkinson Disease Imaging Agent," 2013, PLOS One, vol. 8, Issue 2:e55031, 13 pages.
Bahner, C.T., et al., "Di- and Tri-Methoxystyryl Derivatives of Heterocyclic Nitrogen Compounds," 1981, Arzneimittel-Forschung, 31/3: 404-406 (Abstract Only), 1 page.
Braak, H., et al., "Stages in the Development of Parkinson's Disease-Related Pathology," 2004, Cell Tissue Res., 318:121-134 (Abstract Only), 2 pages.
Chang, E., et al., "Modulation and Detection of Tau Aggregation with Small Molecule Ligands," 2009, Curr Alzheimer Res, 6/5:409-414, 11 pages.
Choi, S.R., et al., "Preclinical Properties of 18F-AV-45: A PET Agent for Aβ Plaques in the Brain," 2009, J Nucl Med, 50/11:1887-1894, 18 pages.
Cui, M., "Past and Recent Progress of Molecular Imaging Probes for β-Amyloid Plaques in the Brain," 2014, Current Medicinal Chemistry, 21:82-11, 31 pages.
Eberling, J.L., et al., "α-Synuclein Imaging: A Critical Need for Parkinson's Disease Research," 2013, J Parkinson's Disease 3, 565-567, 3 pages.
Engel, L.A., et al., "Catalytic Function of PLA2G6 is Impaired by Mutations Associated with Infantile Neuroaxonal Dystrophy but not Dystonia-Parkinsonism," 2010, PLoS One 5: e12897, 7 pages.
Folstein, M.F., et al., ""Mini-Mental State". A Practical Method for Grading the Cognitive State of Patients for the Clinician," 1975, J Psychiatr Res, 12:189-198 (Abstract Only), 3 pages.

(Continued)

*Primary Examiner* — Michael G. Hartley
*Assistant Examiner* — Jagadishwar R Samala
(74) *Attorney, Agent, or Firm* — Stinson Leonard Street LLP

(57) ABSTRACT

The present invention generally relates to various compounds that are useful as α-synuclein ligands. The invention further relates to methods of using these compounds and their radiolabeled analogs for the detection of synucleinopathies, including Parkinson's disease (PD).

20 Claims, 25 Drawing Sheets

(56) References Cited

OTHER PUBLICATIONS

Frost, B., et al, "Propagation of Tau Misfolding from the Outside to the Inside of a Vell," 2009, J. Biol. Chem. 284:2845-12852, 9 pages. http://www.jbc.org.
Galvin, J.E., et al., "The AD8: A Brief Informant Interview to Detect Dementia," 2005, Neurology 65:559-564 (Abstract Only), 2 pages.
Giasson, B.I., "Oxidative Damage Linked to Neurodegeneration by Selective α-Synuclein Nitration in Synucleinopathy Lesions," 2000, Science, 290:985-989 (Abstract Only), 2 pages.
Giasson, B.I., et al., "Mutant and Wild Type Human α-Synucleins Assemble into Elongated Filaments with Distinct Morphologies in Vitro," 1999, J. Biol. Chem., 274:7619-7622, 5 pages.
Gong, L., et al., "Metal-Free Oxidative Olefination of Primary Amines with Benzylic C—H Bonds Through Direct Deamination and C—H Bond Activation," 2014, Org Biomol Chem, 12:6557-6560, 37 pages.
Huang, C., et al., "A New Method for Purification of Recombinant Human α-Synuclein in *Escherichia coli*," 2005, Protein Expr Purif, 42:173-177 (Abstract Only), 2 pages.
Hughes, A.J., et al., "Accuracy of Clinical Diagnosis of Idiopathic Parkinson's Disease: A Clinico-Pathological Study of 100 Cases," 1992, J Neurol Neurosurg Psychiatry, 55:181-184, 5 pages.
Irving, H., et al., "8-Hydroxyquinaldic Acid," 1954, J Chem Soc, 3782-3785 (Abstract Only), 3 pages.
Kotzbauer, P.T., et al., "Fibrillization of α-synuclein and Tau in Familial Parkinson's Disease Caused by the A53T α-Synuclein Mutation," 2004, Exp Neurol, 187:279-288 (Abstract Only), 2 pages.
Kouznetsov, V.V., et al., "Synthesis and Antifungal Activity of Diverse C-2 Pyridinyl and Pyridinylvinyl Dubstituted Quinolines," 2012, Biorg Med Chem, 20/21:6506-6512 (Abstract Only), 1 page.
Kung, H.F., et al., "18F Stilbenes and Styrylpyridines for PET Imaging of Aβ Plaques in Alzheimer's Disease: A Miniperspective," 2010, J. Med. Chem., 53/3:933, 21 pages.
Li, W., et al., "Characterization of Two VQIXXK Motifs for Tau Fibrillization in Vitro," 2006, Biochemistry, 45:15692-15701 (Abstract Only), 2 pages.
Marchiani, A., et al., "Curcumin and Curcumin-Like Molecules: From Spice to Drugs," 2014, Curr Med Chem, 21/2:204-222 (Abstract Only), 1 page.
Marchiani, A., et al., "Small Molecules Interacting with α-Synuclein: Antiaggregating and Cytoprotective Properties," 2013, Amino Acids, 45/2:327-338 (Abstract Only), 2 pages.
Masuda, M., et al., "Small Molecule Inhibitors of α-Synuclein Filament Assembly," 2006, Biochemistry, 45/19:6085-6094.
Neal, K.L., et al., "Development and Screening of Contrast Agents for in Vivo Imaging of Parkinson's Disease," 2013, Mol Imaging Biol, 15/5:585-595 (Abstract Only), 2 pages.
Ono, M., et al., "SPECT Imaging Agents for Detecting Cerebral β-Amyloid Plaques," 2011, International Journal of Mol Imaging, vol. 2011, Article ID 543267, 12 pages.

Ouali, M., et al., "Tautomers of Styrylquinoline Derivatives Containing a Methoxy Substituent: Computation of Their Population in Aqueous Solution and Their Interaction with RSV Sntegrase Catalytic Core," 2000, Acta Biochimica Polonica, 47/1:11-22, 12 pages.
Padakanti, P.K., et al., "Syntheses and Radiosyntheses of Two Carbon-11 Labeled Potent and Selective Radioligands for Imaging Vesicular Acetylcholine Transporter," 2014, Mol Imaging Biol, 16:765-772, 16 pages.
Percino, M.J., et al., "Spectroscopic Characterization of Halogen- and Cyano-Substituted Pyridinevinylenes Synthesized without Catalyst or Solvent," 2010, Chemical Papers, 64/3:360-367 (Abstract Only), 9 pages.
Poirier, R.H., et al.,"Abnormal Condensation of Piperidinium Acetate with Aromatic Aldehydes," 1961, J Org Chem, 26/11:4275-4278 (Abstract Only), 3 pages.
Prabhudesai, S., et al., "A Novel "Molecular Tweezer" Inhibitor of α-Synuclein Neurotoxicity in Vitro and in Vivo," 2012, Neurotherapeutics, 9:464-476, 13 pages.
Rubtsov, M.V., et al., "Derivatives of 2-Styrylquinoline," 1959, J Med Chem, 2/2:113-131 (Abstract Only), 3 pages.
Shi, C., et al., "Ligand-Free Palladium-Catalysed Oxidative Heck Reaction of 4-Vinylpyridine with Arylboronic Acids: Selective Synthesis of (E)-4-Styrylpyridines," 2012, J Chem Res, 36/6:322-325 (Abstract Only) 1 page.
Singh, P.K., et al., "Curcumin Modulates α-Synuclein Aggregation and Toxicity," 2013, ACS Chem Neurosci, 4/3:393-407 (Abstract Only) 2 pages.
Staderini, M., et al., "A Fluorescent Styrylquinoline with Combined Therapeutic and Diagnostic Activities against Alzheimer's and Prion Diseases," 2013, ACS Med Chem Lett, 4:225-229, 5 pages.
Troger, J., et al., "Condensation of Hydroxy- and Methoxyquinaldines as Well as α-Hydroxylepidine with Aromatic Aldehydes," 1925, J. Pract. Chem., 109:88-123, 42 pages.
Vanden Eynde, J.J., et al., "Quaternary Ammonium Salt-Assisted Synthesis of Extended π-Systems from Methyldiazines and Aromatic Aldehydes," 2001, Syn. Commun, 31/20:3167-3173 (Abstract Only), 2 pages.
Werner, L.F., "An Alkylene and Some Alkyl Halides of 2(4-Hydroxy-3-Methoxy-Styryl)Quinoline," 1921, JACS, 43/4:890-891 (Abstract Only), 3 pages.
Yu, L., et al., "Synthesis and in Vitro Evaluation of α-Synuclein Ligands," 2012, Biorg Med Chem, 20:6425-4634 (Abstract Only), 2 pages.
Zhang X., et al., "Dual Functional Small Molecule Probes as Fluorophore and Ligand for Misfolding Proteins," Curr Org Chem, 17/6:580-593, 24 pages.
Zhang, X., et al., "Radiosynthesis and in Vivo Evaluation of Two PET Radioligands for Imaging α-Synuclein," 2014, Appl Sci, 4:66-78, 13 pages.
CAS #925932-97-4, http://www.ebuychem.com/product/EBD686621.html Jan. 30, 2017, 1 page.
"Florbetapir", society of Nuclear Medicine and Molecular Imaging, Jul. 2012, 4 pages.
Patent Abstracts of Japan, JP 08-57457, Applicant Dainippon Printing Co. Ltd., Published, Jun. 18, 1996, Ionic Liquid Crystal Compound, 3 pages.

* cited by examiner

TZ-19-135 R₁=-H, R₂=-H
TZ-19-135 R₁=-H, R₂=-H
TZ-19-137 R₁=-OMe, R₂=-NO₂

TZ-19-139 R₃=-H
TZ-19-141 R₃=-N(CH₃)₂
TZ-19-141 R₃=-N(CH₃)₂

TZ-19-136 R₁=-H, R₂=-H, R₃=-H
TZ-19-138 R₁=-H, R₂=-H, R₃=-N(CH₃)₂
TZ-19-140 R₁=-OMe, R₂=-NO₂, R₃=-N(CH₃)₂

TZ-20-37

TZ-23-52 R = Br
TZ-23-56 R = I

TZ-20-37 R = CO$_2$H
TZ-20-35 R = CO$_2$Me
TZ-20-59 R = NO$_2$
TZ-20-73 R = F
TZ-20-75 R = CF$_3$

TZ-22-25-1   $X^1$ = N, $R^1$ = 2OMe
TZ-22-23-1   $X^1$ = N, $R^1$ = 4OMe
TZ-22-21-1   $X^2$ = N, $R^1$ = 2OMe
TZ-22-19-1   $X^2$ = N, $R^1$ = 4OMe
TZ-22-33-1   $X^4$ = N, $R^1$ = 2OMe
TZ-22-31-1   $X^4$ = N, $R^1$ = 4OMe

TZ-22-1-2   $X^3$ = N, $R^1$ = 4OMe
TZ-22-49-1   $X^3$ = N, $R^1$ = 3OMe
TZ-22-15-1   $X^3$ = N, $R^1$ = 2OMe
TZ-22-35-1   $X^3$ = N, $R^1$ = 4NMe$_2$
TZ-22-37-1   $X^3$ = N, $R^1$ = 4OMe, $R^2$ = 3OMe
TZ-22-47-1   $X^3$ = N, $R^1$ = 4Br

TZ-34-24 2-fural
TZ-34-27 3-fural
TZ-34-26 2-thienyl
TZ-34-28 3-thienyl

| | |
|---|---|
| TZ-36-26-2T | $R_1$= -OCH$_3$, $R_2$= -F |
| TZ-36-28-2T | $R_1$= -OCH$_3$, $R_2$= -OCH$_3$ |
| TZ-36-42 | $R_1$= -OCH$_3$, $R_2$= -Cl |
| TZ-36-14 | $R_1$= -F, $R_2$= -H |
| TZ-36-16 | $R_1$= -Br, $R_2$= -H |
| TZ-36-138 | $R_1$= -OCH(CH$_3$)$_2$, $R_2$= -OCH$_3$ |
| TZ-36-144 | $R_1$= -OCH$_2$OCH$_3$, $R_2$= -OCH$_3$ |
| TZ-36-146 | $R_1$= -OH, $R_2$= -OCH$_3$ |
| TZ-36-148 | $R_1$= -O(CH$_2$)$_2$F, $R_2$= -OCH$_3$ |
| TZ-36-36 | $R_1$= -OCH$_3$, $R_2$= -Br |
| TZ-36-32 | $R_1$= -OCH$_3$, $R_2$= -H |

TZ-36-34   $R_1$= -OCH$_3$, $R_2$= -H
TZ-36-38   $R_1$= -OCH$_3$, $R_2$= -Cl

Figure 16.1
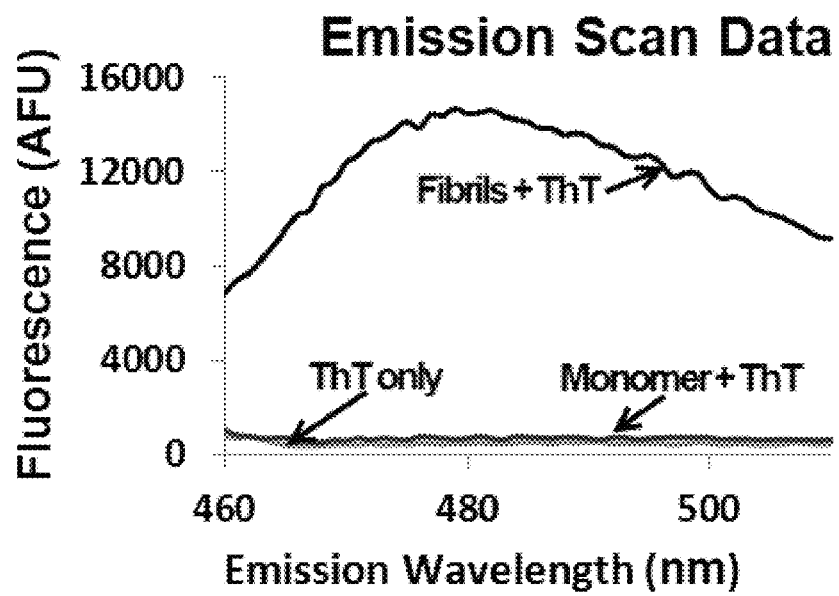
Figure 16.2
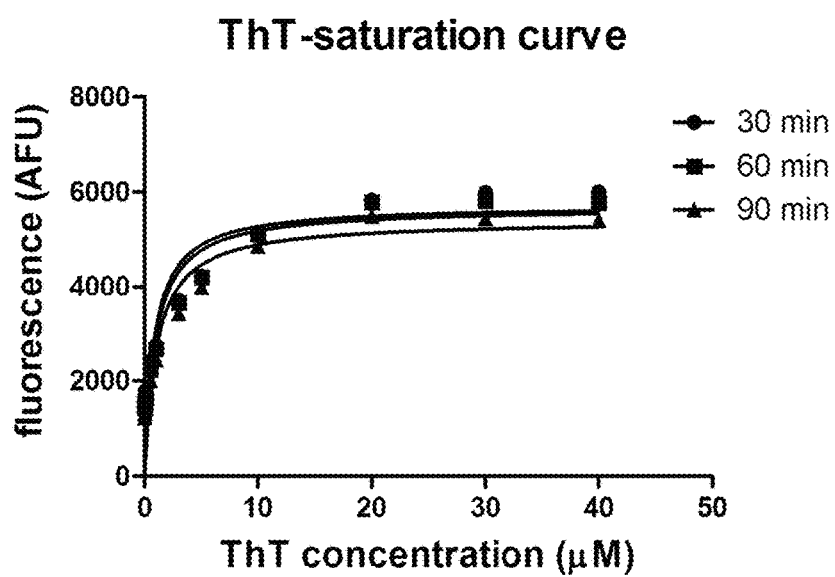

Figure 17.1
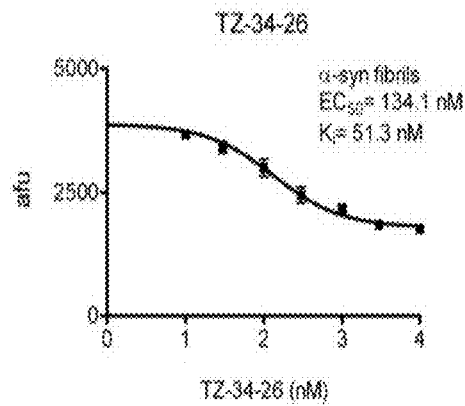
Figure 17.2
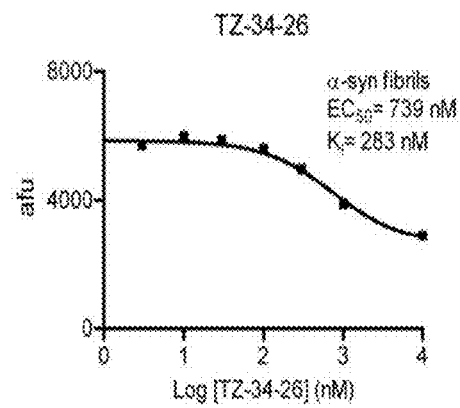
Figure 17.3
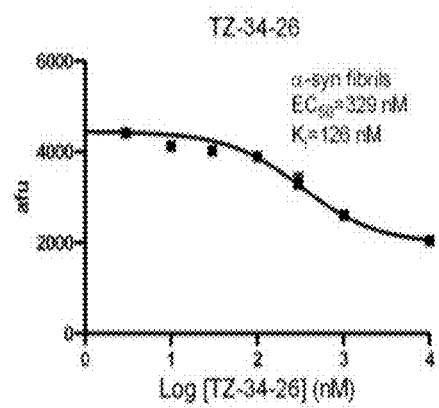
Figure 17.4
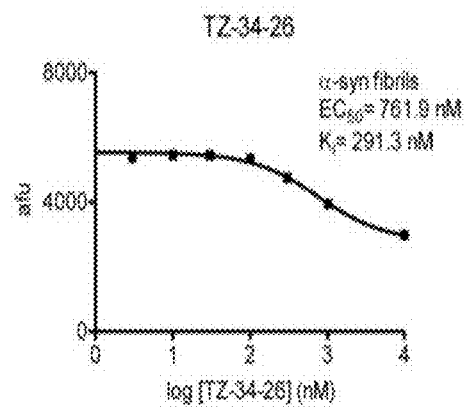
Figure 17.5
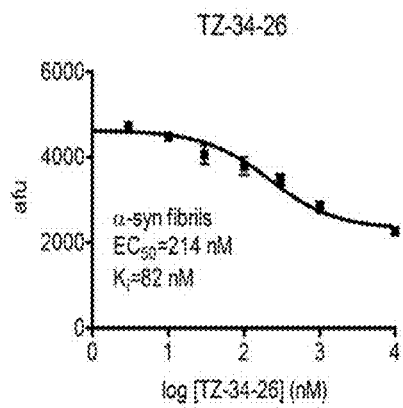
Figure 17.6
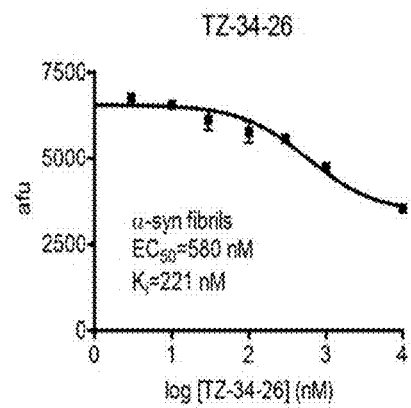

Figure 18.1
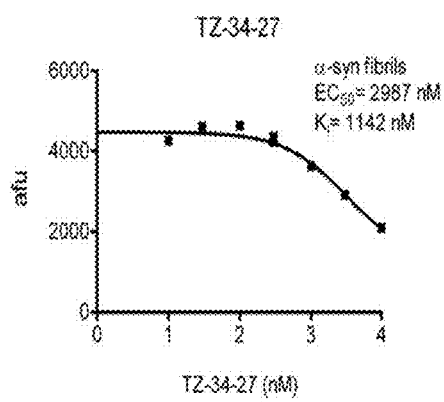
Figure 18.2
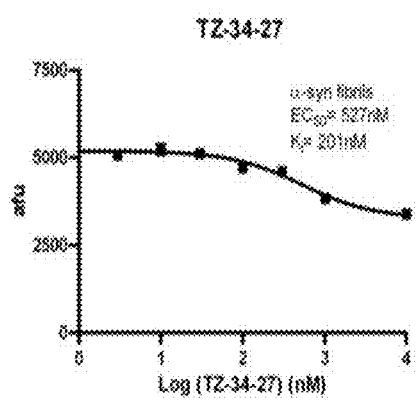
Figure 18.3
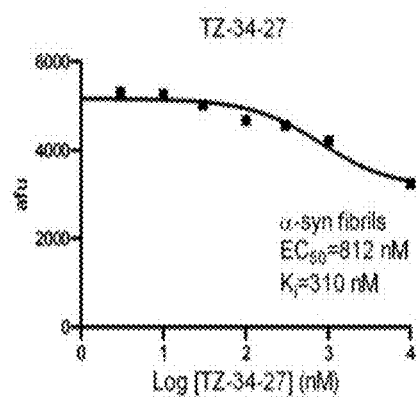

Figure 19.1
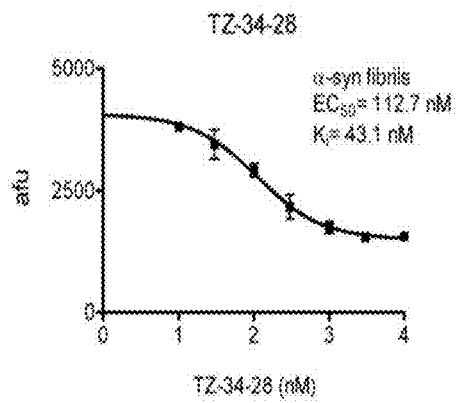
Figure 19.2
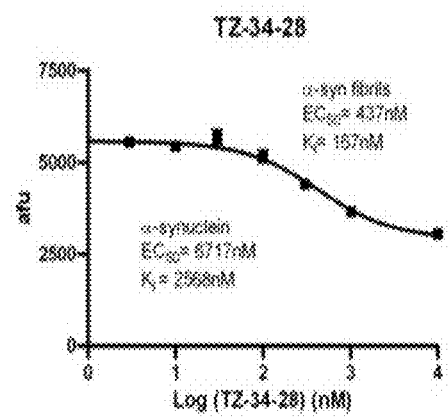
Figure 19.3
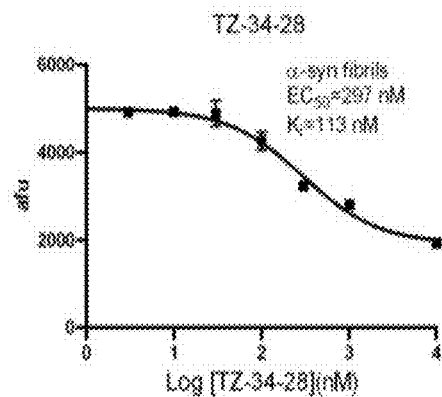
Figure 19.4
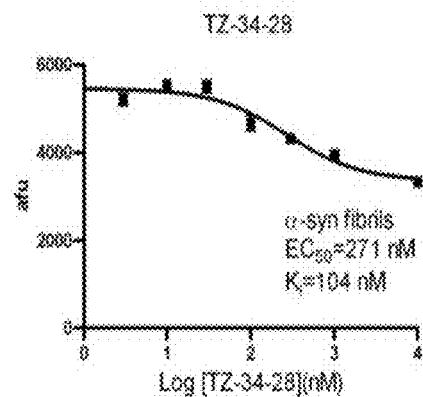
Figure 19.5
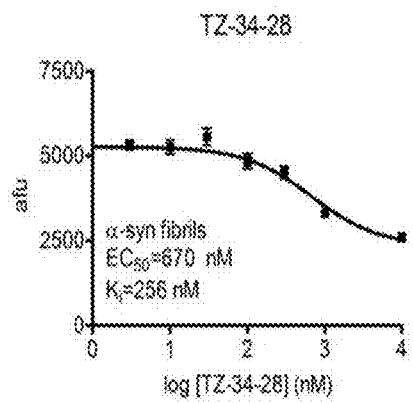
Figure 19.6
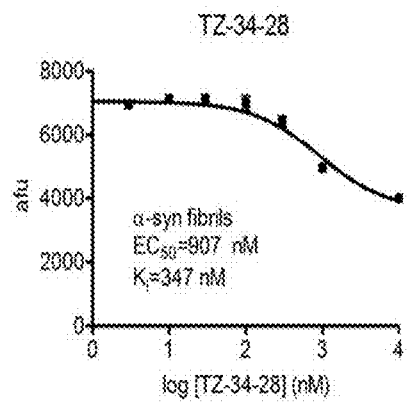

Figure 20.1
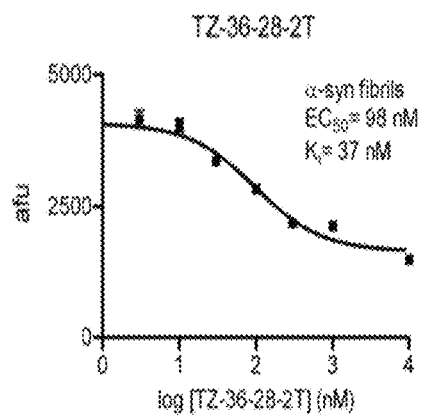
Figure 20.2
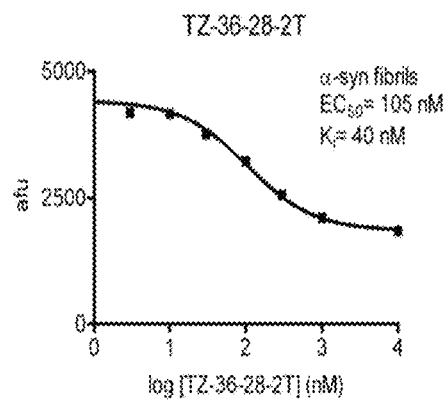
Figure 20.3
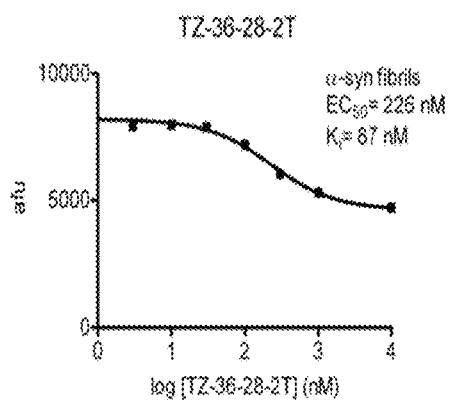
Figure 20.4
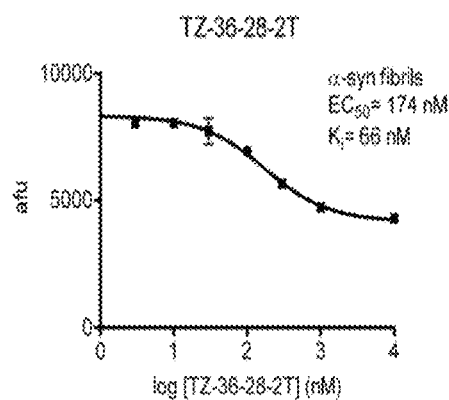

Figure 21.1
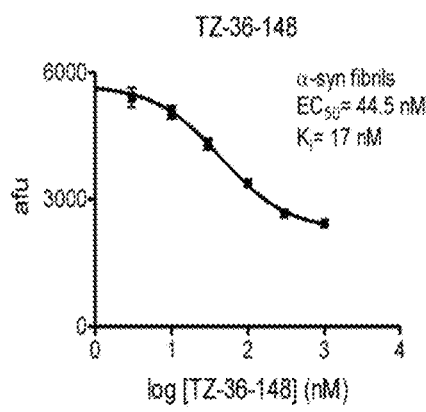
Figure 21.2
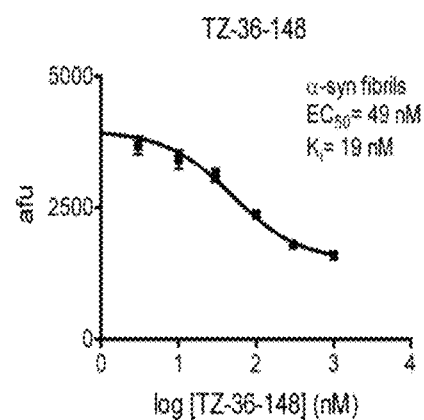
Figure 22.1
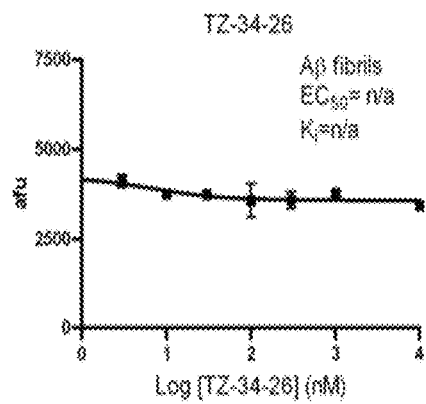
Figure 22.2
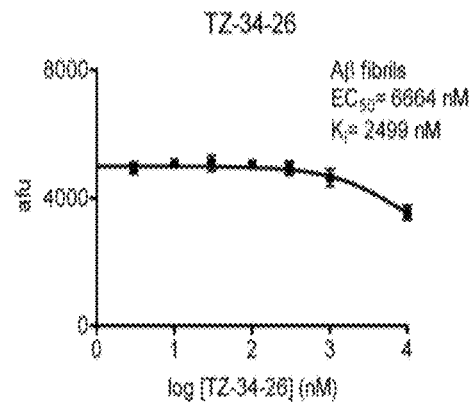

Figure 23.1
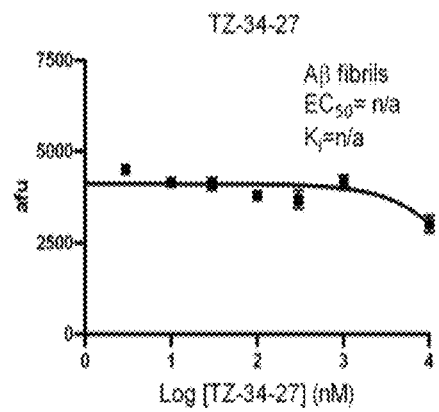
Figure 23.2
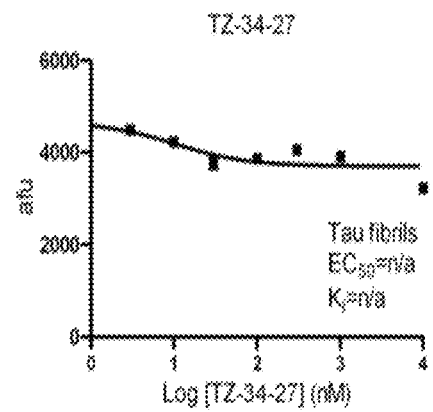
Figure 24.1
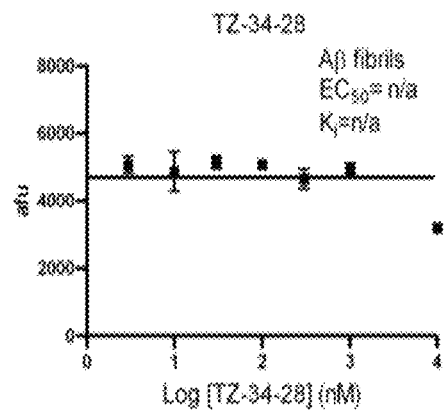
Figure 24.2
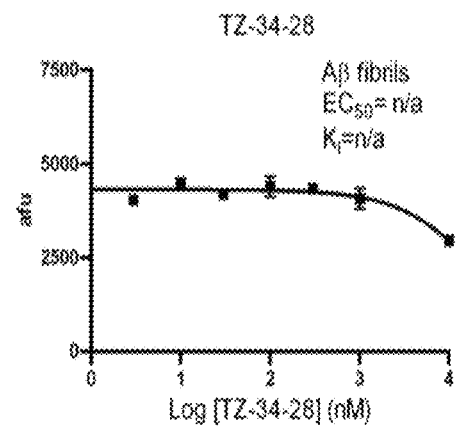
Figure 25.1
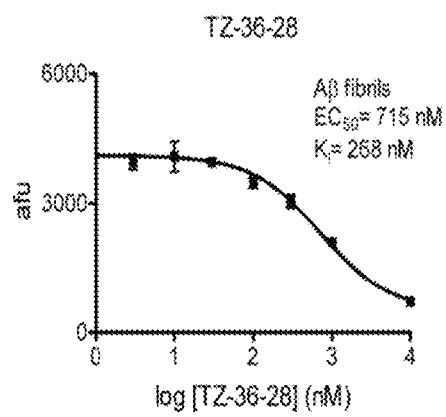

Figure 26.1
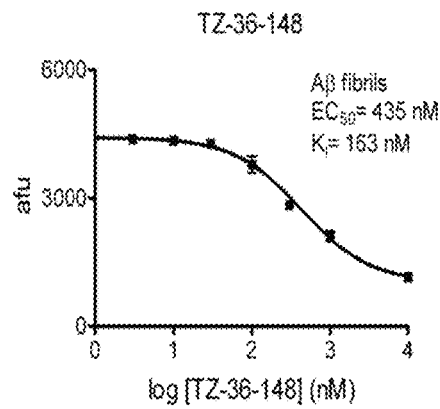
Figure 26.2
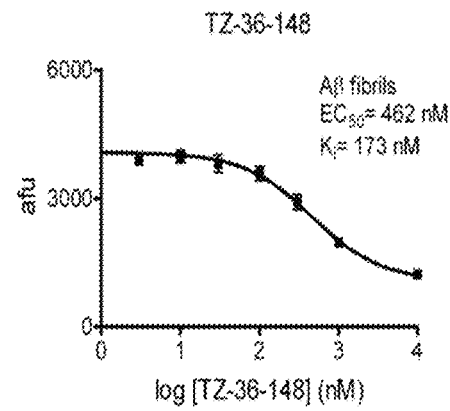
Figure 27.1
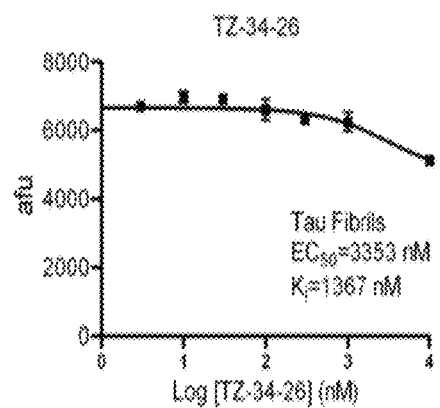
Figure 27.2
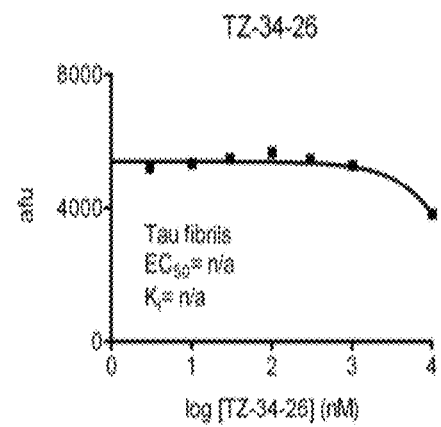
Figure 28.1
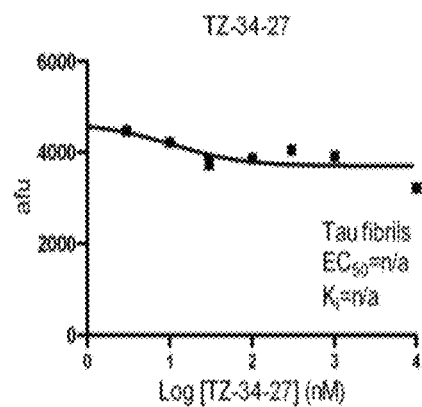

Figure 29.1
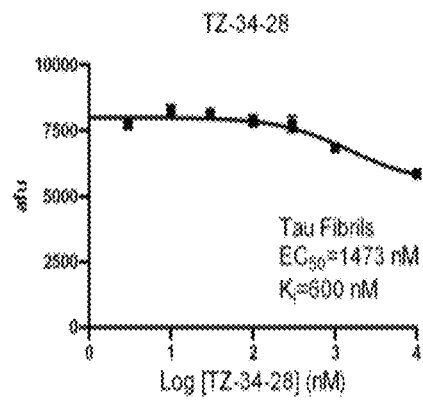
Figure 29.2
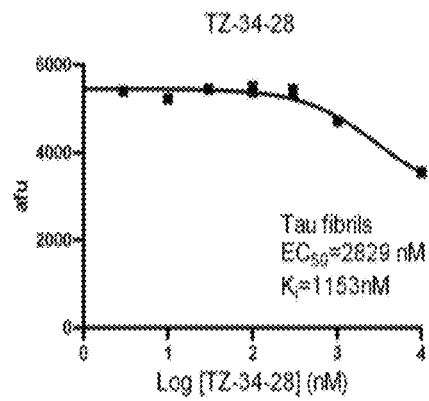
Figure 30.1
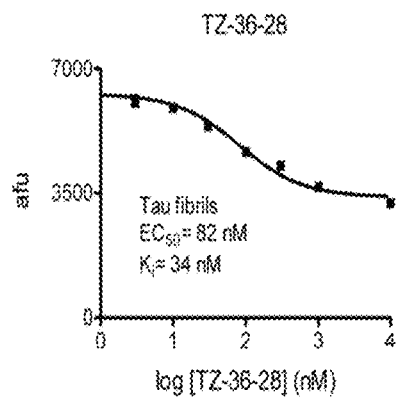
Figure 31.1
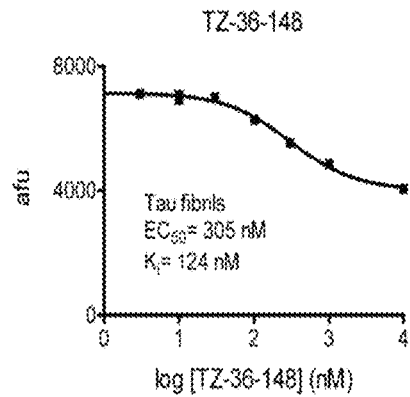
Figure 31.2
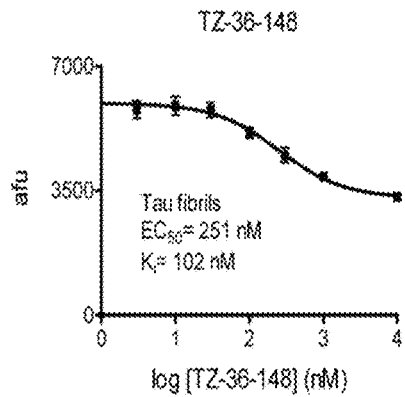

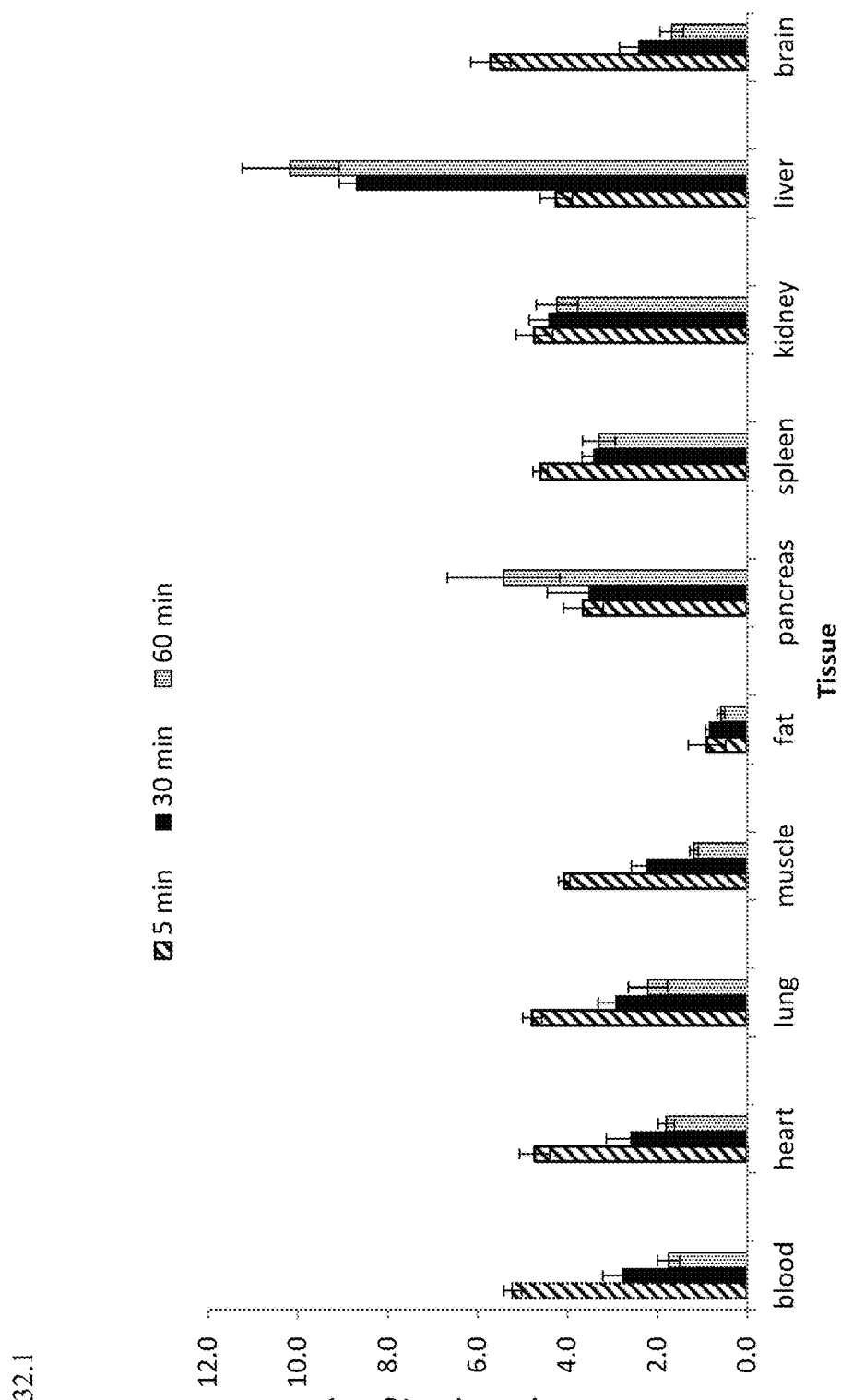
Figure 32.1

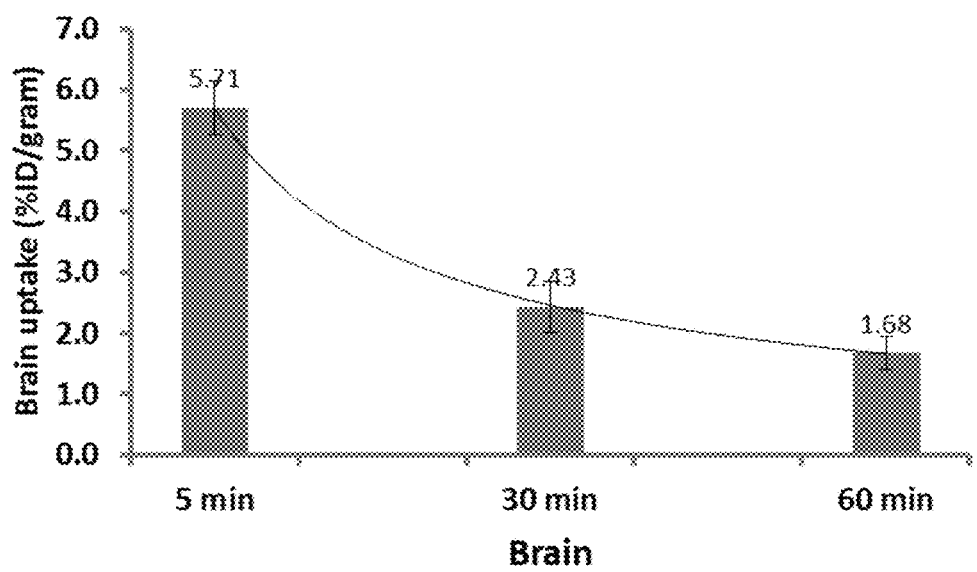
Figure 32.2

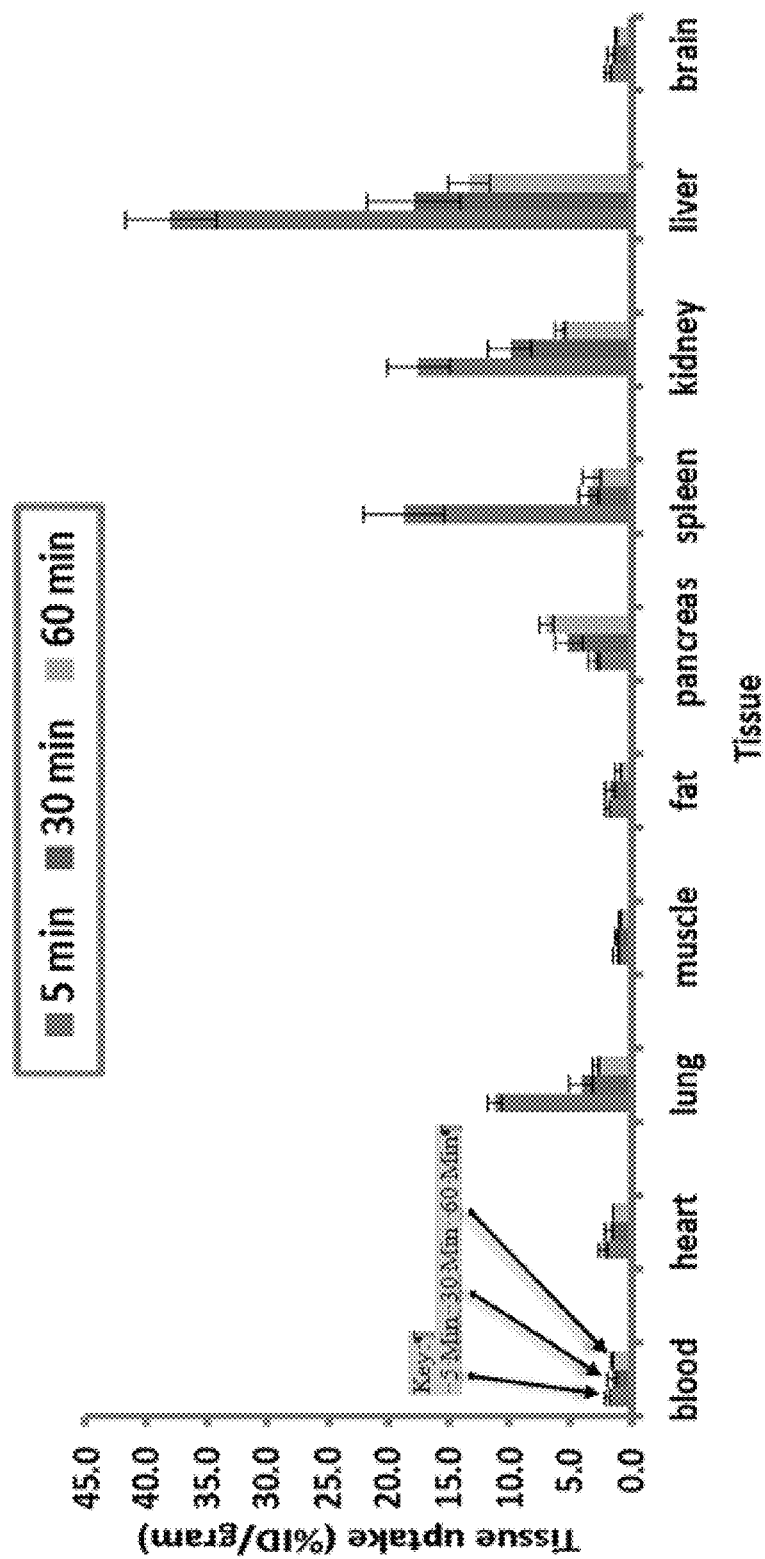
Figure 33.1

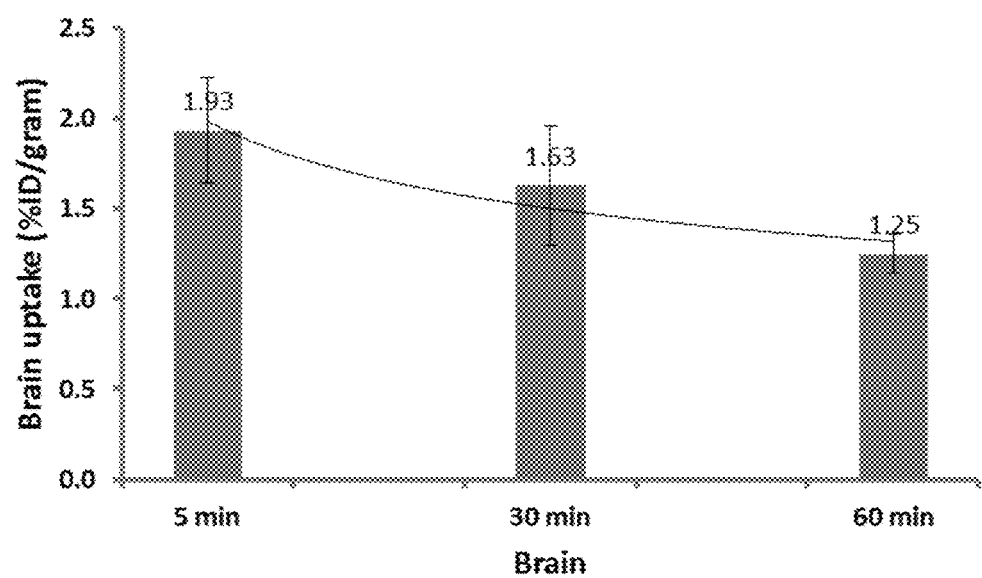
Figure 33.2

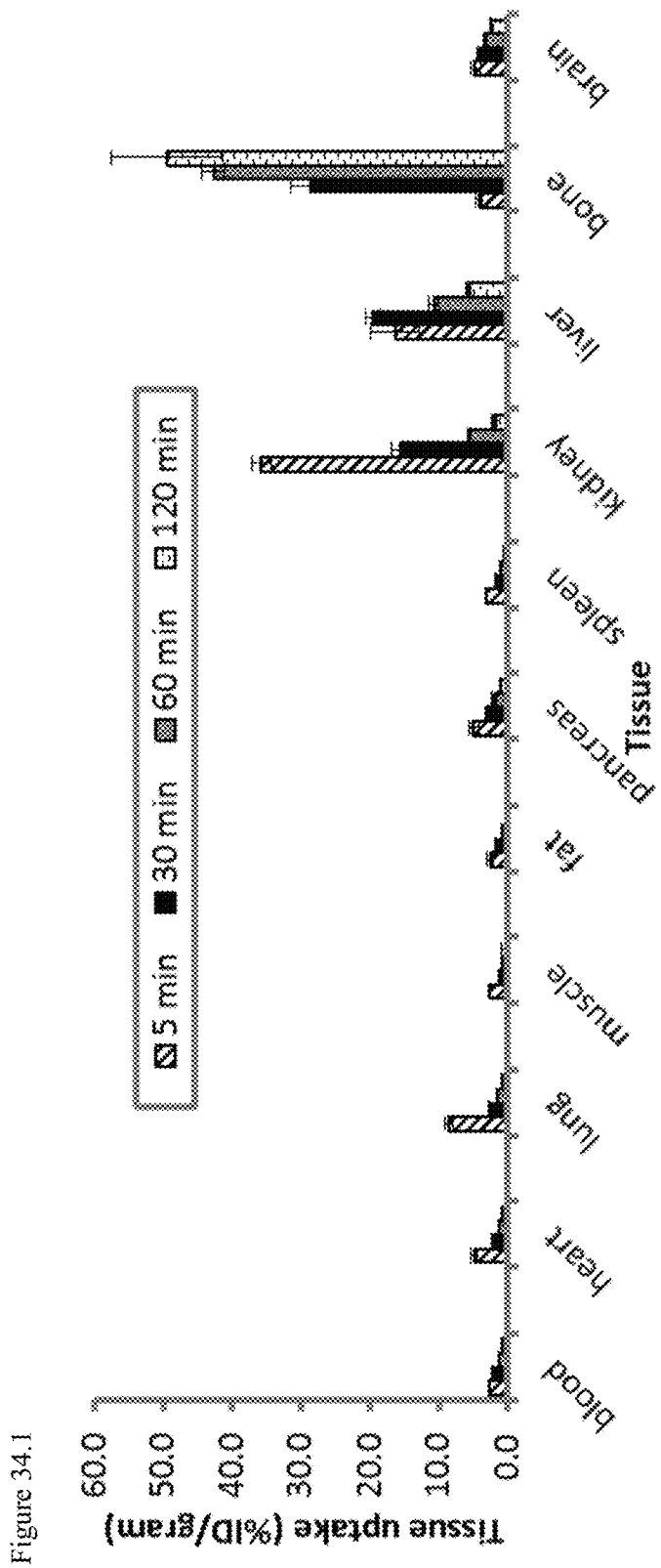
Figure 34.1

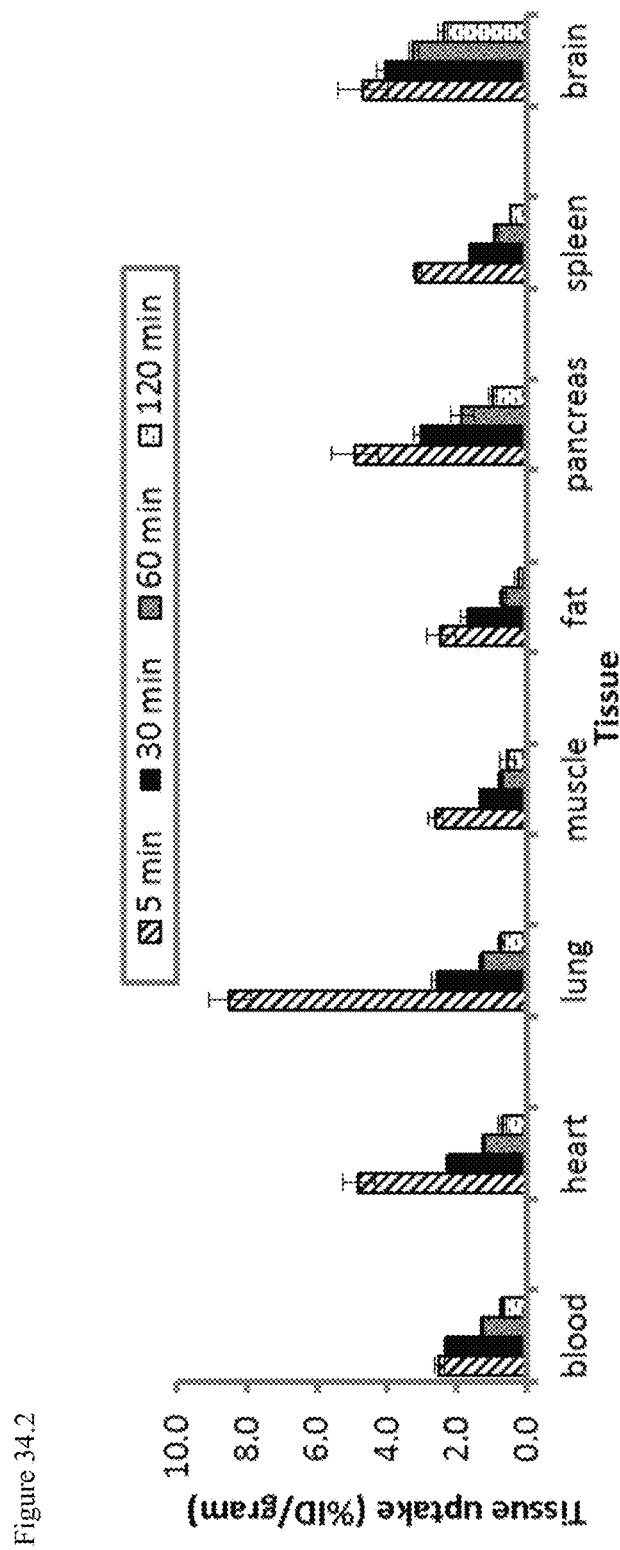
Figure 34.2

Figure 34.3
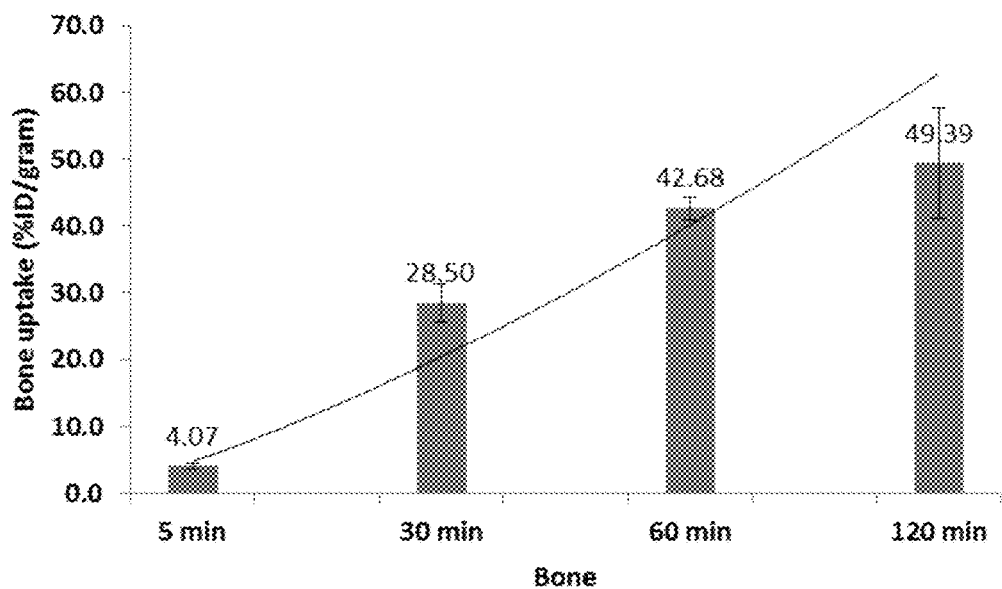
Figure 34.4
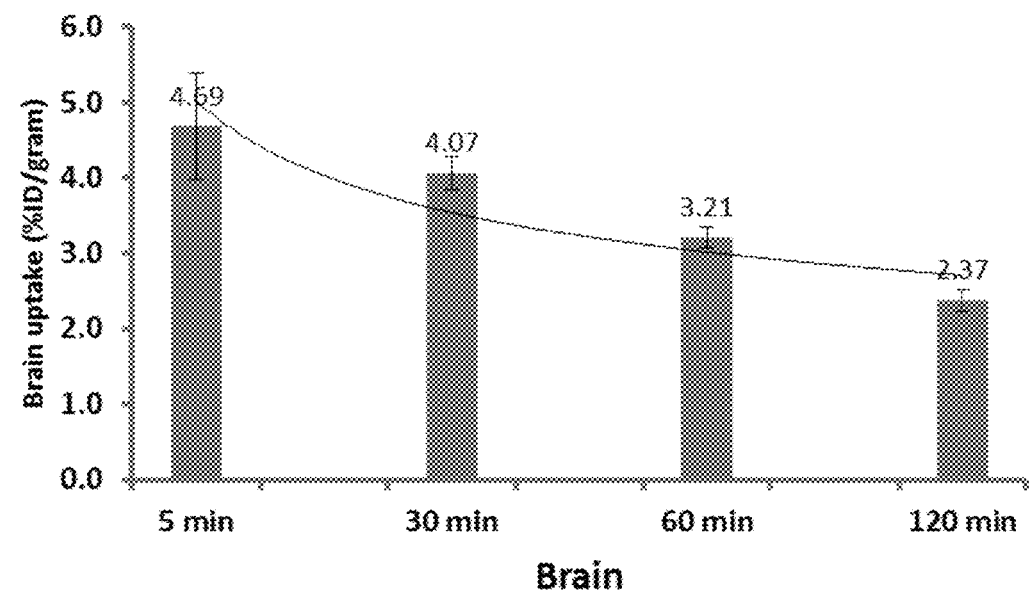

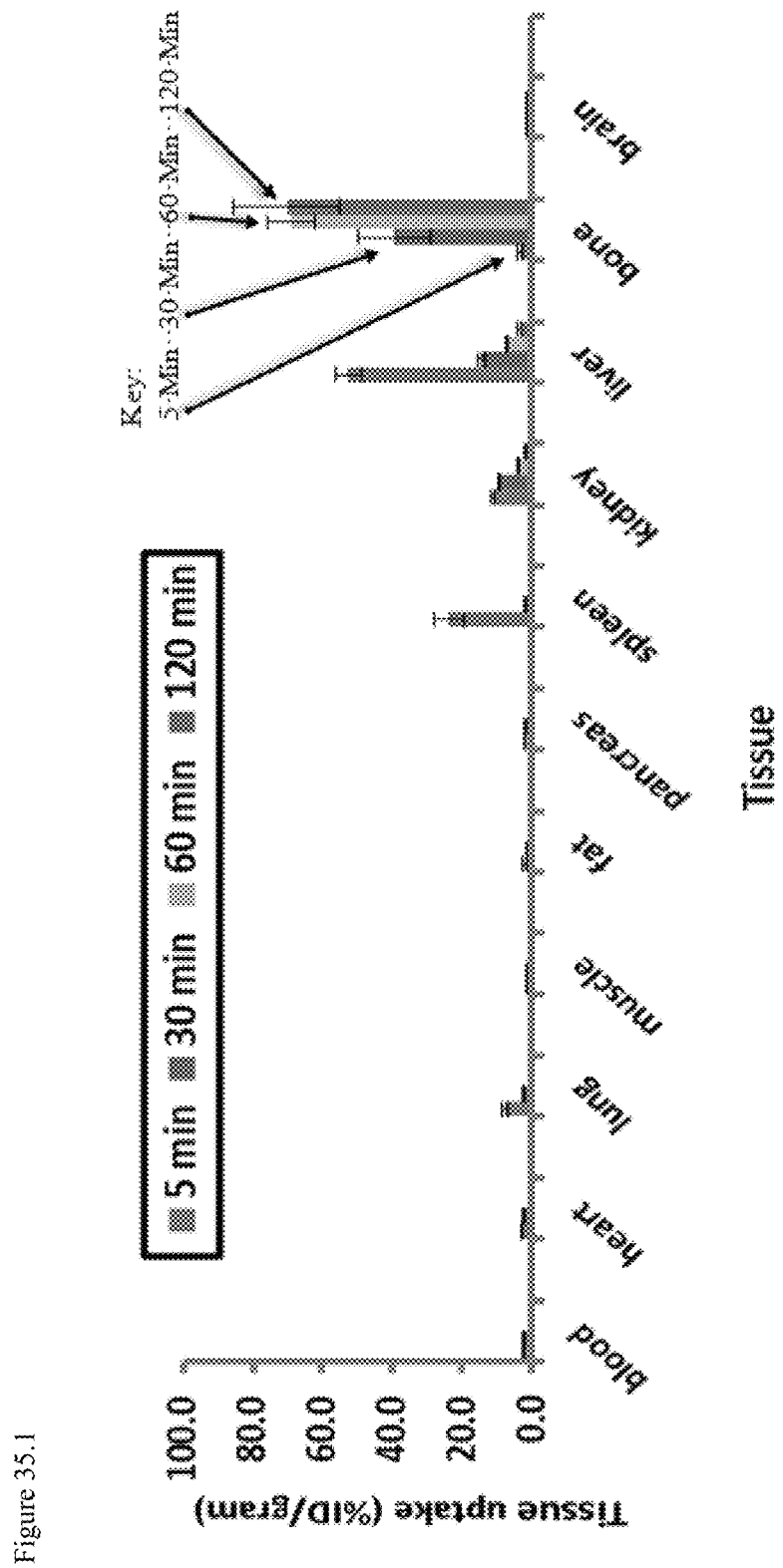
Figure 35.1

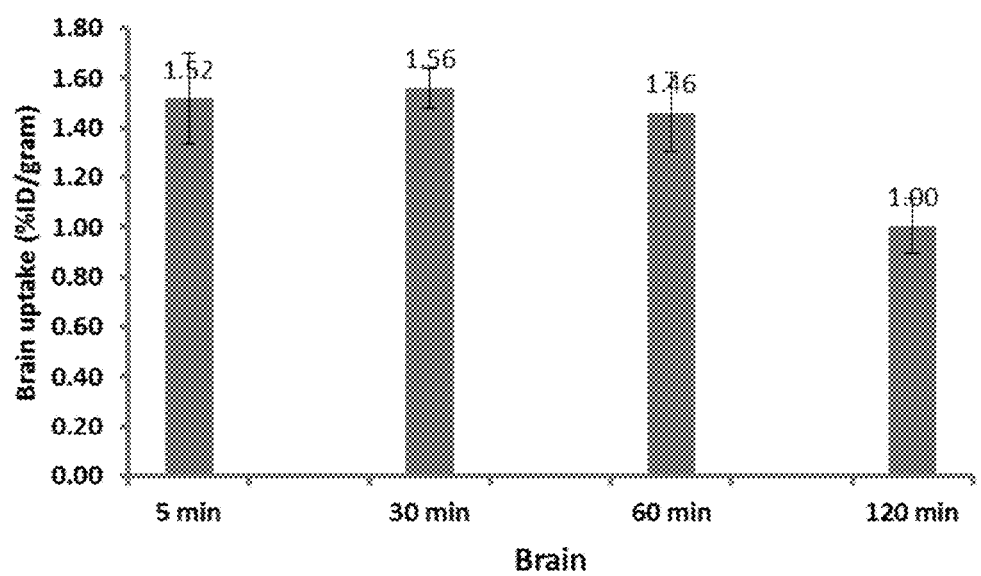
Figure 35.2

ALPHA-SYNUCLEIN LIGANDS

REFERENCE TO RELATED APPLICATIONS

This application claims benefit of U.S. provisional application Ser. No. 62/273,675 filed Dec. 31, 2015, the entire disclosure of which is incorporated herein by reference.

FIELD OF THE INVENTION

The present invention generally relates to various compounds that are useful as α-synuclein ligands. The invention further relates to methods of using these compounds and their radiolabeled analogs for the detection of synucleinopathies, including Parkinson's disease (PD).

BACKGROUND OF THE INVENTION

Neurodegenerative diseases such as Alzheimer's disease, Parkinson's disease (PD), Huntington's disease, amyotrophic lateral sclerosis and prion diseases are debilitating diseases which affect cognition and/or muscle control. These diseases are a subset of protein misfolding diseases. Protein folding is an essential process for protein function in all organisms, and conditions that disrupt protein folding present a threat to cell viability. In some cases, the disease arises because a specific protein is no longer functional when adopting a misfolded state. In other diseases, the pathological state originates because misfolding occurs concomitantly with aggregation, and the underlying aggregates are detrimental.

Even though neurodegenerative diseases such as Alzheimer's and Parkinson's are caused by different proteins, both involve the accumulation of insoluble fibrous protein deposits, called amyloids. For example, Parkinson's Disease (PD), Dementia with Lewy Bodies (DLB), and multiple system atrophy (MSA), which are collectively referred to as "synucleinopathies," have been linked to the accumulation of aggregated forms of the α-synuclein protein in neurons in the brain. As the primary neuropathologic change of PD, the degeneration of dopaminergic neurons occurs in the substantia nigra, as well as Lewy bodies (LB) and Lewy neurites (LN). To date, the pathogenic mechanism of PD has not been fully discovered.

α-Synuclein is a presynaptic terminal protein that consists of 140-amino acid protein that plays an important function in the central nervous system including synaptic vesicle recycling and synthesis, vesicular storage, and neurotransmitter release. It is specifically upregulated in a discrete population of presynaptic terminals of the brain during acquisition-related synaptic rearrangement. α-Synuclein naturally exists in a highly soluble, unfolded state. Evidence suggests that filamentous aggregates of α-synuclein accumulate at the pre-synaptic membrane and trigger synapse dysfunction and neuronal cell death in synucleinopathies, and may be the cause of Parkinson's and DLB. α-Synuclein aggregation has been identified by antibody-immunohistological studies as the major component of Lewy bodies, which are microscopic protein deposits in deteriorating nerve cells. Accumulation of misfolded, fibrillar α-synuclein in Lewy bodies (LB) and Lewy neurites (LN) is considered a hallmark of PD.

The diagnosis of PD is mainly based on the clinical symptoms such as rest tremor, bradykinesia, and rigidity. The current treatment for PD is to slow the disease progression and minimize the disease symptoms in the patients. Therefore, a method of diagnosing PD in the very early stage can greatly help the physicians to design the therapy accordingly, and to slow the disease progression.

There remains a need for improved diagnostic methods for identifying aggregations of misfolded proteins, including α-synuclein for early detection and ongoing monitoring of PD in subjects.

SUMMARY OF THE INVENTION

In various aspects, the present invention is directed to compounds that function as ligands for α-synuclein as well as radiolabeled analogs of these compounds that are useful for diagnosing or monitoring a synucleinopathy in a subject. For example, ligands for α-synuclein of the present invention include compounds of Formulas (I)-(IV)

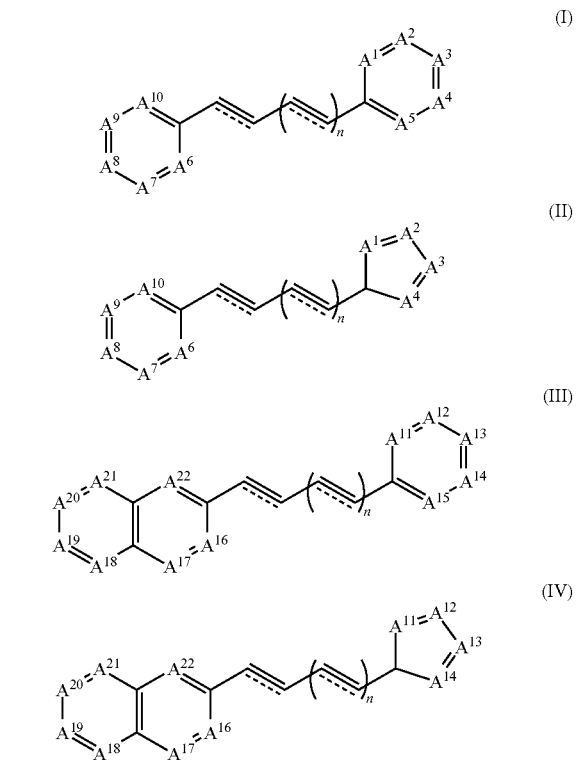

wherein n is 0 or 1; ----- is an optional bond; each $A^1$ is independently C—$R^1$, nitrogen, oxygen, or sulfur; each $A^2$ is independently C—$R^2$, nitrogen, oxygen, or sulfur; each $A^3$ is independently C—$R^3$, nitrogen, oxygen, or sulfur; each $A^4$ is independently C—$R^4$, nitrogen, oxygen, or sulfur; $A^5$ is C—$R^5$, nitrogen, oxygen, or sulfur; each $A^6$ is independently C—$R^6$ or nitrogen; each $A^7$ is independently C—$R^7$ or nitrogen; each $A^8$ is independently C—$R^8$ or nitrogen; each $A^9$ is independently C—$R^9$ or nitrogen; each $A^{10}$ is independently C—$R^{10}$ or nitrogen; each $A^{11}$ is independently C—$R^{11}$, nitrogen, oxygen, or sulfur; each $A^{12}$ is independently C—$R^{12}$, nitrogen, oxygen, or sulfur; each $A^{13}$ is independently C—$R^{13}$, nitrogen, oxygen, or sulfur; each $A^{14}$ is independently C—$R^{14}$, nitrogen, oxygen, or sulfur; $A^{15}$ is C—$R^{15}$, nitrogen, oxygen, or sulfur; each $A^{16}$ is independently C—$R^{16}$ or nitrogen; each $A^{17}$ is independently C—$R^{17}$ or nitrogen; each $A^{18}$ is independently C—$R^{18}$ or nitrogen; each $A^{19}$ is independently C—$R^{19}$ or nitrogen; each $A^{20}$ is independently C—$R^{20}$ or nitrogen; each $A^{21}$ is independently C—$R^{21}$ or nitrogen; each $A^{22}$ is independently C—$R^{22}$ or nitrogen; each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ is independently hydrogen, nitro, halo, hydroxy, carboxyl, substituted or unsubstituted alkyl, substituted or unsubstituted alkoxy, substituted or unsubstituted carboxylate, substituted or unsubstituted amino, substituted or unsubstituted amido, substituted or unsubstituted thiophenyl, or substituted or unsubstituted thiazolyl, or $R^3$ and $R^4$ optionally form a fused 6-membered aromatic ring.

Other ligands for α-synuclein of the present invention include compounds of Formula (V)

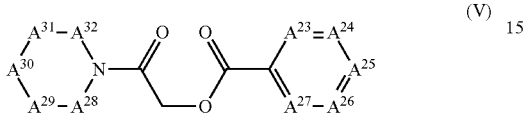

(V)

wherein $A^{23}$ is C—$R^{23}$; $A^{24}$ is C—$R^{24}$; $A^{25}$ is C—$R^{25}$; $A^{26}$ is C—$R^{26}$; $A^{27}$ is C—$R^{27}$; $A^{28}$ is C—$R^{28}$; $A^{29}$ is C—$R^{29}$; $A^{30}$ is C—$R^{30}$; $A^{31}$ is C—$R^{31}$; $A^{32}$ is C—$R^{32}$; and $R^{23}$, $R^{24}$, $R^{25}$, $R^{26}$, $R^{27}$, $R^{28}$, $R^{29}$, $R^{30}$, $R^{31}$, and $R^{32}$ are independently hydrogen, halo, substituted or unsubstituted alkyl, substituted or unsubstituted alkoxy, substituted or unsubstituted aryl, or substituted or unsubstituted benzoyl.

Additional ligands for α-synuclein of the present invention include compounds of Formula (VI)

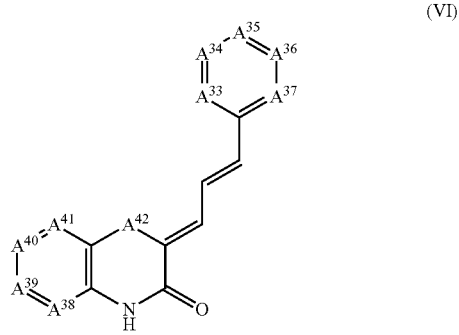

(VI)

wherein $A^{33}$ is C—$R^{33}$; $A^{34}$ is C—$R^{34}$; $A^{35}$ is C—$R^{35}$; $A^{36}$ is C—$R^{36}$; $A^{37}$ is C—$R^{37}$; $A^{38}$ is C—$R^{38}$; $A^{39}$ is C—$R^{39}$; $A^{40}$ is C—$R^{40}$; $A^{41}$ is C—$R^{41}$; $A^{42}$ is oxygen or sulfur; and $R^{33}$, $R^{34}$, $R^{35}$, $R^{36}$, $R^{37}$, $R^{38}$, $R^{39}$, $R^{40}$, and $R^{41}$ is hydrogen, halo, nitro, substituted or unsubstituted alkyl, or substituted or unsubstituted alkoxy.

Further ligands for α-synuclein of the present invention include compounds of Formula (VII)

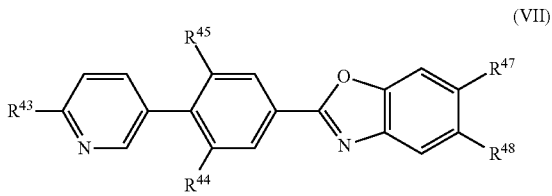

(VII)

wherein $R^{43}$, $R^{44}$, $R^{45}$, $R^{46}$, $R^{47}$, and $R^{48}$ are independently hydrogen, halo, substituted or unsubstituted alkyl, substituted or unsubstituted alkoxy, or substituted or unsubstituted carboxylate.

Still other ligands for α-synuclein of the present invention include compounds of Formula (VIII)

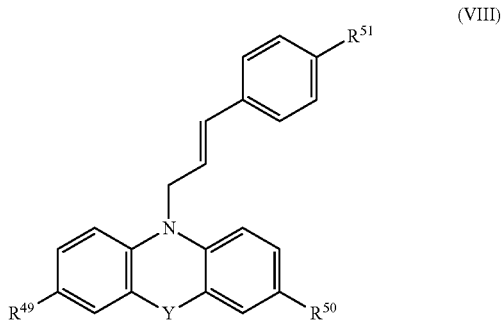

(VIII)

wherein $R^{49}$, $R^{50}$, and $R^{51}$ are independently hydrogen, substituted or unsubstituted alkyl, substituted or unsubstituted alkoxy, substituted or unsubstituted amine, or nitro, and Y is oxygen or sulfur.

Further aspects of the present invention are directed to compounds of Formulas (I)-(VIII) that are radiolabeled, for example, with an isotope useful for positron emission tomography. In other aspects, the present invention is directed to methods for diagnosing or monitoring a synucleinopathy in a human subject comprising administering a radiolabeled compound of Formulas (I)-(VIII) to the human subject; and imaging the subject's brain by positron emission tomography.

Other objects and features will be in part apparent and in part pointed out hereinafter.

BRIEF DESCRIPTION OF THE DRAWINGS

FIG. 16.1 is the fluorescence emission spectra of ThT in buffer alone, in the presence of α-synuclein monomer, and in the presence of α-synuclein fibrils at $\lambda_{em}$=440 nm.

FIG. 16.2 is the saturation curve of thioflavin T (ThT) for α-synuclein fibrils at difference incubation times.

FIG. 17.1 is a plot of the inhibition curve for compound TZ-34-26 in the ThT competition binding assay using α-synuclein fibrils.

FIG. 17.2 is a plot of the inhibition curve for compound TZ-34-26 in the ThT competition binding assay using α-synuclein fibrils.

FIG. 17.3 is a plot of the inhibition curve for compound TZ-34-26 in the ThT competition binding assay using α-synuclein fibrils.

FIG. 17.4 is a plot of the inhibition curve for compound TZ-34-26 in the ThT competition binding assay using α-synuclein fibrils.

FIG. 17.5 is a plot of the inhibition curve for compound TZ-34-26 in the ThT competition binding assay using α-synuclein fibrils.

FIG. 17.6 is a plot of the inhibition curve for compound TZ-34-26 in the ThT competition binding assay using α-synuclein fibrils.

FIG. 18.1 is a plot of the inhibition curve for compound TZ-34-27 in the ThT competition binding assay using α-synuclein fibrils.

FIG. 18.2 is a plot of the inhibition curve for compound TZ-34-27 in the ThT competition binding assay using α-synuclein fibrils.

FIG. 18.3 is a plot of the inhibition curve for compound TZ-34-27 in the ThT competition binding assay using α-synuclein fibrils.

FIG. 19.1 is a plot of the inhibition curve for compound TZ-34-28 in the ThT competition binding assay using α-synuclein fibrils.

FIG. 19.2 is a plot of the inhibition curve for compound TZ-34-28 in the ThT competition binding assay using α-synuclein fibrils.

FIG. 19.3 is a plot of the inhibition curve for compound TZ-34-28 in the ThT competition binding assay using α-synuclein fibrils.

FIG. 19.4 is a plot of the inhibition curve for compound TZ-34-28 in the ThT competition binding assay using α-synuclein fibrils.

FIG. 19.5 is a plot of the inhibition curve for compound TZ-34-28 in the ThT competition binding assay using α-synuclein fibrils.

FIG. 19.6 is a plot of the inhibition curve for compound TZ-34-28 in the ThT competition binding assay using α-synuclein fibrils.

FIG. 20.1 is a plot of the inhibition curve for compound TZ-36-28-2T in the ThT competition binding assay using α-synuclein fibrils.

FIG. 20.2 is a plot of the inhibition curve for compound TZ-36-28-2T in the ThT competition binding assay using α-synuclein fibrils.

FIG. 20.3 is a plot of the inhibition curve for compound TZ-36-28-2T in the ThT competition binding assay using α-synuclein fibrils.

FIG. 20.4 is a plot of the inhibition curve for compound TZ-36-28-2T in the ThT competition binding assay using α-synuclein fibrils.

FIG. 21.1 is a plot of the inhibition curve for compound TZ-36-148 in the ThT competition binding assay using α-synuclein fibrils.

FIG. 21.2 is a plot of the inhibition curve for compound TZ-36-148 in the ThT competition binding assay using α-synuclein fibrils.

FIG. 22.1 is a plot of the inhibition curve for compound TZ-34-26 in the ThT competition binding assay using Aβ fibrils.

FIG. 22.2 is a plot of the inhibition curve for compound TZ-34-26 in the ThT competition binding assay using Aβ fibrils.

FIG. 23.1 is a plot of the inhibition curve for compound TZ-34-27 in the ThT competition binding assay using Aβ fibrils.

FIG. 23.2 is a plot of the inhibition curve for compound TZ-34-27 in the ThT competition binding assay using Aβ fibrils.

FIG. 24.1 is a plot of the inhibition curve for compound TZ-34-28 in the ThT competition binding assay using Aβ fibrils.

FIG. 24.2 is a plot of the inhibition curve for compound TZ-34-28 in the ThT competition binding assay using Aβ fibrils.

FIG. 25.1 is a plot of the inhibition curve from compound TZ-36-28-2T in the ThT competition binding assay using Aβ fibrils.

FIG. 26.1 is a plot of the inhibition curve for compound TZ-36-148 in the ThT competition binding assay using Aβ fibrils.

FIG. 26.2 is a plot of the inhibition curve from compound TZ-36-148 in the ThT competition binding assay using Aβ fibrils.

FIG. 27.1 is a plot of the inhibition curve from compound TZ-34-26 in the ThT competition binding assay using tau fibrils.

FIG. 27.2 is a plot of the inhibition curve from compound TZ-34-26 in the ThT competition binding assay using tau fibrils.

FIG. 28.1 is a plot of the inhibition curve from compound TZ-34-27 in the ThT competition binding assay using tau fibrils.

FIG. 29.1 is a plot of the inhibition curve from compound TZ-34-28 in the ThT competition binding assay using tau fibrils.

FIG. 29.2 is a plot of the inhibition curve from compound TZ-34-28 in the ThT competition binding assay using tau fibrils.

FIG. 30.1 is a plot of the inhibition curve from compound TZ-36-28-2T in the ThT competition binding assay suing tau fibrils.

FIG. 31.1 is a plot of the inhibition curve from compound TZ-36-148 in the ThT competition binding assay suing tau fibrils.

FIG. 31.2 is a plot of the inhibition curve from compound TZ-36-148 in the ThT competition binding assay suing tau fibrils.

FIG. 32.1 is a graph of the biodistribution of compound [$^{11}$C]TZ-20-35 in various tissues in mice.

FIG. 32.2 is a graph of brain uptake of compound [$^{11}$C]TZ-20-35 in mice.

FIG. 33.1 is a graph of the biodistribution of compound [$^{11}$C]TZ-20-83 in various tissues in mice.

FIG. 33.2 is a graph of brain uptake of compound [$^{11}$C]TZ-20-83 in mice.

FIG. 34.1 is a graph of the biodistribution of compound [$^{11}$C]TZ-20-88 in various tissues in mice.

FIG. 34.2 is a graph of the biodistribution of compound [$^{11}$C]TZ-20-88 in various tissues in mice.

FIG. 34.3 is a graph of bone uptake of compound [$^{11}$C]TZ-20-88 in mice.

FIG. 34.4 is a graph of brain uptake of compound [$^{11}$C]TZ-20-88 in mice.

FIG. 35.1 is a graph of the biodistribution of compound [$^{11}$C]TZ-23-92 in various tissues in mice.

FIG. 35.2 is a graph of brain uptake of compound [$^{11}$C]TZ-23-92 in mice.

DESCRIPTION OF THE PREFERRED EMBODIMENTS

Figure 1:
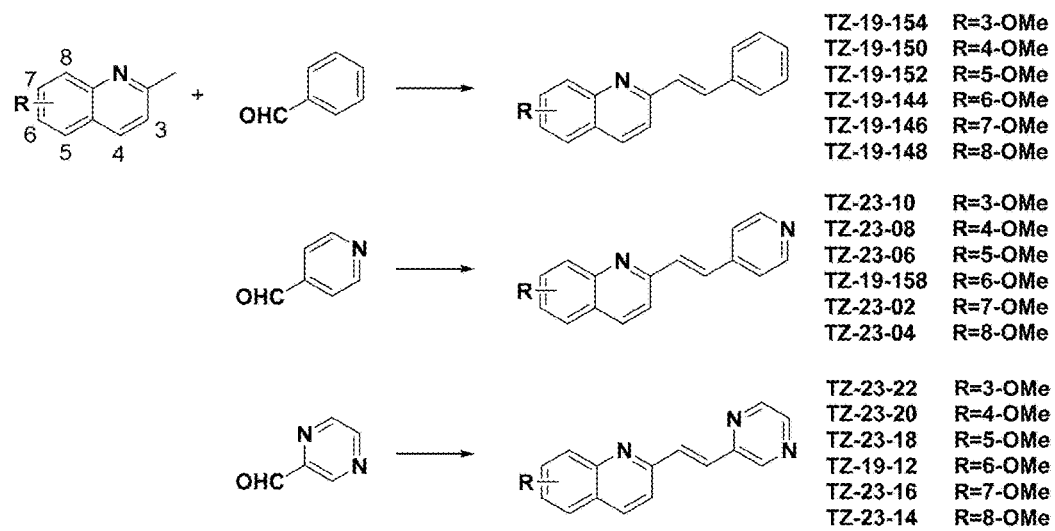
FIG. 1 shows the synthesis scheme for compounds TZ-19-154, TZ-19-150, TZ-19-152, TZ-19-144, TZ-19-146, TZ-19-148, TZ-23-10, TZ-23-08, TZ-23-06, TZ-19-158, TZ-23-02, TZ-23-04, TZ-23-22, TZ-23-20, TZ-23-18, TZ-19-12, TZ-23-16, and TZ-23-14.
Figure 2:
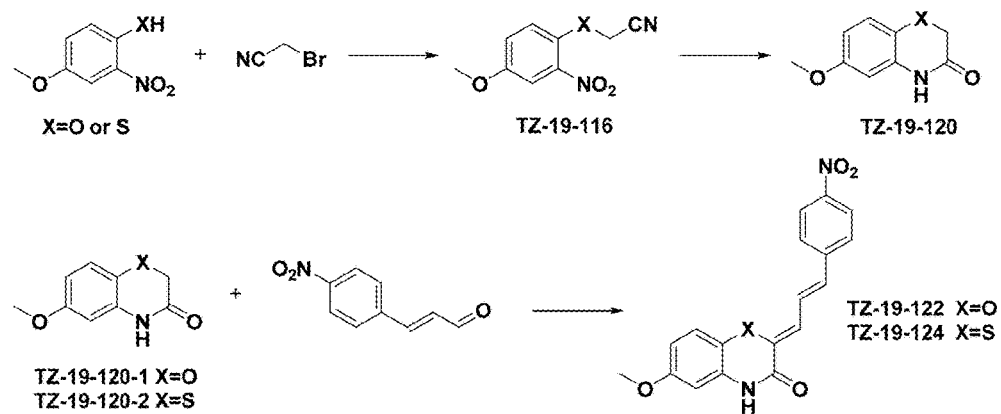
FIG. 2 shows the synthesis scheme for compounds TZ-19-122 and TZ-19-124.
Figure 3:
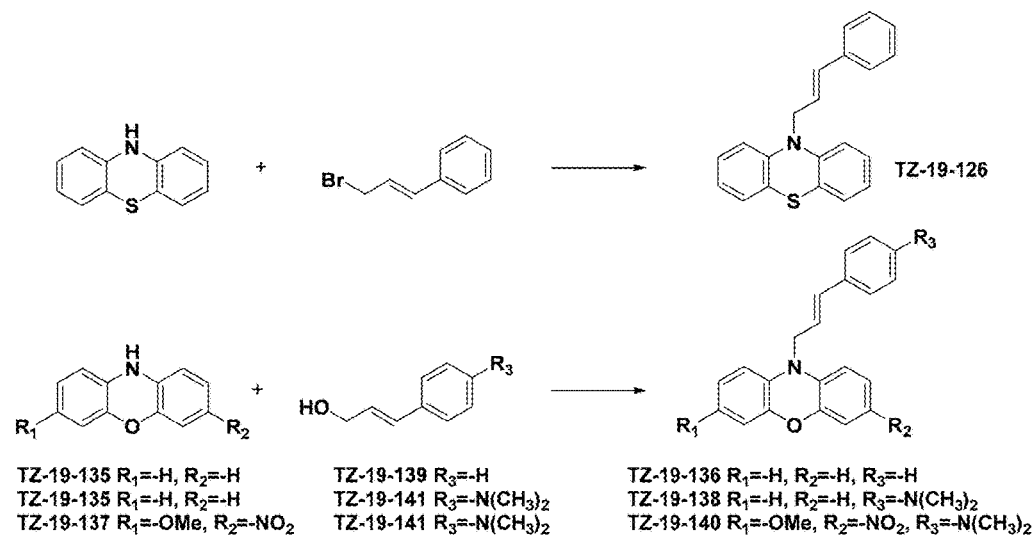
FIG. 3 shows the synthesis scheme for compounds TZ-19-126, TZ-19-136, TZ-19-138, and TZ-19-140.
Figure 4:
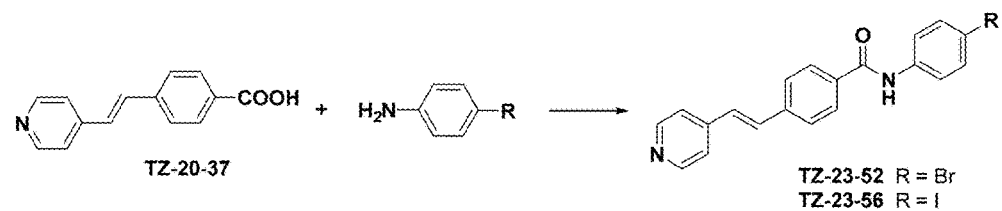
FIG. 4 shows the synthesis scheme for compounds TZ-23-52 and TZ-23-56.
Figure 5:
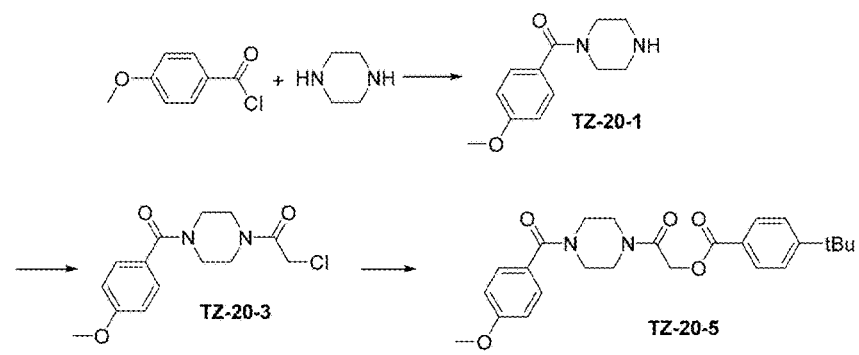
FIG. 5 shows the synthesis scheme for compound TZ-20-5.
Figure 6:
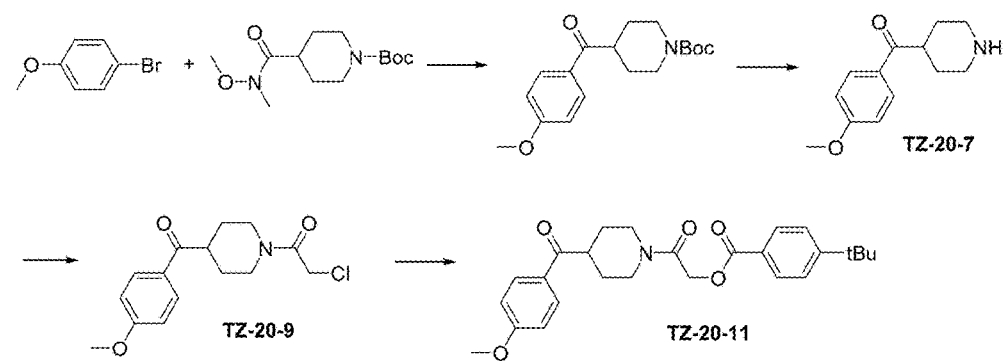
FIG. 6 shows the synthesis scheme for compound TZ-20-11.
Figure 7:
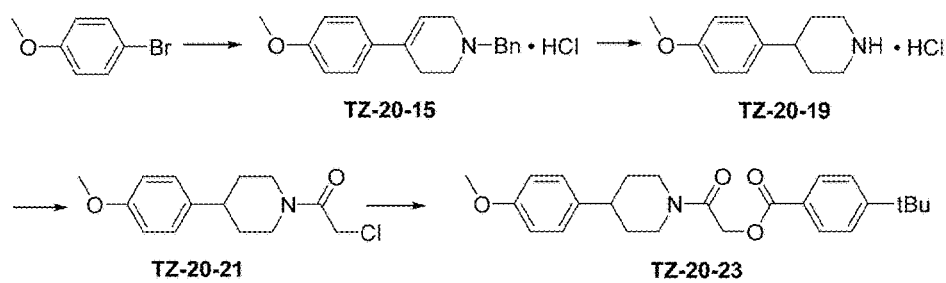
FIG. 7 shows the synthesis scheme for compound TZ-20-23.
Figure 8:
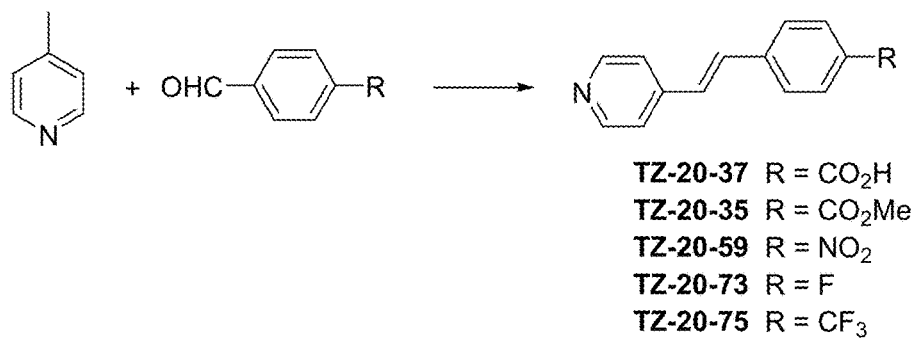
FIG. 8 shows the synthesis scheme for compound TZ-20-37, TZ-20-35, TZ-59, TZ-20-73, and TZ-20-75.
Figure 9:
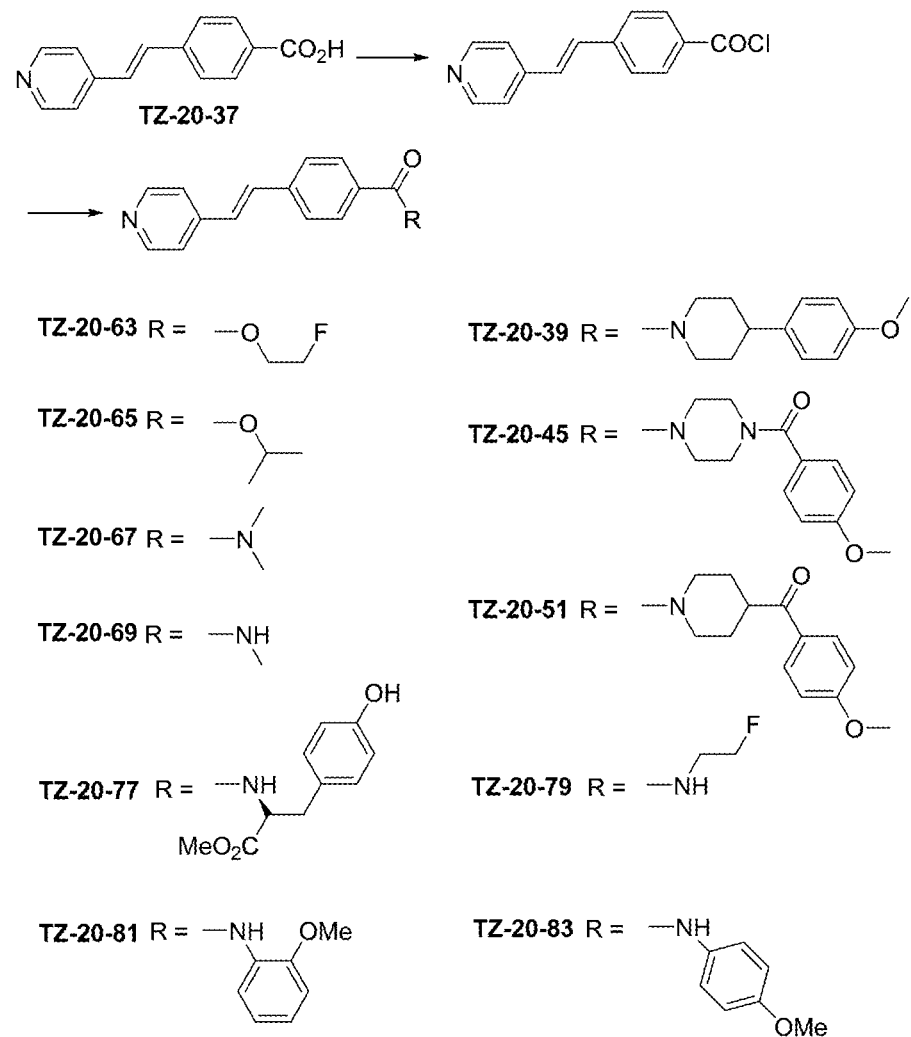
FIG. 9 shows the synthesis scheme for compound TZ-20-63, TZ-20-65, TZ-20-67, TZ-20-69, TZ-20-77, TZ-20-81, TZ-20-39, TZ-20-45, TZ-20-51, TZ-20-79, and TZ-20-83.
Figure 10:
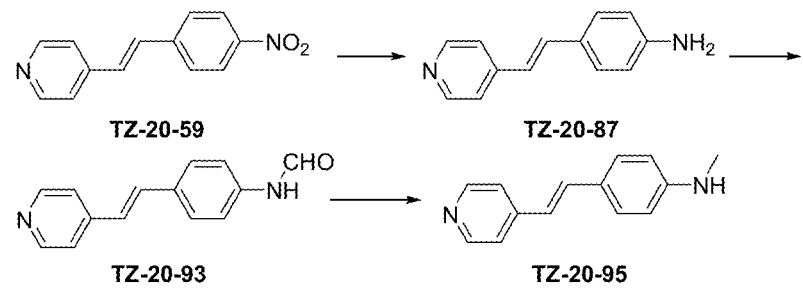
FIG. 10 shows the synthesis scheme for compound TZ-20-95.
Figure 11:
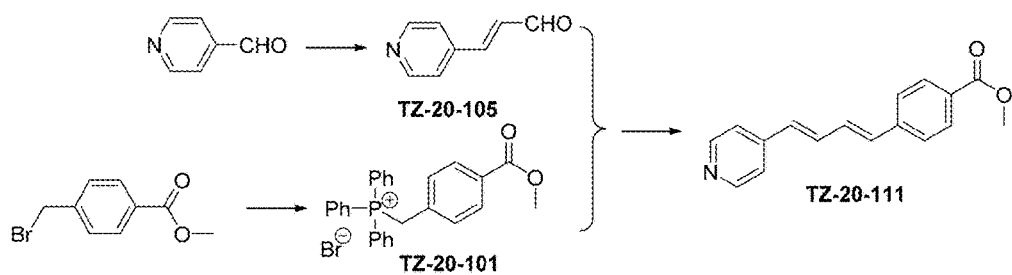
FIG. 11 shows the synthesis scheme for compound TZ-20-111.
Figure 12:
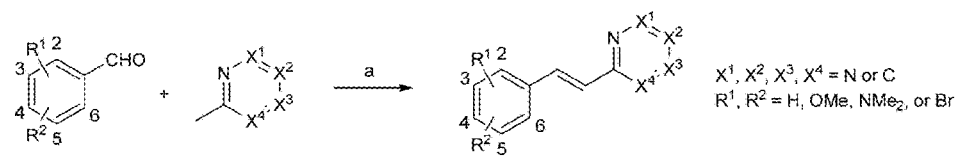
FIG. 12 shows the synthesis scheme for compounds TZ-22-25-1, TZ-22-23-1, TZ-22-21-1, TZ-22-19-1, TZ-22-33-1, TZ-22-31-1, TZ-22-1-2, TZ-22-49-1, TZ-22-15-1, TZ-22-35-1, TZ-22-37-1, and TZ-22-47-1.
Figure 13:
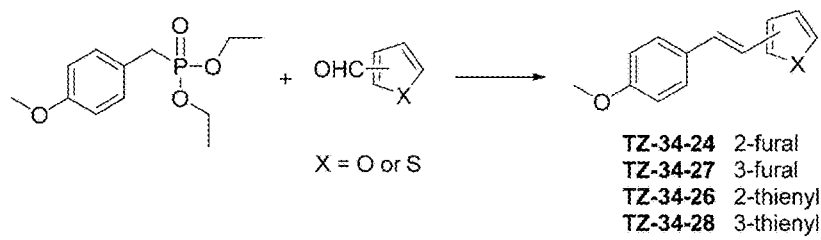
FIG. 13 shows the synthesis scheme for compounds TZ-34-24, TZ-34-27, TZ-34-26, and TZ-34-28.
Figure 14:
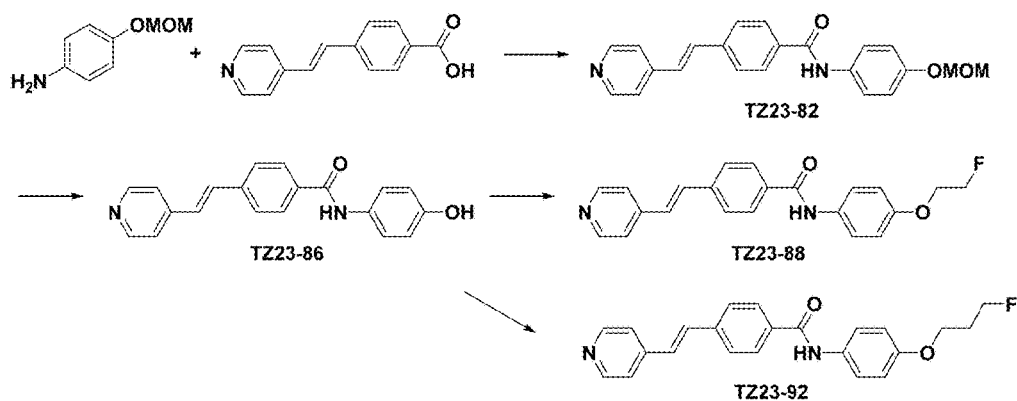
FIG. 14 shows the synthesis scheme for compounds TZ-23-82, TZ-23-88, and TZ-23-92.
Figure 15:
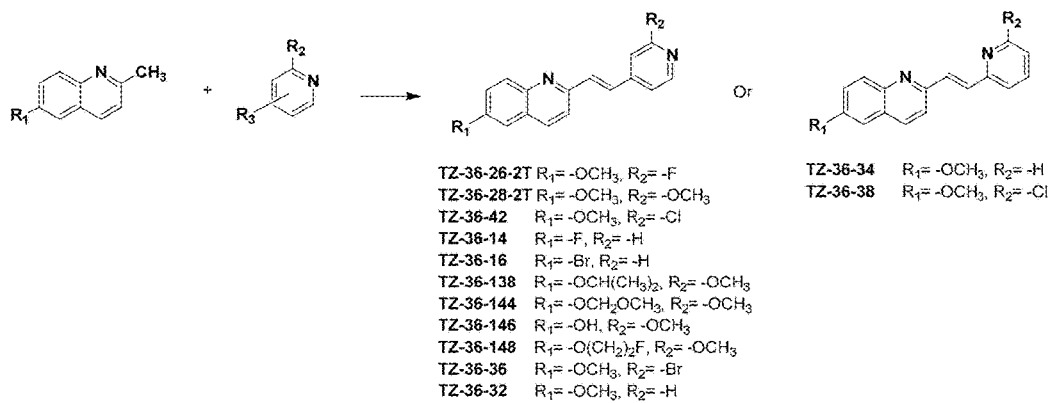
FIG. 15 shows the synthesis scheme for compounds TZ-36-26-2T, TZ-36-28-2T, TZ-36-42, TZ-36-14, TZ-36-16, TZ-36-138, TZ-36-144, TZ-36-146, TZ-36-148, TZ-36-36, TZ-36-32, TZ-36-34, and TZ-36-38.

Generally, the present invention is directed compounds that are useful α-synuclein ligands. The compounds possess sufficient binding affinity to α-synuclein fibrils. Also, various compounds of the present invention are highly selective ligands for α-synuclein as compared to other fibrils such as Aβ-fibrils and tau fibrils. As a result, radiolabeled analogs of the compounds described herein are useful for certain diagnostic methods for synucleinopathies such as PD.

The present invention is also directed to the α-synuclein ligands that are radiolabeled with radionuclides such as carbon-11 and/or fluorine-18 to serve as imaging agents (e.g., positron emission tomography (PET) imaging agents) for quantifying α-synuclein protein aggregation in the brain. The in vivo quantification of α-synuclein protein aggregation in patients is useful not only for diagnosing synucleinopathies such as PD, but also for monitoring disease progression.

As noted, fibrillar α-synuclein imaging is a highly useful marker for disease progression. Thus, an α-synuclein imaging agent provides for accurate enrollment of early stage PD patients into trials of therapeutic interventions targeting disease progression. If progressive accumulation of α-synuclein within individual regions or across multiple brain regions correlates with disease progression, particularly in early and intermediate disease stages, an α-synuclein imaging agent could also greatly improve evaluation of therapeutic efficacy for candidate disease-modifying interventions.

To these ends, applicants have discovered compounds that are useful as α-synuclein ligands.

In accordance with various aspects of the present invention, compounds useful as α-synuclein ligands comprise compounds of Formulas (I)-(IV):

(I)

(II)

(III)

(IV)

wherein n is 0 or 1;

----- is an optional bond;

each $A^1$ is independently C—$R^1$, nitrogen, oxygen, or sulfur;

each $A^2$ is independently C—$R^2$, nitrogen, oxygen, or sulfur;

each $A^3$ is independently C—$R^3$, nitrogen, oxygen, or sulfur;

each $A^4$ is independently C—$R^4$, nitrogen, oxygen, or sulfur;

$A^5$ is C—$R^5$, nitrogen, oxygen, or sulfur;

each $A^6$ is independently C—$R^6$ or nitrogen;

each $A^7$ is independently C—$R^7$ or nitrogen;

each $A^8$ is independently C—$R^8$ or nitrogen;

each $A^9$ is independently C—$R^9$ or nitrogen;

each $A^{10}$ is independently C—$R^{10}$ or nitrogen;

each $A^{11}$ is independently C—$R^{11}$, nitrogen, oxygen, or sulfur;

each $A^{12}$ is independently C—$R^{12}$, nitrogen, oxygen, or sulfur;

each $A^{13}$ is independently C—$R^{13}$, nitrogen, oxygen, or sulfur;

each $A^{14}$ is independently C—$R^{14}$, nitrogen, oxygen, or sulfur;

$A^{15}$ is C—$R^{15}$, nitrogen, oxygen, or sulfur;

each $A^{16}$ is independently C—$R^{16}$ or nitrogen;

each $A^{17}$ is independently C—$R^{17}$ or nitrogen;

each $A^{18}$ is independently C—$R^{18}$ or nitrogen;

each $A^{19}$ is independently C—$R^{19}$ or nitrogen;

each $A^{20}$ is independently C—$R^{20}$ or nitrogen;

each $A^{21}$ is independently C—$R^{21}$ or nitrogen;

each $A^{22}$ is independently C—$R^{22}$ or nitrogen;

each $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ is independently hydrogen, nitro, halo, hydroxy, carboxyl, substituted or unsubstituted alkyl, substituted or unsubstituted alkoxy, substituted or unsubstituted carboxylate, substituted or unsubstituted amino, substituted or unsubstituted amido, substituted or unsubstituted thiophenyl, or substituted or unsubstituted thiazolyl, or $R^3$ and $R^4$ optionally form a fused 6-membered aromatic ring.

Unless otherwise indicated, the alkyl groups described herein are preferably lower alkyl containing from 1 to 20 carbon atoms in the principal chain. They may be straight or branched chain or cyclic. Also, unless otherwise indicated, the alkoxy groups described herein contain saturated or unsaturated, branched or unbranched carbon chains having from 1 to 20 carbon atoms in the principal chain.

In various embodiments, at least one of the aromatic rings of the compounds of (I)-(IV) is a heteroaromatic ring and more particularly, a nitrogen-containing heteroaromatic ring. Accordingly, in these embodiments, at least one or at least two of $A^1, A^2, A^3, A^4, A^5$ is nitrogen; at least one or at least two of $A^{11}, A^{12}, A^{13}, A^{14}, A^{15}$ is nitrogen; and/or at least one or at least two of $A^{16}, A^{17}, A^{18}, A^{19}, A^{20}, A^{21}$ and $A^{22}$ is nitrogen.

In further embodiments, each $A^6$ is independently C—$R^6$; each $A^7$ is independently C—$R^7$; each $A^8$ is independently C—$R^8$; each $A^9$ is independently C—$R^9$; each $A^{10}$ is independently C—$R^{10}$; each $A^{18}$ is independently C—$R^{18}$; each $A^{19}$ is independently C—$R^{19}$; each $A^{20}$ is independently C—$R^{20}$; and each $A^{21}$ is independently C—$R^{21}$.

In various embodiments, each $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}$, and $R^{22}$ is independently hydrogen, halo, nitro, substituted or unsubstituted $C_1$ to $C_6$ alkyl, substituted or unsubstituted $C_1$ to $C_6$ alkoxy, substituted or unsubstituted amino, substituted or unsubstituted amido, or substituted or unsubstituted carboxylate. For example, each $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}$, and $R^{22}$ can be independently hydrogen, nitro, halo, hydroxy, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, amino, $C_1$ to $C_6$ alkyl-substituted amino, amido, $C_1$ to $C_6$ alkyl-substituted amido, $C_1$ to $C_6$ alkyl-substituted carboxylate, or $C_1$ to $C_6$ haloalkyl-substituted carboxylate. In certain embodiments, each $R^1, R^5, R^6, R^{10}, R^{11}, R^{16}$ and $R^{22}$ is hydrogen. In some embodiments, each $R^7, R^8, R^9, R^{17}, R^{18}, R^{19}, R^{20}$, and $R^{21}$ is not hydrogen.

As noted, α-synuclein ligands of the present invention comprise compounds of Formula (I). For example, the compounds of Formula (I) include compounds of the structure of Formula (I-A):

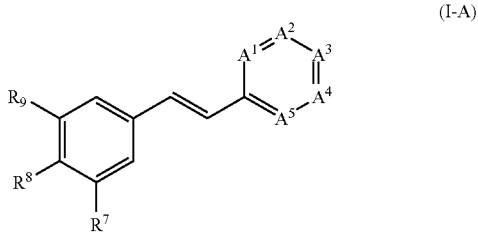

(I-A)

wherein $A^1$ is C—$R^1$ or nitrogen; $A^2$ is C—$R^2$ or nitrogen; $A^3$ is C—$R^3$ or nitrogen; $A^4$ is C—$R^4$ or nitrogen; $A^5$ is C—$R^5$ or nitrogen; and $R^1, R^2, R^3, R^4, R^5, R^7, R^8, R^9$ are independently hydrogen, nitro, halo, hydroxy, carboxyl, substituted or unsubstituted alkyl, substituted or unsubstituted alkoxy, substituted or unsubstituted carboxylate, substituted or unsubstituted amino, or substituted or unsubstituted amido.

In various embodiments, $R^1, R^2, R^3, R^4, R^5, R^6, R^7, R^8, R^9$ are independently hydrogen, nitro, halo, hydroxy, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, amino, $C_1$ to $C_6$ alkyl-substituted amino, amido, $C_1$ to $C_6$ alkyl-substituted amido, $C_1$ to $C_6$ alkyl-substituted carboxylate, or $C_1$ to $C_6$ haloalkyl-substituted carboxylate. In some embodiments, $R^7$ and/or $R^9$ are hydrogen.

In various embodiments, $A^1$ is C—H or nitrogen; $A^2$ is C—H or nitrogen; $A^3$ is C—H or nitrogen; $A^4$ is C—H or nitrogen; and/or $A^5$ is C—H or nitrogen. In certain embodiments, $A^3$ is nitrogen.

The compounds of Formula (I) also include compounds of Formula (I-B):

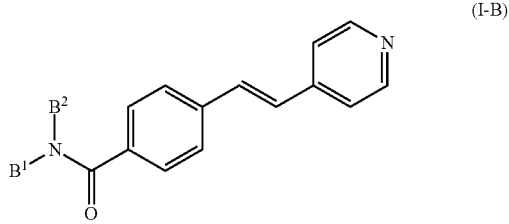

(I-B)

wherein $B^1$ is hydrogen, substituted or unsubstituted $C_1$ to $C_6$ alkyl, substituted or unsubstituted $C_1$ to $C_6$ alkoxy, or substituted or unsubstituted phenyl; $B^2$ is hydrogen, substituted or unsubstituted $C_1$ to $C_6$ alkyl, or substituted or unsubstituted $C_1$ to $C_6$ alkoxy; or $B^1$ and $B^2$ optionally form a six-membered heterocyclic ring.

In various embodiments, $B^1$ is hydrogen, $C_1$ to $C_6$ alkyl, halo-substituted $C_1$ to $C_6$ alkyl, $C_1$ to $C_6$ alkoxy, halo-substituted $C_1$ to $C_6$ alkoxy, phenyl, halo-substituted phenyl, $C_1$ to $C_6$ alkoxy-substituted phenyl, $C_1$ to $C_6$ haloalkoxy-substituted phenyl. In various embodiments, $B^2$ is hydrogen or substituted or unsubstituted $C_1$ to $C_6$ alkyl, or $B^1$ and $B^2$ optionally form a six-membered heterocyclic ring.

In certain embodiments, the compound of Formula (I) is selected from the group consisting of:

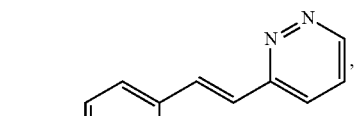

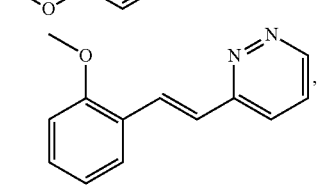

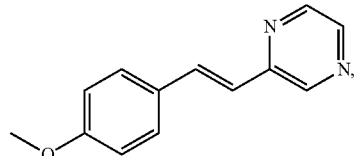

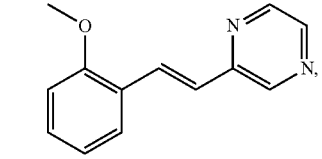

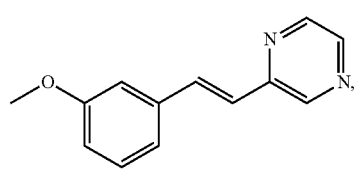

-continued
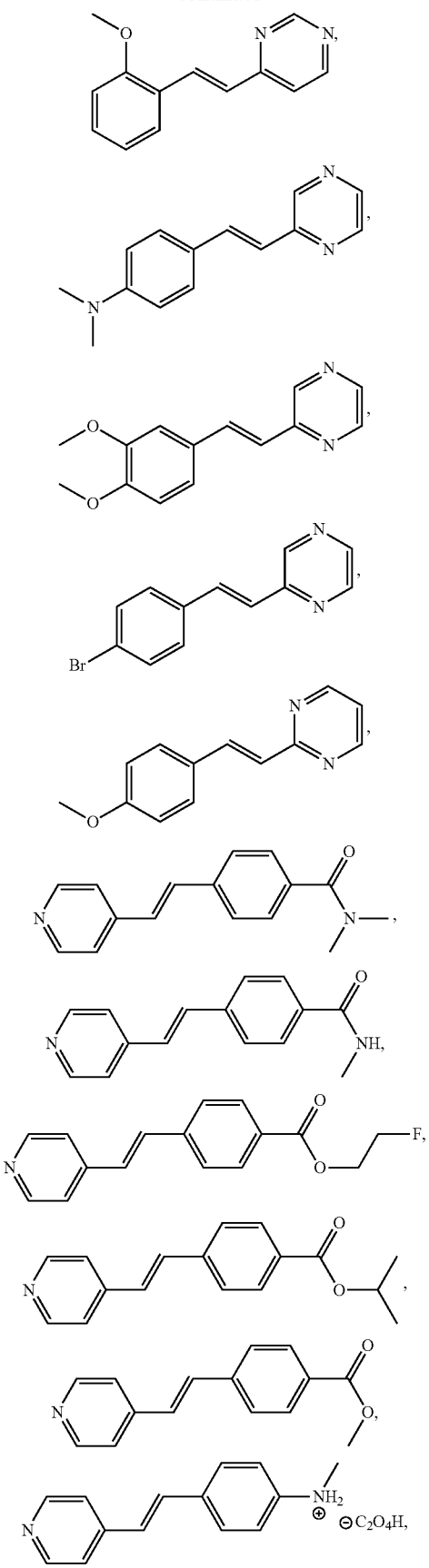
-continued
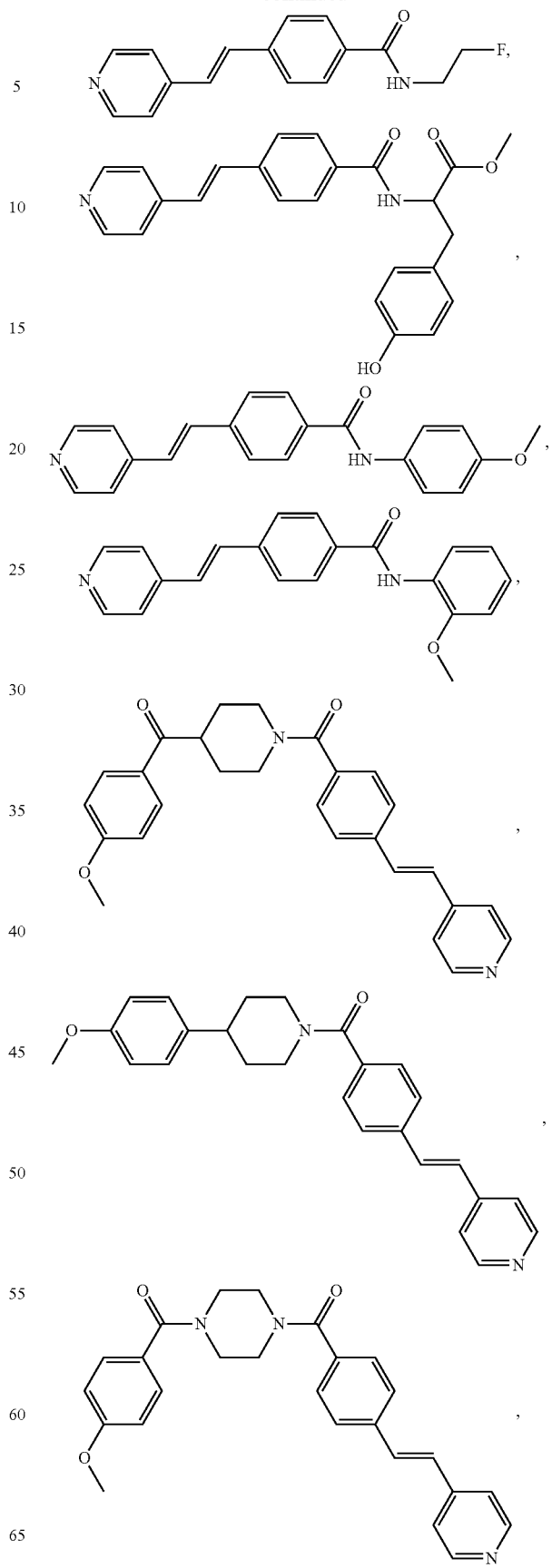

and pharmaceutically acceptable salts thereof.

As noted, α-synuclein ligands of the present invention comprise compounds of Formula (II). In various embodiments, the compound of Formula (II) has the structure of Formula (II-A):

(II-A)

wherein $A^1$ is C—$R^1$, nitrogen, oxygen, or sulfur; $A^2$ is C—$R^2$, nitrogen, oxygen, or sulfur; $A^3$ is C—$R^3$, nitrogen, oxygen, or sulfur; $A^4$ is C—$R^4$, nitrogen, oxygen, or sulfur; and $R^1$, $R^2$, $R^3$, $R^4$, and $R^8$ are independently hydrogen, nitro, halo, hydroxy, carboxyl, substituted or unsubstituted alkyl, substituted or unsubstituted alkoxy, substituted or unsubstituted carboxylate, substituted or unsubstituted amino, or substituted or unsubstituted amido.

In some embodiments, $A^1$ is C—H, nitrogen, oxygen, or sulfur; $A^2$ is C—H, nitrogen, oxygen, or sulfur; $A^3$ is C—H, nitrogen, oxygen, or sulfur; and $A^4$ is C—H, nitrogen, oxygen, or sulfur. In certain embodiments, one of $A^1$, $A^2$, $A^3$, or $A^4$ is nitrogen, oxygen, or sulfur.

In various embodiments, $R^8$ is hydrogen, nitro, halo, hydroxy, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, amino, $C_1$ to $C_6$ alkyl-substituted amino, amido, $C_1$ to $C_6$ alkyl-substituted amido, $C_1$ to $C_6$ alkyl-substituted carboxylate, or $C_1$ to $C_6$ haloalkyl-substituted carboxylate.

In some embodiments, the compound of Formula (II) is selected from the group consisting of:

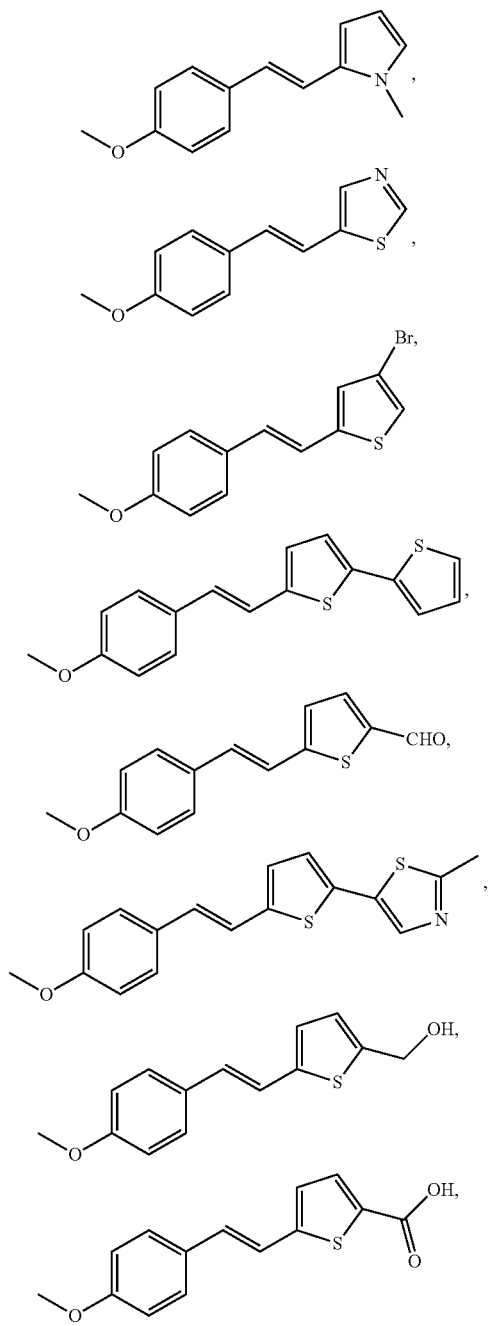

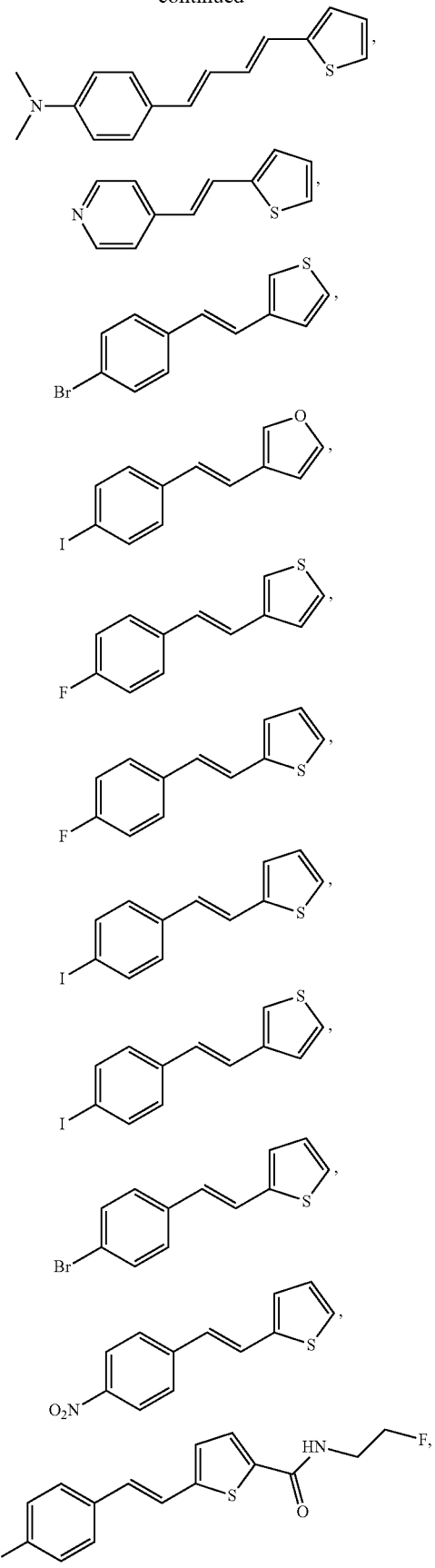

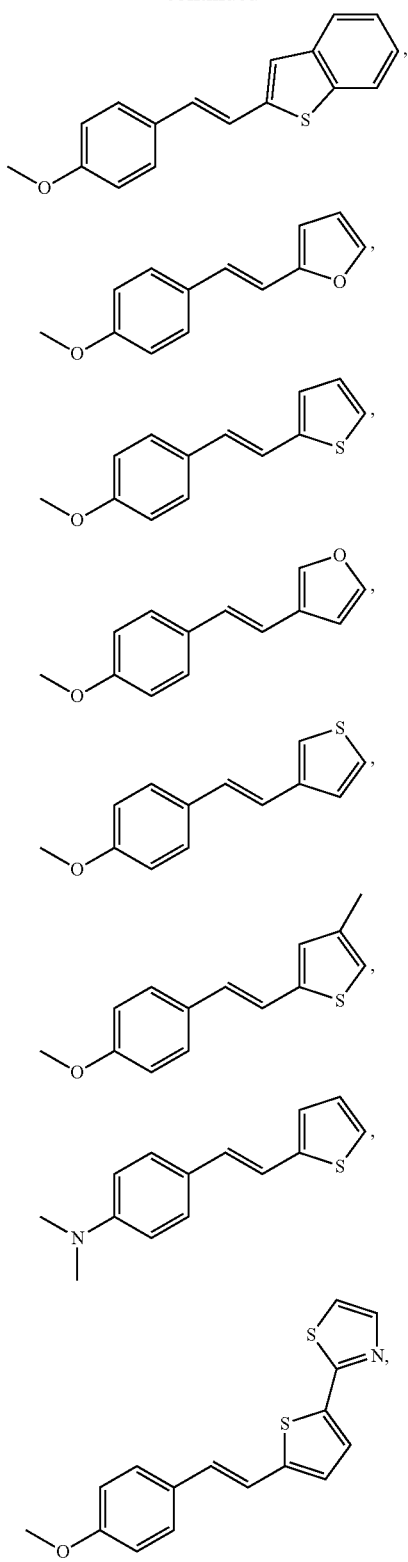

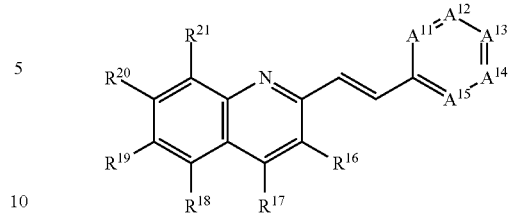

wherein $A^{11}$ is C—$R^{11}$ or nitrogen; $A^{12}$ is C—$R^{12}$ or nitrogen; $A^{13}$ is C—$R^{13}$ or nitrogen; $A^{14}$ is C—$R^{14}$ or nitrogen; $A^{15}$ is C—$R^{15}$ or nitrogen; and $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are independently hydrogen, nitro, halo, hydroxy, carboxyl, substituted or unsubstituted alkyl, substituted or unsubstituted alkoxy, substituted or unsubstituted carboxylate, substituted or unsubstituted amino, or substituted or unsubstituted amido.

In various embodiments, one of $A^{11}$, $A^{12}$, $A^{13}$, $A^{14}$, or $A^{15}$ is nitrogen. In these and other embodiments, $R^{11}$, $R^{12}$, $R^{13}$, $R^{14}$, $R^{15}$, $R^{16}$, $R^{17}$, $R^{18}$, $R^{19}$, $R^{20}$, and $R^{21}$ are independently hydrogen, nitro, halo, hydroxy, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, amino, $C_1$ to $C_6$ alkyl-substituted amino, amido, $C_1$ to $C_6$ alkyl-substituted amido, $C_1$ to $C_6$ alkyl-substituted carboxylate, or $C_1$ to $C_6$ haloalkyl-substituted carboxylate.

In some embodiments, the compound of Formula (III) is selected from the group consisting of:

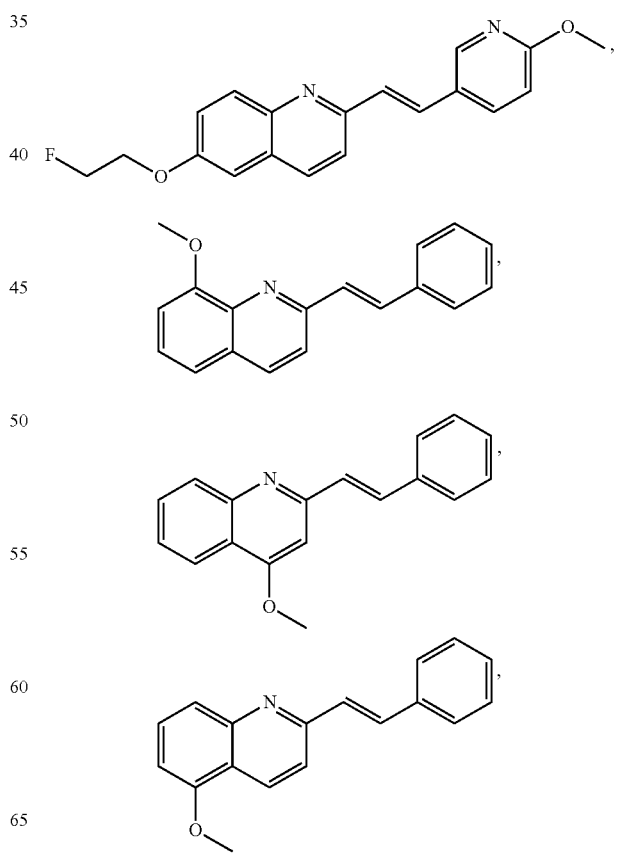

and pharmaceutically acceptable salts thereof.

Ligands of α-synuclein of the present invention also comprise compounds of Formula (III). For example, compounds of Formula (III) include compounds having the structure of Formula (III-A):

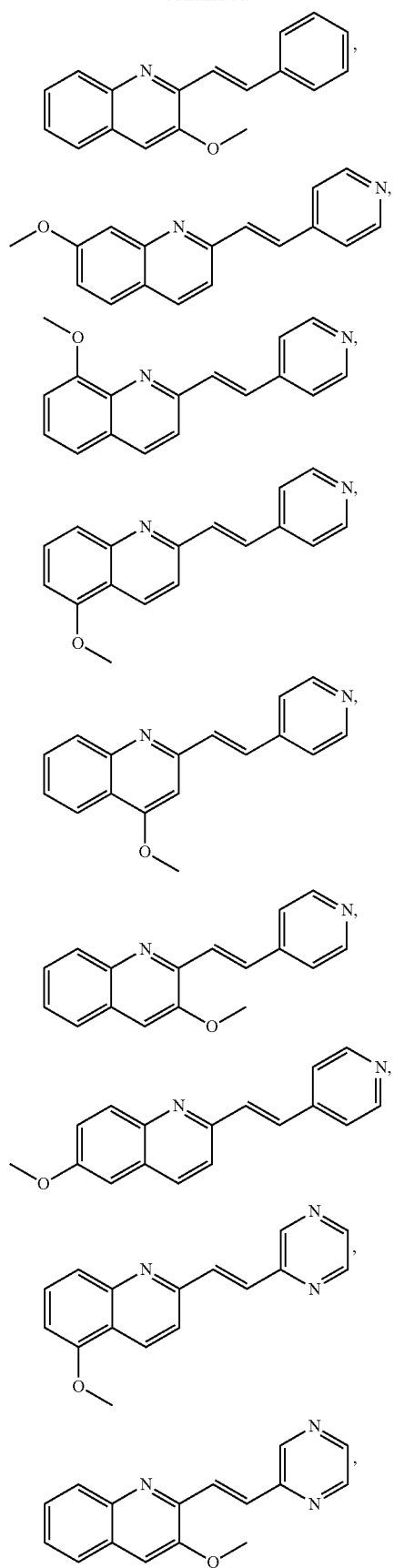
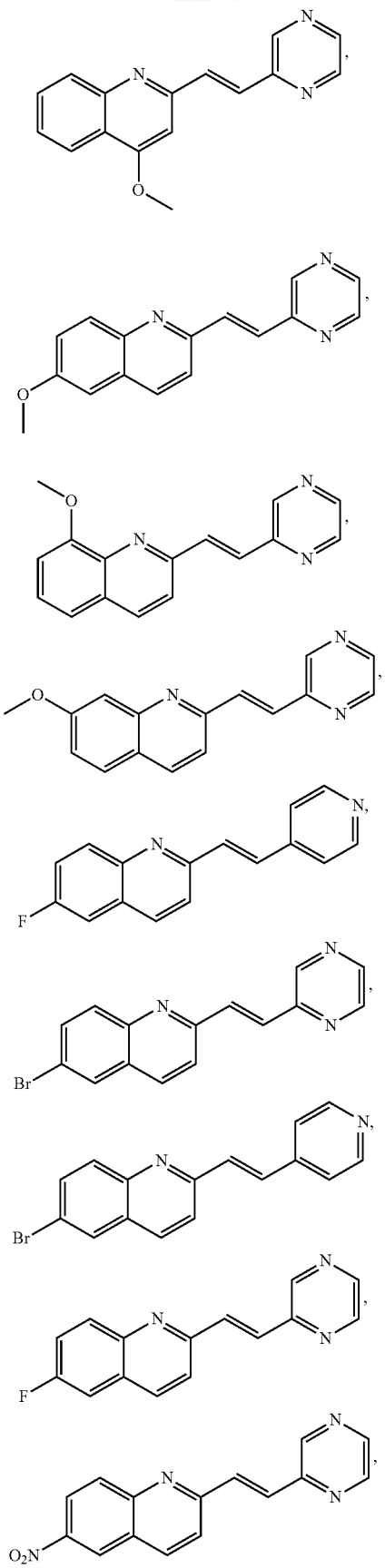

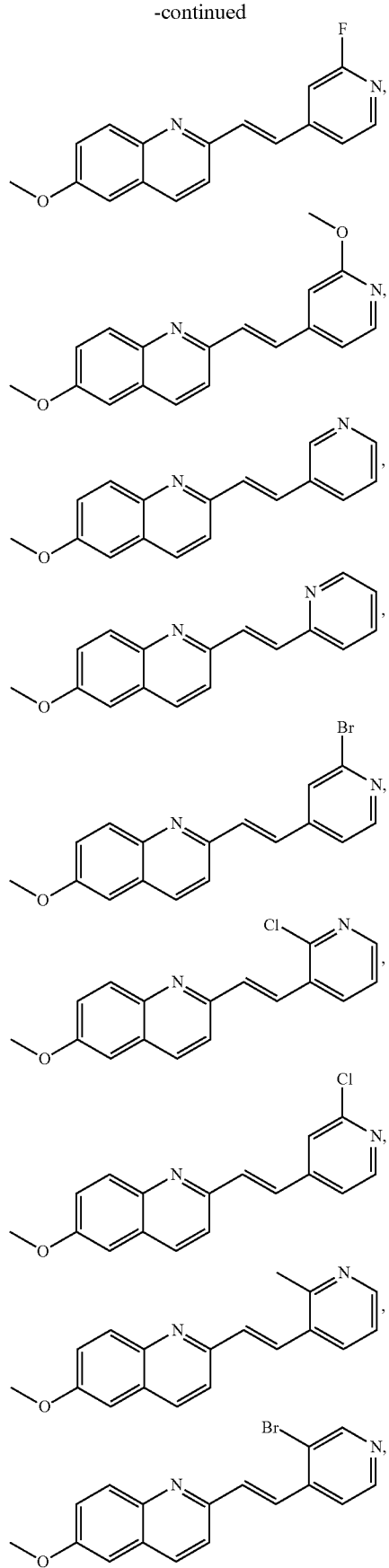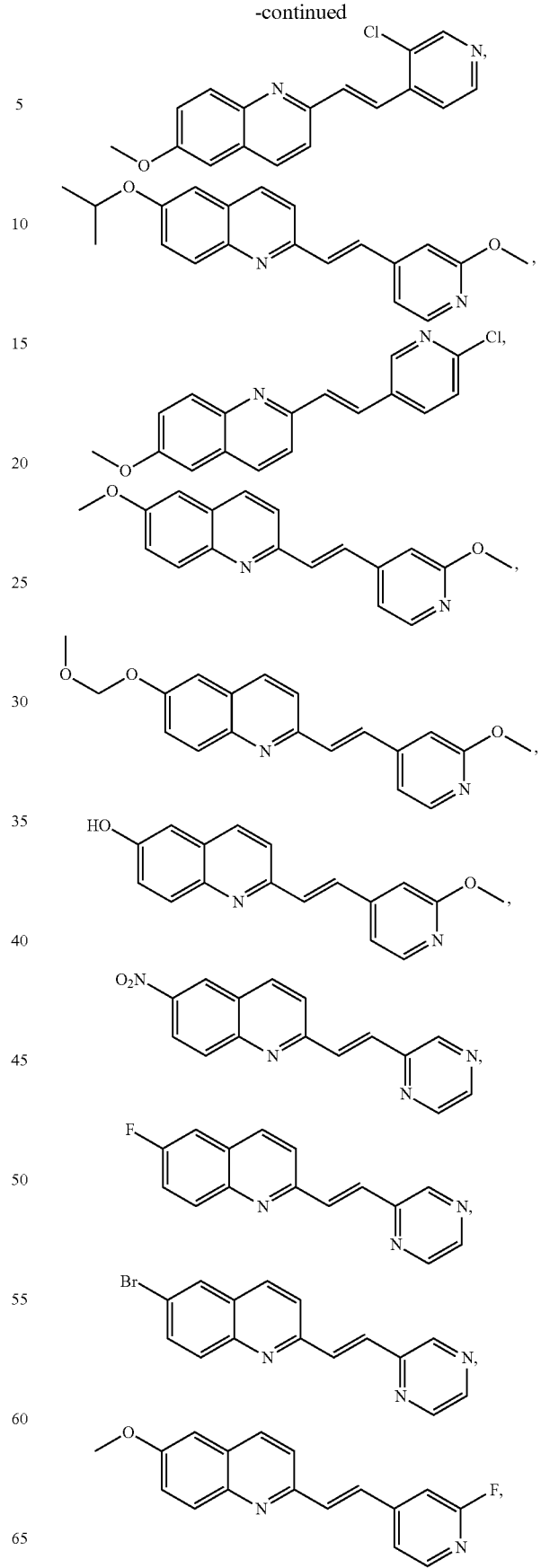

-continued

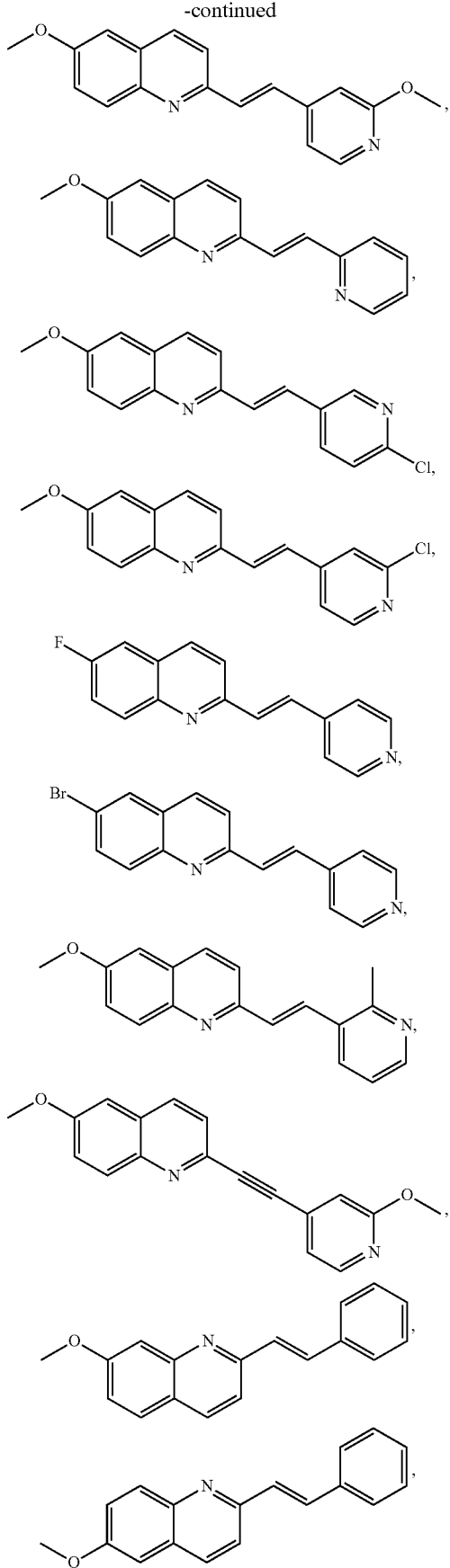

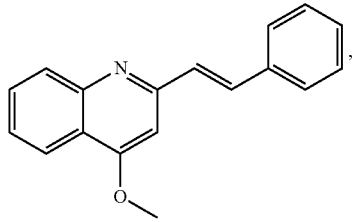

and pharmaceutically acceptable salts thereof.

Ligands of α-synuclein of the present invention also comprise compounds of Formula (IV). For example, compounds of Formula (IV) include compounds having the structure of Formula (IV-A):

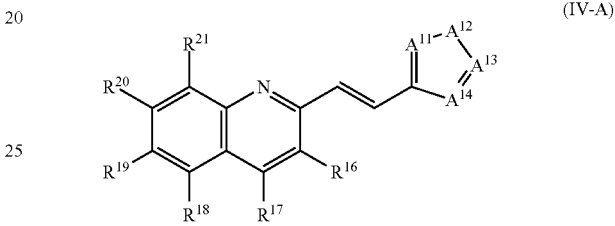

(IV-A)

wherein is C—$R^{11}$ nitrogen, oxygen, or sulfur; $A^{12}$ is C—$R^{12}$ nitrogen, oxygen, or sulfur; $A^{13}$ is C—$R^{13}$ nitrogen, oxygen, or sulfur; $A^{14}$ is C—$R^{14}$ nitrogen, oxygen, or sulfur; and $R^{11}$, $R^{12}$, $R^{13}$, $R^{14}$, $R^{16}$, $R^{17}$, $R^{18}$, $R^{19}$, $R^{20}$, and $R^{21}$ are independently hydrogen, nitro, halo, hydroxy, carboxyl, substituted or unsubstituted alkyl, substituted or unsubstituted alkoxy, substituted or unsubstituted carboxylate, substituted or unsubstituted amino, or substituted or unsubstituted amido.

In various embodiments, $A^{11}$ is C—H, nitrogen, oxygen, or sulfur; $A^{12}$ is C—H, nitrogen, oxygen, or sulfur; $A^{13}$ is C—H, nitrogen, oxygen, or sulfur; and $A^{14}$ is C—H, nitrogen, oxygen, or sulfur. In these and other embodiments, one of $A^{11}$, $A^{12}$, $A^{13}$, or $A^{14}$ is nitrogen, oxygen, or sulfur.

In certain embodiments, the compound of Formula (IV) is selected from the group consisting of

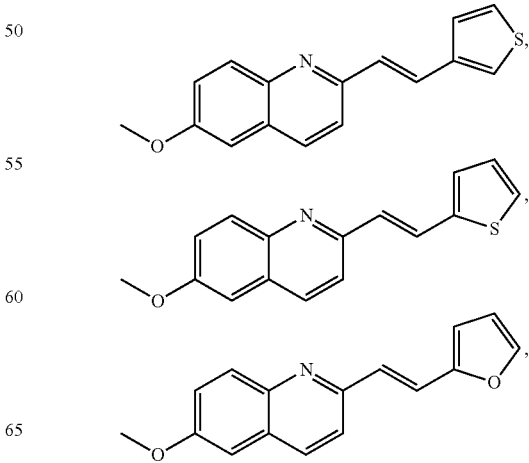

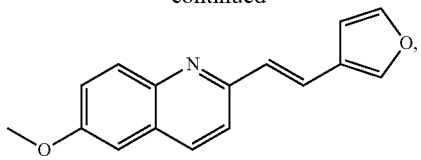

and pharmaceutically acceptable salts thereof.

Ligands of α-synuclein of the present invention also comprise compounds of Formula (V) or a pharmaceutically acceptable salt thereof

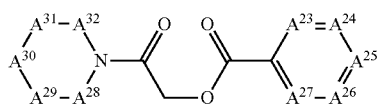
(V)

wherein $A^{23}$ is $C-R^{23}$; $A^{24}$ is $C-R^{24}$; $A^{25}$ is $C-R^{25}$; $A^{26}$ is $C-R^{26}$; $A^{27}$ is $C-R^{27}$; $A^{28}$ is $C-R^{28}$; $A^{29}$ is $C-R^{29}$; $A^{30}$ is $C-R^{30}$ or $N-R^{30}$; $A^{31}$ is $C-R^{31}$; $A^{32}$ is $C-R^{32}$; and $R^{23}$, $R^{24}$, $R^{25}$, $R^{26}$, $R^{27}$, $R^{28}$, $R^{29}$, $R^{30}$, $R^{31}$ and $R^{32}$ are independently hydrogen, halo, substituted or unsubstituted alkyl, substituted or unsubstituted alkoxy, substituted or unsubstituted aryl, or substituted or unsubstituted benzoyl.

In various embodiments, the compound of Formula (V) has the structure of Formula (V-A):

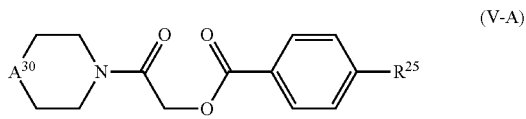
(V-A)

wherein $A^{30}$ is $C-R^{30}$ or $N-R^{30}$; $R^{25}$ is a $C_1$ to $C_6$ alkyl; and $R^{30}$ is a substituted phenyl or substituted benzoyl.

In certain embodiments, the compound of Formula (V) is selected from the group consisting of:

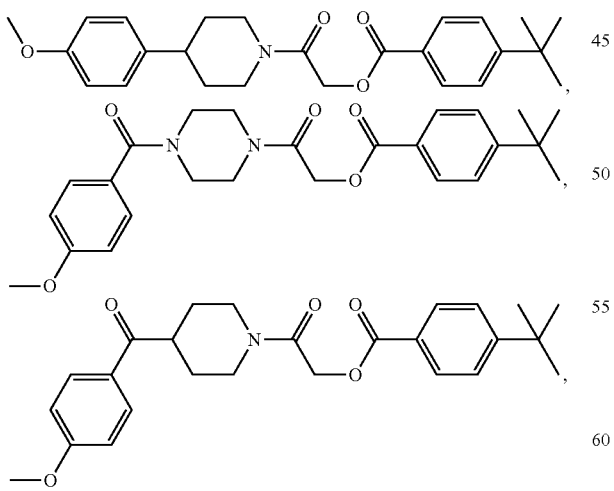

and pharmaceutically acceptable salts thereof.

Compounds useful as α-synuclein ligands also comprise compounds of Formula (VI) or a pharmaceutically acceptable salt thereof

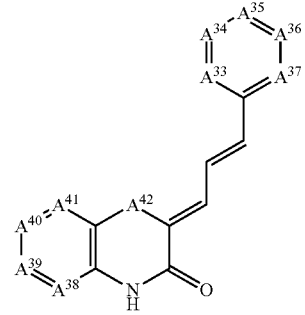
(VI)

wherein $A^{33}$ is $C-R^{33}$; $A^{34}$ is $C-R^{34}$; $A^{35}$ is $C-R^{35}$; $A^{36}$ is $C-R^{36}$; $A^{37}$ is $C-R^{37}$; $A^{38}$ is $C-R^{38}$; $A^{39}$ is $C-R^{39}$; $A^{40}$ is $C-R^{40}$; $A^{41}$ is $C-R^{41}$; $A^{42}$ is oxygen or sulfur; and $R^{33}$, $R^{34}$, $R^{35}$, $R^{36}$, $R^{37}$, $R^{38}$, $R^{39}$, $R^{40}$, and $R^{41}$ is hydrogen, halo, nitro, substituted or unsubstituted alkyl, or substituted or unsubstituted alkoxy.

In various embodiments, $R^{33}$, $R^{34}$, $R^{36}$, $R^{38}$, $R^{40}$, and $R^{41}$ are each hydrogen. In some embodiments, $R^{35}$ and $R^{39}$ are independently nitro or methoxy.

In certain embodiments, the compound of Formula (VI) is selected from a group consisting of:

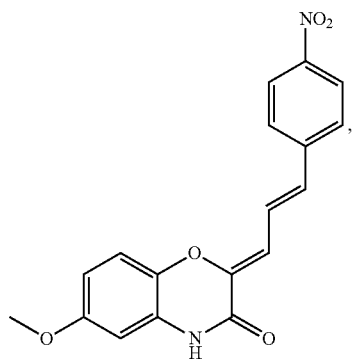

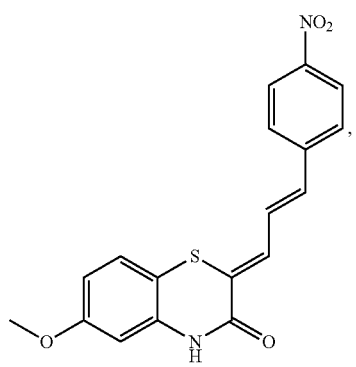

and pharmaceutically acceptable salts thereof.

In accordance with the present invention, compounds useful as α-synuclein ligands also comprise compounds of Formula (VII) or a pharmaceutically acceptable salt thereof:

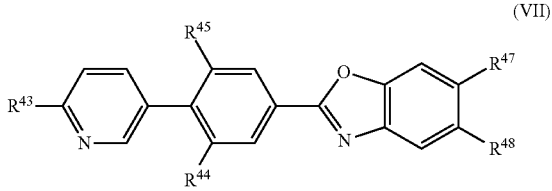

(VII)

wherein $R^{43}$, $R^{44}$, $R^{45}$, $R^{46}$, $R^{47}$, and $R^{48}$ are independently hydrogen, halo, substituted or unsubstituted alkyl, substituted or unsubstituted alkoxy, or substituted or unsubstituted carboxylate.

In various embodiments, $R^{43}$, $R^{44}$, $R^{45}$, $R^{46}$, $R^{47}$, and $R^{48}$ are independently hydrogen, halo, $C_1$ to $C_6$ substituted or unsubstituted alkyl, $C_1$ to $C_6$ substituted or unsubstituted alkoxy, or $C_1$ to $C_6$ substituted or unsubstituted carboxylate. In some embodiments, $R^{43}$, $R^{44}$, $R^{45}$, $R^{46}$, $R^{47}$, and $R^{48}$ are independently hydrogen, bromo, fluoro, hydroxymethyl, or methyl acetate.

In certain embodiments, the compound of Formula (VII) is selected from a group consisting of:

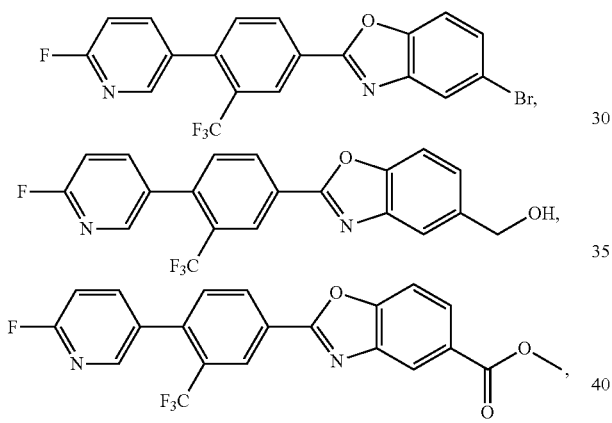

and pharmaceutically acceptable salts thereof.

Ligands of α-synuclein of the present invention also comprise compounds of Formula (VIII)

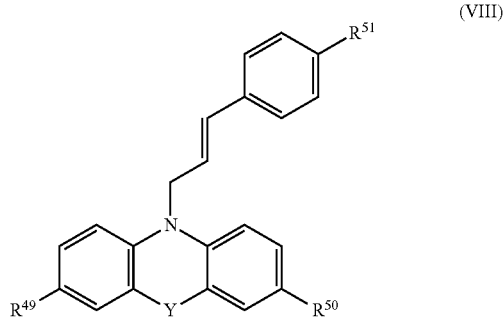

(VIII)

wherein $R^{49}$, $R^{50}$, and $R^{51}$ are independently hydrogen, substituted or unsubstituted alkyl, substituted or unsubstituted alkoxy, substituted or unsubstituted amine, or nitro, and Y is oxygen or sulfur.

In various embodiments, $R^{49}$, $R^{50}$, and $R^{51}$ are independently, hydrogen, $C_1$ to $C_6$ substituted or unsubstituted alkoxy, $C_1$ to $C_6$ substituted or unsubstituted alkoxy, $C_1$ to $C_6$ substituted or unsubstituted amine, or nitro. In some embodiments, $R^{49}$, $R^{50}$, and $R^{51}$ are independently, hydrogen, methoxy, dimethylamine, or nitro.

In some embodiments the compound of Formula (VIII) is selected from a group consisting of:

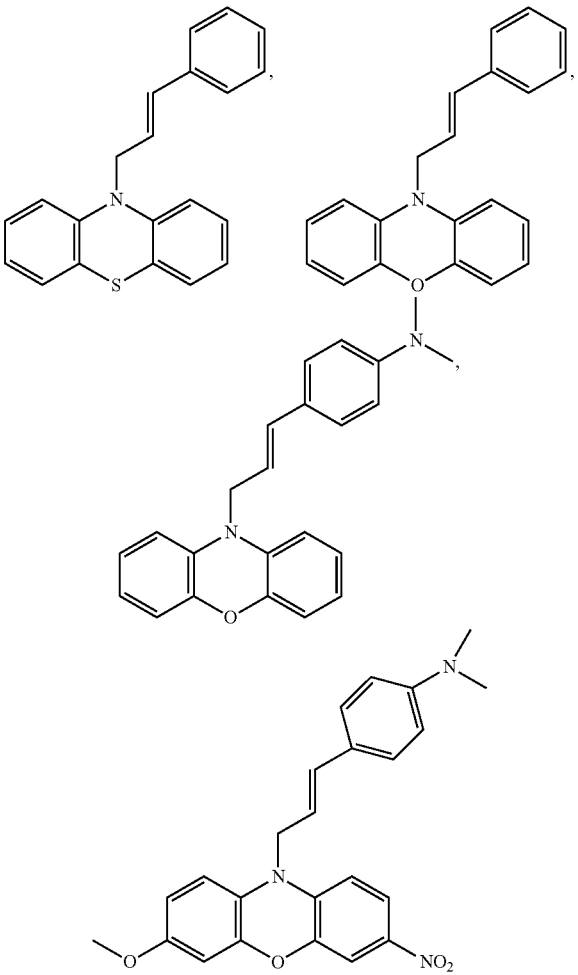

and pharmaceutically acceptable salts thereof.

As noted, the compounds of the present invention possess binding affinity to α-synuclein which is useful for certain diagnostic and monitoring methods for synucleinopathies such as PD. One diagnostic method that is suitable for use with the α-synuclein ligands of the present invention is positron emission tomography (PET). PET is known in the art of nuclear medicine imaging as a non-invasive imaging modality that can provide functional information of a living subject at the molecular and cellular level. PET utilizes biologically active molecules in micromolar or nanomolar concentrations that have been labeled with short-lived positron emitting isotopes. The physical characteristics of the isotopes and the molecular specificity of labeled molecules, combined with the high detection efficacy of modern PET scanners provides a sensitivity for in vivo measurements of indicator concentrations that is several orders of magnitude higher than with other imaging techniques.

In order to make measurements with PET, a biologically active tracer molecule labeled with a positron-emitting isotope is administered to a subject, for example, intravenously, orally, or by inhalation. The subject is then scanned, and axial tomographic slices of regional cerebral tracer accumulation are obtained. This tracer accumulation can be related to cerebral metabolism, blood flow, or binding site concentrations by appropriate mathematical models. Thus, by using a small molecular PET radiotracer which has high affinity and selectivity to α-synuclein protein, the level of α-synuclein aggregation can be quantified. This approach not only improves the diagnostic accuracy of PD, but also provides a tool to monitor the progression of the disease and the efficacy of the treatment, and improve the understanding of disease progression.

Accordingly, the compounds of the present invention, including those represented by Formulas (I)-(VIII), can be labeled with a radioactive isotope (e.g., synthetic radioactive isotopes) including, for example, carbon-11, nitrogen-13, oxygen-15, fluorine-18, bromine-76, iodine-123, and iodine-125 to serve as tracers for quantifying α-synuclein protein aggregation in the brain. In various embodiments, the compounds of Formulas (I)-(VIII) are labeled with a radioactive isotope selected from the group consisting of carbon-11, fluorine-18, iodine-123, and iodine-125. Methods known in the art for radiolabeling the compounds of the present invention may be used. Reagents having a radionuclide that may be used in the preparation radiolabeled compounds of the present invention include for example [$^{11}$C]CH$_3$I.

The present invention is also directed to various pharmaceutical compositions comprising one or more of radiolabeled compounds of Formulas (I)-(VIII). In various embodiments, the pharmaceutical composition comprises from about 0.001 mg to about 10 g of a compound of Formulas (I)-(VIII) and at least about 10 wt. %, at least about 25 wt. %, at least about 50 wt. %, at least about 75 wt. %, at least about 90 wt. %, or at least about 95 wt. % of the compound in the pharmaceutical composition is radiolabeled. The pharmaceutical compositions can also contain one or more excipients.

The compounds of present invention may be formulated in a suitable pharmaceutical delivery medium or vehicle. In various embodiments, the pharmaceutical composition comprises an injectable comprising a compound of the present invention. In other embodiments, the pharmaceutical delivery medium comprises an oral vehicle comprising a compound of the present invention (e.g., capsule, pill, liquid, suspension, etc.).

Further, in accordance with the present invention, methods for diagnosing or monitoring synucleinopathies are provided. In various embodiments, the method for diagnosing or monitoring a synucleinopathy in a human subject comprises administering a radiolabeled compound of Formulas (I)-(VIII) or pharmaceutical composition comprising a radiolabeled compound of Formulas (I)-(VIII) to the human subject; and imaging the subject's brain by positron emission tomography.

Having described the invention in detail, it will be apparent that modifications and variations are possible without departing from the scope of the invention defined in the appended claims.

EXAMPLES

The following non-limiting examples are provided to further illustrate the present invention.

Unless otherwise stated, reagents and chemicals were purchased from Sigma-Aldrich (St. Louis, Mo.) or VWR International, Inc. (Earth city, Mo.) and used without further purification unless otherwise stated. All air and water sensitive reactions were carried out in oven-dried glassware under a nitrogen atmosphere. When reactions involved extractions with DCM (CH$_2$Cl$_2$), chloroform (CHCl$_3$), or ethyl acetate (EtOAc), the organic solvents were dried with anhydrous Na$_2$SO$_4$ and concentrated on a rotary evaporator under reduced pressure. The melting points of all the intermediates and final compounds were determined on a Hake-Buchler melting point apparatus and are uncorrected. $^1$H NMR spectra were obtained on a Varian 400 MHz NMR spectrometer with CDCl$_3$, DMSO-d$_6$, CD$_3$COCD$_3$, or CD$_3$OD as solvents and tetramethylsilane (TMS) was used as the internal standard. The following abbreviations were used to describe peak patterns when appropriate: br s=broad singlet, s=singlet, d=doublet, t=triplet, q=quartet, m=multiplet. The purity of the target compounds was found to be >95%, as determined by elemental analysis or HPLC.

Plate reader and software used for fluorescence scans was TECAN infinite M100 Plate Reader, and i-control 1.7 TECAN software was used to run plate reader. Plate reader and software used for the binding assay was Biotek Synergy 2 Plate Reader, and Gen 5 software was used to run plate reader. Fluorescence filters were Excitation 440/30, Emission 485/20. Optical Setting Top 50% and Sensitivity=60. UV/Vis absorbance scans were acquired on a Beckman Coulter DU 800 spectrophotometer using quartz cuvettes.

Example 1: Synthesis of TZ-19-144

A solution of 6-methoxy-2-methylquinoline (100 mg, 0.58 mmol), p-toluenesulfonamide (98.85 mg, 0.58 mmol) and benzaldehyde (61.2 mg, 0.58 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/Hexane (1:4, v/v) on silica gel, affording TZ-19-144 as a white solid (137 mg, 91%). $^1$H-NMR (400 MHz, CDCl$_3$): δ 8.00 (dd, J=11.5, 9.2 Hz, 2H), 7.68-7.56 (m, 4H), 7.35 (t, J=14.5, 7.1 Hz, 5H), 7.05 (d, J=2.2 Hz, 1H), 3.93 (s, 3H). $^{13}$C NMR (101 MHz, CDCl$_3$) δ 157.65, 153.70, 144.22, 136.82, 135.10, 133.20, 130.77, 129.02, 128.73, 128.35, 128.25, 127.08, 122.32, 119.59, 105.29, 55.46.

Example 2: Synthesis of TZ-19-146

A solution of 7-methoxy-2-methylquinoline (100 mg, 0.58 mmol), p-toluenesulfonamide (98.85 mg, 0.58 mmol) and benzaldehyde (61.2 mg, 0.58 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/Hexane (1:4, v/v) on silica gel, affording TZ-19-146 as a white solid (135 mg, 90%). $^1$H-NMR (400 MHz, CDCl$_3$): δ 8.04 (d, J=8.4 Hz, 1H), 7.77-7.59 (m, 4H), 7.53 (d, J=8.3 Hz, 1H), 7.45-7.29 (m, 5H), 7.15 (d, J=8.8 Hz, 1H), 3.97 (s, 3H). $^{13}$C NMR (101 MHz, CDCl$_3$) δ 156.07, 149.89, 136.50, 135.99, 134.04, 128.97, 128.75, 128.53, 128.45, 127.19, 122.53, 119.30, 117.25, 107.05, 55.51.

Example 3: Synthesis of TZ-19-148

A solution of 8-methoxy-2-methylquinoline (100 mg, 0.58 mmol), p-toluenesulfonamide (98.85 mg, 0.58 mmol) and benzaldehyde (61.2 mg, 0.58 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/Hexane (1:4, v/v) on silica gel, affording TZ-19-148 as colorless oil (133 mg, 89%). $^1$H-NMR (400 MHz, CDCl$_3$): δ 8.05 (d, J=8.6 Hz, 1H), 7.72 (d, J=8.6 Hz, 1H), 7.65-7.46 (m, 4H), 7.43-7.20 (m, 5H), 7.02 (d, J=7.5 Hz, 1H), 4.08 (s, 3H). $^{13}$C NMR (101 MHz, CDCl$_3$) δ 154.61, 154.59, 139.47, 136.02, 135.75, 133.41, 129.15, 128.26, 127.98, 127.82, 126.69, 125.84, 118.90, 118.63, 107.38, 55.58.

Example 4: Synthesis of TZ-19-150

A solution of 4-methoxy-2-methylquinoline (100 mg, 0.58 mmol), p-toluenesulfonamide (98.85 mg, 0.58 mmol) and benzaldehyde (61.2 mg, 0.58 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/Hexane (1:4, v/v) on silica gel, affording TZ-19-148 as colorless oil (133 mg, 89%). $^1$H-NMR (400 MHz, CDCl$_3$): δ 8.11 (d, J=8.2 Hz, 1H), 8.00 (d, J=8.4 Hz, 1H), 7.73-7.56 (m, 4H), 7.49-7.21 (m, 5H), 6.92 (s, 1H), 4.03 (s, 3H). $^{13}$C NMR (101 MHz, cdcl$_3$) δ 157.01, 149.06, 136.45, 133.94, 130.01, 129.49, 128.76, 128.62, 128.54, 127.21, 125.26, 121.67, 120.68, 97.81, 55.57.

Example 5: Synthesis of TZ-19-152

A solution of 5-methoxy-2-methylquinoline (100 mg, 0.58 mmol), p-toluenesulfonamide (98.85 mg, 0.58 mmol) and benzaldehyde (61.2 mg, 0.58 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/Hexane (1:4, v/v) on silica gel, affording TZ-19-152 as white solid (130 mg, 87%). $^1$H-NMR (400 MHz, CDCl$_3$): δ 7.97 (d, J=8.4 Hz, 1H), 7.70-7.55 (m, 4H), 7.46 (d, J=8.4 Hz, 1H), 7.40-7.25 (m, 5H), 7.11 (dd, J=8.9, 1.9 Hz, 1H), 3.92 (s, 3H). $^{13}$C NMR (101 MHz, CDCl$_3$) δ 156.05, 149.89, 136.51, 135.96, 134.02, 128.98, 128.75, 128.52, 128.45, 127.19, 122.53, 119.28, 117.25, 107.07, 55.48.

Example 6: Synthesis of TZ-19-154

A solution of 3-methoxy-2-methylquinoline (100 mg, 0.58 mmol), p-toluenesulfonamide (98.85 mg, 0.58 mmol) and benzaldehyde (61.2 mg, 0.58 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/Hexane (1:4, v/v) on silica gel, affording TZ-19-154 as white solid (130 mg, 87%). $^1$H-NMR (400 MHz, CDCl$_3$): δ 8.11-8.01 (m, 2H), 7.80-7.63 (m, 4H), 7.54 (dd, J=11.2, 4.1 Hz, 1H), 7.46-7.36 (m, 3H), 7.34-7.27 (m, 1H), 3.94 (s, 2H). $^{13}$C NMR (101 MHz, CDCl$_3$) δ 151.45, 148.55, 143.05, 137.13, 135.15, 128.91, 128.68, 128.64, 128.42, 127.53, 126.85, 126.35, 126.24, 121.97, 111.91, 77.37, 77.06, 76.74, 55.41.

Example 7: Synthesis of TZ-19-158

A solution of 6-methoxy-2-methylquinoline (100 mg, 0.57 mmol), p-toluenesulfonamide (98.85 mg, 0.57 mmol) and isonicotinaldehyde (61.8 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-19-158 as white solid (132 mg, 88%). 1H-NMR (400 MHz, CDCl$_3$): 1H NMR (400 MHz, CDCl$_3$) δ 8.53 (d, J=4.7 Hz, 2H), 7.93 (dd, J=19.4, 8.9 Hz, 2H), 7.52 (d, J=8.5 Hz, 1H), 7.44 (s, 2H), 7.36 (d, J=4.7 Hz, 2H), 7.30 (d, J=9.2 Hz, 1H), 6.97 (s, 1H), 3.85 (s, 3H). 13C NMR (101 MHz, CDCl3) δ 158.00, 152.29, 150.29, 144.27, 143.93, 135.24, 133.23, 130.80, 130.19, 128.66, 122.73, 121.20, 119.91, 105.07, 55.54.

Example 8: Synthesis of TZ-23-02

A solution of 7-methoxy-2-methylquinoline (100 mg, 0.57 mmol), p-toluenesulfonamide (98.85 mg, 0.57 mmol) and isonicotinaldehyde (61.8 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-02 (129 mg, 86%). $^1$H-NMR (400 MHz, CDCl$_3$): δ 8.55 (d, J=4.5 Hz, 2H), 8.00 (d, J=8.3 Hz, 1H), 7.60 (d, J=8.9 Hz, 1H), 7.44 (m, 6H), 7.11 (d, J=8.9 Hz, 1H), 3.89 (s, 3H). $^{13}$C NMR (101 MHz, CDCl$_3$) δ 161.09, 154.75, 150.33, 149.92, 143.79, 136.27, 133.21, 131.12, 128.52, 122.92, 121.29, 120.03, 117.67, 107.06, 55.54.

Example 9: Synthesis of TZ-23-04

A solution of 8-methoxy-2-methylquinoline (100 mg, 0.57 mmol), p-toluenesulfonamide (98.85 mg, 0.57 mmol) and isonicotinaldehyde (61.8 mg, 0.57 mmol) in toluene (0.5 mL) was refluxed at 120° C. for 12 h in a reaction tube under nitrogen. After the mixture was cooled to room temperature, the solvent was removed under reduced pressure.

Then the concentrate was purified by column chromatography with EtOAc/DCM (1:2, v/v) on silica gel, affording TZ-23-04 (135 mg, 90%). $^1$H-NMR (400 MHz, CDCl$_3$): δ 8.58 (d, J=4.8 Hz, 2H), 8.10 (d, J=8.6 Hz, 1H), 7.74-7.59 (m, 2H), 7.52-7.31 (m, 5H), 7.04 (d, J=7.6 Hz, 1H), 4.06 (s, 3H). $^{13}$C NMR (101 MHz, CDCl$_3$) δ 155.22, 153.80, 150.29, 143.81, 140.01, 136.55, 133.84, 131.02, 128.66, 127.01, 121.27, 119.46, 119.41, 108.08, 56.12.

Example 10: Synthesis of TZ-23-06

A solution of 5-methoxy-2-methylquinoline (100 mg, 0.57 mmol), p-toluenesulfonamide (98.85 mg, 0.57 mmol) and isonicotinaldehyde (61.8 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-06 (128 mg, 85%). $^1$H-NMR (400 MHz, CDCl$_3$): δ 8.76-8.43 (m, 2H), 7.97 (d, J=8.4 Hz, 1H), 7.67-7.30 (m, 7H), 7.11 (dd, J=8.9, 2.1 Hz, 1H), 3.90 (s, 3H). $^{13}$C NMR (101 MHz, CDCl$_3$) δ 154.69, 150.27, 149.87, 143.75, 136.21, 133.17, 131.05, 128.49, 122.87, 121.26, 119.98, 117.63, 107.04, 55.49.

Example 11: Synthesis of TZ-23-08

A solution of 4-methoxy-2-methylquinoline (100 mg, 0.57 mmol), p-toluenesulfonamide (98.85 mg, 0.57 mmol)

and isonicotinaldehyde (61.8 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-08 (120 mg, 80%). $^1$H-NMR (400 MHz, CDCl$_3$): δ 8.58 (d, J=4.8 Hz, 2H), 8.11 (d, J=8.2 Hz, 1H), 7.98 (d, J=8.5 Hz, 1H), 7.66 (t, J=7.6 Hz, 1H), 7.46 (dt, J=15.4, 11.1 Hz, 5H), 6.90 (s, 1H), 4.05 (s, 3H). $^{13}$C NMR (101 MHz, CDCl$_3$) δ 162.62, 155.70, 150.31, 148.99, 143.71, 133.70, 131.06, 130.25, 128.78, 125.80, 121.73, 121.29, 120.84, 98.32, 55.67.

Example 12: Synthesis of TZ-23-10

A solution of 3-methoxy-2-methylquinoline (100 mg, 0.57 mmol), p-toluenesulfonamide (98.85 mg, 0.57 mmol) and isonicotinaldehyde (61.8 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-10 (128 mg, 85%). $^1$H-NMR (400 MHz, CDCl$_3$): δ 8.59 (d, J=5.5 Hz, 2H), 8.02 (d, J=8.3 Hz, 1H), 7.90 (s, 2H), 7.68 (d, J=7.9 Hz, 1H), 7.60-7.42 (m, 4H), 7.37 (s, 1H), 3.98 (s, 3H). $^{13}$C NMR (101 MHz, CDCl$_3$) δ 151.56, 150.22, 147.26, 144.30, 142.99, 132.14, 129.08, 129.04, 127.11, 126.95, 126.40, 126.29, 121.57, 112.30, 55.49.

Example 13: Synthesis of TZ-23-12

A solution of 6-methoxy-2-methylquinoline (100 mg, 0.57 mmol), p-toluenesulfonamide (98.85 mg, 0.57 mmol) and pyrazine-2-carbaldehyde (61.5 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-12 (127 mg, 85%). $^1$H-NMR (400 MHz, CDCl$_3$): δ 8.73 (d, J=1.3 Hz, 1H), 8.61-8.48 (m, 1H), 8.41 (d, J=2.5 Hz, 1H), 7.99 (dd, J=15.6, 8.9 Hz, 2H), 7.81 (dd, J=70.7, 15.9 Hz, 2H), 7.56 (d, J=8.5 Hz, 1H), 7.44-7.29 (m, 1H), 7.02 (d, J=2.8 Hz, 1H), 3.90 (s, 3H). $^{13}$C NMR (101 MHz, CDCl$_3$) δ 158.00, 152.10, 150.82, 144.45, 144.36, 144.25, 143.24, 135.23, 134.77, 130.93, 128.79, 128.40, 122.74, 120.91, 104.99, 55.53.

Example 14: Synthesis of TZ-23-16

A solution of 7-methoxy-2-methylquinoline (100 mg, 0.57 mmol), p-toluenesulfonamide (98.85 mg, 0.57 mmol) and pyrazine-2-carbaldehyde (61.5 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-16 (120 mg, 80%). $^1$H-NMR (400 MHz, CDCl$_3$): δ 8.69 (d, J=1.3 Hz, 1H), 8.59-8.48 (m, 1H), 8.38 (d, J=2.4 Hz, 1H), 8.00 (d, J=8.3 Hz, 1H), 7.80 (dd, J=50.7, 15.9 Hz, 2H), 7.60 (d, J=8.9 Hz, 1H), 7.43 (d, J=8.3 Hz, 1H), 7.35 (d, J=2.4 Hz, 1H), 7.10 (d, J=8.9 Hz, 1H), 3.90 (s, 3H). $^{13}$C NMR (101 MHz, CDCl$_3$) δ 161.04, 154.55, 150.66, 149.97, 144.49, 144.36, 143.40, 136.25, 134.75, 129.21, 128.48, 123.07, 120.05, 118.68, 107.12, 55.50.

Example 15: Synthesis of TZ-23-14

A solution of 8-methoxy-2-methylquinoline (100 mg, 0.57 mmol), p-toluenesulfonamide (98.85 mg, 0.57 mmol) and pyrazine-2-carbaldehyde (61.5 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-14 (130 mg, 87%). $^1$H-NMR (400 MHz, CDCl$_3$): δ 8.89-8.71 (m, 1H), 8.57 (dt, J=2.7, 1.4 Hz, 1H), 8.44 (t, J=2.1 Hz, 1H), 8.07 (dd, J=17.8, 12.4 Hz, 2H), 7.83-7.66 (m, 2H), 7.53-7.32 (m, 2H), 7.06 (d, J=7.6 Hz, 1H), 4.09 (s, 3H). $^{13}$C NMR (101 MHz, CDCl$_3$) δ 155.28, 153.59, 150.80, 144.47, 144.17, 143.33, 140.45, 136.65, 135.01, 129.66, 128.82, 127.03, 120.64, 119.43, 108.06, 56.15.

Example 16: Synthesis of TZ-23-18

A solution of 5-methoxy-2-methylquinoline (100 mg, 0.57 mmol), p-toluenesulfonamide (98.85 mg, 0.57 mmol) and pyrazine-2-carbaldehyde (61.5 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-18 (123 mg, 82%). $^1$H-NMR (400 MHz, CDCl$_3$): δ 8.75 (d, J=1.4 Hz, 1H), 8.64-8.50 (m, 1H), 8.43 (d, J=2.4 Hz, 1H), 8.09 (dd, J=46.9, 23.7 Hz, 2H), 7.81 (dd, J=47.4, 15.9 Hz, 2H), 7.71-7.61 (m, 1H), 7.54-7.38 (m, 1H), 6.93 (s, 1H), 4.07 (s, 3H). $^{13}$C NMR (101 MHz, CDCl$_3$) δ 162.64, 155.53, 150.61, 149.06, 144.48, 144.30, 143.44, 135.26, 130.20, 129.38, 128.91, 125.79, 121.69, 120.89, 99.32, 55.66.

Example 17: Synthesis of TZ-23-20

A solution of 4-methoxy-2-methylquinoline (100 mg, 0.57 mmol), p-toluenesulfonamide (98.85 mg, 0.57 mmol) and pyrazine-2-carbaldehyde (61.5 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-20 (124 mg, 83%). $^1$H NMR (400 MHz, CDCl$_3$) δ 8.67 (d, J=1.4 Hz, 1H), 8.49 (dd, J=2.2, 1.6 Hz, 1H), 8.36 (d, J=2.5 Hz, 1H), 7.96 (d, J=8.4 Hz, 1H), 7.83 (d, J=15.9 Hz, 1H), 7.70 (d, J=15.9 Hz, 1H), 7.56 (d, J=8.9 Hz, 1H), 7.39 (d, J=8.4 Hz, 1H), 7.32 (d, J=2.4 Hz, 1H), 7.08 (dd, J=8.9, 2.5 Hz, 1H), 3.87 (s, 3H). $^{13}$C NMR (101 MHz, CDCl$_3$) δ 161.02, 154.52, 150.64, 149.95, 144.48, 144.36, 143.39, 136.23, 134.74, 129.19, 128.47, 123.05, 120.04, 118.67, 107.10, 55.50.

Example 18: Synthesis of TZ-23-22

A solution of 3-methoxy-2-methylquinoline (100 mg, 0.57 mmol), p-toluenesulfonamide (98.85 mg, 0.57 mmol) and pyrazine-2-carbaldehyde (61.5 mg, 0.57 mmol) in toluene (0.5 mL) was refluxed at 120° C. for 12 h in a reaction tube under nitrogen. After the mixture was cooled to room temperature, the solvent was removed under reduced pressure. Then the concentrate was purified by column chromatography with EtOAc/DCM (1:2, v/v) on silica gel, affording TZ-23-22 (133 mg, 89%). $^1$H-NMR (400 MHz, CDCl$_3$): δ 8.67 (d, J=1.2 Hz, 1H), 8.59-8.46 (s, 1H), 8.36 (d, J=2.4 Hz, 1H), 8.28 (d, J=15.7 Hz, 1H), 8.03-7.90 (m, 2H), 7.68-7.57 (m, 1H), 7.54-7.36 (m, 2H), 7.29 (s, 1H), 3.89 (s, 3H). $^{13}$C NMR (101 MHz, CDCl$_3$) δ 151.80, 150.96, 147.23, 144.83, 144.54, 143.35, 142.97, 129.94, 129.20, 129.16, 128.33, 127.04, 126.97, 126.26, 112.25, 55.43.

Example 19: Synthesis of TZ-19-122

A mixture of (E)-3-(4-nitrophenyl)acrylaldehyde (197 mg, 1.12 mmol) and 6-methoxy-2H-benzo[b][1,4]oxazin-3 (4H)-one (TZ19-120-1) (100 mg, 0.56 mmol) was dissolved in acetic anhydride (2 mL) and triethyl amine (1 mL), and was refluxed for 7 h, left overnight at room temperature. The reaction mixture was poured into crushed ice, extracted methylene chloride, dried with Na$_2$SO$_4$, filtered, and concentrated. The solvent was removed under reduced pressure and the concentrate was purified by column chromatography on silica gel, affording TZ-19-122 (122 mg, 65%). $^1$H-NMR (400 MHz, DMSO-d$_6$): δ 11.08 (s, 1H), 8.17 (d, J=8.5 Hz, 2H), 7.80 (d, J=8.2 Hz, 2H), 7.56-7.40 (m, 1H), 7.12 (d, J=8.5 Hz, 1H), 7.02 (d, J=15.8 Hz, 1H), 6.68-6.40 (m, 3H), 3.62 (s, 3H).

Example 20: Synthesis of TZ-19-124

A mixture of (E)-3-(4-nitrophenyl)acrylaldehyde (181 mg, 1.02 mmol) and 6-methoxy-2H-benzo[b][1,4]thiazin-3 (4H)-one (TZ19-120-2) (100 mg, 0.56 mmol) was dissolved in acetic anhydride (2 mL) and triethyl amine (1 mL), and was refluxed for 7 h, left overnight at room temperature. The reaction mixture was poured into crushed ice, extracted methylene chloride, dried with Na$_2$SO$_4$, filtered, and concentrated. The solvent was removed under reduced pressure and the concentrate was purified by column chromatography on silica gel, affording TZ-19-124 (126 mg, 70%). $^1$H-NMR (400 MHz, DMSO-d$_6$): δ 10.84 (s, 1H), 8.19 (d, J=8.5 Hz, 2H), 7.82 (d, J=8.7 Hz, 2H), 7.46-7.10 (m, 3H), 6.96 (d, J=8.7 Hz, 1H), 6.89 (s, 1H), 6.77 (d, J=7.8 Hz, 1H), 3.64 (s, 3H).

Example 21: Synthesis of TZ-19-126

10H-phenothiazine (100 mg, 0.50 mmol) was slowly added to a suspension of NaH (15 mg, 0.60 mmol) in DMF at 0° C. The stirring continued at room temperature for 1 h. The solution was cooled to 0° C. again and (E)-(3-bromoprop-1-en-1-yl)benzene (98 mg, 0.5 mmol) added slowly. The reaction mixture was allowed to warm to an ambient temperature. After completion of reaction, reaction mixture was diluted in water and organics extracted with ethyl acetate. Organic layer was washed with water, brine, dried over Na$_2$SO$_4$, filtered, and concentrated. The solvent was removed under reduced pressure and the concentrate was purified by column chromatography on silica gel, affording TZ-19-126 (110 mg, 70%). $^1$H-NMR (400 MHz, CDCl$_3$): δ 7.40-7.08 (m, 5H), 6.97 (dd, J=14.0, 7.5 Hz, 4H), 6.86-6.68 (m, 4H), 6.47 (d, J=16.2 Hz, 1H), 6.26 (d, J=16.2 Hz, 1H), 4.54 (d, J=2.0 Hz, 2H).

Example 22: Synthesis of TZ-19-136

A mixture of 10H-phenoxazine (TZ-19-135) (100 mg, 0.54 mmol), (E)-3-phenylprop-2-en-1-ol (TZ-19-139) (88 mg, 0.65 mmol), Pd(OAc)$_2$ (1.23 mg, 0.005 mmol), PPh$_3$ (5.73 mg, 0.021 mmol), Ti(OPr$^i$)$_4$ (38.78 mg, 0.14 mmol), and MS 4 Å (200 mg) in benzene (5 mL) was refluxed under nitrogen for 3 h. After cooling, the reaction mixture was filtered through Celite and the solvent was distilled under reduced pressure. Then the concentrate was purified by column chromatography with hexane/EtOAc (5:1, v/v) on silica gel, affording TZ-19-136 (110 mg, 68%). $^1$H NMR (400 MHz, CDCl$_3$) δ 7.47-7.16 (m, 5H), 6.83-6.72 (m, 2H), 6.68 (s, 4H), 6.58 (d, J=16.1 Hz, 1H), 6.50 (d, J=7.9 Hz, 2H), 6.24 (dt, J=16.2, 3.9 Hz, 1H), 4.31 (s, 2H).

Example 23: Synthesis of TZ-19-138

A mixture of 10H-phenoxazine (TZ-19-135) (100 mg, 0.54 mmol), (E)-3-(4-(dimethylamino)phenyl)prop-2-en-1-ol (TZ-19-139) (116 mg, 0.65 mmol), Pd(OAc)$_2$ (1.23 mg, 0.005 mmol), PPh$_3$ (5.73 mg, 0.021 mmol), Ti(OPr$^i$)$_4$ (38.78 mg, 0.14 mmol), and MS 4 Å (200 mg) in benzene (5 mL) was refluxed under nitrogen for 3 h. After cooling, the reaction mixture was filtered through Celite and the solvent was distilled under reduced pressure. Then the concentrate was purified by column chromatography with hexane/EtOAc (5:1, v/v) on silica gel, affording TZ-19-138 (140 mg, 75%). $^1$H-NMR (400 MHz, CDCl$_3$): δ 7.16 (d, J=8.4 Hz, 2H), 6.73-6.63 (m, 2H), 6.63-6.50 (m, 6H), 6.49-6.33 (m, 3H), 5.99-5.85 (m, 1H), 4.19 (d, J=2.0 Hz, 2H), 2.85 (s, 6H).

Example 24: Synthesis of TZ-19-140

A mixture of 3-methoxy-7-nitro-10H-phenoxazine (TZ-19-137) (70 mg, 0.27 mmol), (E)-3-(4-(dimethylamino) phenyl)prop-2-en-1-ol (TZ-19-141) (58 mg, 0.33 mmol), Pd(OAc)$_2$ (0.007 mg, 0.002 mmol), PPh$_3$ (2.84 mg, 0.011 mmol), Ti(OPr$^i$)$_4$ (19.26 mg, 0.07 mmol), and MS 4 Å (200 mg) in benzene (5 mL) was refluxed under nitrogen for 3 h. After cooling, the reaction mixture was filtered through Celite and the solvent was distilled under reduced pressure. Then the concentrate was purified by column chromatography with hexane/EtOAc (5:1, v/v) on silica gel, affording TZ-19-140 (80 mg, 70%). $^1$H-NMR (400 MHz, CDCl$_3$): δ 7.70 (d, J=8.6 Hz, 1H), 7.46 (s, 1H), 7.23 (d, J=8.6 Hz, 2H), 6.63 (d, J=8.3 Hz, 2H), 6.56-6.39 (m, 3H), 6.34 (s, 2H), 5.94 (d, J=16.0 Hz, 1H), 4.29 (s, 2H), 3.71 (s, 3H), 2.93 (s, 6H).

Example 25: Synthesis of TZ-23-52

To a solution of (E)-4-(2-(pyridin-4-yl)vinyl)benzoic acid (200 mg, 0.89 mmol) in thionyl chloride (80 ml) under nitrogen atmosphere. The reaction mixture was stirred overnight and excess thionyl chloride was removed under vacuum. The acid chloride was dissolved in dichloromethane (15 ml) and 4-bromoaniline (229 mg, 1.35 mmol) was added. To this stirred mixture, triethylamine (5 ml in 7 ml dichloromethane) was added slowly and stirred overnight. After evaporation, the residue was dissolved in dichloromethane (30 ml) and washed with 1N sodium hydroxide. The organic phase was dried by sodium sulfate and concentrate in vacuum. The residue was purified by silica gel column chromatography with EtOAc/DCM (1:1, v/v) and gave the title compound with 75% yield. $^1$H NMR (400 MHz, DMSO-d$_6$) δ 10.36 (s, 1H), 8.55 (d, J=6.1 Hz, 2H), 7.97 (d, J=8.4 Hz, 2H), 7.76 (dd, J=15.8, 8.7 Hz, 4H), 7.66-7.47 (m, 5H), 7.41 (s, 1H).

Example 26: Synthesis of TZ-23-56

To a solution of (E)-4-(2-(pyridin-4-yl)vinyl)benzoic acid (200 mg, 0.89 mmol) in thionyl chloride (80 ml) under nitrogen atmosphere. The reaction mixture was stirred overnight and excess thionyl chloride was removed under vacuum. The acid chloride was dissolved in dichloromethane (15 ml) and 4-iodoaniline (295 mg, 1.35 mmol) was added. To this stirred mixture, triethylamine (5 ml in 7 ml dichloromethane) was added slowly and stirred overnight. After evaporation, the residue was dissolved in dichloromethane (30 ml) and washed with 1N sodium hydroxide. The organic phase was dried by sodium sulfate and concentrate in vacuum. The residue was purified by silica gel column chromatography with EtOAc/DCM (1:1, v/v) and gave the title compound with 60% yield. $^1$H NMR (400 MHz, DMSO-d$_6$) δ 10.33 (s, 1H), 8.54 (s, 2H), 7.97 (d, J=8.1 Hz, 2H), 7.78 (d, J=8.2 Hz, 2H), 7.72-7.50 (m, 7H), 7.39 (d, J=16.4 Hz, 1H).

Example 27: Synthesis of TZ-20-1

To a 250 mL flask 11.20 g (130 mmol) piperazine was added to 2N HCl 50 mL with stirring at 50° C. following added dropwise of 4-Methoxybenzoyl chloride 8.53 g (50 mmol, 6.88 mL). After 1 h the reaction mixture was concentrated in vacuum. 40% NaOH was added to the residue with pH 12 and then extracted with DCM (3×30 mL). Followed dryness and concentration in vacuum, the residue was separated with silica gel chromatography (DCM:methanol:TEA=180:20:1) afforded the desired compound in colorless oil with 30% yield. $^1$H NMR (400 MHz, CDCl$_3$) δ 7.33 (d, J=8.3 Hz, 1H), 6.86 (d, J=8.4 Hz, 1H), 3.78 (s, 2H), 3.55 (s, 2H), 2.82 (s, 2H), 2.08 (s, 1H). $^{13}$C NMR (101 MHz, CDCl$_3$) δ 170.24, 160.54, 128.93, 127.72, 113.56, 55.21, 49.01 (br.), 46.07, 43.39 (br.).

Example 28: Synthesis of TZ-20-3

To a solution of (4-methoxyphenyl)(piperazin-1-yl)methanone (TZ-20-1) (3.30 g, 14.9 mmol) in THF 80 mL was added dropwise chloroacetyl chloride (1.69 g, 17.9 mmol) at 0° C. under nitrogen. The reaction was allowed to warm to room temperature stirring for 1 h. The reaction mixture was extracted with DCM (3×50 mL). The organic layer was washed with saturated NH$_4$Cl and brine, dried over anhydrous NaSO$_4$. After filtration and concentration in vacuum, the crude product obtained was used directly for next step without purification (faint yellow oil, 96% yield). $^1$H NMR (400 MHz, CDCl$_3$) δ 7.39 (d, J=8.5 Hz, 2H), 6.92 (d, J=8.5 Hz, 2H), 4.08 (s, 2H), 3.83 (s, 3H), 3.72-3.56 (m, 8H). $^{13}$C NMR (101 MHz, CDCl$_3$) δ 170.59, 165.31, 161.11, 129.22, 126.86, 113.85, 55.36, 46.04 (br.), 42.18 (br.), 40.68.

Example 29: Synthesis of TZ-20-5

To 50 mL of acetonitrile was added 2-chloro-1-(4-(4-methoxybenzoyl)piperazin-1-yl)ethanone (TZ-20-3) (3.42 g, 11.5 mmol), 4-tert butyl benzoic acid (2.46 g, 13.8 mmol) and TEA (2.40 mL). The mixture was refluxed for 2 h. After cooling, the mixture was filtrated and the filtrate was concentrated in vacuum. To the residue was added ice-water, and precipitated crystals was recrystallized from 40% ethanol solution to give faint yellow crystal with about 50% yield. Melting point: 158.6-159.4° C. $^1$H NMR (400 MHz, CDCl$_3$) δ 8.02 (d, J=8.4 Hz, 2H), 7.47 (d, J=8.4 Hz, 2H), 7.40 (d, J=8.7 Hz, 2H), 6.93 (d, J=8.7 Hz, 2H), 4.97 (s, 2H), 3.84 (s, 3H), 3.72-3.53 (m, 8H), 1.34 (s, 9H). $^{13}$C NMR (101 MHz, CDCl$_3$) δ 170.56, 166.00, 165.38, 161.05, 157.13, 129.72, 129.19, 126.86, 126.29, 125.41, 113.81, 61.73, 55.32, 44.69, 42.00, 35.07, 31.01.

Example 30: Synthesis of TZ-20-7

4-Bromoanisole (2.06 g, 11.0 mmol, 1.38 mL) was treated with BuLi (0.94 g, 14.7 mmol, 9.18 mL) in dry THF (40 mL) at −78° C. for 30 min., then tert-Butyl 4-(methoxy(methyl)carbamoyl)-piperidine-1-carboxylate (2.00 g, 7.34 mmol) in dry THF (30 mL) was added dropwise under nitrogen. The reaction was allowed to warm to room temperature overnight. Sat. NH$_4$Cl was used to quench the reaction followed extraction with EA. The organic layer was washed with brine, dried over, filtrated, and concentrated in vacuum. The residue was purified via silica gel chromatography affording desired compound (DCM:EA=19:1). TFA (5 mL) was added dropwise to the solution of the compound in DCM (30 mL) at ice bath and the reaction was allowed to warm to room temperature overnight. Removing DCM and TFA in vacuum and the residue was added 2N HCl (10 mL) and DCM (50 mL) stirring for 1 h. The mixture was extracted with ether (3×10 mL). The water layer was treated with 6N NaOH (1 mL) to pH 12 and then extracted with DCM (3×10 mL). The organic layer was washed with saturated NH$_4$Cl and brine, dried over anhydrous NaSO$_4$. After filtration and concentration in vacuum, the crude product obtained was used directly for next step without purification (colorless oil, 50% yield for 2 steps). $^1$H NMR (300 MHz, CDCl$_3$): δ 1.53-1.84 (m, 2H), 2.72-2.81 (m, 2H), 3.11-3.21 (m, 3H), 3.31-3.41 (m, 1H), 3.88 (s, 3H), 6.95 (d, J=9.0 Hz, 2H), 7.94 (d, J=9.0 Hz, 2H).

Example 31: Synthesis of TZ-20-9

(4-methoxyphenyl)(piperidin-4-yl)methanone (TZ-20-7) (0.70 g, 3.19 mmol), chloroacetyl chloride (0.53 mL, 6.66 mmol), and dry THF (20 mL). The procedure was same as the synthesis of TZ-20-3. Colorless oil, 92% yield. $^1$H NMR (400 MHz, CDCl$_3$) δ 7.93 (d, J=8.4 Hz, 2H), 6.95 (d, J=8.4 Hz, 2H), 4.49 (d, J=13.0 Hz, 1H), 4.09 (s, 2H), 3.94 (d, J=13.4 Hz, 1H), 3.87 (s, 3H), 3.48 (s, 1H), 3.30 (s, 1H), 2.94 (t, J=11.8 Hz, 1H), 1.91 (brs, 3H), 1.73-1.69 (m, 1H). $^{13}$C NMR (101 MHz, CDCl$_3$) δ 199.82, 164.98, 163.63, 130.53, 128.45, 113.95, 55.50, 45.78, 42.42, 41.77, 41.04, 28.48, 28.44.

Example 32: Synthesis of TZ-20-11

2-chloro-1-(4-(4-methoxybenzoyl)piperidin-1-yl)ethanone (TZ-20-9) (150 mg, 0.51 mmol), 4-tert-butyl benzoic acid (136 mg, 0.76 mmol), TEA (123 mg, 1.01 mmol, 0.14 mL) and THF, (20 mL). The procedure was same as the synthesis of TZ-20-5. Colorless oil, 93% yield. $^1$H NMR (400 MHz, CDCl$_3$) δ 8.02 (d, J=8.0 Hz, 2H), 7.92 (d, J=8.4 Hz, 2H), 7.44 (d, J=8.0 Hz, 2H), 6.94 (d, J=8.4 Hz, 2H), 4.96 (q, J=14.0 Hz, 2H), 4.51 (d, J=13.1 Hz, 1H), 3.85 (s, 3H), 3.82 (s, 1H), 3.53-3.40 (m, 1H), 3.25 (t, J=10.7 Hz, 1H), 2.93 (t, J=11.9 Hz, 1H), 1.93-1.90 (m, 3H), 1.77-1.63 (m, 1H), 1.32 (s, 9H). $^{13}$C NMR (101 MHz, CDCl$_3$) δ 199.85, 166.13, 164.96, 163.60, 156.93, 130.54, 129.78, 128.43, 126.59, 125.36, 113.94, 61.91, 55.49, 44.07, 42.58, 41.51, 35.08, 31.06, 28.47. FIRMS: Calculate for C$_{26}$H$_{32}$NO$_5$ (M+H$^+$): 438.2275; Found: 438.2276.

Example 33: Synthesis of TZ-20-15

A solution of 4-methoxybromobenzen 6.0 g (32.1 mmol, 2.0 mL), in THF (100 mL) was added dropwise to a stirred mixture of Mg (780 mg, 32.1 mmol) and I$_2$ (catalytic amount) at r.t for 1 h, then refluxed for 2 h under nitrogen. Cooling to 0° and added dropwise a solution of 1-benzyl-4-piperidinone (5.5 g, 29.2 mmol) in THF (50 mL) at ice bath. The reaction was allowed warm to r.t. overnight. Sat. NH$_4$Cl 50 mL and water 20 mL were added to the mixture and stirred for 30 min and then, separated the oil layer and extracted water layer with EA (3×30 mL). Combined the organic phase and washed with brine, dried with anhydrate NaSO$_4$, filtered and concentrated in vacuum. The residue was dissolved in a mixture of 1,4-dioxane (50 mL) and 6N HCl (100 mL), then refluxed for 10 h. Concentrated in vacuum, the residue was triturated with ether afforded solid crude product, then purified it via recrystallization (95% ethanol) to yield white solid compound 1.1 g. Concentrated the filtrate and treated with base (6N NaOH), extracted with EA (3×30 mL), washed with brine, dried with anhydrate, NaSO$_4$, filtered, concentrated in vacuum and separated via silica gel chromatography (EA:hexane=2:3) afforded white solid (non-salt product) 2.2 g. Total yield was about 43%. M.p.: 228.1-229.3° C. (hydrochloride). $^1$H NMR (400 MHz, CD$_3$OD) δ 7.56-7.45 (m, 5H), 7.38 (d, J=8.6 Hz, 2H), 6.88 (d, J=8.6 Hz, 2H), 5.99 (s, 1H), 4.41 (s, 2H), 3.82 (s, 2H), 3.76 (s, 3H), 3.27 (s, 3H), 2.83 (s, 2H). $^{13}$C NMR (101 MHz, CD$_3$OD) δ 161.48, 136.38, 132.26, 131.32, 130.47, 127.36, 114.96, 114.44, 60.67, 55.74, 51.65, 50.12, 25.67.

Example 34: Synthesis of TZ-20-19

A solution of 1-benzyl-4-(4-methoxyphenyl)-1,2,3,6-tetrahydropyridine hydrochloride (TZ-20-15) (1.0 g, 3.6 mmol) in a mixture of methanol (20 mL) and water (18 mL) was hydrogenated in presence of 10% Pd—C (300 mg) under H$_2$ (70 psi) at r.t. for 8 h. Filtered the catalysis and the filtrate was concentrated in vacuum afforded white solid. M.p.: 204.9-206.0° C. (hydrochloride). $^1$H NMR (400 MHz, DMSO-d$_6$) δ 6.93 (d, J=8.3 Hz, 2H), 6.68 (d, J=8.2 Hz, 2H), 3.50 (s, 3H), 3.11 (d, J=12.3 Hz, 2H), 2.74 (brs, 2H), 2.55-2.54 (m, 1H), 2.30 (s, 1H), 1.62 (m, 4H). $^{13}$C NMR (101 MHz, DMSO-d$_6$) M57.95, 136.88, 127.64, 114.05, 55.18, 43.65, 38.26, 29.71.

Example 35: Synthesis of TZ-20-21

To a solution of 4-(4-methoxyphenyl)piperidine hydrochloride (TZ-20-19) (1.1 g, 4.8 mmol) and TEA (1.35 mL, 9.7 mmol) in THF 60 mL was added dropwise chloroacetyl chloride (821 mg, 7.3 mmol, 0.58 mL) at 0° C. under nitrogen. The reaction was allowed to warm to room temperature stirring for 2 h. The reaction mixture was extracted with DCM (3×50 mL). The organic layer was washed with saturated NH$_4$Cl and brine, dried over anhydrous NaSO$_4$. After filtration and concentration in vacuum, the crude product was purified via silica gel chromatography (hexane:EA=1:3) to yield desired compound (faint yellow oil, 74% yield). $^1$H NMR (400 MHz, CDCl$_3$) δ 7.11 (d, J=8.0 Hz, 2H), 6.85 (d, J=8.0 Hz, 2H), 4.70 (d, J=12.4 Hz, 1H), 4.21-4.02 (m, overlap, 2H), 3.95 (d, J=12.4 Hz, 1H), 3.78 (s, 3H), 3.21 (t, J=13.1 Hz, 1H), 2.84-2.59 (m, 2H), 1.90 (t, J=14.4 Hz, 2H), 1.74-1.56 (m, 2H). $^{13}$C NMR (101 MHz, CDCl$_3$) δ 165.08, 158.04, 136.81, 127.46, 113.80, 55.14, 46.98, 42.98, 41.42, 40.97, 33.73, 32.74.

Example 36: Synthesis of TZ-20-23

To 50 mL of acetonitrile was added 2-chloro-1-(4-(4-methoxyphenyl)piperidin-1-yl)ethanone (TZ-20-21) (390 mg, 1.4 mmol), 4-tert butyl benzoic acid (389 mg, 2.2 mmol) and TEA (0.4 mL, 2.9 mmol). The mixture was refluxed for 4 h. After cooling, the mixture was filtered and the filtrate was concentrated in vacuum. The desired compound was obtained via silica gel chromatography (hexane:EA=3:1) in white solid with 76% yield. M.p.: 101.0-102.2° C. $^1$H NMR (400 MHz, CDCl$_3$) δ 8.06 (d, J=5.4 Hz, 2H), 7.47 (d, J=5.6 Hz, 2H), 7.11 (brs, 2H), 6.87 (brs, 2H), 5.00 (s, 2H), 4.75 (d, J=10.7 Hz, 1H), 3.79 (brs, overlap, 4H), 3.20 (brs, 1H), 2.71 (brs, 2H), 1.90 (brs, 2H), 1.67 (brs, 2H), 1.34 (s, 9H). $^{13}$C NMR (101 MHz, CDCl$_3$) δ 166.17, 164.78, 58.11, 156.88, 137.04, 129.76, 127.54, 126.61, 125.32, 113.87, 61.89, 55.20, 45.25, 42.74, 41.71, 35.05, 33.87, 32.81, 31.04. Elemental Analysis: Calculated for C$_{25}$H$_{31}$NO$_4$: C, 73.32, H, 7.63, N, 3.42; Found: C, 73.21, H, 7.78, N, 3.44.

Example 37: Synthesis of TZ-20-35

4-Picoline (0.89 mL, 9.1 mmol) and methyl 4-formylbenzoate (1.50 g, 9.1 mmol) were refluxed in 25 mL acetic anhydride for 16 hours. The mixture was then cooled to ambient temp, and poured onto 200 mL of ice water. The solid was collected from filtration, and washed repeatedly with water. The desired compound was obtained via silica gel chromatograph (EA:methanol=16:1). $^1$H NMR (400 MHz, DMSO-d$_6$) δ 8.57 (d, J=3.6 Hz, 2H), 7.98 (d, J=7.5 Hz, 2H), 7.78 (d, J=7.5 Hz, 2H), 7.61 (overlap, 3H), 7.40 (d, J=16.4 Hz, 1H), 3.85 (s, 3H). $^{13}$C NMR (101 MHz, DMSO-d$_6$) δ 165.88, 150.12, 143.74, 140.83, 131.74, 129.66, 129.12, 128.76, 127.23, 121.10, 52.16. HRMS: calculated for C$_{15}$H$_{14}$NO$_2$ [M+H$^+$]: 240.1019; Found: 240.1015.

Example 38: Synthesis of TZ-20-37

Synthesis was performed in a similar fashion as described in Example 37. Faint yellow solid in 70% yield. $^1$H NMR (400 MHz, DMSO-d$_6$) δ 13.00 (brs, 1H), 8.55 (d, J=4.3 Hz, 2H), 7.93 (d, J=7.3 Hz, 2H), 7.74 (d, J=7.8 Hz, 2H), 7.63-7.59 (overlap, 3H), 7.39 (d, J=16.8 Hz, 1H). $^{13}$C NMR (101 MHz, DMSO-d$_6$) δ 167.43, 150.25, 144.30, 140.70, 132.59, 130.81, 130.24, 128.78, 127.69, 121.83.

Example 39: Synthesis of TZ-20-59

Synthesis was performed in a similar fashion as described in Example 37. $^1$H NMR (400 MHz, CDCl$_3$) δ 8.62 (s, 2H), 8.23 (d, J=7.0 Hz, 2H), 7.67 (d, J=7.1 Hz, 2H), 7.39 (s, 2H), 7.33 (d, J=16.6 Hz, 1H), 7.16 (d, J=16.2 Hz, 1H). $^{13}$C NMR (101 MHz, CDCl$_3$) δ 150.43, 147.39, 143.31, 142.42, 130.58, 130.44, 127.48, 124.19, 121.08. HRMS: calculated for C$_{13}$H$_{11}$N$_2$O$_2$ [M+H$^+$]: 227.0815; Found: 227.0810.

Example 40: Synthesis of TZ-20-73

Synthesis was performed in a similar fashion as described in Example 37. $^1$H NMR (400 MHz, CD$_3$OD) δ 8.47 (d, J=5.1 Hz, 2H), 7.66 (dd, J=7.7, 5.9 Hz, 2H), 7.57 (d, J=5.2 Hz, 2H), 7.49 (d, J=16.4 Hz, 1H), 7.18-7.06 (m, 3H). $^{13}$C NMR (101 MHz, CD$_3$OD) δ 164.45 (J=252), 150.32, 147.47, 134.10, 134.07, 130.18 (J=8.0), 126.41, 122.52, 116.70 (J=22). HRMS: calculated for C$_{13}$H$_{11}$FN [M+H$^+$]: 200.0870; Found: 200.0864.

Example 41: Synthesis of TZ-20-75

Synthesis was performed in a similar fashion as described in Example 37. $^1$H NMR (400 MHz, DMSO-d$_6$) δ 8.62-8.53

(m, 2H), 7.86 (d, J=8.0 Hz, 2H), 7.76 (d, J=8.0 Hz, 2H), 7.63 (d, J=16.6 Hz, 1H), 7.60-7.57 (m, 2H), 7.42 (d, J=16.5 Hz, 1H). $^{13}$C NMR (101 MHz, DMSO-d$_6$) δ 150.40, 144.13, 140.51, 131.79, 129.10, 128.84 (q, J=32.3 Hz), 127.98, 126.00 (q, J=4.0 Hz), 124.56 (q, J=272.7 Hz), 121.55. HRMS: calculated for C$_{14}$H$_{11}$F$_3$N [M+H$^+$]: 250.0838; Found: 250.0829.

Example 42: Synthesis of TZ-20-63

The mixture of (E)-4-(2-(Pyridin-4-yl)vinyl)benzoic acid 150 mg (0.66 mmol), 1-bromo-2-fluoroethane 0.05 mL (0.66 mmol) and TEA 1 mL in acetonitrile (10 mL) was stirred for 12 hours at room temperature under nitrogen. Adding 10 g silica gel to the mixture to make slurry and removing TEA and solvent under vacuum, the desired compound was obtained via chromatography (EA:hexane=5:1) in white solid with 45% yield. $^1$H NMR (400 MHz, CDCl$_3$) δ 8.61 (d, J=4.3 Hz, 2H), 8.09 (d, J=8.0 Hz, 2H), 7.61 (d, J=8.1 Hz, 2H), 7.38 (d, J=4.4 Hz, 2H), 7.32 (d, J=16.3 Hz, 1H), 7.13 (d, J=16.3 Hz, 1H), 4.81 (s, 1H), 4.69 (s, 1H), 4.61 (s, 1H), 4.54 (s, 1H). $^{13}$C NMR (101 MHz, CDCl$_3$) δ 165.85, 150.30, 143.85, 140.74, 131.81, 130.25, 129.38, 28.58, 126.85, 120.96, 81.39 (d, J=170.5 Hz), 63.81 (d, J=20.1 Hz). HRMS: calculated for C$_{16}$H$_{15}$FNO$_2$ [M+H$^+$]: 272.1081; Found: 272.1078.

Example 43: Synthesis of TZ-20-65

(E)-4-(2-(Pyridin-4-yl)vinyl)benzoic acid 150 mg (0.66 mmol) was added to SOCl$_2$ (15 mL) stirring 24 hours at room temperature under nitrogen. After removing SOCl$_2$ under vacuum, the mixture of TEA (1.0 mL) and 2-propanol (15 mL) was added dropwise at ice bath, and then the reaction was allowed to warm to room temperature for 24 hours. Adding 10 g silica gel to the mixture to make slurry and removing TEA and solvent under vacuum, the desired compound was obtained via chromatography (EA: hexane=5:1) in white solid with 60% yield. $^1$H NMR (400 MHz, CDCl$_3$) δ 8.62 (d, J=2.7 Hz, 2H), 8.06 (d, J=8.0 Hz, 2H), 7.61 (d, J=8.0 Hz, 2H), 7.51 (d, J=3.6 Hz, 2H), 7.40 (d, J=16.4 Hz, 1H), 7.14 (d, J=16.4 Hz, 1H), 5.26 (dt, J=12.4, 6.2 Hz, 1H), 1.39 (s, 3H), 1.37 (s, 3H). $^{13}$C NMR (101 MHz, CDCl$_3$) δ 165.53, 148.05, 146.24, 139.70, 133.89, 131.19, 130.09, 127.37, 127.00, 121.51, 68.61, 21.94. HRMS: calculated for C$_{17}$H$_{18}$NO$_2$ [M+H$^+$]: 268.1332; Found: 268.1332.

Example 44: Synthesis of TZ-20-51

(E)-4-(2-(Pyridin-4-yl)vinyl)benzoic acid 150 mg (0.66 mmol) was added to SOCl$_2$ (15 mL) stirring 24 hours at room temperature under nitrogen. After removing SOCl$_2$ under vacuum, the mixture of TEA (1.0 mL) and (4-methoxyphenyl)(piperidin-4-yl)methanone hydrochloride (TZ-20-7) 140 mg (0.64 mmol) in DCM (20 mL) was added dropwise at ice bath under nitrogen, then the reaction was allowed to warm to room temperature for 24 hours. Adding 10 g silica gel to the mixture to make slurry and removing TEA and solvent under vacuum, the desired compound was obtained via chromatography (EA: hexane=5:1) in faint yellow solid with 70% yield. $^1$H NMR (400 MHz, CDCl$_3$) δ 8.60 (d, J=4.0, 2H), 7.96 (d, J=8.5 Hz, 2H), 7.59 (d, J=7.9 Hz, 2H), 7.46 (d, J=7.9 Hz, 2H), 7.39 (d, J=4.8 Hz, 2H), 7.31 (d, J=16.4 Hz, 1H), 7.07 (d, J=16.3 Hz, 1H), 6.97 (d, J=8.5 Hz, 2H), 4.71 (brs, 1H), 3.88 (s, overlep, 4H), 3.53 (brs, 1H), 3.13 (br, 2H), 2.01 (brs, 1H), 1.83 (br, 3H). $^{13}$C NMR (101 MHz, CDCl$_3$) δ 200.05, 169.85, 163.62, 150.03, 144.32, 137.40, 136.05, 132.26, 130.55, 128.47, 127.54, 127.19, 127.02, 120.96, 113.94, 55.50, 47.21 (br), 42.88, 41.91 (br), 28.76 (br). HRMS: calculated for C$_{27}$H$_{27}$N$_2$O$_3$ [M+H$^+$]: 427.2016; Found: 427.2008.

Example 45: Synthesis of TZ-20-69

Synthesis was performed in a similar fashion as described in Example 44. $^1$H NMR (400 MHz, CD$_3$OD) δ 8.62 (brs, 2H), 7.88-7.86 (overlep, 4H), 7.77 (d, J=8.3 Hz, 2H), 7.73 (d, J=16.6 Hz, 1H), 7.40 (d, J=16.4 Hz, 1H), 2.93 (s, 3H). $^{13}$C NMR (101 MHz, CD$_3$OD) δ 169.94, 151.13, 146.99, 140.19, 137.24, 136.10, 128.85, 128.74, 127.52, 123.73, 26.95. HRMS: calculated for C$_{15}$H$_{15}$N$_2$O [M+H$^+$]: 239.1179; Found: 239.1180.

Example 46: Synthesis of TZ-20-67

Synthesis was performed in a similar fashion as described in Example 44. $^1$H NMR (400 MHz, CDCl$_3$) δ 8.59 (d, J=4.2 Hz, 2H), 7.57 (d, J=8.1 Hz, 2H), 7.45 (d, J=8.1 Hz, 2H), 7.37 (d, J=5.5 Hz, 2H), 7.30 (d, J=16.4 Hz, 1H), 7.05 (d, J=16.3 Hz, 1H), 3.12 (s, 3H), 3.01 (s, 3H). $^{13}$C NMR (101 MHz, CDCl$_3$) δ 171.03, 150.24, 144.17, 137.30, 136.29, 132.17, 127.74, 127.18, 126.86, 120.89, 39.57, 35.40. HRMS: calculated for C$_{16}$H$_{17}$N$_2$O [M+H$^+$]: 253.1335; Found: 253.1337.

Example 47: Synthesis of TZ-20-39

Synthesis was performed in a similar fashion as described in Example 44. $^1$H NMR (400 MHz, CDCl$_3$) δ 8.60 (s, 2H), 7.59 (d, J=7.7 Hz, 2H), 7.48 (d, J=7.7 Hz, 2H), 7.38 (d, J=3.9 Hz, 2H), 7.31 (d, J=16.4 Hz, 1H), 7.15 (d, J=8.1 Hz, 2H), 7.07 (d, J=16.3 Hz, 1H), 6.87 (d, J=8.1 Hz, 2H), 4.88 (s, 1H), 3.90 (s, 1H), 3.80 (s, 3H), 3.15 (s, 1H), 2.87 (s, 1H), 2.75 (t, J=11.7 Hz, 1H), 1.99-1.54 (m, 4H). $^{13}$C NMR (101 MHz, CDCl$_3$) δ 169.79, 158.16, 150.17, 144.23, 137.34, 137.19, 136.28, 132.20, 127.57, 127.19, 127.00, 120.91, 113.92, 109.99, 55.25, 48.37 (br), 42.83 (br), 41.87 (br), 34.17 (br), 33.10 (br). HRMS: calculated for C$_{26}$H$_{27}$N$_2$O$_2$ [M+H$^+$]: 399.2067; Found: 399.2061.

Example 48: Synthesis of TZ-20-45

Synthesis was performed in a similar fashion as described in Example 44. $^1$H NMR (400 MHz, CDCl$_3$) δ 8.60 (d, J=3.8 Hz, 2H), 7.59 (d, J=7.6 Hz, 2H), 7.45 (d, J=8.2 Hz, 2H), 7.40 (overlep, 4H), 7.30 (d, J=16.7 Hz, 1H), 7.07 (d, J=16.6 Hz, 1H), 6.93 (d, J=8.4 Hz, 2H), 3.84 (s, 3H), 3.68 (brs, 8H). $^{13}$C NMR (101 MHz, CDCl$_3$) δ 170.63, 170.10, 161.05, 150.26, 144.01, 137.92, 134.98, 131.89, 129.24, 127.79, 127.63, 127.11, 126.94, 120.93, 113.84, 55.38, 47.73 (br), 42.27 (br). HRMS: calculated for C$_{26}$H$_{26}$N$_3$O$_3$ [M+H$^+$]: 428.1969; Found: 428.1963.

Example 49: Synthesis of TZ-20-77

(E)-4-(2-(Pyridin-4-yl)vinyl)benzoic acid 150 mg (0.66 mmol) was added to SOCl$_2$ (15 mL) stirring 24 hours at room temperature under nitrogen. After removing SOCl$_2$ under vacuum, the solution L-tyrosine methyl ester 129 mg (0.66 mmol) in DCM (10 mL) and DMF (5 mL) was added and stirred at ice bath under nitrogen. The reaction was allowed warm to room temperature for 2 h. Adding 10 mL water and then 2N NaOH. When pH=6 to 7, the mixture was extracted with DCM (3×20 mL), washing with brine, drying with anhydride sodium sulfate, and removing solvent under vacuum, the desired compound was obtained via chromatography (EA) in white solid with 45% yield. $^1$H NMR (400 MHz, CD$_3$OD) δ 8.45 (d, J=5.9 Hz, 2H), 7.74 (d, J=8.2 Hz, 2H), 7.64 (d, J=8.4 Hz, 2H), 7.55 (d, J=6.1 Hz, 2H), 7.47 (d, J=16.4 Hz, 1H), 7.23 (d, J=16.4 Hz, 1H), 7.05 (d, J=8.3 Hz, 2H), 6.69 (d, J=8.2 Hz, 2H), 4.77 (dd, J=9.2, 5.7 Hz, 1H), 3.69 (d, J=0.5 Hz, 1H), 3.17 (dd, J=13.9, 5.7 Hz, 1H), 3.01 (dd, J=13.9, 9.3 Hz, 1H). $^{13}$C NMR (101 MHz, CD$_3$OD) δ 173.78, 169.59, 157.39, 150.39, 147.02, 140.97, 134.97, 134.07, 131.22, 129.01, 128.66, 128.21, 122.71, 116.27, 56.20, 52.75, 37.40. HRMS: calculated for C$_{24}$H$_{23}$N$_2$O$_4$ [M+H$^+$]: 403.1652; Found: 403.1635.

Example 50: Synthesis of TZ-20-79

E)-4-(2-(Pyridin-4-yl)vinyl)benzoic acid 150 mg (0.66 mmol) was added to SOCl$_2$ (15 mL) stirring 24 hours at room temperature under nitrogen. After removing SOCl$_2$ under vacuum, added 10 mL DMF and then TEA (1.0 mL), fluoroethylamine hydrochloride 131 mg (1.32 mmol) in 5 mL DMF was added dropwise at −10° C. The reaction was allowed to warm to room temperature for 3 hours. After removing solvent under vacuum, added 20 mL DCM and filtered. The filtrate was washed with sat. Na$_2$CO$_3$, dried and concentrated. The desired compound was obtained via chromatography (EA) in white solid with 80% yield. $^1$H NMR (400 MHz, CDCl$_3$) δ 8.53 (d, J=5.5 Hz, 2H), 7.75 (d, J=8.3 Hz, 2H), 7.54 (d, J=8.3 Hz, 2H), 7.31 (d, J=6.0 Hz, 2H), 7.21 (d, J=12.0 Hz, 1H), 7.03 (d, J=16.3 Hz, 1H), 6.55 (brs, 1H), 4.56 (dt, J=47.4, 4.7 Hz, 2H), 3.73 (ddd, J=28.4, 10.2, 5.1 Hz, 2H). $^{13}$C NMR (101 MHz, CDCl$_3$) δ 166.95, 150.29, 143.99, 139.37, 133.80, 131.84, 128.04, 127.55, 127.08, 120.93, 82.82 (d, J=66.4 Hz), 40.45 (d, J=19.4 Hz). HRMS: calculated for C$_{16}$H$_{16}$F N$_2$O [M+H$^+$]: 271.1241; Found: 271.1230.

Example 51: Synthesis of TZ-20-81

(E)-4-(2-(Pyridin-4-yl)vinyl)benzoic acid 150 mg (0.66 mmol) was added to SOCl$_2$ (15 mL) stirring 24 hours at room temperature under nitrogen. After removing SOCl$_2$ under vacuum, added 10 mL DMF and then TEA (1.0 mL), 2-methoxyaniline 122 mg (0.11 mL, 0.99 mmol) in 5 mL DMF was added dropwise at −10° C. The reaction was allowed to warm to room temperature for 3 hours. After removing solvent under vacuum, added 20 mL DCM and filtered. The filtrate was washed with sat. Na$_2$CO$_3$, dried and concentrated. The desired compound was obtained via chromatography (EA) in faint yellow solid with 70% yield. $^1$H NMR (400 MHz, CDCl$_3$) δ 8.61-8.52 (m, 4H), 7.91 (d, J=8.3 Hz, 2H), 7.64 (d, J=8.2 Hz, 2H), 7.38 (d, J=5.8 Hz, 2H), 7.32 (d, J=16.3 Hz, 1H), 7.12-7.07 (overlap, 2H), 7.02 (t, J=7.2 Hz, 1H), 6.93 (d, J=8.0 Hz, 1H), 3.93 (s, 3H). $^{13}$C NMR (101 MHz, CDCl$_3$) δ 164.51, 150.21, 148.08, 144.06, 139.36, 135.00, 131.92, 128.04, 127.64, 127.61, 127.21, 123.97, 121.20, 120.98, 119.82, 109.91, 55.81. HRMS: calculated for C$_{21}$H$_{19}$N$_2$O$_2$ [M+H$^+$]: 331.1441; Found: 331.1427.

Example 52: Synthesis of TZ-20-83

(E)-4-(2-(Pyridin-4-yl)vinyl)benzoic acid 150 mg (0.66 mmol) was added to SOCl$_2$ (15 mL) stirring 24 hours at room temperature under nitrogen. After removing SOCl$_2$ under vacuum, added 10 mL DMF and then TEA (1.0 mL), 4-methoxyaniline 122 mg (0.11 mL, 0.99 mmol) in 5 mL DMF was added dropwise at −10° C. The reaction was allowed to warm to room temperature for 3 hours. After removing solvent under vacuum, added 20 mL DCM and filtered. The filtrate was washed with sat. Na$_2$CO$_3$, dried and concentrated. The desired compound was obtained via chromatography (EA) in faint yellow solid with 50% yield. $^1$H NMR (400 MHz, DMSO-d$_6$) δ 10.17 (s, 1H), 8.58 (d, J=5.9 Hz, 2H), 8.00 (d, J=8.3 Hz, 2H), 7.80 (d, J=8.3 Hz, 2H), 7.69-7.61 (m, 5H), 7.41 (d, J=16.5 Hz, 1H), 6.94 (d, J=9.0 Hz, 2H), 3.75 (s, 3H). $^{13}$C NMR (101 MHz, DMSO-d$_6$) δ 164.96, 156.00, 150.26, 144.66, 139.44, 135.01, 132.69, 132.53, 128.53, 128.18, 127.38, 122.47, 121.53, 114.16, 55.60. FIRMS: calculated for C$_{21}$H$_{19}$N$_2$O$_2$ [M+H$^+$]: 331.1441; Found: 331.1428.

Example 53: Synthesis of TZ-20-87

SnCl$_2$ 3.3 g (18 mmol) was added to a solution of (E)-4-(4-nitrostyryl)pyridine 420 mg (1.8 mmol) in HCl (20 mL), refluxed for 2 h, cooled to r.t., and the precipitate was filtered and dried in air. The residue was mixed with dry NaHCO$_3$, water (5 mL) was added, stirred and the precipitate filtered off. The desired compound obtained was purified by column chromatography (hex:MeOH=4:1) with yellow crystal in 80 yield. $^1$H NMR (400 MHz, DMSO-d$_6$) δ 8.48-8.43 (m, 2H), 7.46-7.41 (overlap, 2H), 7.38-7.30 (overlap, 3H), 6.86 (d, J=16.4 Hz, 1H), 6.57 (d, J=8.5 Hz, 2H), 5.49 (s, 2H). $^{13}$C NMR (101 MHz, DMSO-d$_6$) δ 150.22, 150.21, 145.67, 134.17, 128.92, 124.02, 120.59, 120.21, 114.18.

Example 54: Synthesis of TZ-20-93

A solution of 4-(2-(pyridin-4-yl)ethyl)aniline (520 mg, 2.65 mmol) and formic acid (0.1 mL, 2.75 mmol) was stirred at 85° C. overnight. The reaction mixture was dispersed between DCM and saturated aqueous sodium bicarbonate and the organic layer was separated, washed with brine, dried over anhydrous sodium sulfate, filtered and concentrated under vacuum. The residue was purified by flash column chromatography (hexane/EtOAc=1-4:1) to yield the title compound as a white solid in 70% yield. $^1$H NMR (400 MHz, DMSO-d$_6$) δ 10.34 (s, 1H), 8.52 (d, J=5.8 Hz, 2H), 8.31 (d, J=1.6 Hz, 1H), 7.63 (pseudo q, 4H), 7.55-7.51 (m, 2H), 7.48 (d, J=16.8 Hz, 1H), 7.15 (d, J=16.5 Hz, 1H).

Example 55: Synthesis of TZ-20-95

Lithium aluminum hydride (LAH) (40 mg, 1.08 mmol) was added dropwise at 0° C. with stirring to a solution of TZ-20-93 (80 mg, 0.36 mmol) in THF (10 mL). The reaction mixture was gradually warmed to room temperature, and was stirred at room temperature overnight. The resulting mixture was quenched by the addition of saturated ammonium chloride solution. The mixture was then extracted with EA. The combined organic extracts were washed with water then brine, dried over anhydrous sodium sulfate, filtered and concentrated under vacuum. The residue was purified by flash column chromatography to yield the title compound as a white solid in 40% yield. $^1$H NMR (400 MHz, DMSO-d$_6$) δ 8.45 (d, J=5.6 Hz, 2H), 7.45 (d, J=5.8 Hz, 2H), 7.39 (overlap, 3H), 6.88 (d, J=16.4 Hz, 1H), 6.55 (d, J=8.5 Hz, 2H), 6.09 (s, 1H), 2.71 (s, 3H). $^{13}$C NMR (101 MHz, DMSO-d$_6$) δ 151.02, 150.04, 145.85, 134.30, 128.94, 123.85, 120.61, 120.15, 112.00, 29.88. HRMS: calculated for C$_{14}$H$_{15}$N$_2$[M+H$^+$]: 211.1230; Found: 211.1240.

Example 56: Synthesis of TZ-20-101

A solution of 4-(2-(pyridin-4-yl)ethyl)aniline (520 mg, 2.65 mmol) and formic acid (0.1 mL, 2.75 mmol) was stirred at 85° C. overnight. The reaction mixture was dispersed between DCM and saturated aqueous sodium bicarbonate and the organic layer was separated, washed with brine, dried over anhydrous sodium sulfate, filtered and concentrated under vacuum. The residue was purified by flash column chromatography (hexane/EtOAc=1-4:1) to yield the title compound as a white solid in 70% yield. $^1$H NMR (400 MHz, DMSO-d$_6$) δ 8.14-7.46 (m, 17H), 7.11 (d, J=6.4 Hz, 2H), 5.28 (d, J=16.3 Hz, 2H), 3.82 (s, 3H).

Example 57: Synthesis of TZ-20-105

A solution of 4-pridinecarboxaldehyde 1.0 g (0.89 mL, 9.43 mmol) and (formylmethylene)triphenylphosphorane in anhydrous toluene 60 mL was heated at 80° C. for 20 h under nitrogen. The mixture was cooled to ambient temperature and evaporated under vacuum. The residue was extracted with ice-cooled diethyl ether, triphenylphosphine oxide remains behind. The ethereal was evaporated to dryness, the residue dissolved in DCM and extracted with 1 M aqueous hydrochloric acid. The acid layer was dried, evaporated to dryness and purified by column chromatography (EA:HEX=1:1 to 3:1) to yield the title compound as a white solid in 80% yield. $^1$H NMR (400 MHz, CDCl$_3$) δ 9.78 (d, J=7.5 Hz, 1H), 8.72 (dd, J=4.5, 1.6 Hz, 2H), 7.47-7.37 (m, overlap, 3H), 6.84 (dd, J=16.1, 7.5 Hz, 1H). $^{13}$C NMR (101 MHz, CDCl$_3$) δ 192.94, 150.74, 148.97, 140.97, 131.96, 121.83.

Example 58: Synthesis of TZ-20-111

To the mixture of TZ-20-101 384 mg (0.77 mmol) and THF (5 mL) cooled to −35° C., n-BuLi (0.38 mL, 0.62 mmol) was added dropwise and stirred for 1 h under nitrogen, then cooled to −78° C. A solution of (E)-3-(pyridin-4-yl)acrylaldehyde in THF (5 mL) was added dropwise and stirred for 10 min. the reaction was allowed to warm to ambient temperature for 24 h. 5 mL water and 10 mL diethyl ether was added to quench the reaction and washed with brine, dried over anhydrous sodium sulfate, filtered and concentrated under vacuum. The residue was purified by flash column chromatography (hexane/EtOAc=3-9:1) to yield the title compound as a white solid in 40% yield. $^1$H NMR (400 MHz, CDCl$_3$) δ 8.56 (d, J=4.8 Hz, 2H), 8.01 (d, J=8.2 Hz, 2H), 7.51 (d, J=8.2 Hz, 2H), 7.29 (d, J=4.8 Hz, 2H), 7.13 (dd, J=15.1, 10.6 Hz, 1H), 7.05 (dd, J=14.9, 10.7 Hz, 1H), 6.79 (d, J=15.2 Hz, 1H), 6.64 (d, J=15.0 Hz, 1H), 3.92 (s, 3H). $^{13}$C NMR (101 MHz, CDCl$_3$) δ 166.70, 150.21, 144.17, 141.08, 134.38, 132.97, 131.33, 130.52, 130.02, 129.39, 126.46, 120.68, 52.12. HRMS: calculated for C$_{17}$H$_{16}$NO$_2$[M+H$^+$]: 266.1176; Found: 260.1166.

Example 59: Synthesis of TZ-22-1-2

2-methylpyrazine (0.18 mL, 2.0 mmol), 4-methoxybenzaldehyde (0.24 mL, 2.0 mmol) and 50% solution of tetrabutylammoniumsulfate in water (0.23 mL, 0.2 mmol) were added to 2 mL 5N NaOH stirring under nitrogen. The reaction was carried on at 105° C. for 48 h. After cooling to r.t., the mixture was extracted with DCM (3×20 mL), and then the oil phase was washed with water and brine, dried over Na$_2$SO$_4$, concentrated via vacuum. The desired compound was obtained via silica gel chromatograph (EA:hexane=1:2). Faint yellow solid in 43% yield. M.p.: 101.4-102.3° C. $^1$H NMR (400 MHz, CDCl$_3$) δ 8.61 (d, J=1.0 Hz, 1H), 8.51 (s, 1H), 8.37 (d, J=2.3 Hz, 1H), 7.70 (d, J=16.1 Hz, 1H), 7.54 (d, J=8.7 Hz, 2H), 7.02 (d, J=16.1 Hz, 1H), 6.93 (d, J=8.7 Hz, 2H), 3.85 (s, 3H). $^{13}$C NMR (101 MHz, CDCl$_3$) δ 160.32, 151.60, 144.21, 143.54, 142.26, 134.70, 128.78, 128.72, 121.74, 114.25, 55.33. Anal. Calcd for C$_{13}$H$_{12}$N$_2$O: C, 73.56; H, 5.70; N, 13.20. Found: C, 73.12; H, 5.79; N, 12.30.

Example 60: Synthesis of TZ-22-15-1

Synthesis was performed in a similar fashion as described in Example 59. Faint yellow solid in 81% yield. M.p.: 55.8-56.8° C. $^1$H NMR (400 MHz, CDCl$_3$) δ 8.67 (s, 1H), 8.54 (s, 1H), 8.38 (s, 1H), 8.06 (d, J=16.2 Hz, 1H), 7.63 (d, J=7.6 Hz, 1H), 7.32 (t, J=7.7 Hz, 1H), 7.24 (d, J=17.0 Hz, 2H), 7.00 (t, J=7.5 Hz, 1H), 6.94 (d, J=8.2 Hz, 1H), 3.92 (s, 3H). $^{13}$C NMR (101 MHz, CDCl$_3$) δ 157.74, 151.83, 144.24, 143.65, 142.35, 130.36, 130.06, 127.69, 124.75, 120.71, 111.00, 109.82, 55.46. Anal. Calcd for C$_{13}$H$_{12}$N$_2$O: C, 73.56; H, 5.70; N, 13.20. Found: C, 73.26; H, 5.61; N, 12.99.

Example 61: Synthesis of TZ-22-49-1

Synthesis was performed in a similar fashion as described in Example 59. Colorless oil in 6% yield. $^1$H NMR (400 MHz, CDCl$_3$) δ 8.65 (s, 1H), 8.55 (s, 1H), 8.41 (d, J=2.1 Hz, 1H), 7.72 (d, J=16.1 Hz, 1H), 7.32 (t, J=7.9 Hz, 1H), 7.17 (m, 3H), 6.90 (d, J=6.7 Hz, 1H), 3.86 (s, 3H). $^{13}$C NMR (101 MHz, CDCl$_3$) δ 159.88, 151.21, 144.32, 143.75, 142.78, 137.39, 135.05, 129.79, 124.29, 119.99, 114.76, 112.31, 55.27. Anal. Calcd for C$_{13}$H$_{12}$N$_2$O: C, 73.56; H, 5.70; N, 13.20. Found: C, 73.26; H, 5.61; N, 12.99.

Example 62: Synthesis of TZ-22-19-1

Synthesis was performed in a similar fashion as described in Example 59. Faint yellow solid in 53% yield. M.p.: 102.2-102.6° C. $^1$H NMR (400 MHz, CDCl$_3$) δ 9.13 (s, 1H), 8.64 (d, J=5.3 Hz, 1H), 7.84 (d, J=15.9 Hz, 1H), 7.56 (d, J=8.5 Hz, 2H), 7.28 (d, J=5.4 Hz, 1H), 6.98-6.84 (m, 3H), 3.85 (s, 3H). $^{13}$C NMR (101 MHz, CDCl$_3$) δ 162.53, 158.79, 157.15, 137.08, 129.20, 128.24, 124.90, 123.15, 118.36, 114.32, 55.35. Anal. Calcd for C$_{13}$H$_{12}$N$_2$O: C, 73.56; H, 5.70; N, 13.20. Found: C, 73.43; H, 5.63; N, 13.20.

Example 63: Synthesis of TZ-22-21-1

Synthesis was performed in a similar fashion as described in Example 59. Faint yellow solid in 47% yield. M.p.: 78.3-78.9° C. $^1$H NMR (400 MHz, CDCl$_3$) δ 9.16 (s, 1H), 8.64 (d, J=5.3 Hz, 1H), 8.19 (d, J=16.2 Hz, 1H), 7.62 (d, J=7.6 Hz, 1H), 7.39-7.28 (m, 2H), 7.14 (d, J=16.2 Hz, 1H), 6.99 (t, J=7.5 Hz, 1H), 6.94 (d, J=8.3 Hz, 1H), 3.92 (s, 4H). $^{13}$C NMR (101 MHz, CDCl$_3$) δ 162.93, 158.86, 157.92, 157.08, 132.72, 130.66, 128.02, 126.14, 124.46, 120.75, 118.34, 111.05, 55.46. Anal. Calcd for C$_{13}$H$_{12}$N$_2$O: C, 73.56; H, 5.70; N, 13.20. Found: C, 73.46; H, 5.65; N, 13.16.

Example 64: Synthesis of TZ-22-23-1

Synthesis was performed in a similar fashion as described in Example 59. Faint yellow solid in 22% yield. M.p.: 123.9-124.7° C. $^1$H NMR (400 MHz, CDCl$_3$) δ 9.03 (d, J=4.5 Hz, 1H), 7.65 (d, J=16.5 Hz, 1H), 7.60 (d, J=8.6 Hz, 1H), 7.56 (d, J=8.3 Hz, 2H), 7.42 (dd, J=8.0, 4.7 Hz, 1H), 7.22 (d, J=16.4 Hz, 1H), 6.94 (d, J=8.2 Hz, 2H), 3.85 (s, 3H). $^{13}$C NMR (101 MHz, CDCl$_3$) δ 160.36, 158.51, 149.37, 134.69, 128.75, 128.64, 126.34, 123.66, 122.83, 114.27, 55.36. Anal. Calcd for C$_{13}$H$_{12}$N$_2$O: C, 73.56; H, 5.70; N, 13.20. Found: C, 73.12; H, 5.79; N, 12.30.

Example 65: Synthesis of TZ-22-25-1

Synthesis was performed in a similar fashion as described in Example 59. Faint yellow solid in 65% yield. M.p.: 98.7-99.4° C. $^1$H NMR (400 MHz, CDCl$_3$) δ 9.02 (d, J=4.6 Hz, 1H), 7.97 (d, J=16.7 Hz, 1H), 7.70 (d, J=8.6 Hz, 1H), 7.66 (d, J=7.6 Hz, 1H), 7.43 (overlap, 2H), 7.32 (t, J=7.8 Hz, 1H), 7.00 (t, J=7.5 Hz, 1H), 6.93 (d, J=8.3 Hz, 1H), 3.90 (s, 3H). $^{13}$C NMR (101 MHz, CDCl$_3$) δ 158.92, 157.49, 149.49, 130.19, 130.18, 127.47, 126.31, 125.73, 124.83, 123.60, 120.80, 110.98, 55.46. Anal. Calcd for C$_{13}$H$_{12}$N$_2$O: C, 73.56; H, 5.70; N, 13.20. Found: C, 73.12; H, 5.79; N, 12.30.

Example 66: Synthesis of TZ-22-31-1

Synthesis was performed in a similar fashion as described in Example 59. Faint yellow solid in 56% yield. M.p.: 98.5-99.7° C. $^1$H NMR (400 MHz, CDCl$_3$) δ 8.70 (d, J=4.6 Hz, 2H), 7.94 (d, J=15.9 Hz, 1H), 7.58 (d, J=8.2 Hz, 2H), 7.09 (overlap, 2H), 6.93 (d, J=8.2 Hz, 2H), 3.85 (s, 3H). $^{13}$C NMR (101 MHz, CDCl$_3$) δ 165.16, 160.45, 157.01, 137.69, 129.10, 125.07, 118.16, 114.22, 55.33. Anal. Calcd for C$_{13}$H$_{12}$N$_2$O: C, 73.56; H, 5.70; N, 13.20. Found: C, 73.46; H, 5.65; N, 13.16.

Example 67: Synthesis of TZ-22-33-1

Synthesis was performed in a similar fashion as described in Example 59. Faint yellow solid in 55% yield. M.p.: 68.2-69.0° C. $^1$H NMR (400 MHz, CDCl$_3$) δ 8.72 (d, J=4.8 Hz, 2H), 8.32 (d, J=16.2 Hz, 1H), 7.66 (d, J=7.6 Hz, 1H), 7.39-7.28 (m, 2H), 7.08 (t, J=4.8 Hz, 1H), 6.99 (t, J=7.5 Hz, 1H), 6.93 (d, J=8.3 Hz, 1H), 3.92 (s, 3H). $^{13}$C NMR (101 MHz, CDCl$_3$) δ 165.39, 157.91, 156.99, 133.38, 130.22, 128.12, 127.92, 124.89, 120.66, 118.24, 110.95, 55.41. Anal. Calcd for C$_{13}$H$_{12}$N$_2$O: C, 73.56; H, 5.70; N, 13.20. Found: C, 73.46; H, 5.65; N, 13.16.

Example 68: Synthesis of TZ-22-35-1

Synthesis was performed in a similar fashion as described in Example 59. Faint yellow solid in 60% yield. M.p.: 115.2-117.0° C. $^1$H NMR (400 MHz, CDCl$_3$) δ 8.58 (s, 1H), 8.47 (s, 1H), 8.31 (d, J=2.0 Hz, 1H), 7.67 (d, J=16.0 Hz, 1H), 7.49 (d, J=8.6 Hz, 2H), 6.94 (d, J=16.0 Hz, 1H), 6.71 (d, J=8.6 Hz, 2H), 3.01 (s, 6H). $^{13}$C NMR (101 MHz, CDCl$_3$) δ 152.23, 150.89, 144.10, 143.34, 141.52, 135.38, 128.67, 124.09, 119.19, 112.07, 40.24.

Example 69: Synthesis of TZ-22-37-1

Synthesis was performed in a similar fashion as described in Example 59. Faint yellow oil in 50% yield. $^1$H NMR (400 MHz, CDCl$_3$) δ 8.62 (s, 1H), 8.51 (s, 1H), 8.36 (d, J=2.2 Hz, 1H), 7.67 (d, J=16.1 Hz, 1H), 7.14 (overlap, 2H), 7.02 (d, J=16.1 Hz, 1H), 6.88 (d, J=8.5 Hz, 1H), 3.94 (s, 3H), 3.91 (s, 3H). $^{13}$C NMR (101 MHz, CDCl$_3$) δ 151.55, 150.01, 149.12, 144.25, 143.40, 142.22, 135.02, 129.00, 121.92, 121.32, 111.08, 109.04, 55.92, 55.85.

Example 70: Synthesis of TZ-22-43-1

Synthesis was performed in a similar fashion as described in Example 59. Faint yellow solid in 50% yield. M.p.: 111.2-112.6° C. $^1$H NMR (400 MHz, CDCl$_3$) δ 8.63 (s, 1H), 8.54 (s, 1H), 8.42 (d, J=2.1 Hz, 1H), 7.69 (d, J=16.1 Hz, 1H), 7.52 (d, J=8.4 Hz, 2H), 7.46 (d, J=8.4 Hz, 2H), 7.14 (d, J=16.1 Hz, 1H). $^{13}$C NMR (101 MHz, CDCl$_3$) δ 150.84, 144.38, 143.83, 142.99, 134.93, 133.81, 131.99, 128.70, 124.59, 122.92.

Example 71: Synthesis of TZ-22-47-1

Synthesis was performed in a similar fashion as described in Example 59. Faint yellow solid in 50% yield. M.p.: 111.2-112.6° C. 1H NMR (400 MHz, CDCl3) δ 8.63 (s, 1H), 8.54 (s, 1H), 8.42 (d, J=2.1 Hz, 1H), 7.69 (d, J=16.1 Hz, 1H), 7.52 (d, J=8.4 Hz, 2H), 7.46 (d, J=8.4 Hz, 2H), 7.14 (d, J=16.1 Hz, 1H). 13C NMR (101 MHz, CDCl3) δ 150.84, 144.38, 143.83, 142.99, 134.93, 133.81, 131.99, 128.70, 124.59, 122.92.

Example 72: Synthesis of TZ-34-24

Under an ice-bath, sodium methoxide (54 mg, 1 mmol) was added to a diethyl (4-methoxybenzyl)phosphonate (129 mg, 0.5 mmol) solution in anhydrous THF (2 mL). The mixture was stirred at 0° C. for 30 minutes. Then 2-furaldehyde (96 mg, 1 mmol) in anhydrous THF (1 mL) was syringed by drops. After injection, the ice-bath was removed; the reaction was stirred at room temperature for overnight. The solvent was evaporated in vacuum and the residue was purified by silica gel flash column chromatography (hexane/ethyl acetate=40/1, v/v) to afford compound TZ-34-24 as a yellow solid, 72% yield; 1H NMR (400 MHz, CDCl$_3$) δ 7.30 (d, J=8.4 Hz, 2H), 7.29 (d, J=9.2 Hz, 1H), 6.90 (d, J=16.4 Hz, 1H), 6.79 (d, J=8.4 Hz, 2H), 6.67 (d, J=16.0 Hz, 1H), 6.31 (dd, J=3.2 Hz, 2.0 Hz, 1H), 6.20 (d, J=3.2 Hz, 1H), 3.71 (s, 3H); 13C NMR (100.6 MHz, CDCl$_3$) δ 159.3, 153.6, 141.7, 129.8, 127.6, 126.8, 114.6, 114.2, 111.6, 107.7, 55.3.

Example 73: Synthesis of TZ-34-27

Synthesis was performed in a similar fashion as described in Example 72. It was obtained as yellow solid, 84% yield. 1H NMR (400 MHz, CDCl$_3$) δ 7.50 (s, 1H), 7.40 (d, J=4.0 Hz, 1H), 7.39 (d, J=6.8 Hz, 2H), 6.88 (d, J=8.4 Hz, 2H), 6.81 (d, J=16.0 Hz, 1H), 6.77 (d, J=16.4 Hz, 1H), 6.65 (d, J=1.6 Hz, 1H), 3.81 (s, 3H); 13C NMR (100.6 MHz, CDCl$_3$) δ 159.1, 143.6, 140.5, 130.2, 128.0, 127.3, 124.7, 116.3, 114.1, 107.4, 55.3.

Example 74: Synthesis of TZ-34-26

Synthesis was performed in a similar fashion as described in Example 72. It was obtained as light yellow solid, 57% yield. 1H NMR (400 MHz, CDCl$_3$) δ 7.41 (d, J=8.8 Hz, 2H), 7.17 (d, J=4.4 Hz, 1H), 7.12 (d, J=16.0 Hz, 1H), 7.04 (d, J=5.2 Hz, 1H), 7.00 (dd, J=5.2 Hz, 3.6 Hz, 1H), 6.91 (d, J=16.0 Hz, 1H), 6.90 (d, J=8.4 Hz, 2H), 3.82 (s, 3H); 13C NMR (100.6 MHz, CDCl$_3$) δ 159.3, 143.3, 129.8, 128.0, 127.6, 127.5, 125.4, 123.7, 119.8, 114.2, 55.3.

Example 75: Synthesis of TZ-34-28

Synthesis was performed in a similar fashion as described in Example 72. It was obtained as light yellow solid, yellow solid, 71% yield. 1H NMR (400 MHz, CDCl$_3$) δ 7.41 (d, J=8.8 Hz, 2H), 7.33 (d, J=5.2 Hz, 1H), 7.30 (d, J=4.8 Hz, 1H), 7.21 (s, 1H), 7.99 (dd, J=16.4 Hz, 1H), 6.91 (d, J=16.8 Hz, 1H), 6.89 (d, J=8.8 Hz, 2H), 3.82 (s, 3H); 13C NMR (100.6 MHz, CDCl$_3$) δ 159.2, 140.4, 130.5, 128.2, 127.5, 126.0, 124.9, 121.5, 120.9, 114.1, 55.3.

Example 76: Synthesis of TZ-23-82

In a solution of 4-(methoxymethoxy)aniline (408 mg, 2.66 mmol), BOPCl (1.13 g, 4.44 mmol) and triethylamine (1 mL) in DCM (40 mL), (E)-4-(2-(pyridin-4-yl)vinyl)benzoic acid (400 mg, 1.78 mmol) was added. The reaction mixture was stirred overnight at room temperature. The reaction mixture was washed with saturated aqueous Na$_2$CO$_3$ and brine. The organic phase was dried over Na$_2$SO$_4$ and concentrated under vacuum. The crude product was purified by column chromatography with DCM/MeOH (15:1, v/v) to afford TZ-23-82 as a yellow solid (448 mg, 70%). 1H-NMR (400 MHz, DMSO-d$_6$): δ 10.19 (s, 1H), 8.56 (m, 2H), 8.00 (d, J=8.0 Hz, 2H), 7.80 (d, J=8.4 Hz, 2H), 7.68-7.59 (m, 5H), 7.40 (d, J=16.5 Hz, 1H), 7.02 (m, 2H), 5.10 (s, 2H), 3.30 (s, 3H).

Example 78: Synthesis of TZ-23-86

TFA (0.5 mL) was added into a solution of TZ-23-82 (0.1 mmol) in DCM column at 0° C. The mixture was allowed to reach room temperature and was further stirred for 24 h. The solvent was evaporated, and crude compound was taken up in a saturated aq. NaHCO$_3$ solution and extracted by DCM. The organic layers were combined and dried over Na$_2$SO4, filtered, and the solvent was evaporated to dryness. The residue was purified by chromatograph using DCM/MeOH (15:1, v/v) to give the desired compound as yellow solid (268 mg, 85%). 1H-NMR (400 MHz, DMSO-d$_6$): δ 10.05 (s, 1H), 9.29 (s, 1H), 8.57 (m, 2H), 7.97 (m, 2H), 7.78 (m, 2H), 7.64-7.52 (m, 5H), 7.40 (d, J=16.5 Hz, 1H), 6.75 (m, 2H).

Example 79: Synthesis of TZ-23-88

To a solution of TZ-23-86 (30 mg, 0.94 mmol) and 2-fluoroethyl 4-methylbenzenesulfonate (41.39 mg, 0.18 mmol) in acetonitrile (20 mL), Cs$_2$CO$_3$ (61.79 g, 0.18 mmol) was added. The mixture was stirred at 80° C. overnight. To the cooled reaction, saturated NH$_4$Cl solution was then added. The reaction mixture was extracted with DCM. The organic phase was washed with brine, dried over Na$_2$SO$_4$, and evaporated to dryness. The residue was purified by chromatograph using DCM/MeOH (15:1, v/v) to give the desired compound as a yellow solid (25 mg, 70%). 1H NMR (400 MHz, DMSO-d$_6$) δ 9.89 (s, 1H), 8.28 (d, J=4.5 Hz, 2H), 7.70 (d, J=7.5 Hz, 2H), 7.51 (d, J=7.6 Hz, 2H), 7.44-7.26 (m, 5H), 7.12 (d, J=16.5 Hz, 1H), 6.67 (d, J=8.1 Hz, 2H), 4.50 (d, J=2.8 Hz, 1H), 4.38 (d, J=2.6 Hz, 1H), 3.95 (d, J=2.6 Hz, 1H), 3.88 (s, 1H).

Example 80: Synthesis of TZ-23-92

Synthesis was performed in a similar fashion as described in Example 79. It was obtained as a yellow solid (24 mg, 65%). 1H NMR (400 MHz, DMSO-d$_6$) δ 10.18 (s, 1H), 8.57 (d, J=5.6 Hz, 2H), 8.00 (d, J=8 Hz, 2H), 7.80 (d, J=8.4 Hz, 2H), 7.69-7.59 (m, 5H), 7.40 (d, J=16.5 Hz, 1H), 6.95 (d, J=8.8 Hz, 2H), 4.67 (t, 1H), 4.55 (t, 1H), 4.05 (m, 2H), 2.15-2.05 (m, 2H).

Example 81: Synthesis of TZ-36-20

A solution of 2-methyl-6-nitroquinoline (200 mg, 1.06 mmol), p-toluenesulfonamide (182 mg, 1.06 mmol) and pyrazine-2-carbaldehyde (114 mg, 1.06 mmol) in toluene (4 mL) was refluxed at 120° C. for 12 h in a reaction tube under N$_2$. After the mixture was cooled to room temperature, the solvent was removed under reduced pressure. Then the concentrate was purified by column chromatography with EtOAc/Hexane (1:4, v/v) on silica gel, affording TZ36-20 as a yellow solid (182 mg, 62%). $^1$H NMR (400 MHz, DMSO-d$_6$) δ 8.98 (d, J=21.2 Hz, 2H), 8.70 (d, J=7.5 Hz, 1H), 8.58 (s, 1H), 8.43 (d, J=9.0 Hz, 1H), 8.06 (ddd, J=44.2, 30.4, 12.5 Hz, 2H).

Example 82: Synthesis of TZ-36-22

A solution of 6-fluoro-2-methylquinoline (200 mg, 1.24 mmol), p-toluenesulfonamide (212 mg, 1.24 mmol) and pyrazine-2-carbaldehyde (134 mg, 1.24 mmol) in toluene (4 mL) was refluxed at 120° C. for 12 h in a reaction tube under N$_2$. After the mixture was cooled to room temperature, the solvent was removed under reduced pressure. Then the concentrate was purified by column chromatography with EtOAc/Hexane (1:4, v/v) on silica gel, affording TZ-36-22 as a light yellow solid (211 mg, 68%). $^1$H NMR (400 MHz, DMSO-d$_6$) δ 8.93 (d, J=1.4 Hz, 1H), 8.67 (dd, J=2.4, 1.5 Hz, 1H), 8.55 (d, J=2.5 Hz, 1H), 8.38 (d, J=8.6 Hz, 1H), 8.07 (dd, J=9.3, 5.5 Hz, 1H), 7.93 (dd, J=15.5, 6.2 Hz, 3H), 7.77 (dd, J=9.4, 2.9 Hz, 1H), 7.66 (td, J=8.9, 2.9 Hz, 1H).

Example 83: Synthesis of TZ-36-24

A solution of 6-bromo-2-methylquinoline (200 mg, 0.9 mmol), p-toluenesulfonamide (154 mg, 0.9 mmol) and pyrazine-2-carbaldehyde (98 mg, 0.9 mmol) in toluene (4 mL) was refluxed at 120° C. for 12 h in a reaction tube under N$_2$. After the mixture was cooled to room temperature, the solvent was removed under reduced pressure. Then the concentrate was purified by column chromatography with EtOAc/Hexane (1:4, v/v) on silica gel, affording TZ-36-24 as a yellow solid (168 mg, 60%). $^1$H NMR (400 MHz, DMSO-d$_6$) δ 8.93 (d, J=1.4 Hz, 1H), 8.67 (dd, J=2.4, 1.5 Hz, 1H), 8.56 (d, J=2.4 Hz, 1H), 8.36 (d, J=8.6 Hz, 1H), 8.24 (d, J=2.2 Hz, 1H), 7.98-7.90 (m, 4H), 7.85 (dd, J=9.0, 2.3 Hz, 1H).

Example 84: Synthesis of TZ-36-28-2T

A solution of 6-methoxy-2-methylquinoline (200 mg, 1.15 mmol), p-toluenesulfonamide (197 mg, 1.15 mmol) and 2-methoxyisonicotinaldehyde (158 mg, 1.15 mmol) in toluene (5 mL) was refluxed at 120° C. for 12 h in a reaction tube under N$_2$. After the mixture was cooled to room temperature, the solvent was removed under reduced pressure. Then the concentrate was purified by column chromatography with EtOAc/Hexane (1:4, v/v) on silica gel, affording TZ36-28-2T as a white solid (239 mg, 71%). $^1$H NMR (400 MHz, CDCl$_3$) δ 8.15 (dd, J=5.4, 2.4 Hz, 1H), 8.12-7.98 (m, 2H), 7.63 (t, J=8.0 Hz, 1H), 7.57-7.45 (m, 2H), 7.42-7.34 (m, 1H), 7.09 (ddd, J=18.5, 4.9, 2.1 Hz, 2H), 6.86 (s, 1H), 3.94 (dd, J=8.6, 2.1 Hz, 6H).

Example 85: Synthesis of TZ-36-34

A solution of 6-methoxy-2-methylquinoline (200 mg, 1.15 mmol), p-toluenesulfonamide (197 mg, 1.15 mmol) and picolinaldehyde (124 mg, 1.15 mmol) in toluene (5 mL) was refluxed at 120° C. for 12 h in a reaction tube under $N_2$. After the mixture was cooled to room temperature, the solvent was removed under reduced pressure. Then the concentrate was purified by column chromatography with EtOAc/DCM (1:2, v/v) on silica gel, affording TZ-36-34 as a yellow solid (208 mg, 69%). $^1$H NMR (400 MHz, $CDCl_3$) δ 8.65-8.57 (m, 1H), 7.98 (dd, J=8.8, 6.2 Hz, 2H), 7.81-7.61 (m, 3H), 7.59 (d, J=8.6 Hz, 1H), 7.51 (dd, J=7.9, 0.8 Hz, 1H), 7.33 (dd, J=9.2, 2.8 Hz, 1H), 7.15 (ddd, J=7.4, 4.8, 1.1 Hz, 1H), 7.01 (d, J=2.7 Hz, 1H), 3.88 (s, 3H).

Example 86: Synthesis of TZ-34-71

Under an ice-bath, sodium methoxide (130 mg, 2.4 mmol) was added to a diethyl (thiophen-2-ylmethyl)phosphonate (562 mg, 2.4 mmol) solution in anhydrous THF (1.5 mL). The mixture was stirred for at 0° C. for 30 minutes. Then 4-(dimethylamino)benzaldehyde (120 mg, 0.8 mmol) in anhydrous THF was syringed by drops. After addition, removed the ice-bath and kept stirring overnight at room temperature. The solvent was evaporated in vacuum and the residue was purified by silica gel flash column chromatography to afford the target compound as exclusive E configuration. 20% yield, yellow solid. $^1$H NMR (400 MHz, $CD_3COCD_3$) δ 7.38 (d, J=9.2 Hz, 2H), 7.24 (d, J=5.2 Hz, 1H), 7.14 (d, J=16.0 Hz, 1H), 7.04 (d, J=3.2 Hz, 1H), 6.98 (dd, J=4.8 Hz, 3.2 Hz, 1H), 6.87 (d, J=16.4 Hz, 1H), 6.73 (d, J=8.8 Hz, 2H), 2.95 (s, 6H); $^{13}$C NMR (100.6 MHz, $CDCl_3$) δ 150.3, 143.8, 128.5, 127.5, 127.4, 127.3, 124.8, 123.1, 117.4, 112.4, 39.6.

Example 87: Synthesis of TZ-36-38

A solution of 6-methoxy-2-methylquinoline (200 mg, 1.15 mmol), p-toluenesulfonamide (197 mg, 1.15 mmol) and 6-chloronicotinaldehyde (163 mg, 1.15 mmol) in toluene (5 mL) was refluxed at 120° C. for 12 h in a reaction tube under $N_2$. After the mixture was cooled to room temperature, the solvent was removed under reduced pressure. Then the concentrate was purified by column chromatography with EtOAc/Hexane (1:4, v/v) on silica gel, affording TZ-36-38 as a yellow solid (232 mg, 68%). $^1$H NMR (400 MHz, $CDCl_3$) δ 8.56 (d, J=1.9 Hz, 1H), 8.04 (dd, J=21.0, 7.7 Hz, 2H), 7.90 (d, J=8.3 Hz, 1H), 7.59 (dd, J=8.7, 6.4 Hz, 2H), 7.49-7.30 (m, 3H), 7.06 (s, 1H), 3.99 (d, J=50.0 Hz, 3H).

Example 88: Synthesis of TZ-36-42

A solution of 6-methoxy-2-methylquinoline (200 mg, 1.15 mmol), p-toluenesulfonamide (197 mg, 1.15 mmol) and 2-chloroisonicotinaldehyde (163 mg, 1.15 mmol) in toluene (5 mL) was refluxed at 120° C. for 12 h in a reaction tube under $N_2$. After the mixture was cooled to room temperature, the solvent was removed under reduced pressure. Then the concentrate was purified by column chromatography with EtOAc/DCM (1:2, v/v) on silica gel, affording TZ-36-42 as a yellow solid (242 mg, 71%). $^1$H NMR (400 MHz, $CDCl_3$) δ 8.37 (d, J=5.2 Hz, 1H), 8.04 (dd, J=24.6, 8.9 Hz, 2H), 7.59 (d, J=8.5 Hz, 1H), 7.50 (d, J=20.6 Hz, 3H), 7.42-7.34 (m, 2H), 7.07 (d, J=2.7 Hz, 1H), 4.00 (d, J=50.8 Hz, 3H).

Example 89: Synthesis of TZ-36-46

A solution of 6-methoxy-2-methylquinoline (200 mg, 1.15 mmol), p-toluenesulfonamide (197 mg, 1.15 mmol) and 3-bromoisonicotinaldehyde (214 mg, 1.15 mmol) in toluene (5 mL) was refluxed at 120° C. for 12 h in a reaction tube under $N_2$. After the mixture was cooled to room temperature, the solvent was removed under reduced pressure. Then the concentrate was purified by column chromatography with EtOAc/DCM (1:4, v/v) on silica gel, affording TZ-36-46 as a yellow solid (247 mg, 63%). $^1$H NMR (400 MHz, $CDCl_3$) δ 8.76 (t, J=3.6 Hz, 1H), 8.52 (d, J=5.1 Hz, 1H), 8.17 (d, J=8.6 Hz, 2H), 7.89-7.60 (m, 4H), 7.43 (d, J=9.2 Hz, 1H), 7.11 (s, 1H), 3.95 (d, J=2.1 Hz, 3H).

Example 90: Synthesis of TZ-36-48

A solution of 6-methoxy-2-methylquinoline (200 mg, 1.15 mmol), p-toluenesulfonamide (197 mg, 1.15 mmol) and 3-chloroisonicotinaldehyde (163 mg, 1.15 mmol) in toluene (5 mL) was refluxed at 120° C. for 12 h in a reaction tube under $N_2$. After the mixture was cooled to room temperature, the solvent was removed under reduced pressure. Then the concentrate was purified by column chromatography with EtOAc/Hexane (1:4, v/v) on silica gel, affording TZ-36-48 as a yellow solid (255 mg, 65%). $^1$H NMR (400 MHz, $CDCl_3$) δ 8.61 (s, 1H), 8.47 (d, J=5.1 Hz, 1H), 8.07 (dd, J=16.7, 8.9 Hz, 2H), 7.87 (d, J=16.4 Hz, 1H), 7.72 (d, J=8.5 Hz, 1H), 7.65-7.54 (m, 2H), 7.39 (d, J=9.2 Hz, 1H), 7.28-7.21 (m, OH), 7.07 (s, 1H), 3.91 (d, J=13.2 Hz, 3H).

Example 91: Synthesis of TZ-36-30

A solution of 6-methoxy-2-methylquinoline (200 mg, 1.15 mmol), p-toluenesulfonamide (197 mg, 1.15 mmol) and thiophene-3-carbaldehyde (122 mg, 1.15 mmol) in toluene (5 mL) was refluxed at 140° C. for 12 h in a reaction tube under $N_2$. After the mixture was cooled to room temperature, the solvent was removed under reduced pressure. Then the concentrate was purified by column chromatography with EtOAc/DCM (1:10, v/v) on silica gel, affording TZ-36-30 as a yellow solid (212 mg, 91%). $^1$H NMR (400 MHz, DMSO-$d_6$) δ 8.19 (d, J=8.6 Hz, 1H), 7.84 (d, J=9.5 Hz, 1H), 7.76-7.67 (m, 3H), 7.62-7.53 (m, 2H), 7.31 (ddd, J=35.2, 20.7, 9.6 Hz, 3H), 3.87 (s, 3H).

Example 92: Synthesis of TZ-36-50

A solution of 6-methoxy-2-methylquinoline (200 mg, 1.15 mmol), p-toluenesulfonamide (197 mg, 1.15 mmol) and thiophene-2-carbaldehyde (122 mg, 1.15 mmol) in toluene (5 mL) was refluxed at 140° C. for 12 h in a reaction tube under $N_2$. After the mixture was cooled to room temperature, the solvent was removed under reduced pressure. Then the concentrate was purified by column chromatography with EtOAc/DCM (1:10, v/v) on silica gel, affording TZ-36-50 as a yellow solid (212 mg, 69%). $^1$H NMR (400 MHz, DMSO-$d_6$) δ 8.18 (d, J=8.6 Hz, 1H), 7.87 (dd, J=25.5, 12.6 Hz, 2H), 7.73 (d, J=8.6 Hz, 1H), 7.54 (d, J=5.0 Hz, 1H), 7.41-7.24 (m, 3H), 7.17-6.98 (m, 2H), 3.86 (s, 3H).

Example 93: Synthesis of TZ-36-52

A solution of 6-methoxy-2-methylquinoline (200 mg, 1.15 mmol), p-toluenesulfonamide (197 mg, 1.15 mmol) and furan-3-carbaldehyde (122 mg, 1.15 mmol) in toluene (0.5 mL) was refluxed at 140° C. for 12 h in a reaction tube under N₂. After the mixture was cooled to room temperature, the solvent was removed under reduced pressure. Then the concentrate was purified by column chromatography with EtOAc/DCM (1:10, v/v) on silica gel, affording TZ-36-52 as a yellow solid (203 mg, 70%). ¹H NMR (400 MHz, DMSO-d₆) δ 8.18 (d, J=8.6 Hz, 1H), 7.83 (d, J=9.1 Hz, 1H), 7.73 (dd, J=11.6, 4.9 Hz, 2H), 7.57 (d, J=16.1 Hz, 1H), 7.41-7.25 (m, 2H), 7.13 (d, J=16.2 Hz, 1H), 6.72 (d, J=3.3 Hz, 1H), 6.57 (dd, J=3.3, 1.8 Hz, 1H), 3.87 (d, J=5.3 Hz, 3H).

Example 94: Synthesis of TZ-36-14

A solution of 6-fluoro-2-methylquinoline (200 mg, 1.24 mmol), p-toluenesulfonamide (212 mg, 1.24 mmol) and isonicotinaldehyde (132 mg, 1.24 mmol) in toluene (5 mL) was refluxed at 120° C. for 12 h in a reaction tube under N₂. After the mixture was cooled to room temperature, the solvent was removed under reduced pressure. Then the concentrate was purified by column chromatography with EtOAc/DCM (1:4, v/v) on silica gel, affording TZ-36-14 as a yellow solid (201 mg, 65%). ¹H NMR (400 MHz, DMSO-d₆) δ 8.58 (d, J=5.6 Hz, 2H), 8.37 (d, J=8.6 Hz, 1H), 8.10-8.00 (m, 1H), 7.92 (d, J=8.6 Hz, 1H), 7.83-7.71 (m, 3H), 7.70-7.58 (m, 3H).

Example 95: Synthesis of TZ-36-16

A solution of 6-bromo-2-methylquinoline (200 mg, 0.9 mmol), p-toluenesulfonamide (154 mg, 0.9 mmol) and isonicotinaldehyde (97 mg, 0.9 mmol) in toluene (5 mL) was refluxed at 120° C. for 12 h in a reaction tube under N₂. After the mixture was cooled to room temperature, the solvent was removed under reduced pressure. Then the concentrate was purified by column chromatography with EtOAc/Hexane (1:4, v/v) on silica gel, affording TZ-36-16 as a yellow solid (182 mg, 65%). ¹H NMR (400 MHz, DMSO-d₆) δ 8.59 (dd, J=4.5, 1.6 Hz, 2H), 8.36 (d, J=8.6 Hz, 1H), 8.25 (d, J=2.2 Hz, 1H), 7.93 (dd, J=8.8, 2.1 Hz, 2H), 7.89-7.81 (m, 1H), 7.76 (d, J=22.1 Hz, 2H), 7.71-7.63 (m, 2H).

Example 96: Synthesis of TZ-36-40

A solution of 6-methoxy-2-methylquinoline (200 mg, 1.15 mmol), p-toluenesulfonamide (197 mg, 1.15 mmol) and 2-chloronicotinaldehyde (163 mg, 1.15 mmol) in toluene (5 mL) was refluxed at 120° C. for 12 h in a reaction tube under N₂. After the mixture was cooled to room temperature, the solvent was removed under reduced pressure. Then the concentrate was purified by column chromatography with EtOAc/DCM (1:2, v/v) on silica gel, affording TZ-36-40 as a yellow solid (246 mg, 72%). ¹H NMR (400 MHz, CDCl₃) δ 8.32 (dd, J=4.6, 1.2 Hz, 1H), 8.12-8.03 (m, 2H), 7.99 (d, J=9.2 Hz, 1H), 7.85 (d, J=16.4 Hz, 1H), 7.71 (d, J=8.6 Hz, 1H), 7.47-7.34 (m, 2H), 7.27 (dd, J=7.8, 4.7 Hz, 1H), 7.06 (d, J=2.7 Hz, 1H), 3.93 (s, 3H).

Example 97: Synthesis of TZ-36-44

197 mg, 1.15 mmol) and 2-methylnicotinaldehyde (140 mg, 1.15 mmol) in toluene (5 mL) was refluxed at 120° C. for 12 h in a reaction tube under N₂. After the mixture was cooled to room temperature, the solvent was removed under reduced pressure. Then the concentrate was purified by column chromatography with EtOAc/DCM (1:1, v/v) on silica gel, affording TZ-36-44 as a white solid (207 mg, 65%). ¹H NMR (400 MHz, CDCl₃) δ 8.43 (dd, J=4.6, 2.3 Hz, 1H), 8.12-7.89 (m, 3H), 7.80 (dd, J=16.2, 3.0 Hz, 1H), 7.62 (dd, J=8.6, 3.8 Hz, 1H), 7.43-7.13 (m, 4H), 7.06 (t, J=3.0 Hz, 1H), 3.93 (d, J=2.8 Hz, 3H), 2.74 (d, J=3.5 Hz, 3H).

Example 98: Synthesis of TZ-36-138

Compound 2-methylquinolin-6-ol (1.0 g, 6.28 mmol), 2-bromopropane (772 mg, 6.28 mmol) and K₂CO₃ (1.74 g, 12.56 mmol) was mixed in acetone (70 mL) and was refluxed for 24 h. The solvent was removed and water was added. The crude product solution was extracted with ethyl acetate. The organic extract was concentrated in vacuum. The residue was purified by silica gel column chromatography to get 6-isopropoxy-2-methylquinoline, TZ36-134 (1.0 g, 80%). 1H NMR (400 MHz, CDCl₃) δ 7.84 (dt, J=3.7, 2.1 Hz, 2H), 7.26-7.19 (m, 1H), 7.14 (dd, J=8.4, 1.8 Hz, 1H), 6.97 (d, J=2.5 Hz, 1H), 4.67-4.51 (m, 1H), 2.62 (s, 3H), 1.32 (s, 6H).

A solution of TZ36-134 (200 mg, 0.99 mmol), p-toluenesulfonamide (170 mg, 0.99 mmol) and 2-methoxyisonicotinaldehyde (137 mg, 0.99 mmol) in toluene (8 mL) was refluxed at 120° C. for 12 h in a reaction tube under N₂. After the mixture was cooled to room temperature, the solvent was removed under reduced pressure. Then the concentrate was purified by column chromatography with EtOAc/DCM (1:4, v/v) on silica gel, affording TZ36-138 as a yellow liquid (238 mg, 75%). 1H NMR (400 MHz, CDCl₃) δ 8.09 (t, J=5.6 Hz, 1H), 7.93 (dd, J=17.2, 8.6 Hz, 2H), 7.52 (dd, J=10.6, 8.6 Hz, 1H), 7.42 (d, J=10.0 Hz, 2H), 7.27 (m, 1H), 7.01 (m, 2H), 6.80 (d, J=6.0 Hz, 1H), 4.62 (dd, J=12.8, 6.2 Hz, 1H), 3.89 (s, 3H), 1.34 (s, 6H).

Example 99: Synthesis of TZ-36-142

2-methoxy-4-((trimethylsilyl)ethynyl)pyridine (1.8 g, 10.28 mmol) was dissolved in 50 mL of dry THF and TBAF.3H₂O (12.0 g, 38.03 mmol) was added at −10° C. After stirring for 2 h, water was added and aqueous layer was extracted with DCM. The organic layer was dried over Na₂SO₄ and filtered through a plug of celite. Evaporation of solvents and purification by column chromatography with EtOAc/hexane (1:9, v/v) on silica gel, affording 4-Ethynyl-2-methoxypyridine TZ-36-140 as a colorless solid (400 mg, 38%). ¹H NMR (400 MHz, cdcl₃) δ 8.01 (d, J=5.2 Hz, 1H), 6.89-6.76 (m, 1H), 6.72 (s, 1H), 3.91-3.75 (m, 3H), 3.13 (s, 1H). To a solution of 2-chloro-6-methoxyquinoline (400 mg, 2.07 mmol) in THF (30 mL) was added PdCl₂(PPh₃)₂ (72 mg, 0.11 mmol), CuI (50 mg, 0.25 mmol). The reaction mixture was stirred for 5 min and TEA (0.3 mL) and TZ36-140 (203 mg, 2.48 mmol) were added. After the resulting mixture was stirred at 80° C. for 24 h, it was allowed to cool to room temperature and filtered through a pad of celite by the aid of EtOAc. The filtrate was treated with water and extracted with EtOAc. The organic layer was washed with water and brine, dried over Na2SO4. Evaporation of solvents and purification by column chromatography with EtOAc/hexane (1:10, v/v) on silica gel, affording TZ-36-142 (390 mg, 65%). 1H NMR (400 MHz, CDCl₃) δ 8.11 (s, 1H), 7.98 (t, J=9.7 Hz, 2H), 7.51 (d, J=8.4 Hz, 1H), 7.34 (d, J=9.3 Hz, 1H), 7.01 (s, 2H), 6.91 (s, 1H), 3.89 (s, 6H).

Example 100: Synthesis of TZ-36-144

A solution of 6-(methoxymethoxy)-2-methylquinoline (600 mg, 2.95 mmol), p-toluenesulfonamide (505 mg, 2.95 mmol) and 2-methoxyisonicotinaldehyde (404 mg, 2.95 mmol) in toluene (8 mL) was refluxed at 120° C. for 12 h in a reaction tube under $N_2$. After the mixture was cooled to room temperature, the solvent was removed under reduced pressure. Then the concentrate was purified by column chromatography with EtOAc/DCM (1:2, v/v) on silica gel, affording TZ-36-144 as a white solid (808 mg, 85%). $^1$H NMR (400 MHz, CDCl$_3$) δ 8.12 (t, J=5.0 Hz, 1H), 8.04-7.91 (m, 2H), 7.57 (t, J=7.9 Hz, 1H), 7.45 (dd, J=6.1, 2.2 Hz, 2H), 7.40 (m, 1H), 7.30 (t, J=4.0 Hz, 1H), 7.11-7.03 (m, 1H), 6.83 (d, J=4.7 Hz, 1H), 5.33-5.20 (m, 2H), 3.92 (s, 3H), 3.48 (s, 3H).

Example 101: Synthesis of TZ-36-148

6-(2-fluoroethoxy)-2-methylquinoline (200 mg, 0.97 mmol) was dissolved in the presence of acetic anhydride, then added 2-methoxyisonicotinaldehyde (133 mg, 0.97 mmol), the reaction mixture was stirred at gentle reflux for 12 h. The reaction mass was subjected to simple distillation, removing the solvent, the product obtained were purified by column chromatography on silica gel with DCM:EA (10:1, v/v) to afford TZ36-148 as a yellow solid (259 mg, 82%). 1H NMR (400 MHz, CDCl$_3$) δ 8.17-8.12 (m, 2H), 7.69-7.65 (m, 1H), 7.59-7.53 (m, 2H), 7.48-7.43 (m, 1H), 7.25-7.23 (m, 1H), 7.14-7.09 (m, 2H), 6.88-6.87 (m, 1H), 4.91-4.75 (m, 2H), 4.38-4.31 (m, 2H), 3.96 (s, 3H).

Example 102: Synthesis of TZ-36-54

A solution of 6-methoxy-2-methylquinoline (200 mg, 1.15 mmol), p-toluenesulfonamide (197 mg, 1.15 mmol) and furan-3-carbaldehyde (122 mg, 1.15 mmol) in toluene (5 mL) was refluxed at 140° C. for 12 h in a reaction tube under $N_2$. After the mixture was cooled to room temperature, the solvent was removed under reduced pressure. Then the concentrate was purified by column chromatography with EtOAc/DCM (1:10, v/v) on silica gel, affording TZ-36-54 as a yellow solid (208 mg, 72%). $^1$H NMR (400 MHz, DMSO-d$_6$) δ 8.17 (d, J=8.6 Hz, 1H), 7.96 (s, 1H), 7.82 (d, J=9.1 Hz, 1H), 7.75-7.54 (m, 3H), 7.38-7.25 (m, 2H), 7.12 (d, J=16.2 Hz, 1H), 6.95 (d, J=1.9 Hz, 1H), 3.86 (s, 3H).

Example 103: Synthesis of TZ-34-58

To a solution of the phosphate (1.3 eq.) in DMF was added sodium methoxide (1.5 eq.) at 0° C. under nitrogen. 30 min later, aldehyde (1.0 eq.) in DMF was added dropwise to the solution, the mixture was stirred overnight at room temperature (or at 60° C. if required). Cold water/methanol (v/v, 1/1) was added to quench the reaction, the resulting mixture was filtered and the remaining solid was washed with cold water/methanol, cold methanol respectively, the residue was dried under vacuum to afford the target compound. 81% yield, light yellow solid. $^1$H NMR (400 MHz, CD$_3$COCD$_3$) δ 7.56-7.45 (m, 7H), 7.30 (d, J=16.4 Hz, 1H), 7.06 (d, J=16.8 Hz, 1H; $^{13}$C NMR (100.6 MHz, acetone-d6) δ 140.0, 136.9, 131.6, 128.0, 127.0, 126.4, 124.9, 123.9, 123.2, 120.4.

Example 104: Synthesis of TZ-34-59

Synthesis was performed in a similar fashion as described in Example 103. 55% yield, white solid. $^1$H NMR (400 MHz, CD$_3$COCD$_3$) δ 7.60-7.56 (m, 2H), 7.46 (d, J=2.0 Hz, 2H), 7.45 (s, 1H), 7.22 (d, J=16.4 Hz, 1H), 7.12 (d, J=8.8 Hz, 2H), 7.09 (d, J=16.8 Hz, 1H); $^{13}$C NMR (100.6 MHz, CD$_3$COCD$_3$) δ 163.3, 134.1, 127.9, 127.2, 126.3, 124.9, 122.9, 122.7, 115.5, 115.2. 55% yield, white solid. $^1$H NMR (400 MHz, CD$_3$COCD$_3$) δ 7.60-7.56 (m, 2H), 7.46 (d, J=2.0 Hz, 2H), 7.45 (s, 1H), 7.22 (d, J=16.4 Hz, 1H), 7.12 (d, J=8.8 Hz, 2H), 7.09 (d, J=16.8 Hz, 1H); $^{13}$C NMR (100.6 MHz, CD$_3$COCD$_3$) δ 163.3, 134.1, 127.9, 127.2, 126.3, 124.9, 122.9, 122.7, 115.5, 115.2.

Example 105: Synthesis of TZ-34-60

Synthesis was performed in a similar fashion as described in Example 103. 63% yield, light yellow solid. $^1$H NMR (400 MHz, CD$_3$COCD$_3$) δ 7.62-7.58 (m, 2H), 7.36 (d, J=16.0 Hz, 1H), 7.35 (d, J=6.4 Hz, 1H), 7.16 (d, J=3.6 Hz, 1H), 7.14-7.09 (m, 2H), 7.03 (dd, J=4.8 Hz, 3.2 Hz, 1H), 6.97 (d, J=16.0 Hz, 1H); $^{13}$C NMR (100.6 MHz, CD$_3$COCD$_3$) δ 162.2 (d, J=920.1 Hz), 142.6, 133.6, 128.0, 127.6, 126.7, 124.6, 121.9, 115.5, 115.3.

Example 106: Synthesis of TZ-34-63

Synthesis was performed in a similar fashion as described in Example 103. 85% yield, white solid. $^1$H NMR (400 MHz, CD$_3$COCD$_3$) δ 7.13 (d, J=8.4 Hz, 2H), 7.46 (d, J=16.4 Hz, 1H), 7.37 (d, J=8.4 Hz, 2H), 7.36 (d, J=6.8 Hz, 1H), 7.19 (br, 1H), 7.04 (d, J=4.0 Hz, 1H), 6.93 (d, J=16.4 Hz, 1H); $^{13}$C NMR (100.6 MHz, CD$_3$COCD$_3$) δ 142.4, 137.7, 136.9, 128.2, 127.7, 127.0, 126.6, 125.1, 122.9, 91.9.

Example 107: Synthesis of TZ-34-64

Synthesis was performed in a similar fashion as described in Example 103. 86% yield, white solid. $^1$H NMR (400 MHz, CDCl$_3$) δ 7.65 (d, J=8.8 Hz, 2H), 7.31 (t, J=1.2 Hz, 2H), 7.26 (t, J=1.6 Hz, 1H), 7.19 (d, J=8.4 Hz, 2H), 7.10 (d, J=16.4 Hz, 1H), 6.84 (d, J=16.0 Hz, 1H); $^{13}$C NMR (100.6 MHz, CDCl$_3$) δ 139.7, 137.7, 136.9, 128.0, 127.4, 126.3, 124.8, 123.6, 122.9, 92.5.

Example 108: Synthesis of TZ-34-30

To a solution of the diethyl (4-methoxybenzyl)phosphonate (194 mg, 0.75 mmol) and tert-butyl 2-formyl-1H-pyrrole-1-carboxylate (98 mg, 0.5 mmol) in THF (2 mL) was added potassium tert-butoxide (252 mg, 2.25 mmol) in portions at 0° C. 30 min later, the reaction was stirred overnight at room temperature. The mixture was concentrated and subjected to silica gel chromatography to afford (E)-2-(4-methoxystyryl)-1H-pyrrole with Boc deprotected. 51% yield, pale solid; $^1$H NMR (400 MHz, CD$_3$OD) δ 7.39-7.37 (m, 2H), 6.91 (d, J=16.0 Hz, 1H), 6.86-6.84 (m, 2H), 6.76 (d, J=16.0 Hz, 1H), 6.61 (t, J=2.0 Hz, 1H), 6.35 (dd, J=4.0 Hz, 2.0 Hz, 1H), 6.01 (t, J=2.8 Hz, 1H), 3.77 (s, 3H), 3.65 (s, 3H); $^{13}$C NMR (100.6 MHz, CD$_3$OD) δ 158.9, 132.0, 130.8, 126.6, 124.8, 122.7, 115.0, 113.6, 107.3, 105.3, 54.2, 32.6.

Example 109: Synthesis of TZ-34-35

Synthesis was performed in a similar fashion as described in Example 108. 16% yield, white solid; $^1$H NMR (400 MHz, CD$_3$COCD$_3$) δ 7.46 (d, J=8.8 Hz, 2H), 7.87 (s, 1H), 7.53 (d, J=8.8 Hz, 2H), 7.35 (d, J=16.4 Hz, 1H), 6.99 (d, J=16.4 Hz, 1H), 6.95 (d, J=8.8 Hz, 2H), 3.31 (s, 3H); $^{13}$C NMR (100.6 MHz, CD$_3$COCD$_3$) δ 159.9, 151.2, 141.5, 138.2, 131.4, 129.3, 127.8, 116.1, 114.2, 54.7.

Example 110: Synthesis of TZ-34-35

Synthesis was performed in a similar fashion as described in Example 108. 41% yield, white solid; $^1$H NMR (400

MHz, CDCl$_3$) δ 7.30 (d, J=8.8 Hz, 2H), 6.94 (s, 1H), 6.89 (d, J=16.0 Hz, 1H), 6.84 (s, 1H), 6.80 (d, J=8.8 Hz, 2H), 6.78 (d, J=16.0 Hz, 1H), 3.73 (s, 3H); $^{13}$C NMR (100.6 MHz, CDCl$_3$) δ 159.6, 144.1, 129.2, 129.1, 127.9, 127.2, 120.6, 118.4, 114.2, 110.1, 55.3.

Example 111: Synthesis of TZ-34-40

Synthesis was performed in a similar fashion as described in Example 108. 35% yield, yellow solid. $^1$H NMR (400 MHz, CDCl$_3$) δ 7.31 (d, J=8.8 Hz, 2H), 7.12 (d, J=4.2 Hz, 1H), 7.09 (d, J=3.6 Hz, 1H), 6.96 (d, J=14.0 Hz, 1H), 6.97-6.92 (m, 2H), 6.83 (d, J=3.6 Hz, 1H), 6.83 (d, J=8.8 Hz, 2H), 6.77 (d, J=16.0 Hz, 1H), 6.74 (s, 3H); $^{13}$C NMR (100.6 MHz, CDCl$_3$) δ 159.4, 142.3, 137.6, 135.5, 129.7, 128.0, 127.9, 127.6, 126.4, 124.3, 124.1, 123.5, 119.6, 114.2, 55.3.

Example 112: Synthesis of TZ-34-41

Phosphorus trichloride (367 mg, 2.4 mmol) was added to a solution of compound TZ-34-26 (260 mg, 1.2 mmol) in DMF (3 mL) at 0° C., after the addition, the reaction was stirred at room temperature for 1 h and at 80° C. for 3 hours. Iced water was added to quench the reaction. The pH of the mixture was adjusted to 7.0 by the addition of 10% aqueous sodium hydroxide solution. The mixture was extracted with EtOAc, the combined organic layer was washed with water, sodium chloride successively. The concentrated residue was purified by silica gel chromatography using hexane/EtOAc as the eluent to afford the aldehyde. 84% yield, yellow solid. $^1$H NMR (400 MHz, CDCl$_3$) δ 9.82 (s, 1H), 7.62 (d, J=4.0 Hz, 1H), 7.42 (d, J=9.6 Hz, 2H), 7.09 (d, J=15.6 Hz, 1H), 7.08 (d, J=4.4 Hz, 1H), 7.04 (d, J=16.0 Hz, 1H), 6.89 (d, J=8.8 Hz, 2H), 3.82 (s, 3H); $^{13}$C NMR (100.6 MHz, CDCl$_3$) δ 182.5, 160.2, 1531, 141.0, 137.3, 132.6, 128.6, 128.3, 125.9, 118.7, 114.3, 55.3.

Example 113: Synthesis of TZ-34-43

Synthesis was performed in a similar fashion as described in Example 127. 20% yield, yellow solid. $^1$H NMR (400 MHz, CDCl$_3$) δ 7.38 (d, J=8.8 Hz, 2H), 7.29 (d, J=4.0 Hz, 1H), 7.15 (s, 1H), 7.05 (d, J=16.0 Hz, 1H), 6.94 (d, J=3.6 Hz, 1H), 6.88 (d, J=16.4 Hz, 1H), 6.87 (d, J=8.8 Hz, 2H), 3.81 (s, 3H), 2.74 (s, 3H); $^{13}$C NMR (100.6 MHz, CDCl$_3$) δ 166.1, 159.3, 149.4, 142.9, 136.2, 129.7, 128.1, 127.6, 126.3, 124.4, 119.8, 114.2, 110.8, 55.3, 19.2.

Example 114: Synthesis of TZ-34-46

To a solution of compound TZ-34-41 (160 mg, 0.66 mmol) in THF/MeOH (v/v=1/1, 6 mL) was added sodium borohydride (50 mg, 1.3 mmol) in portions at 0° C. The mixture was warmed to room temperature and stirred for another 2 hours. The mixture was concentrated in vacuum and subjected to silica gel chromatography using hexane/EtOAc to afford compound TZ-34-46. 83% yield, yellow solid. $^1$H NMR (400 MHz, CD$_3$COCD$_3$) δ 7.47 (d, J=8.4 Hz, 2H), 7.19 (d, J=16.8 Hz, 1H), 6.91 (d, J=8.8 Hz, 2H), 6.90 (d, J=2.4 Hz, 1H), 6.85 (d, J=16.4 Hz, 1H), 6.84 (d, J=5.6 Hz, 1H), 4.71 (s, 2H), 4.41 (br, 1H), 3.79 (s, 3H); $^{13}$C NMR (100.6 MHz, CD$_3$COCD$_3$) δ 159.5, 144.7, 142.5, 129.8, 127.5, 127.1, 125.4, 124.7, 120.1, 114.1, 59.2, 54.7.

Example 115: Synthesis of TZ-34-93

To a solution of compound TZ-34-26 (108 mg, 0.5 mmol) in THF (5 mL) was added n-butyllithium in hexane (1.6 M, 0.35 mL) at −78° C. 1 hour later, dry ice (1 g, 22.7 mmol) was added to the reaction in one portion, the reaction was continued for another one hour and was quench with saturated ammonium chloride solution. The mixture was concentrated in vacuum and subjected to silica gel chromatography using CH$_2$Cl$_2$/MeOH as the eluent to afford the carboxylic acid TZ-34-93. 95% yield, yellow solid. $^1$H NMR (400 MHz, CD$_3$COCD$_3$) δ 7.66 (br, 1H), 7.53 (d, J=8.8 Hz, 2H), 7.26 (d, J=16.4 Hz, 1H), 7.16 (br, 1H), 7.12 (d, J=16.4 Hz, 1H), 6.93 (d, J=9.2 Hz, 2H), 3.80 (s, 3H); $^{13}$C NMR (100.6 MHz, CDCl$_3$) δ 160.1, 150.1, 134.2, 130.9, 129.0, 128.1, 125.9, 118.9, 114.2, 54.7.

Example 116: Thioflavin T Fluorescence Assay for α-Synuclein Fibrils Binding

The binding affinity of a compound to α-synuclein was measured by an indirect method that comprises a competitive assay using the fluorescent dye Thioflavin T (ThT), which has the structure shown below.

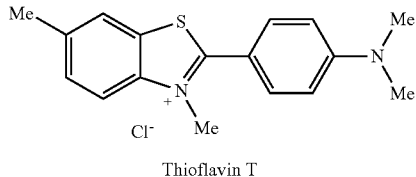

Thioflavin T

ThT is a benzothiazole dye that exhibits enhanced fluorescence upon binding to amyloid fibrils, and is used for the selective staining and identification of amyloid fibrils both in vitro and ex vivo. The changes in the fluorescent properties of ThT upon binding to amyloid fibrils include a shift in its excitation state and an increase in quantum yield. ThT in protic solvents principally absorbs at 340 nm with an emission maximum at 445 nm. Upon binding to amyloid fibrils, a peak at approximately 440 nm becomes dominant with the fluorescent emission maximum shifted to 480 nm. This is accompanied by a strong enhancement of the fluorescence.

The ThT fluorescence emission spectrum has been confirmed to be consistent with reported data. ThT incubated with α-synuclein fibrils prepared as described in this Example has a maximum fluorescence emission wavelength ($\lambda_{em}$) of 485 nm and an excitation wavelength ($\lambda_{ex}$) of 440 nm. No increase in fluorescence emission is observed when ThT is incubated in the presence of monomeric α-synuclein or in α-synuclein free buffer. Furthermore, the ratio of ThT's fluorescence intensity in the presence of α-synuclein fibrils compared to ThT's fluorescence intensity in either monomeric α-synuclein or α-synuclein free buffer has been observed to be about 30-fold.

α-Synuclein recombinant protein was produced in E. coli. BL21(DE3)RIL E. coli were transformed with a pRK172 bacterial expression plasmid containing the human α-synuclein coding sequence. Freshly transformed BL21 colonies were inoculated into 2 L baffled flasks containing 250 mL sterilized TB (1.2% bactotryptone, 2.4% yeast extract, 0.4% glycerol, 0.17 M KH$_2$PO$_4$, 0.72 M K$_2$HPO$_4$) with 50 µg/ml ampicillin, and incubated overnight at 37° C. with shaking. Overnight cultures were pelleted by centrifugation at 3,900×g for 10 min at 25° C. Bacterial pellets were resuspended in 20 mL osmotic shock buffer (30 mM Tris-HCl, 2 mM EDTA, 40% sucrose, pH 7.2) by gentle vortexing and incubated at room temperature for 10 minutes. The cell suspension was then centrifuged at 8,000×g for 10 min at 25° C. and the pellet was resuspended in 22.5 mL cold $H_2O$ before adding 9.4 µL 2 M $MgCl_2$ to each tube. The suspension was incubated on ice for 3 min prior to centrifugation at 20,000×g for 15 min at 4° C. The supernatant was transferred to a fresh tube, streptomyocin was added to a final concentration of 10 mg/mL, and then centrifuged at 20,000×g for 15 min at 4° C. The supernatant from this step was collected and dithiothreitol (DTT) and Tris-HCl were added to final concentrations of 1 mM and 20 mM respectively, before boiling for 10 min to precipitate heat-sensitive proteins, which were pelleted at 20,000×g for 15 minutes at 4° C. The supernatant was collected and filtered through a 0.45 µm surfactant free cellulose acetate filter (Corning, Corning, N.Y.) before loading onto a 1 mL DEAE Sepharose column equilibrated in 20 mM Tris-HCl pH 8, 1 mM EDTA, and 1 mM DTT. The DEAE column was washed with 20 mM Tris-HCl pH 8, 1 mM EDTA, 1 mM DTT before eluting α-synuclein protein in 20 mM Tris-HCl, pH 8, buffer with 1 mM EDTA, 1 mM DTT and 0.3 M NaCl. The purified α-synuclein protein was dialyzed overnight in 10 mM Tris-HCl, pH 7.6, 50 mM NaCl, and 1 mM DTT. Preparations contained greater than 95% α-synuclein protein as determined by SDS-PAGE and BCA assay with a typical yield of 30 mg protein per 250 ml culture.

The purified, recombinant α-synuclein monomer (2 mg/mL) was incubated in Tris-HCl (20 mM) and NaCl (100 mM) while shaking at 1000 rpm in an Eppendorf Thermomixer in a 37° C. temperature-controlled room for 72 hours. To determine the concentration of fibrils, the reaction mixture (100 µL) was centrifuged at 18,000×g for 10 minutes to separate fibrils from monomer. The α-synuclein monomer and other soluble proteins in the supernatant were removed, and the fibril pellet was resuspended in 100 µL solution of Tris-HCl (20 mM) and NaCl (100 mM). This fibril suspension was used in a bicinchoninic acid (BCA) protein assay along with a bovine serum albumin (BSA) standard curve to determine the concentration of fibrils in the 72 hour fibril reaction mixture.

To prepare the fibrils for performing binding assays, the fibril reaction mixture prepared above was centrifuged at 18,000×g for 10 minutes. The supernatant was discarded and the fibril pellet was resuspended in Tris-HCl buffer (30 nM, pH=7.4) to achieve the desired concentration (3 or 6 µM) of fibrils for use in the assay.

The ThT solution (6 µM) in Tris-HCl buffer (30 nM, pH=7.4, 40 µL) was added to each of three cells in a 96 cell plate for fluorescence detection containing α-synuclein fibrils suspension (3.0 µM) in the Tris-HCl buffer (30 nM, pH=7.4, 40 µL). The mixture was incubated at room temperature for 1 hour on the shaking plate. The reaction plate was scanned by the excitation wavelength range from 430 to 465 nm. The maximum excitation wavelength ($\lambda_{ex}$) was determined according to the fluorescent intensity-excitation wavelength curve. At ($\lambda_{ex}$), the emission wavelength was scanned to get maximum emission wavelength ($\lambda_{em}$). Then $\lambda_{ex}$ and $\lambda_{em}$ for the free ThT and ThT-monomeric α-synuclein was determined by the procedure described above. See FIG. 16.1 for fluorescence emission spectra scan data at $\lambda_{ex}$=440 nm and the ThT saturation curve, respectively. See FIG. 16.2 for the saturation curve of ThT (3 µM) for α-synuclein fibrils (1.5 µM) in Tris buffer (30 mM, pH=7.4) at different incubation times: 30 min (circle), 60 min (square), 90 min (triangle) at room temperature. The $K_d$ for ThioT binding to fibrils was 948 nM and the $B_{max}$ was 5672 afu.

ThT solutions of various concentration from 10 nM to 40 µM in Tris-HCl buffer (30 nM, pH=7.4, 40 µL) were added to a 96 cell plate containing α-synuclein fibrils (3.0 µM) in the Tris-HCl buffer (30 nM, pH=7.4, 40 µL). The mixture was incubated at room temperature for 1 hour on the shaking plate. The fluorescent intensity for each cell was measured by the fluorescence reader at $\lambda_{ex}$ and $\lambda_{em}$. The ThT-α-synuclein fibrils saturation curve and $K_d$ value were produced by the software Prism 5. The $K_d$ value for ThT binding to α-synuclein fibrils has been determined to be 948±271 nM.

Once the ThT-α-synuclein saturation binding curve and dissociation constant ($K_d$) were determined the competitive assay for determining the binding affinity of various test compounds was conducted. ThT solution (12 µM) in Tris-HCl buffer (30 nM, pH=7.4, 20 µL) was added to a 96 cell plate containing α-synuclein fibrils (6.0 µM) in the Tris-HCl buffer (30 nM, pH=7.4, 20 µL) and test compounds listed in Table 1 at various concentrations (from 1 nM to 10 µM) in Tris-HCl buffer (30 nM, pH=7.4, 40 µL) with 10% dimethyl sulfoxide. The mixture was incubated at room temperature for 60 minutes on the shaking plate. The fluorescent intensity for each cell was measured by the fluorescence reader at $\lambda_{ex}$ and $\lambda_{em}$. The $K_i$ value for each compound was calculated by the corresponding inhibition curve.

Table 1 shows the α-synuclein binding affinity data for a series of compounds that bind to α-synuclein fibrils, as determined by the ThT competition assay. The inhibitor that binds with highest affinity to α-synuclein fibrils has the lowest dissociation constant ($K_i$). As can be seen from Table 1, compound TZ-23-52 had a $K_i$ of 10.39 nM, and was one of the most potent ligand in the series.

$EC_{50}$ values for each compound were determined by fitting the data to the equation Y=Bottom+(Top-Bottom)/$(1+(X-\text{Log } EC_{50})^{-Hillcoefficient})$ using nonlinear regression by Kaleidagraph software, where Top and Bottom are the Y values for the top and bottom plateaus of the binding curve. The $K_i$ values were derived from the $EC_{50}$ values using the Cheng-Prusoff equation: $K_i=EC_{50}/(1+[\text{radioligand}]/K_d)$. See FIGS. 17.1-31.2 for the inhibition curves for each compound in the ThioT competitive binding assay.

Although fluorescence quenching can potentially interfere with measurement of competitive binding, the data for the individual compounds closely fit a competitive binding model. Absorbance spectra were measured at the $EC_{50}$ concentration for each compound. Absorbance was less than 0.001 in the range of 400-500 nM for all of the compounds, indicating that absorbance at the excitation or emission wavelengths did not interfere with the fluorescence assay.

TABLE 1

Binding affinity ($K_i$) of certain quinolone, N-substituted phenyl amides, and styryl pyridinyl derivatives determined using ThT competitive assays for α-synuclein fibrils.

| Compound No. | Structure | $K_i$ (nM) α-syn | α-syn (avg) | $EC_{50}$ (nM) $EC_{50}$ | $EC_{50}$ (avg) | LogP[b] |
|---|---|---|---|---|---|---|
| TZ-19-122 | | 598.2 | 598.2 | N/A | N/A | 3.82 |
| TZ-19-124 | | 253.9 | 253.9 | N/A | N/A | 4.73 |
| TZ-19-126 | | 3878 | 3878 | N/A | N/A | 5.83 |
| TZ-19-136 | | 3061 | 3061 | N/A | N/A | 4.46 |

TABLE 1-continued

Binding affinity (K$_i$) of certain quinolone, N-substituted phenyl amides, and styryl pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-19-138 | 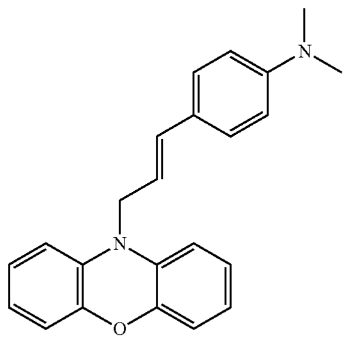 [SMILES: CN(C)c1ccc(/C=C/CN2c3ccccc3Oc3ccccc32)cc1] | 3091.3 | 3091.3 | N/A | N/A | 4.75 |
| TZ-19-140 | 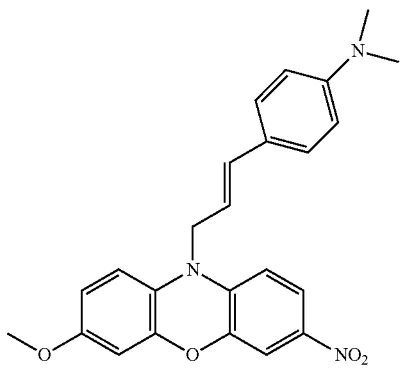 | 466.95 | 466.95 | N/A | N/A | N/A |
| TZ-19-144 | 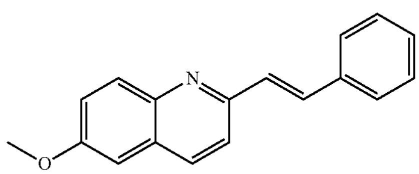 [SMILES: COc1ccc2nc(/C=C/c3ccccc3)ccc2c1] | 195.8 | 195.8 | N/A | N/A | 4.61 |
| TZ-19-146 | 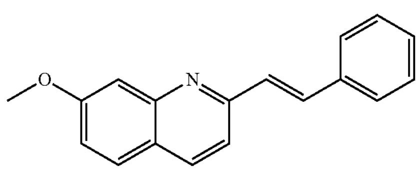 [SMILES: COc1ccc2ccc(/C=C/c3ccccc3)nc2c1] | 665.7 | 665.7 | N/A | N/A | 4.61 |
| TZ-19-148 | 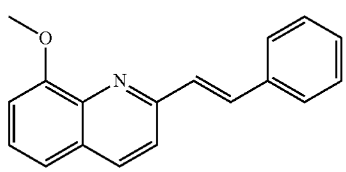 [SMILES: COc1cccc2ccc(/C=C/c3ccccc3)nc12] | 614 | 614 | N/A | N/A | 4.61 |
| TZ-19-150 | 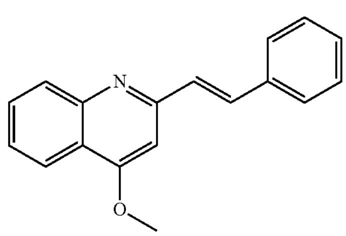 [SMILES: COc1cc(/C=C/c2ccccc2)nc2ccccc12] | ND | ND | N/A | N/A | 4.61 |

TABLE 1-continued

Binding affinity (K$_i$) of certain quinolone, N-substituted phenyl amides, and styryl pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-19-152 | 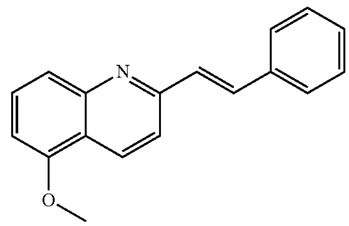 [SMILES: COc1cccc2nc(/C=C/c3ccccc3)ccc12] | 532.2 | 532.2 | N/A | N/A | 4.61 |
| TZ-19-154 | 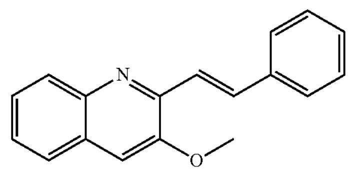 [SMILES: COc1cc2ccccc2nc1/C=C/c1ccccc1] | N/A | N/A | N/A | N/A | 4.61 |
| TZ-19-158 | 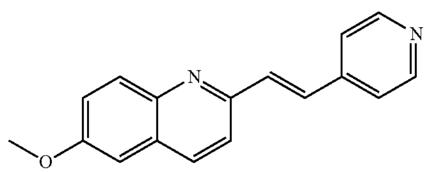 [SMILES: COc1ccc2nc(/C=C/c3ccncc3)ccc2c1] | 29.15 | 29.15 | N/A | N/A | 3.27 |
| TZ-23-02 | 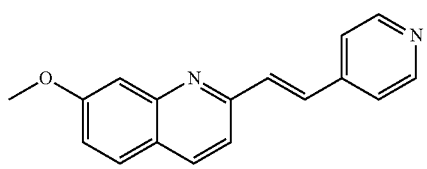 [SMILES: COc1ccc2ccc(/C=C/c3ccncc3)nc2c1] | 71.79 | 71.79 | N/A | N/A | 3.27 |
| TZ-23-04 | 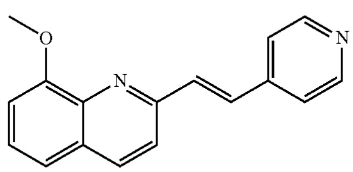 [SMILES: COc1cccc2ccc(/C=C/c3ccncc3)nc12] | N/A | N/A | N/A | N/A | 3.27 |
| TZ-23-06 | 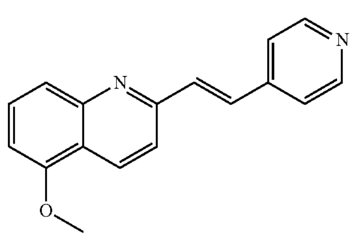 [SMILES: COc1cccc2nc(/C=C/c3ccncc3)ccc12] | 96.34 | 96.34 | N/A | N/A | 3.27 |
| TZ-23-08 | 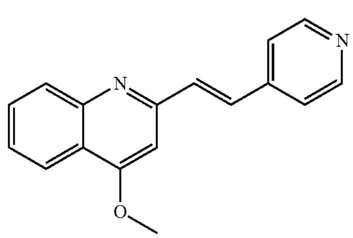 [SMILES: COc1cc(/C=C/c2ccncc2)nc2ccccc12] | N/A | N/A | N/A | N/A | 3.27 |

TABLE 1-continued

Binding affinity (K$_i$) of certain quinolone, N-substituted phenyl amides, and styryl pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-23-10 | | N/A | N/A | N/A | N/A | 3.27 |
| TZ-23-12 | | 36.4 | 36.4 | N/A | N/A | 2.35 |
| TZ-23-14 | | N/A | N/A | N/A | N/A | 2.35 |
| TZ-23-16 | | 3182 | 3182 | N/A | N/A | 2.35 |
| TZ-23-18 | | N/A | N/A | N/A | N/A | 2.35 |
| TZ-23-20 | | 3026 | 3026 | N/A | N/A | 2.35 |
| TZ-23-22 | | N/A | N/A | N/A | N/A | 2.35 |

TABLE 1-continued

Binding affinity (K$_i$) of certain quinolone, N-substituted phenyl amides, and styryl pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-23-52 | 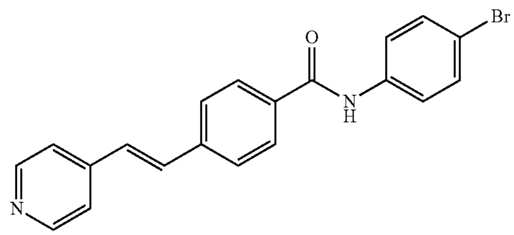 [SMILES: O=C(Nc1ccc(Br)cc1)c1ccc(/C=C/c2ccncc2)cc1] | 10.39 | 10.39 | N/A | N/A | 4.52 |
| TZ-23-56 | 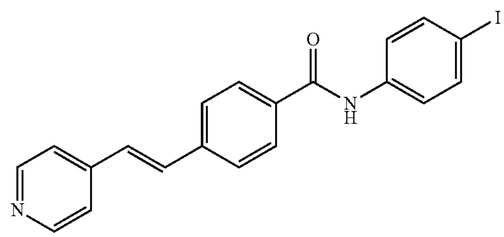 [SMILES: O=C(Nc1ccc(I)cc1)c1ccc(/C=C/c2ccncc2)cc1] | 19.78 | 19.78 | N/A | N/A | 5.05 |
| TZ-22-1-2 | 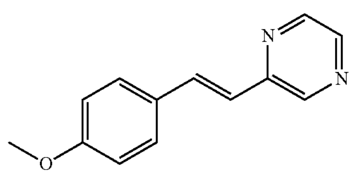 [SMILES: COc1ccc(/C=C/c2cnccn2)cc1] | 31.93 | 31.93 | N/A | N/A | N/A |
| TZ-22-15-1 | 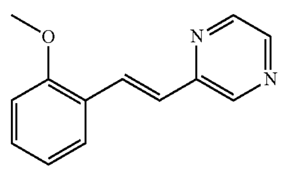 [SMILES: COc1ccccc1/C=C/c1cnccn1] | N/A | N/A | N/A | N/A | N/A |
| TZ-22-19-1 | 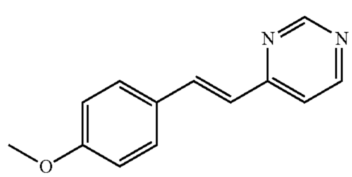 [SMILES: COc1ccc(/C=C/c2ccncn2)cc1] | 154.3 | 154.3 | N/A | N/A | N/A |
| TZ-22-21-1 | 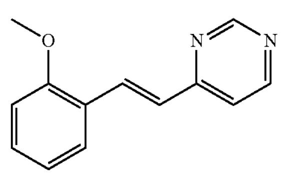 [SMILES: COc1ccccc1/C=C/c1ccncn1] | N/A | N/A | N/A | N/A | N/A |
| TZ-22-23-1 | 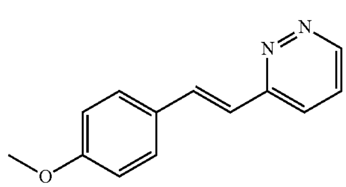 [SMILES: COc1ccc(/C=C/c2cccnn2)cc1] | 1137 | 1137 | N/A | N/A | N/A |

TABLE 1-continued

Binding affinity (K$_i$) of certain quinolone, N-substituted phenyl amides, and styryl pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-22-25-1 | 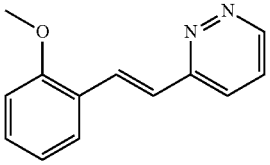 [SMILES: COc1ccccc1/C=C/c1cccnn1] | N/A | N/A | N/A | N/A | N/A |
| TZ-22-31-1 | 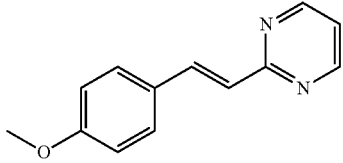 [SMILES: COc1ccc(/C=C/c2ncccn2)cc1] | 2768 | 2768 | N/A | N/A | N/A |
| TZ-22-33-1 | 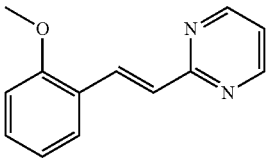 [SMILES: COc1ccccc1/C=C/c1ncccn1] | N/A | N/A | N/A | N/A | N/A |
| TZ-22-35-1 | 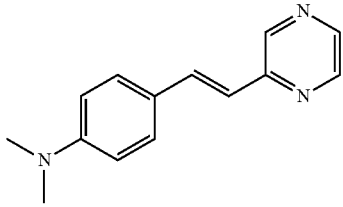 [SMILES: CN(C)c1ccc(/C=C/c2cnccn2)cc1] | 697.8 | 697.8 | N/A | N/A | N/A |
| TZ-22-37-1 | 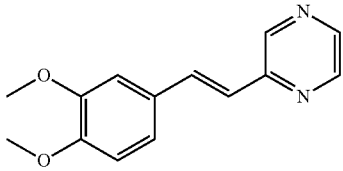 [SMILES: COc1ccc(/C=C/c2cnccn2)cc1OC] | 212.7 | 212.7 | N/A | N/A | N/A |
| TZ-22-47-1 | 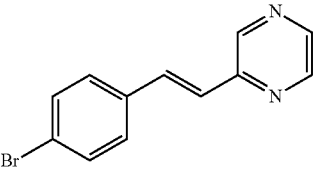 [SMILES: Brc1ccc(/C=C/c2cnccn2)cc1] | 76.71 | 76.71 | N/A | N/A | N/A |
| TZ-22-49-1 | 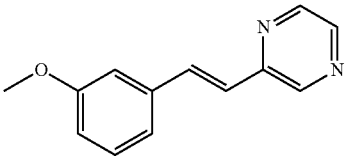 [SMILES: COc1cccc(/C=C/c2cnccn2)c1] | 116.7 | 116.7 | N/A | N/A | N/A |
| TZ-20-5 | 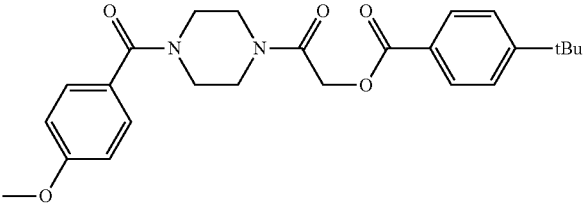 | N/A | N/A | N/A | N/A | 3.44 |

TABLE 1-continued

Binding affinity (K$_i$) of certain quinolone, N-substituted phenyl amides, and styryl pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-20-11 | 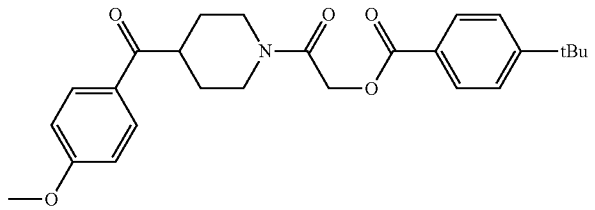 [SMILES: COc1ccc(C(=O)C2CCN(C(=O)COC(=O)c3ccc(C(C)(C)C)cc3)CC2)cc1] | 5089 | 5089 | N/A | N/A | 4.07 |
| TZ-20-23 | 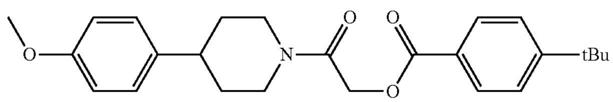 | 109.4 | 109.4 | N/A | N/A | 4.77 |
| TZ-20-35 | 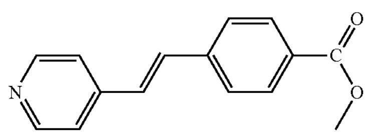 [SMILES: COC(=O)c1ccc(/C=C/c2ccncc2)cc1] | 16.06 | 16.06 | N/A | N/A | 2.71 |
| TZ-20-39 | 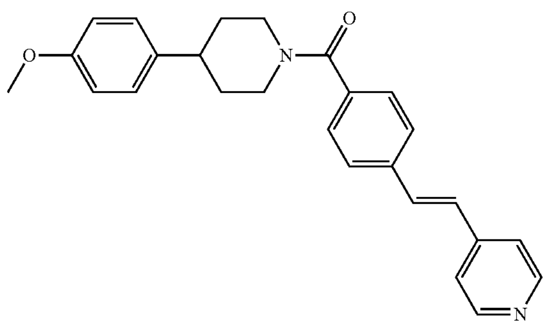 [SMILES: COc1ccc(C2CCN(C(=O)c3ccc(/C=C/c4ccncc4)cc3)CC2)cc1] | 2455 | 2455 | N/A | N/A | 4.39 |
| TZ-20-45 | 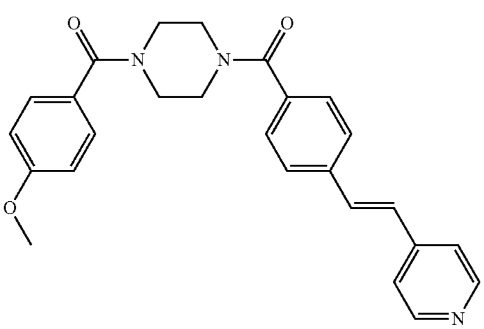 [SMILES: COc1ccc(C(=O)N2CCN(C(=O)c3ccc(/C=C/c4ccncc4)cc3)CC2)cc1] | 181.1 | 181.1 | N/A | N/A | 3.06 |
| TZ-20-51 | 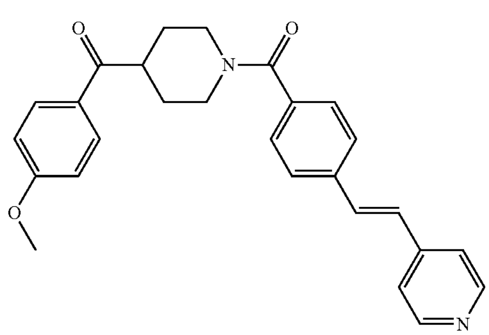 [SMILES: COc1ccc(C(=O)C2CCN(C(=O)c3ccc(/C=C/c4ccncc4)cc3)CC2)cc1] | 183.9 | 183.9 | N/A | N/A | 3.69 |

TABLE 1-continued

Binding affinity (K$_i$) of certain quinolone, N-substituted phenyl amides, and styryl pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-20-59 | 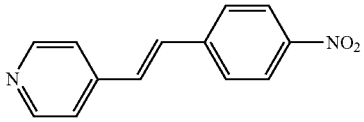 | 52.8 | 52.8 | N/A | N/A | 2.89 |
| TZ-20-63 | 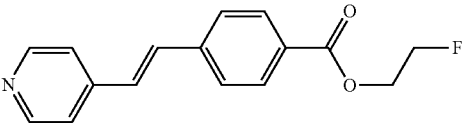 [SMILES: O=C(OCCF)c1ccc(/C=C/c2ccncc2)cc1] | 95.96 | 95.96 | N/A | N/A | 2.9 |
| TZ-20-65 | 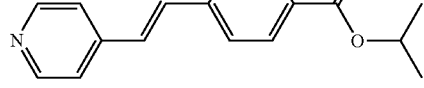 | 75.56 | 75.56 | N/A | N/A | 3.36 |
| TZ-20-67 | 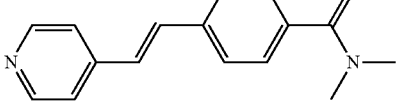 | N/A | N/A | N/A | N/A | 2.27 |
| TZ-20-69 | 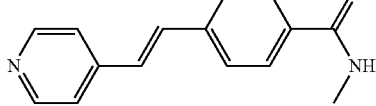 | 85.63 | 85.63 | N/A | N/A | 2.03 |
| TZ-20-73 | 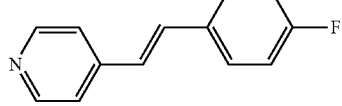 | 431.5 | 431.5 | N/A | N/A | 3.05 |
| TZ-20-75 | 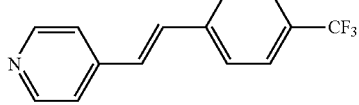 | 36.82 | 36.82 | N/A | N/A | 3.81 |
| TZ-20-77 | 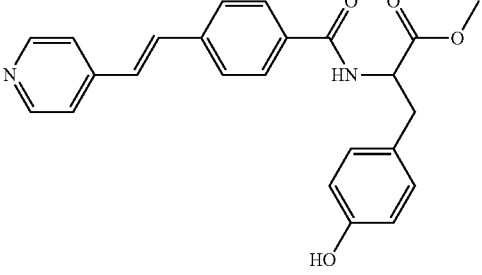 | 523.3 | 523.3 | N/A | N/A | 3.34 |
| TZ-20-79 | 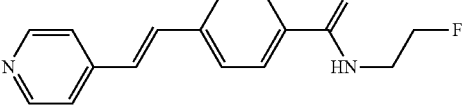 | 115.3 | 115.3 | N/A | N/A | 2.22 |

TABLE 1-continued

Binding affinity ($K_i$) of certain quinolone, N-substituted phenyl amides, and styryl pyridinyl derivatives determined using ThT competitive assays for α-synuclein fibrils.

| Compound No. | Structure | Ki (nM) α-syn | α-syn (avg) | EC$_{50}$ | EC$_{50}$ (avg) | LogP[b] |
|---|---|---|---|---|---|---|
| TZ-20-81 | 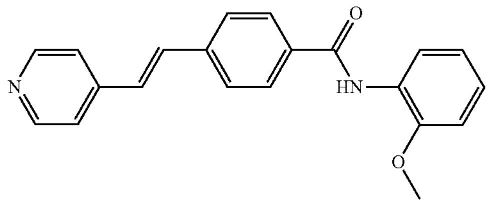 [SMILES: COc1ccccc1NC(=O)c1ccc(/C=C/c2ccncc2)cc1] | 149.7 | 149.7 | N/A | N/A | 3.57 |
| TZ-20-83 | 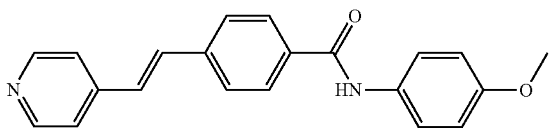 [SMILES: COc1ccc(NC(=O)c2ccc(/C=C/c3ccncc3)cc2)cc1] | 19.14 | N/A | N/A | N/A | 3.57 |
| TZ-20-97 | 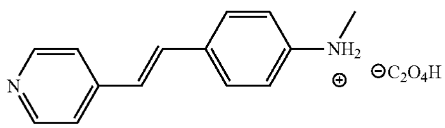 | 33.9 | N/A | N/A | N/A | |
| TZ-20-111 | 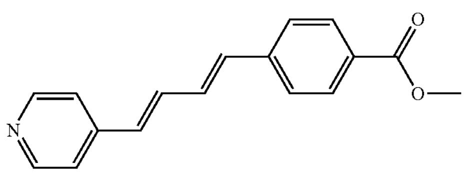 [SMILES: COC(=O)c1ccc(/C=C/C=C/c2ccncc2)cc1] | 56 | N/A | N/A | N/A | 3.22 |
| TZ-23-88 | 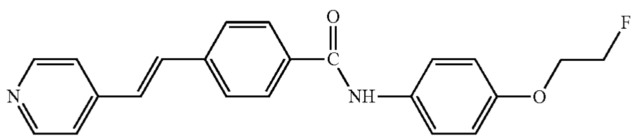 [SMILES: O=C(Nc1ccc(OCCF)cc1)c1ccc(/C=C/c2ccncc2)cc1] | 24.29, 40 | 32.14 | 63.54 104 | 83.77 | N/A |
| TZ-31-108 | 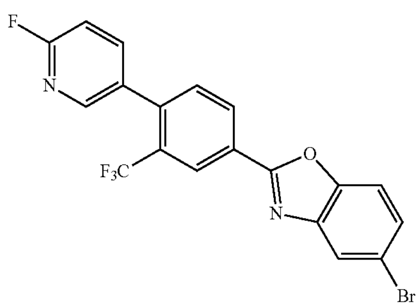 [SMILES: Fc1ccc(-c2ccc(-c3nc4cc(Br)ccc4o3)cc2C(F)(F)F)cn1] | 1539 | 1539 | 4026 | 4026 | N/A |
| TZ-31-123 | 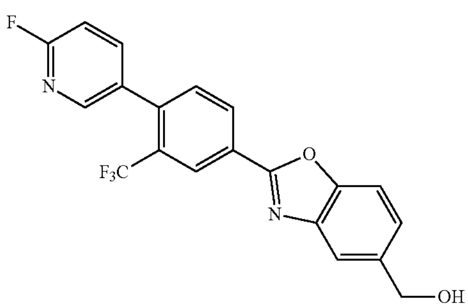 [SMILES: OCc1ccc2oc(-c3ccc(-c4ccc(F)nc4)c(C(F)(F)F)c3)nc2c1] | 31358 | 31358 | 82016 | 82016 | N/A |

TABLE 1-continued
Binding affinity (K$_i$) of certain quinolone, N-substituted phenyl amides, and styryl pyridinyl derivatives determined using ThT competitive assays for α-synuclein fibrils.
| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-31-125 | 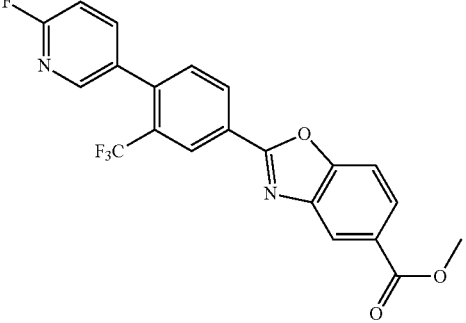 | 1562 | 1562 | 4086 | 4086 | N/A |
| TZ-23-14 | 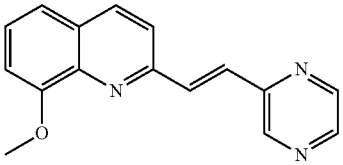 [SMILES: COc1cccc2ccc(/C=C/c3cnccn3)nc12] | N/A | N/A | N/A | N/A | N/A |
| TZ-34-30 | 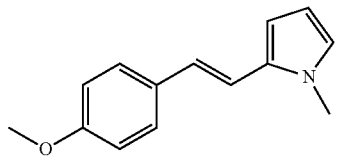 [SMILES: COc1ccc(/C=C/c2cccn2C)cc1] | 72, 230, 270 | 190.66 | 188, 601, 707 | 498.66 | 2.88 |
| TZ-34-35 | 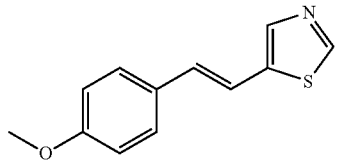 | 313, 333 | 323 | 819, 871 | 845 | 2.89 |
| TZ-34-39 | 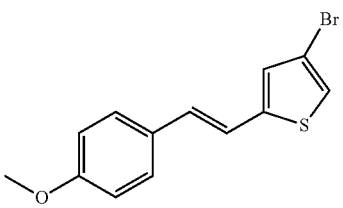 [SMILES: COc1ccc(/C=C/c2cc(Br)cs2)cc1] | 233, 278 | 255.5 | 609, 727 | 668 | 4.91 |
| TZ-34-40 | 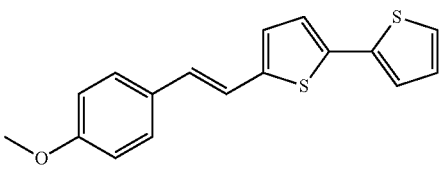 [SMILES: COc1ccc(/C=C/c2ccc(-c3cccs3)s2)cc1] | 500, 400 | 450 | 1307, 1046 | 1176.5 | 5.79 |
| TZ-34-41 | 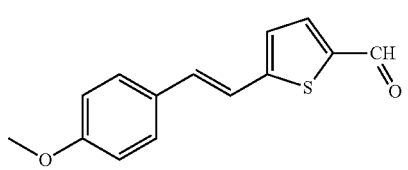 [SMILES: COc1ccc(/C=C/c2ccc(C=O)s2)cc1] | 148 | 148 | 387 | 387 | 3.88 |

TABLE 1-continued

Binding affinity (K$_i$) of certain quinolone, N-substituted phenyl amides, and styryl pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-34-43 | | 318, 27, 59, 133 | 134.25 | 832, 70, 155, 347 | 351 | 5.28 |
| TZ-34-46 | | 105, 110 | 107.5 | 275, 287 | 281 | 3.56 |
| TZ-34-93 | | N/A | N/A | N/A | N/A | 3.69 |
| TZ-34-97 | | 69 | 69 | 180 | 180 | 5.01 |
| TZ-34-100 | | 604 | 604 | 1579 | 1579 | 2.87 |
| TZ-34-58 | | 319 | 319 | 834 | 834 | 4.98 |
| TZ-34-86 | | 117, 152 | 134.5 | 306, 398 | 352 | 4.14 |
| TZ-34-87 | | 884 | 884 | 2312 | 2312 | 5.13 |

TABLE 1-continued
Binding affinity (K$_i$) of certain quinolone, N-substituted phenyl amides, and styryl pyridinyl derivatives determined using ThT competitive assays for α-synuclein fibrils.
| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-34-59 | 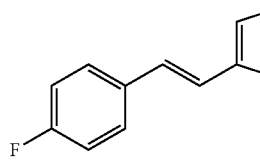 | 860 | 860 | 2250 | 2250 | 4.31 |
| TZ-34-60 | 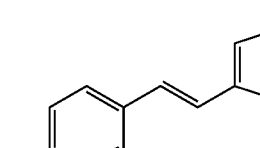 | 1000 | 1000 | 1000 | 1000 | 4.36 |
| TZ-34-63 | 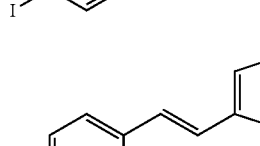 | 80 | 80 | 208 | 208 | 5.56 |
| TZ-34-64 | 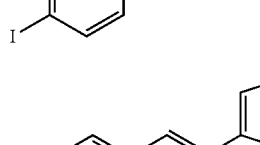 | 115 | 115 | 300 | 300 | 5.51 |
| TZ-34-55 | 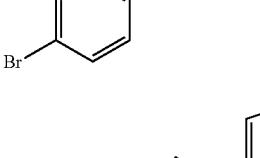 | 198 | 198 | 519 | 519 | 5.04 |
| TZ-34-74 | 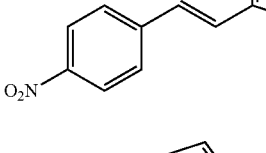 | 55 | 55 | 145 | 145 | 4.24 |
| TZ-34-94 | 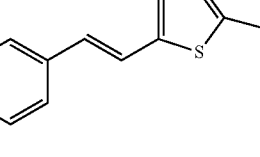 | 223, 61, 197 | 160.33 | 583, 160, 514 | 419 | 3.47 |
| TZ-34-24 | 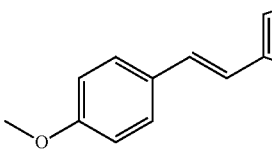 | 610, 163, 262 | 345 | 1595, 426, 686 | 902.33 | 2.71 |

TABLE 1-continued

Binding affinity ($K_i$) of certain quinolone, N-substituted phenyl amides, and styryl pyridinyl derivatives determined using ThT competitive assays for α-synuclein fibrils.

| Compound No. | Structure | $K_i$ (nM) α-syn | α-syn (avg) | $EC_{50}$ (nM) $EC_{50}$ | $EC_{50}$ (avg) | LogP[b] |
|---|---|---|---|---|---|---|
| TZ-34-26 | 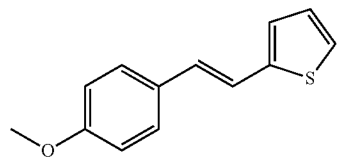 | 51.3, 283, 126, 291.3, 82, 221 | 175.76 | 134.1, 739, 329, 761.9, 214, 580 | 459.67 | 4.08 |
| TZ-34-27 | 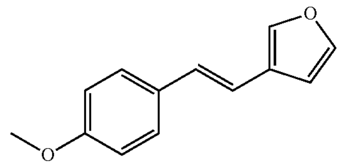 | 1142, 201, 310 | 551 | 2987, 527, 812 | 1442 | 2.66 |
| TZ-34-28 | 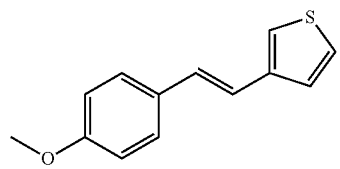 | 43.1, 167, 113, 104, 256, 347 | 171.68 | 112.7, 437, 297, 271, 670, 907 | 449.12 | 4.02 |
| TZ-34-38 | 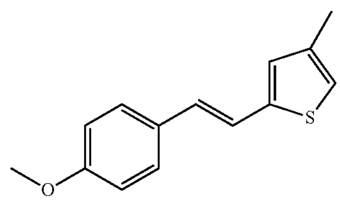 [SMILES: COc1ccc(/C=C/c2cc(C)cs2)cc1] | 387, 114, 256 | 252.33 | 1012, 299, 671 | 660.67 | 4.57 |
| TZ-36-20 | 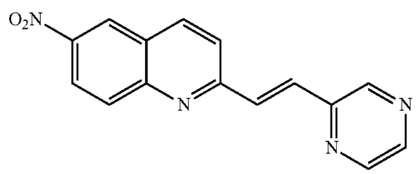 [SMILES: O=[N+]([O-])c1ccc2nc(/C=C/c3cnccn3)ccc2c1] | 926 | 926 | 2422 | 2422 | 2.74 |
| TZ-36-22 | 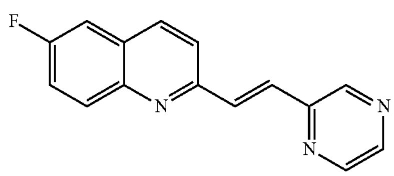 [SMILES: Fc1ccc2nc(/C=C/c3cnccn3)ccc2c1] | 109 | 109 | 286 | 286 | 2.64 |
| TZ-36-24 | 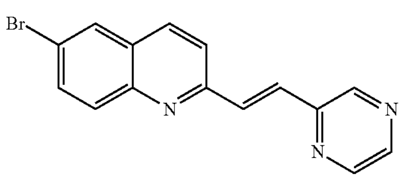 [SMILES: Brc1ccc2nc(/C=C/c3cnccn3)ccc2c1] | 453 | 453 | 1185 | 1185 | 3.31 |
| TZ-36-26-2T | 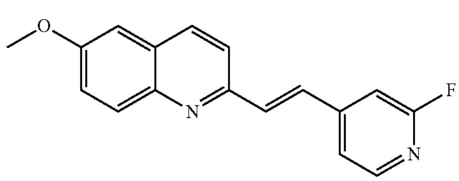 [SMILES: COc1ccc2nc(/C=C/c3ccnc(F)c3)ccc2c1] | 1484, 33, 200, 21 | 434.5 | 3880, 87, 523, 54 | 1136 | 3.89 |

TABLE 1-continued
Binding affinity (K$_i$) of certain quinolone, N-substituted phenyl amides, and styryl pyridinyl derivatives determined using ThT competitive assays for α-synuclein fibrils.
| Compound No. | Structure | Ki (nM) α-syn | α-syn (avg) | EC$_{50}$ (nM) EC$_{50}$ | EC$_{50}$ (avg) | LogP[b] |
|---|---|---|---|---|---|---|
| TZ-36-28-2T | 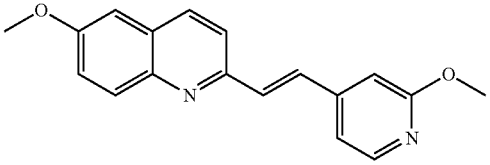 | 37, 40, 87, 66, 29 | 51.8 | 98, 105, 226, 174, 76 | 135.8 | 3.86 |
| TZ-36-34 | 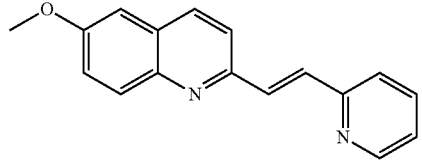 [SMILES: COc1ccc2nc(/C=C/c3ccccn3)ccc2c1] | 193 | 193 | 504 | 504 | 3.69 |
| TZ-34-71 | 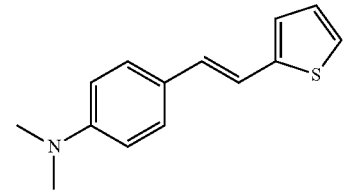 [SMILES: CN(C)c1ccc(/C=C/c2cccs2)cc1] | N/A | N/A | N/A | N/A | 4.49 |
| TZ-36-38 | 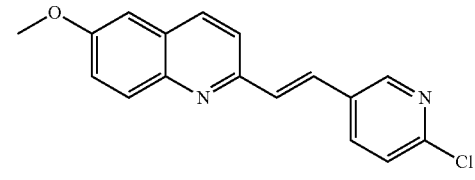 [SMILES: COc1ccc2nc(/C=C/c3ccc(Cl)nc3)ccc2c1] | 31, 47 | 39 | 80, 122 | 101 | 4.17 |
| TZ-36-42 | 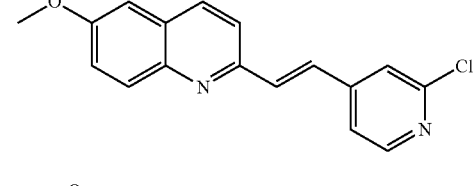 | 52, 56 | 54 | 136, 145 | 140.5 | 4.17 |
| TZ-36-46 | 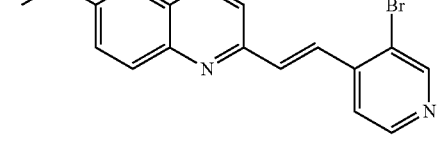 | 140, 195 | 167.5 | 365, 509 | 437 | 4.1 |
| TZ-36-48 | 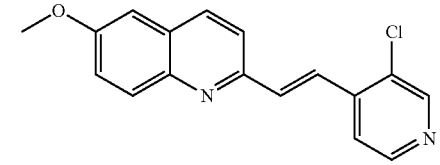 [SMILES: COc1ccc2nc(/C=C/c3ccncc3Cl)ccc2c1] | 414 | 414 | 1083 | 1083 | 3.83 |
| TZ-36-30 | 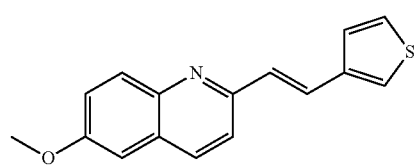 [SMILES: COc1ccc2nc(/C=C/c3ccsc3)ccc2c1] | 122 | 122 | 320 | 320 | 4.53 |

TABLE 1-continued
Binding affinity (K$_i$) of certain quinolone, N-substituted phenyl amides, and styryl pyridinyl derivatives determined using ThT competitive assays for α-synuclein fibrils.
| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-36-50 | 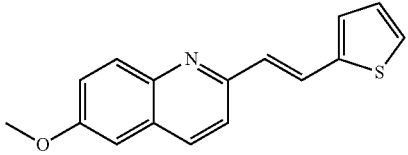 [SMILES: COc1ccc2nc(/C=C/c3cccs3)ccc2c1] | 403 | 403 | 1055 | 1055 | 4.59 |
| TZ-36-52 | 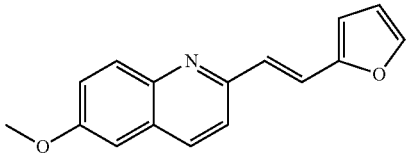 [SMILES: COc1ccc2nc(/C=C/c3ccco3)ccc2c1] | 316 | 316 | 827 | 827 | 3.22 |
| TZ-36-14 | 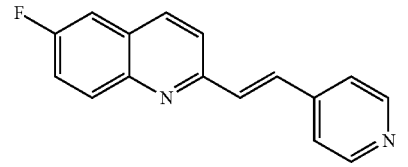 [SMILES: Fc1ccc2nc(/C=C/c3ccncc3)ccc2c1] | N/A | N/A | N/A | N/A | 3.55 |
| TZ-36-16 | 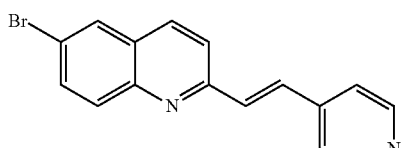 | N/A | N/A | N/A | N/A | 4.22 |
| TZ-36-40 | 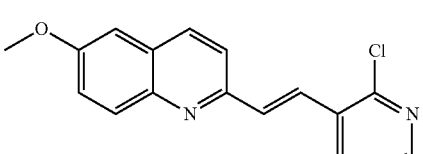 | 62 | 62 | 163 | 163 | 4.17 |
| TZ-36-44 | 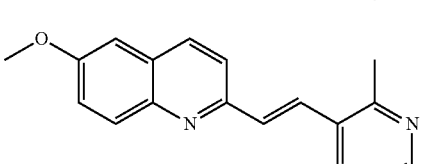 | 289 | 289 | 755 | 755 | 3.97 |
| TZ-36-138 | 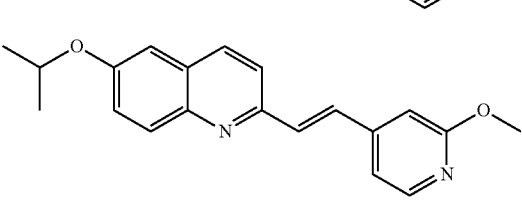 | 49 | 49 | 128 | 128 | N/A |
| TZ-36-144 | 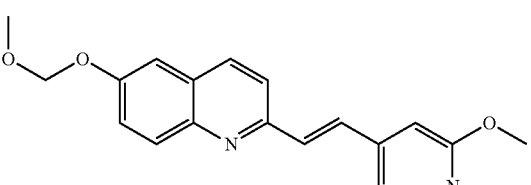 | 42 | 42 | 110 | 110 | N/A |

TABLE 1-continued
Binding affinity (K$_i$) of certain quinolone, N-substituted phenyl amides, and styryl pyridinyl derivatives determined using ThT competitive assays for α-synuclein fibrils.
| Compound No. | Structure | Ki (nM) α-syn | α-syn (avg) | EC$_{50}$ (nM) EC$_{50}$ | EC$_{50}$ (avg) | LogP[b] |
|---|---|---|---|---|---|---|
| TZ-36-146 | 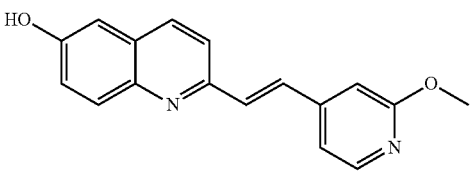 [SMILES: COc1cc(/C=C/c2ccc3cc(O)ccc3n2)ccn1] | 233, 21 | 127 | 609, 56 | 332.5 | N/A |
| TZ-36-148 | 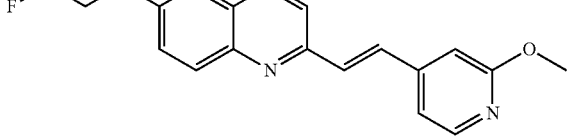 | 17, 19 | 18 | 44.5, 49 | 46.75 | N/A |
| TZ-36-32 | 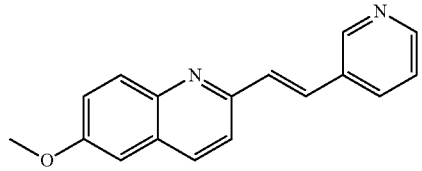 [SMILES: COc1ccc2nc(/C=C/c3cccnc3)ccc2c1] | 34, 26 | 30 | 90, 67 | 78.5 | N/A |
| TZ-36-36 | 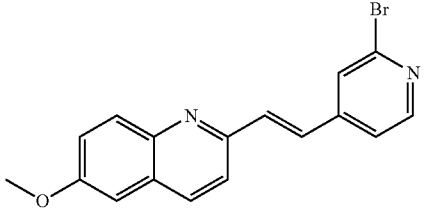 [SMILES: COc1ccc2nc(/C=C/c3ccnc(Br)c3)ccc2c1] | 128, 175 | 151.5 | 335, 457 | 396 | N/A |
| TZ-36-54 | 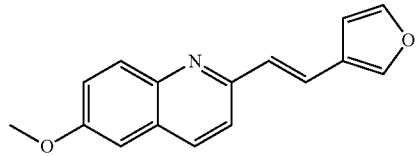 [SMILES: COc1ccc2nc(/C=C/c3ccoc3)ccc2c1] | 65, 72 | 68.5 | 169, 188 | 178.5 | N/A |
| TZ-36-138 | 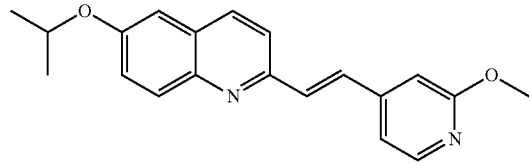 [SMILES: COc1cc(/C=C/c2ccc3cc(OC(C)C)ccc3n2)ccn1] | 49 | 49 | N/A | N/A | 4.83 |
| TZ-36-142 | 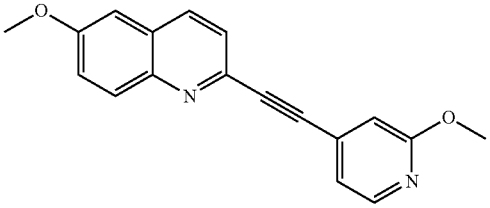 | 233 | 233 | 609 | 609 | 3.84 |

TABLE 1-continued

Binding affinity (K$_i$) of certain quinolone, N-substituted phenyl amides, and styryl
pyridinyl derivatives determined using ThT competitive assays for α-synuclein fibrils.

| Compound No. | Structure | Ki (nM) α-syn | Ki (nM) α-syn (avg) | EC$_{50}$ (nM) EC$_{50}$ | EC$_{50}$ (nM) EC$_{50}$ (avg) | LogP[b] |
|---|---|---|---|---|---|---|
| TZ-36-144 | 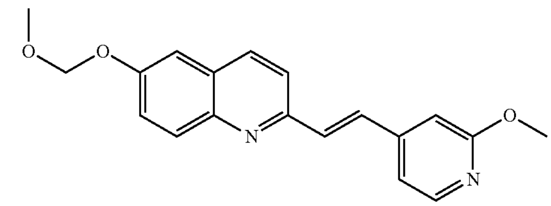 [SMILES: COCOc1ccc2nc(/C=C/c3ccnc(OC)c3)ccc2c1] | 42 | 42 | N/A | N/A | 3.35 |
| TZ-36-146 | 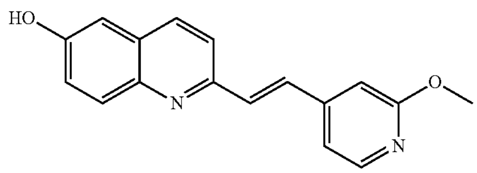 [SMILES: COc1cc(/C=C/c2ccc3cc(O)ccc3n2)ccn1] | 233, 21 | 127 | N/A | N/A | 3.58 |
| TZ-36-148 | 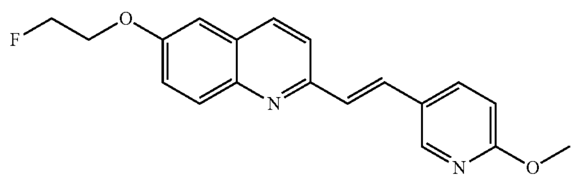 [SMILES: COc1ccc(/C=C/c2ccc3cc(OCCF)ccc3n2)cn1] | 17, 19 | 18 | N/A | N/A | 4.40 |
| TZ-36-32 | 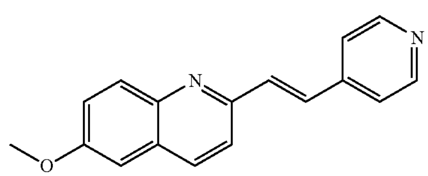 [SMILES: COc1ccc2nc(/C=C/c3ccncc3)ccc2c1] | 34, 26 | 30 | N/A | N/A | 3.29 |
| TZ-36-36 | 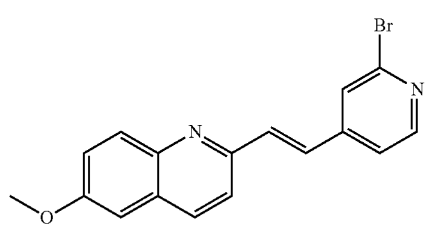 [SMILES: COc1ccc2nc(/C=C/c3ccnc(Br)c3)ccc2c1] | 128, 175 | 151.5 | N/A | N/A | 4.16 |
| TZ-36-54 | 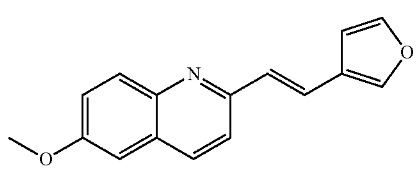 [SMILES: COc1ccc2nc(/C=C/c3ccoc3)ccc2c1] | 65, 72 | 68.5 | N/A | N/A | 4.05 |
| TZ-37-96 | 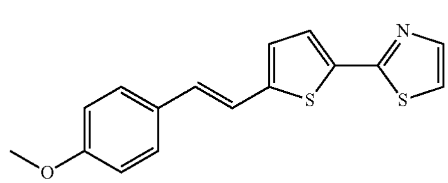 [SMILES: COc1ccc(/C=C/c2ccc(-c3nccs3)s2)cc1] | 102, 95 | 98.5 | N/A | N/A | 5.54 |

See FIGS. 17.1-21.2 for the inhibition curves of select compounds in the ThioT competitive binding assay.

Example 116: Thioflavin T Fluorescence Assay for Aβ-Synuclein Fibrils Binding

Aβ-synuclein recombinant protein was produced in *E. coli*. Additional preparation was performed in a similar fashion to Example 115. Thioflavin T fluorescence assays were performed in a similar fashion to Example 115.

Table 2 shows the Aβ-fibrils binding affinity data for a series of quinolone, N-substituted phenyl amides, and styryl pyridinyl derivatives, as determined by the ThT competition assay. The inhibitor that binds with highest affinity to Aβ fibrils has the lowest dissociation constant ($K_i$). As can be seen from Table 2, that compound TZ-36-148 has a $K_i$ value of 168±5 nM and was one of the most potent ligand in the series.

TABLE 2

Binding affinity ($K_i$) of certain quinolone, N-substituted phenyl amides, and styryl pyridinyl derivatives determined using ThT competitive assays for Aβ fibrils.

| Compound No. | Structure | Ki (nM) Aβ | Aβ (avg) | EC₅₀(nM) EC₅₀ | EC₅₀ (avg) | LogP[b] |
|---|---|---|---|---|---|---|
| TZ-34-43 | | 320 | 320 | 854 | 854 | 5.28 |
| TZ-34-24 | | 960.7, 814.6 | 887.65 | 2562, 1999 | 2280.5 | 2.71 |
| TZ-34-26 | | 2499 | 2499 | 6664 | 6664 | 4.08 |
| TZ-34-27 | | N/A | N/A | N/A | N/A | 2.66 |
| TZ-34-28 | | N/A | N/A | N/A | N/A | 4.02 |
| TZ-36-28-2T | | 268 | 268 | 715 | 715 | 3.86 |
| TZ-36-146 | | N/A | N/A | N/A | N/A | 3.58 |

TABLE 2-continued

Binding affinity (K$_i$) of certain quinolone, N-substituted phenyl amides, and styryl pyridinyl derivatives determined using ThT competitive assays for Aβ fibrils.

| Compound No. | Structure | Aβ Ki (nM) | Aβ (avg) | EC$_{50}$ | EC$_{50}$ (avg) | LogP$^b$ |
|---|---|---|---|---|---|---|
| TZ-36-148 | (structure) | 163, 173 | 168 | 435, 462 | 448.5 | 4.40 |

See FIGS. 22.1-26.2 for the inhibition curves of select compounds in the ThioT competitive binding assay.

Example 117: Thioflavin T Fluorescence Assay for Tau Fibrils Binding

Tau fibril recombinant protein was produced in *E. coli*. Additional preparation was performed in a similar fashion to Example 115. Thioflavin T fluorescence assays were performed in a similar fashion to Example 115.

Table 3 shows the tau fibrils binding affinity data for a series of quinolone, N-substituted phenyl amides, and styryl pyridinyl derivatives, as determined by the ThT competition assay.

The inhibitor that binds with highest affinity to tau fibrils has the lowest dissociation constant (K$_i$). As can be seen from Table 3, compound TZ-36-28-2T had a Ki value 34 nM and was one of the most potent ligand in the series.

TABLE 3

Binding affinity (K$_i$) of certain quinolone, N-substituted phenyl amides, and styryl pyridinyl derivatives determined using ThT competitive assays for tau fibrils.

| Compound No. | Structure | Tau Ki (nM) | Tau (avg) | EC$_{50}$ | EC$_{50}$ (avg) | LogP$^b$ |
|---|---|---|---|---|---|---|
| TZ-34-43 | (structure) | 512 | 512 | 1256 | 1256 | 5.28 |
| TZ-34-26 | (structure) | 1367 | 1367 | 3353 | 3353 | 4.08 |
| TZ-34-27 | (structure) | N/A | N/A | N/A | N/A | 2.66 |
| TZ-34-28 | (structure) | 600, 1153 | 876.5 | 1473, 2829 | 2151 | 4.02 |

TABLE 3-continued

Binding affinity ($K_i$) of certain quinolone, N-substituted phenyl amides, and styryl pyridinyl derivatives determined using ThT competitive assays for tau fibrils.

| Compound No. | Structure | Ki (nM) Tau | Tau (avg) | EC$_{50}$m (nM) EC$_{50}$ | EC$_{50}$ (avg) | LogP[b] |
|---|---|---|---|---|---|---|
| TZ-36-28-2T | 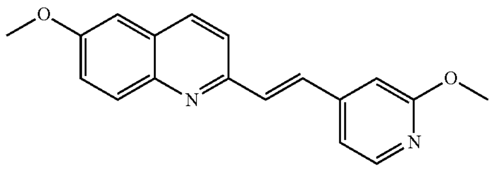 | 34 | 34 | 82 | 82 | 3.86 |
| TZ-36-146 | 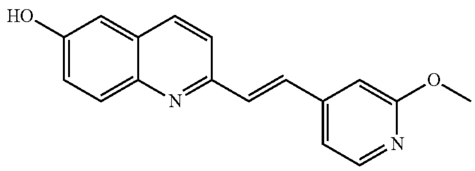 [SMILES: COc1cc(/C=C/c2ccc3cc(O)ccc3n2)ccn1] | 124, 102 | 113 | 305, 251 | 278 | |
| TZ-36-148 | 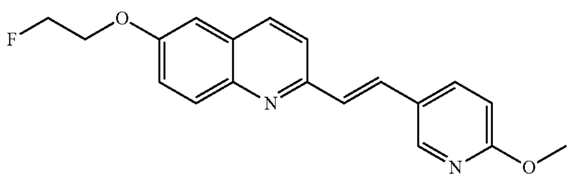 [SMILES: COc1ccc(/C=C/c2ccc3cc(OCCF)ccc3n2)cn1] | 124, 102 | 63 | | | |

See FIGS. 27.1-31.2 for the inhibition curves of select compounds in the ThioT competitive binding assay.

Example 118: Preparation of [$^{11}$C]Methyl Iodide

Production of [$^{11}$C]CH$_3$I followed the reported method [Padakanti P. K., Zhang X., Li J., Parsons S. M., Perlmutter J. S. and Tu Z. (2014) Syntheses and radiosyntheses of two Carbon-11 labeled potent and selective radioligands for imaging vesicular acetylcholine transporter. *Molecular Imaging and Biology*, 16:765-772]. Briefly, [$^{11}$C]CH$_3$I was produced on-site from [$^{11}$C]CO$_2$ using a GE PETtrace MeI Microlab (GE Healthcare). Up to 1.4 Ci of [$^{11}$C]carbon dioxide was produced from the JSW BC-16/8 cyclotron by irradiating a gas target of 0.5% O$_2$ in N$_2$ for 15-30 min with a 40 µA beam of 16 MeV protons in the Barnard Cyclotron Facility of Washington University School of Medicine. After the GE PETtrace MeI Microlab system converted the [$^{11}$C] CO$_2$ to [$^{11}$C]CH$_4$ using a nickel catalyst [Shimalite-Ni (reduced), Shimadzu, Japan P.N.221-27719] in the presence of hydrogen gas at 360° C.; the [$^{11}$C]CH$_4$ was further converted to [$^{11}$C]CH$_3$I by reaction with iodine in the gas phase at 690° C. Approximately 12 min following the end-of-bombardment (EOB), several hundred millicuries of [$^{11}$C]CH$_3$I were delivered in the gas phase to the hot cell where the radiosynthesis was accomplished.

Example 119: Preparation of Radioligand [$^{11}$C]TZ-20-35

[$^{11}$C]CH$_3$I was bubbled for a period of 2-3 min into a solution of (E)-4-(2-(pyridin-4-yl)vinyl)benzoic acid (2 mg) with TRITON B (3 µL) in DMF (0.30 mL) at room temperature. When the trapping of radioactivity was complete, the sealed reaction vessel was heated at 70° C. for 5 min. After the heating source was removed, 1.8 mL of the HPLC mobile phase that was composed of acetonitrile/0.1 M ammonium formate buffer (50/50, v/v), pH=6.5, was added into to the reaction vessel. The mixture was loaded onto a reversed phase HPLC system (Agilent Zorbax, SB-C18 column, 250×10 mm, flow rate: 4.0 mL/min) to purify the [$^{11}$C] TZ-20-35. Under these conditions, the product was collected from 15.75 min to 17.09 min into a vial that contained 50 mL aseptic water. The retention time for the precursor was 3.8 min. After finishing the collection, the collected fraction was passed through a C-18 Plus SEP-PAC cartridge to remove the mobile phase solvent, whereby [$^{11}$C] TZ-20-35 was retained on the cartridge. Then the SEP-PAC cartridge was rinsed using 10 mL of sterile water. Finally, the [$^{11}$C]TZ-20-35 trapped on the SEP-PAC was eluted with 0.6 mL of ethanol, following with 5.4 mL 0.9% sodium chloride solution, passing through a 0.22µ (Whatman Puradisc 13 mm syringe filter) sterile filter into a sterile pyrogen-free glass vial. The total synthesis time was ~45 min.

Quality Control

An aliquot of sample was assayed by an analytical HPLC system (Agilent Zorbax, SB-C18 column, 250×4.6 mm), UV at 254 nm; mobile phase consists of acetonitrile/0.1 M, pH 6.5 ammonium formate buffer (64/36, v/v). At this condition, the retention time for [$^{11}$C] TZ-20-35 was approximately 4.48 min at a flow rate of 1.5 mL/min. The sample was authenticated by co-injecting with the cold standard TZ-20-35 solution. The radiochemical purity was >99%, the chemical purity was >95%, the labeling yield was 42-48% (n=10, decay corrected) and the specific activity was >800 Ci/mmol (decay corrected to end of synthesis).

Example 120: Preparation of Radioligand [$^{11}$C]TZ-20-83

[$^{11}$C]CH$_3$I was bubbled for a period of 2-3 min into a solution of (E)-N-(4-hydroxyphenyl)-4-(2-(pyridin-4-yl)vinyl)benzamide (1 mg) with NaH (10 mg in 1 ml DMF, 50 µL) in DMF (0.20 mL) at room temperature. When the trapping of radioactivity was complete, the sealed reaction vessel was heated at 80° C. for 5 min. After the heating source was removed, 1.8 mL of the HPLC mobile phase that was composed of acetonitrile/0.1 M ammonium formate buffer (40/60, v/v), pH=4.5, was added into to the reaction vessel. The mixture was loaded onto a reversed phase HPLC system (Agilent Zorbax, SB-C18 column, 250×10 mm, flow rate: 4.0 mL/min). Under these conditions, the product was collected from 13.71 min to 15.86 min into a vial that contained 50 mL aseptic water. The retention time for the precursor was 6.30 min. After finishing the collection, the collected fraction was passed through a C-18 Plus SEP-PAC cartridge to remove the mobile phase solvent, whereby [$^{11}$C] TZ-20-83 was retained on the cartridge. Then the SEP-PAC cartridge was rinsed using 10 mL of sterile water. Finally, the [$^{11}$C] TZ-20-83 trapped on the SEP-PAC was eluted with 0.6 mL of ethanol, following with 5.4 mL 0.9% sodium chloride solution, passing through a 0.22µ (Whatman Puradisc 13 mm syringe filter) sterile filter into a sterile pyrogen-free glass vial. The total synthesis time was ~45 min.

Quality Control

An aliquot of sample was assayed by an analytical HPLC system (Agilent Zorbax, SB-C18 column, 250×4.6 mm), UV at 254 nm; mobile phase consists of acetonitrile/0.1 M, pH6.5 ammonium formate buffer (55/45, v/v). At this condition, the retention time for [$^{11}$C] TZ-20-83 was approximately 4.42 min at a flow rate of 1.5 mL/min. The sample was authenticated by co-injecting with the cold standard TZ-20-83 solution. The radiochemical purity was >99%, the chemical purity was >95%, the labeling yield was 30-35% (n=10, decay corrected) and the specific activity was >800 Ci/mmol (decay corrected to end of synthesis).

Example 121: Preparation of Radioligand [$^{18}$F]TZ-23-88

A two-step strategy was applied for the radiosynthesis of [$^{18}$F]TZ-23-88. The radioactive intermediate [$^{18}$F]fluoroethyltosylate was first synthesized through a typical fluorination of tosylate substrate. Treating ethylene glycol ditosylate with [$^{18}$F]fluoride, potassium carbonate and KRYPTOFIX 222 (4,7,13,16,21,24-Hexaoxa-1,10-diazabicyclo[8.8.8] hexacosane) gave [$^{18}$F]fluoroethyltosylate in good yield (60-70%, decay corrected) after HPLC purification. Then mixed the [$^{18}$F]fluoroethyl tosylate with the mixture of precursor and cesium carbonate in DMSO, and heated for 15 min, obtained sufficiently dose of [$^{18}$F]TZ-23-88, the labeling yield was 60-68% (n=3, decay corrected).

[$^{18}$F]Fluoride was produced in our institution by $^{18}$O(p, n)$^{18}$F reaction through proton irradiation of enriched $^{18}$O water (95%) using a RDS111 cyclotron (Siemens/CTI Molecular Imaging, Knoxville, Tenn.). [$^{18}$F]Fluoride is first passed through an ion-exchange resin and then is eluted with 0.02 M potassium carbonate ($K_2CO_3$) solution.

After heated for 15 minutes, the reaction mixture was diluted with 3.0 mL of HPLC mobile phase (50:50 Acetonitrile/0.1 M ammonium formate buffer (pH ~6.5)) and passed through an alumina Neutral SEP-PAC Plus cartridge. The crude product was then loaded onto an Agilent SB-C18 semi-preparative HPLC column (250 mm×10 mm) with a UV detector set at 254 nm. The HPLC system used a 5 mL injection loop. With 50:50 Acetonitrile/0.1 M ammonium formate buffer (pH ~6.5) as eluent at 4.0 mL/min flow rate, the retention time of the product was 9.5-10 min. The retention time of the precursor was 23-24 min. In situ monitored by the radioactivity detector, the HPLC collection was diluted with ~50 mL sterile water and the diluted collection went through a C-18 SEP-PAC Plus cartridge to trap the [$^{18}$F]fluoroethyl tosylate on the SEP-PAC. The trapped product was eluted with diethyl ether (2.5 mL).

The eluted solution formed two phases, the top ethereal phase was transferred out, and the bottom aqueous phase was extracted with another 1 mL of ether. The combined ether solution was passed through a set of two SEP-PAC Plus dry cartridges into a reaction vessel. After the ether was evaporated with a nitrogen stream at 25° C., 2 mg of precursor was dissolved in 250 µL DMSO and was transferred to a vial containing 2.0 mg $Cs_2CO_3$. After vortexed for 1 min, the $Cs_2CO_3$ saturated/suspended solution was added into the reaction tube containing the activity. The tube was capped and briefly swirled with a vortex, and then was kept at 90° C. for 15 min. Subsequently, the residual was diluted with 3 mL HPLC mobile phase (45:55 acetonitrile/ 0.1 M formate solution (pH ~6.5)) and loaded onto a Semi-Prep HPLC system for purification. The HPLC system contains a 5 mL injection loop, a LUNA C-18 column, a UV detector at 254 nm and a radioactivity detector. With 45:55 acetonitrile/0.1 M formate solution (pH ~6.5) as eluent, at 4.0 mL/min flow rate, the retention time of the product was 23-25 min, whereas the retention time of the precursor was 9.0 min. After the HPLC collection was diluted with ~50 mL sterile water, the product was trapped on a C-18 SEP-PAC Plus cartridge. The trapped product was eluted with ethanol (0.6 mL) followed by 5.4 mL of 0.9% saline. After sterile filtration into a glass vial, the final product was ready for quality control (QC) analysis and animal studies. An aliquot of sample was assayed by an analytical HPLC system (Agilent Zorbax, SB-C18 column, 250×4.6 mm), UV at 254 nm; mobile phase consists of acetonitrile/0.1 M, ammonium formate buffer. At this condition, the retention time for [$^{18}$F]TZ-23-88 was approximately 4.3 min at a flow rate of 1.5 mL/min. The sample was authenticated by co-injecting with the cold standard TZ-23-88 solution. The radiochemical purity was >99%, the chemical purity was 81%, the labeling yield was 60-68% (n=3, decay corrected) and the specific activity was >2000 Ci/mmol (decay corrected to end of synthesis). The entire procedure took ~3 h.

Example 122: Preparation of Radioligand [$^{18}$F]TZ-23-92

A two-step strategy was applies for the radiosynthesis of [$^{18}$F]TZ-23-92. The radioactive intermediate [$^{18}$F] 3-(fluoro-18F)propyl 4-methylbenzenesulfonate was first synthesized through a typical fluorination of tosylate substrate. Treating propane-1,3-diyl bis(4-methylbenzenesulfonate) with [$^{18}$F]fluoride, potassium carbonate and KRYPTOFIX 222 gave [$^{18}$F] 3-(fluoro-18F)propyl 4-methylbenzenesulfonate in good yield (48-58%, decay corrected) after HPLC purification. Then mixed 3-(fluoro-18F)propyl 4-methylbenzenesulfonate with the mixture of precursor, (E)-N-(4-hydroxyphenyl)-4-(2-(pyridin-4-yl)vinyl)benzamide (1.2 mg) and cesium carbonate in DMSO, and heated for 15 min, obtained sufficiently dose of [$^{18}$F]TZ-23-92, the labeling yield was 42-49% (n=3, decay corrected).

[$^{18}$F]Fluoride was produced in our institution by $^{18}$O(p, n)$^{18}$F reaction through proton irradiation of enriched $^{18}$O water (95%) using a RDS111 cyclotron (Siemens/CTI Molecular Imaging, Knoxville, Tenn.). [$^{18}$F]Fluoride is first passed through an ion-exchange resin and then is eluted with 0.02 M potassium carbonate ($K_2CO_3$) solution.

A sample of ~150 mCi [$^{18}$F]/fluoride was added to a reaction vessel containing KRYPTOFIX 222 (6.5-7.0 mg). The syringe was washed with 2×0.4 mL ethanol. The resulting solution was evaporated under nitrogen flow with a bath temperature of 110° C. To the mixture acetonitrile (3×1.0 mL) was added and water was azeotropically removed by evaporation. After all the water was removed, 5.0-5.5 mg of the corresponding precursor propane-1,3-diyl bis(4-methylbenzenesulfonate) was dissolved in acetonitrile (200 μL) under vortex, and the precursor solution was transferred into the reaction vessel containing [$^{18}$F]fluoride/KRYPTOFIX/K$_2$CO$_3$. The reaction tube was capped and the reaction mixture was briefly mixed, and then subjected to heating in an oil bath that was preheated to 100° C. for 15 min.

After heated for 15 minutes, the reaction mixture was diluted with 3.0 mL of HPLC mobile phase (50:50 Acetonitrile/0.1 M ammonium formate buffer (pH ~6.5)) and passed through an alumina Neutral SEP-PAC Plus cartridge. The crude product was then loaded onto an Agilent SB-C-18 semi-preparative HPLC column (250 mm×10 mm) with a UV detector set at 254 nm. The HPLC system used a 5 mL injection loop. With 50:50 Acetonitrile/0.1 M ammonium formate buffer (pH ~6.5) as eluent at 4.0 mL/min flow rate, the retention time of the product was 11-13 min. In situ monitored by the radioactivity detector, the HPLC collection was diluted with ~50 mL sterile water and the diluted collection went through a C-18 SEP-PAC Plus cartridge to trap the [$^{18}$F] 3-(fluoro-18F)propyl 4-methylbenzenesulfonate on the SEP-PAC. The trapped product was eluted with diethyl ether (2.5 mL).

The eluted solution formed two phases, the top ethereal phase was transferred out, and the bottom aqueous phase was extracted with another 1 mL of ether. The combined ether solution was passed through a set of two SEP-PAC Plus dry cartridges into a reaction vessel. After the ether was evaporated with a nitrogen stream at 25° C., 2 mg of precursor was dissolved in 250 μL DMSO and was transferred to a vial containing 2.0 mg Cs$_2$CO$_3$. After vortexed for 1 min, the Cs$_2$CO$_3$ saturated/suspended solution was added into the reaction tube containing the activity. The tube was capped and briefly swirled with a vortex, and then was kept at 90° C. for 15 min. Subsequently, the residual was diluted with 3 mL HPLC mobile phase (45:55 acetonitrile/0.1 M formate solution (pH ~6.5)) and loaded onto a Semi-Prep HPLC system for purification. The HPLC system contains a 5 mL injection loop, an Luna C-18 column, a UV detector at 254 nm and a radioactivity detector. With 45:55 acetonitrile/0.1 M formate solution (pH ~6.5) as eluent, at 4.0 mL/min flow rate, the retention time of the product was 24 to 28 min, whereas the retention time of the precursor was 8 to 9.5 min. After the HPLC collection was diluted with ~50 mL sterile water, the product was trapped on a C-18 SEP-PAC Plus cartridge. The trapped product was eluted with ethanol (0.6 mL) followed by 5.4 mL of 0.9% saline. After sterile filtration into a glass vial, the final product was ready for quality control (QC) analysis and animal studies. An aliquot of sample was assayed by an analytical HPLC system (Agilent Zorbax, SB-C18 column, 250×4.6 mm), UV at 254 nm; mobile phase consists of acetonitrile/0.1 M, pH4.5 ammonium formate buffer (60/40, v/v). At this condition, the retention time for [$^{18}$F]TZ-23-92 was approximately 4.7 min at a flow rate of 1.5 mL/min. The sample was authenticated by co-injecting with the cold standard TZ-23-92 solution. The radiochemical purity was >99%, the chemical purity was 95%, the labeling yield was 42-49% (n=3, decay corrected) and the specific activity was >2000 Ci/mmol (decay corrected to end of synthesis). The entire procedure took ~3 h.

Example 123: Biodistribution of [$^{11}$C]TZ-20-35 in Male Balb/C Mice

For the biodistribution studies, 100~130 μCi of [$^{11}$C]TZ-20-35 in ~100 μL of 10% ethanol/saline solution (v/v) was injected via the tail vein into mature male Balb/C mice (19-24 g) under anesthesia (2.5% isoflurane in oxygen at a flow rate of 1 mL/min). A group of at least four rats were used for each time point. At 5 min, 30 min, 60 min post injection, the rats were anesthetized and euthanized. The whole brain was quickly harvested. At the same time, samples of blood, heart, lung, liver, spleen, pancreas, kidney, muscle, fat, and tail were dissected. All the tissue samples were collected in tared tubes and counted in an automated gamma counter (Beckman Gamma 8000 well counter) with standards, prepared by diluting the injectate. The counted tissues were then weighed, and the % ID/g was calculated (Table 4).

TABLE 4

Biodistribution of [$^{11}$C]TZ-20-35 in male Balb/C mice[a]

| Organ | Time | | |
|---|---|---|---|
| | 5 min | 30 min | 60 min |
| Blood | 5.21 ± 0.20 | 2.79 ± 0.43 | 1.75 ± 0.25 |
| Heart | 4.72 ± 0.34 | 2.61 ± 0.54 | 1.80 ± 0.18 |
| Lung | 4.78 ± 0.21 | 2.94 ± 0.38 | 2.21 ± 0.44 |
| Muscle | 4.06 ± 0.13 | 2.25 ± 0.33 | 1.18 ± 0.10 |
| Fat | 0.90 ± 0.42 | 0.86 ± 0.07 | 0.58 ± 0.09 |
| Pancreas | 3.64 ± 0.44 | 3.54 ± 0.90 | 5.42 ± 1.25 |
| Spleen | 4.60 ± 0.16 | 3.44 ± 0.23 | 3.30 ± 0.36 |
| Kidney | 4.73 ± 0.41 | 4.43 ± 0.42 | 4.23 ± 0.47 |
| Liver | 4.25 ± 0.36 | 8.72 ± 0.37 | 10.17 ± 1.08 |
| Brain | 5.71 ± 0.44 | 2.43 ± 0.41 | 1.68 ± 0.26 |

[a]% ID/g values (mean ± SD) with n = 4 rats per group.

The result shows the initial uptakes of all organs except for fat were homogeneous (FIG. 32.1). Probably because it has the radioactive metabolite and the metabolite was able to enter all organs. The brain uptake (% ID/gram) reached 5.71% at 5 min, and it deceased to 2.43 and 1.68 (% ID/gram) at 30 and 60 min (FIG. 32.2). Although the Brain uptake and the washout kinetics were very good, maybe the metabolite can enter the brain. In addition, the organ recovery (% ID/gram) was very low at 30 min and 60 min (52% at 30 min, and 34% at 60 min), probably because the radioactive metabolite entered the urine.

Example 124: Biodistribution of [$^{11}$C]TZ-20-83 in Male Balb/C Mice

The biodistribution studies were performed in a similar fashion as described in Example 123. The counted tissues were then weighed, and the % ID/g was calculated (Table 5).

TABLE 5

Biodistribution of [$^{11}$C]TZ-20-83 in male Balb/C mice[a]

| Organ | Time | | |
|---|---|---|---|
| | 5 min | 30 min | 60 min |
| Blood | 1.93 ± 0.15 | 1.59 ± 0.42 | 1.56 ± 0.12 |
| Heart | 2.31 ± 0.37 | 1.79 ± 0.35 | 1.48 ± 0.05 |
| Lung | 11.22 ± 0.59 | 4.10 ± 0.96 | 2.93 ± 0.22 |
| Muscle | 1.18 ± 0.24 | 1.17 ± 0.23 | 0.92 ± 0.14 |
| Fat | 1.94 ± 0.20 | 1.73 ± 0.36 | 1.05 ± 0.22 |
| Pancreas | 3.09 ± 0.39 | 5.10 ± 1.09 | 6.96 ± 0.51 |
| Spleen | 18.77 ± 3.38 | 3.49 ± 0.84 | 3.21 ± 0.76 |
| Kidney | 17.55 ± 2.61 | 9.98 ± 1.76 | 5.82 ± 0.47 |
| Liver | 37.98 ± 3.78 | 17.94 ± 3.86 | 13.36 ± 1.75 |
| Brain | 1.93 ± 0.29 | 1.63 ± 0.33 | 1.25 ± 0.11 |

[a]% ID/g values (mean ± SD) with n = 4 rats per group.

The results as illustrated by FIGS. 33.1 and 33.2, shows the brain uptake (% ID/gram) reached 1.93% at 5 min, and it deceased to 1.63 and 1.25 (% ID/gram) at 30 and 60 min, which means brain uptake and washout aren't significant. Although liver has the highest accumulation, the organ recovery (% ID/gram) was very low at 30 min and 60 min (58% at 30 min, and 38% at 60 min).

Example 125: Biodistribution of [$^{18}$F]TZ-23-88 in Male Balb/C Mice

The biodistribution studies were performed in a similar fashion as described in Example 123. The counted tissues were then weighed, and the % ID/g was calculated (Table 6).

TABLE 6

Biodistribution of [$^{18}$F]TZ-23-88 in male Balb/C mice[a]

| Organ | Time | | | |
|---|---|---|---|---|
| | 5 min | 30 min | 60 min | 120 min |
| Blood | 2.50 ± 0.13 | 2.30 ± 0.05 | 1.28 ± 0.06 | 0.70 ± 0.05 |
| Heart | 4.82 ± 0.47 | 2.23 ± 0.06 | 1.23 ± 0.05 | 0.71 ± 0.12 |
| Lung | 8.50 ± 0.60 | 2.57 ± 0.15 | 1.31 ± 0.07 | 0.71 ± 0.09 |
| Muscle | 2.60 ± 0.19 | 1.35 ± 0.04 | 0.75 ± 0.07 | 0.55 ± 0.21 |
| Fat | 2.43 ± 0.42 | 1.70 ± 0.17 | 0.69 ± 0.10 | 0.23 ± 0.12 |
| Pancreas | 4.91 ± 0.68 | 3.02 ± 0.19 | 1.84 ± 0.33 | 0.98 ± 0.10 |
| Spleen | 3.12 ± 0.12 | 1.59 ± 0.08 | 0.90 ± 0.07 | 0.47 ± 0.04 |
| Kidney | 35.67 ± 1.48 | 15.72 ± 1.06 | 5.59 ± 0.29 | 1.94 ± 0.29 |
| Liver | 16.30 ± 3.53 | 19.56 ± 0.97 | 10.71 ± 0.80 | 5.59 ± 0.39 |
| Bone | 4.07 ± 0.50 | 28.50 ± 2.81 | 42.68 ± 1.69 | 49.39 ± 8.21 |
| Brain | 4.69 ± 0.70 | 4.07 ± 0.21 | 3.21 ± 0.14 | 2.37 ± 0.14 |

[a]% ID/g values (mean ± SD) with n = 4 rats per group.

The results as indicated in FIGS. 34.1, 34.2, 34.4, and 34.4, shows the bone uptake (% ID/gram) reached 4.07 at 5 min, but it increased to 28.50%, 42.68% and 49.39% at 30 min, 60 min and 120 min. It indicated that there is strong defluorination in the mice. The brain uptake (% ID/gram) reached 4.59% at 5 min, which means the radiotracer [$^{18}$F]TZ-23-88 can cross the blood brain barrier and enter the brain; and the brain uptake then decreased to 4.07, 3.21 and 2.37 (% ID/gram) at 30, 60 and 120 min.

Example 126: Biodistribution of [$^{18}$F]TZ-23-92 in Male Balb/C Mice

The biodistribution studies were performed in a similar fashion as described in Example 123. The counted tissues were then weighed, and the % ID/g was calculated (Table 7).

TABLE 7

Biodistribution of [$^{18}$F]TZ-23-92 in male Balb/C mice[a]

| Organ | Time | | | |
|---|---|---|---|---|
| | 5 min | 30 min | 60 min | 120 min |
| Blood | 2.40 ± 0.39 | 2.42 ± 0.19 | 0.84 ± 0.05 | 0.32 ± 0.02 |
| Heart | 2.93 ± 0.34 | 2.19 ± 0.19 | 0.90 ± 0.07 | 0.31 ± 0.02 |
| Lung | 7.70 ± 0.85 | 2.30 ± 0.25 | 0.83 ± 0.05 | 0.36 ± 0.03 |
| Muscle | 1.47 ± 0.16 | 1.30 ± 0.16 | 0.55 ± 0.06 | 0.33 ± 0.26 |
| Fat | 1.79 ± 0.55 | 1.34 ± 0.30 | 0.58 ± 0.13 | 0.29 ± 0.10 |
| Pancreas | 2.03 ± 0.19 | 1.87 ± 0.23 | 0.98 ± 0.08 | 0.61 ± 0.13 |
| Spleen | 23.73 ± 4.54 | 1.69 ± 0.15 | 0.61 ± 0.04 | 0.24 ± 0.01 |
| Kidney | 11.17 ± 0.41 | 9.10 ± 0.34 | 3.87 ± 0.36 | 1.67 ± 0.23 |
| Liver | 52.44 ± 3.84 | 14.47 ± 1.13 | 7.00 ± 0.33 | 3.50 ± 0.48 |
| Bone | 3.31 ± 0.74 | 39.48 ± 10.28 | 68.78 ± 6.75 | 70.20 ± 15.04 |
| Brain | 1.52 ± 0.18 | 1.56 ± 0.08 | 1.46 ± 0.16 | 1.00 ± 0.11 |

[a]% ID/g values (mean ± SD) with n = 4 rats per group.

The result as illustrated in FIGS. 35.1 and 35.2 shows the bone uptake (% ID/gram) reached 3.31 at 5 min, but it increased to 39.47%, 68.78% and 70.20% at 30 min, 60 min and 120 min. The brain uptake (% ID/gram) reached 1.51% at 5 min which means it can cross BBB and enter the brain; and the brain uptake was slowly decreased to 1.55, 1.46 and 1.0 (% ID/gram) at 30, 60 and 120 min.

Example 127: Preparation of Radioligand [$^{11}$C]TZ-36-28-2T

[$^{11}$C]CH$_3$I was bubbled for a period of 2-3 min into a solution of (E)-2-(2-(2-methoxypyridin-4-yl)vinyl)quinolin-6-ol (~1 mg) with 5 N NaOH (3 uL) in DMF (0.25 mL) at room temperature. When the trap of radioactivity was complete, the sealed reaction vessel was heated at 85° C. for 5 min. After the heating source was removed, 1.8 mL of the HPLC mobile phase that was composed of acetonitrile/0.1 M ammonium formate buffer (50/50, v/v), pH=4.5, was added into to the reaction vessel. The mixture was loaded onto a reversed phase HPLC system (Agilent Zorbax, SB-C18 column, 250×10 mm, flow rate: 4.0 mL/min) to purify the [$^{11}$C]TZ-36-28. Under these conditions, the product was collected from 20 min to 22 into a vial that contained 50 mL aseptic water. The retention time for the precursor was 6.0-7.6 min. After finishing the collection, the collected fraction was passed through a C-18 Plus SEP-PAC cartridge to remove the mobile phase solvent, whereby [$^{11}$C] TZ-36-28-2T was retained on the cartridge. Then the SEP-PAK cartridge was rinsed using 10 mL of sterile water. Finally, the [$^{11}$C]TZ-36-28-2T trapped on the SEP-PAK was eluted with 2 mL of ethanol, passing through a 0.22µ (Whatman Puradisc 13 mm syringe filter) sterile filter into a sterile pyrogen-free glass vial. The total synthesis time was ~45 min.

Quality Control

An aliquot of sample was assayed by an analytical HPLC system (Agilent Zorbax, SB-C18 column, 250×4.6 mm), UV at 254 nm; mobile phase consists of acetonitrile/0.1 M, pH4.5 ammonium formate buffer (69/31, v/v). At this condition, the retention time for [$^{11}$C]TZ-36-28-2T was approximately 5.1 min at a flow rate of 1.5 mL/min. The sample was authenticated by co-injecting with the cold standard TZ-36-28-2T solution. The radiochemical purity was >99%, the chemical purity was >95%, the labeling yield was 40-43% (n=10, decay corrected) and the specific activity was >800 Ci/mmol (decay corrected to end of synthesis).

Example 128: Preparation of Radioligand [$^{11}$C]TZ-20-35

[$^{11}$C]CH$_3$I was bubbled for a period of 2-3 min into a solution of (E)-4-(2-(pyridin-4-yl)vinyl)benzoic acid (2 mg) with Triton B (3 uL) in DMF (0.30 mL) at room temperature. When the trap of radioactivity was complete, the sealed reaction vessel was heated at 70° C. for 5 min. After the heating source was removed, 1.8 mL of the HPLC mobile phase that was composed of acetonitrile/0.1 M ammonium formate buffer (50/50, v/v), pH=6.5, was added into to the reaction vessel. The mixture was loaded onto a reversed phase HPLC system (Agilent Zorbax, SB-C18 column, 250×10 mm, flow rate: 4.0 mL/min) to purify the [$^{11}$C]TZ-20-35. Under these conditions, the product was collected from 15.75 min to 17.09 into a vial that contained 50 mL aseptic water. The retention time for the precursor was 3.8 min. After finishing the collection, the collected fraction was passed through a C-18 Plus SEP-PAK cartridge to remove the mobile phase solvent, whereby [$^{11}$C]TZ-20-35 was retained on the cartridge. Then the SEP-PAK cartridge was rinsed using 10 mL of sterile water. Finally, the [$^{11}$C] morphine trapped on the SEP-PAK was eluted with 0.6 mL of ethanol, following with 5.4 mL 0.9% sodium chloride solution, passing through a 0.22µ (Whatman Puradisc 13 mm syringe filter) sterile filter into a sterile pyrogen-free glass vial. The total synthesis time was ~45 min.

Quality Control

[$^{11}$C]TZ-20-35 An aliquot of sample was assayed by an analytical HPLC system (Agilent Zorbax, SB-C18 column, 250×4.6 mm), UV at 254 nm; mobile phase consists of acetonitrile/0.1 M, pH6.5 ammonium formate buffer (64/36, v/v). At this condition, the retention time for [$^{11}$C]TZ-20-35 was approximately 4.48 min at a flow rate of 1.5 mL/min. The sample was authenticated by co-injecting with the cold standard TZ-20-35 solution. The radiochemical purity was >99%, the chemical purity was >95%, the labeling yield was 42-48% (n=10, decay corrected) and the specific activity was >800 Ci/mmol (decay corrected to end of synthesis).

Example 129: Preparation of Radioligand [$^{18}$F]TZ-36-148

[$^{18}$F]Fluoride was produced in our institution by $^{18}$O(p, n)$^{18}$F reaction through proton irradiation of enriched $^{18}$O water (95%) using a RDS111 cyclotron (Siemens/CTI Molecular Imaging, Knoxville, Tenn.). [$^{18}$F]Fluoride is first passed through an ion-exchange resin and then is eluted with 0.02 M potassium carbonate (K$_2$CO$_3$) solution. [$^{18}$F]fluoride (~200 mCi) was added to a reaction vessel containing KRYPTOFIX 222 (8.0-10.0 mg). The syringe was washed with 2×0.4 mL ethanol. The resulting solution was evaporated under nitrogen flow in a 110° C. oil bath. To the mixture, acetonitrile (3×1.0 mL) was added and all the solvent was azeotropically removed by evaporation. 5.0-5.5 mg of the corresponding precursor 1,2-ethylene ditosylate was dissolved in acetonitrile (200 µL) and the precursor solution was transferred into the reaction vessel containing [$^{18}$F]fluoride/KRYPTOFIX/K$_2$CO$_3$. The reaction tube was capped and the reaction mixture was briefly mixed, and heated in a 100° C. oil bath for 15 min.

After the reaction was complete, the reaction mixture was diluted with 3.0 mL of HPLC mobile phase (50% Acetonitrile in 0.1 M ammonium formate buffer (pH ~6.5)). The mixture was loaded through an alumina Neutral SEP-PAK Plus cartridge to an Agilent SB-C18 semi-preparative HPLC column (250 mm×10 mm). With a UV detector set at 254 nm and 50:50 Acetonitrile/0.1 M ammonium formate buffer (pH ~6.5) as eluent at 4.0 mL/min flow rate, the retention time of the product was 9.5-10 min. The retention time of the precursor was 23-24 min. [$^{18}$F]fluoroethyl tosylate was collected in a vial of sterile water (50 mL). The aqueous solution was passed through C18 SEP-PAK Plus (Waters, WAT020515) by applying nitrogen pressure. The trapped product was eluted with diethyl ether (2.5 mL).

The eluted solution had two phases. The top ether phase was transferred into another vial, and the bottom aqueous phase was extracted with another 1 mL of ether which was later transferred into the ether vial. The combined ether solution was passed through a set of two SEP-PAC Plus dry cartridges into a reaction vessel. A nitrogen line was applied to the vial and ether was evaporated under nitrogen. A solution of 2 mg precursor (TZ-36-146), 2.0 mg Cs$_2$CO$_3$ in 200 µL DMSO was transferred to the reaction tube containing the activity. The tube was capped and briefly swirled on a vortex, and then was heated at 90° C. for 15 min. Subsequently, the reaction mixture was diluted with 3 mL HPLC mobile phase (62% acetonitrile in 0.1 M ammonium formate solution (pH ~4.5)) and loaded onto an Agilent SB C-18 column (250 mm×10 mm). With a UV detector set at 254 nm and 4 mL/min flow rate, the retention time of the product was 12 min. The activity was collected in a vial of sterile water (50 mL). The aqueous solution was passed through C18 SEP-PAC Plus cartridge (Waters, WAT020515) by applying nitrogen pressure and the activity was trapped on the cartridge. The trapped product was eluted with ethanol (0.6 mL) followed by 5.4 mL of 0.9% saline. After sterile filtration into a glass vial, the final product was ready for quality control (QC) analysis and animal studies. A small amount of sample (~0.2 mL) was taken for quality control analysis which was performed on an analytical Agilent SB-C18 column (4.6×250 mm, 5 µm) using mobile phase: 75% acetonitrile in 0.1 M ammonium formate buffer (pH 4.5); flow rate 1.5 ml/min; UV wavelength 254 nm. The $t_R$ of the product is 5 minutes. The sample was authenticated by co-injecting with the cold standard TZ-36-148 solution. The radiochemical purity was >99%, the chemical purity was >95%, the labeling yield was 10-20% (n=3, decay corrected) and the specific activity was 0.7-5 Ci/µmol.

Example 130: Competition Binding Assays with α-Synuclein, Aβ-Fibrils, and Tau Fibrils Preparation of Recombinant α-Synuclein and Tau Protein Recombinant protein was produced in *E. coli* using protocols based on previously described methods for α-synuclein [Giasson, B. I., et al., "Mutant and wild type human alpha-synucleins assemble into elongated filaments with distinct morphologies in vitro," 1999, *J. Biol. Chem.*, 274: 7619-7622; Huang, C., et al., "A new method for purification of recombinant human alpha-synuclein in *Escherichia coli*,"

2005, Protein Expr Purif, 42:173-177; Yu, L., et al, "Synthesis and in vitro evaluation of á-synuclein ligands," 2012, *Bioorg. Med. Chem.*, 20:4625-4634] and tau [Li, W., et al., "Characterization of two VQIXXK motifs for tau fibrillization in vitro," 2006, *Biochemistry*, 45:15692-15701]. BL21 (DE3)RIL *E. coli* were transformed with a pRK172 bacterial expression plasmid containing the human α-synuclein coding sequence. Freshly transformed BL21 colonies were inoculated into 2 L baffled flasks containing 250 ml sterilized TB (1.2% bactotryptone, 2.4% yeast extract, 0.4% glycerol, 0.17 M $KH_2PO_4$, 0.72 M $K_2HPO_4$) with 50 µg/ml ampicillin, and incubated overnight at 37° C. with shaking. Overnight cultures were centrifuged at 3,900×g for 10 min at 25° C. and the bacterial pellets were resuspended by gentle vortexing in 20 ml osmotic shock buffer (30 mM Tris-HCl, 2 mM EDTA, 40% Sucrose, pH 7.2) and then incubated at room temperature for 10 min. The cell suspension was then centrifuged at 8,000×g for 10 min at 25° C. and the pellet was resuspended in 22.5 ml cold $H_2O$ before adding 9.4 µl 2 M $MgCl_2$ to each tube. The suspension was incubated on ice for 3 min prior to centrifugation at 20,000×g for 15 min at 4° C. After the supernatant was transferred to a fresh tube, streptomycin was added to a final concentration of 10 mg/ml and centrifuged at 20,000×g for 15 min at 4° C. The supernatant from this step was collected and dithiothreitol (DTT) and Tris-HCl pH 8.0 were added to final concentrations of 1 mM and 20 mM respectively, before boiling for 10 min to precipitate heat-sensitive proteins, which were pelleted at 20,000×g for 15 min at 4° C. The supernatant was collected and filtered through a 0.45 µm surfactant-free cellulose acetate filter (Corning) before loading onto a 1 ml DEAE Sepharose column equilibrated in 20 mM Tris-HCl pH 8.0, 1 mM EDTA, and 1 mM DTT. The DEAE column was washed with 20 mM Tris-HCl pH 8.0, 1 mM EDTA, 1 mM DTT before eluting α-synuclein protein in 20 mM Tris-HCl pH 8.0 buffer with 1 mM EDTA, 1 mM DTT and 0.3 M NaCl. Purified α-synuclein protein was dialyzed overnight in 10 mM Tris-HCl pH 7.6, 50 mM NaCl, 1 mM DTT. Preparations contained greater than 95% α-synuclein protein as determined by sodium dodecyl sulfate polyacrylamide gel electrophoresis (SDS-PAGE) and bicinchoninic acid (BCA) protein assay (Thermo Scientific, Rockford, Ill.), with a typical yield of 30 mg protein per 250 ml culture.

Recombinant tau protein was produced in *E. coli*. BL21 (DE3)RIL *E. coli* were transformed with a pRK172 bacterial expression plasmid encoding a human tau fragment containing the four microtubule binding repeats (amino acids 243-375) [Frost, B., et al, "Propagation of tau misfolding from the outside to the inside of a cell," 2009, *J. Biol. Chem.* 284: 2845-12852]. Cultures were inoculated and grown overnight as above for α-synuclein protein production. Purified tau protein was prepared using the method described in reference [Li, W., et al., "Characterization of two VQIXXK motifs for tau fibrillization in vitro," 2006, *Biochemistry*, 45:15692-15701] and dialyzed overnight in 100 mM sodium acetate pH 7.0.

Preparation of Recombinant α-Synuclein Fibrils

Purified recombinant α-synuclein monomer (2 mg/ml) was incubated in 20 mM Tris-HCl, pH 8.0, 100 mM NaCl for 72 h at 37 C with shaking at 1000 rpm in an Eppendorf Thermomixer. To determine the concentration of fibrils, the fibril reaction mix was centrifuged at 15,000×g for 15 min to separate fibrils from monomer. The concentration of α-synuclein monomer in the supernatant was determined in a BCA protein assay according to the manufacturer's instructions, using a bovine serum albumin (BSA) standard curve. The measured decrease in α-synuclein monomer concentration was used to determine the concentration of fibrils in the 72 h fibril reaction mixture.

Preparation of $Aβ_{1-42}$ Fibrils

Synthetic $Aβ_{42}$ peptide (1 mg) (Bachem, Torrance, Calif.) was first dissolved in 50 µl DMSO. An additional 925 µl of $mQ-H_2O$ was added. Finally, 25 µl 1M Tris-HCl pH 7.6 was added to bring the final peptide concentration to 222 µM (1 mg/ml) [16]. The dissolved peptide was incubated for 30 h at 37° C. with shaking at 1000 rpm in an Eppendorf Thermomixer. Fibril formation was confirmed by ThioT fluorescence. To determine the concentration of fibrils, the fibril reaction mix was centrifuged at 15,000×g for 15 min to separate fibrils from monomer. The concentration of Aβ monomer in the supernatant was determined in a BCA protein assay using a BSA standard curve that contained DMSO at a percentage equivalent to the samples.

Preparation of Recombinant Tau Fibrils

Purified recombinant tau monomer (300 µg/ml) was incubated in 20 mM Tris-HCl pH 8.0, 100 mM NaCl, 25 µM low molecular weight heparin, 0.5 mM DTT for 48 h at 37° C. with shaking at 1000 rpm in an Eppendorf Thermomixer. To determine the concentration of fibrils, the fibril reaction mixer was centrifuged at 15,000×g for 15 min to separate fibrils from monomer. The concentration of tau monomer in the supernatant was determined in a BCA protein assay along with a BSA standard curve. The measured decrease in monomer concentration was used to determine the concentration of tau fibrils in the 48 h fibril reaction mixture.

Preparation of α-Synuclein, $Aβ_{1-42}$, and Tau Fibrils for Binding and Competition Assays The prepared fibril mixture was centrifuged at 15,000×g for 15 min to prepare fibrils for binding assays. The supernatant was discarded and the fibril pellet was resuspended in 30 mM Tris-HCl pH 7.4, 0.1% BSA to achieve the desired concentration of fibrils for use in the assay.

Competitive Binding

A fixed concentration (1 µM) of α-syn, Aβ, or tau fibrils were incubated for 2 h at 37° C. with increasing concentrations of ThioT in 30 mM Tris-HCl pH 7.4, 0.1% BSA in a reaction volume of 150 µl. Nonspecific binding was determined in a duplicate set of binding reactions containing the same concentration of ThioT with no fibrils. Fluorescence was determined in a Biotek plate reader using a 440/30 excitation filter and a 485/20 emission filter. All data points were performed in triplicate. The dissociation constant ($K_d$) and the maximal number of binding sites ($B_{max}$) values were determined by fitting the data to the equation $Y=B_{max}*X/(X+K_d)$ by nonlinear regression using Graphpad Prism software (version 4.0). Under the conditions used for these studies we determined that the affinity constants ($K_d$) of ThioT for α-syn, Aβ and tau fibrils were 1850 nM, 32 nM, and 2700 nM respectively. The results are shown in Table 8.

TABLE 8

Comparison of $K_d$ values for certain quinolone, N-substituted phenyl amides, and styryl pyridinyl derivatives in a competitive binding assay with α-synuclein, $Aβ_{1-42}$, and tau fibrils.

| | α-synuclein | | $Aβ_{1-42}$ fibrils | | Tau fibrils | |
|---|---|---|---|---|---|---|
| Compound | $K_d$ (nM) | $B_{max}$ (pmol/ nmol) | $K_d$ (nM) | $B_{max}$ (pmol/ nmol) | $K_d$ (nM) | $B_{max}$ (pmol/ nmol) |
| [$^{11}$C]TZ-37-74 | 77 | 12 | | | | |
| [$^{11}$C]TZ-36-28-2T | 30 | 51 | | | | |
| [$^{18}$F]TZ-36-148 | 90 | 29 | 98 | 28 | 51 | 58 |

The results in Table 8 show, of the compounds tested, compound TZ-36-28-2T had the lowest $K_d$ of 30 nM against α-synuclein fibrils.

Thioflavin T Competition Assays

A fixed concentration (1 µM) of α-syn, Aβ, or tau fibrils were incubated for 2 h at 37° C. with increasing concentrations of ThioT in 30 mM Tris-HCl pH 7.4, 0.1% BSA in a reaction volume of 150 µl. Nonspecific binding was determined in a duplicate set of binding reactions containing the same concentration of ThioT with no fibrils. Fluorescence was determined in a Biotek plate reader using a 440/30 excitation filter and a 485/20 emission filter. All data points were performed in triplicate. The dissociation constant ($K_d$) and the maximal number of binding sites ($B_{max}$) values were determined by fitting the data to the equation $Y=B_{max}*X/(X+K_d)$ by nonlinear regression using Graphpad Prism software (version 4.0). Under the conditions used for these studies we determined that the affinity constants ($K_d$) of ThioT for α-syn, Aβ and tau fibrils were 1850 nM, 32 nM, and 2700 nM respectively Competition assays used a fixed concentration of α-syn, Aβ, or tau fibrils (1 µM), consisting of 3 µM, 50 nM and 4 µM of ThioflavinT respectively. The competitor ligand was diluted in 30 mM Tris-HCl pH 7.4, 0.1% BSA and added to the reactions in varying concentrations. To optimize the determination of selectivity, assays for all three fibril species were set up in parallel using a common set of intermediate compound dilutions for each analog. Reactions were incubated at room temperature for 1.5 h before quantifying bound ligand as described above for the saturation binding assay. Fluorescence was determined in a Biotek plate reader using a 440/30 excitation filter and a 485/20 emission filter. All data points were performed in triplicate. Nonspecific fluorescence was measured in parallel reactions containing ThioT plus each concentration of competitor but no fibrils, and these measurements were subtracted from the reactions with fibrils to yield fibril-specific fluorescence. Data were analyzed using Graphpad. Prism software (version 4.0) to obtain $EC_{50}$ values by fitting the data to the equation $Y=bottom+(top-bottom)/(1+10^{(x-log\ EC50)})$. The results are shown in Table 9.

Washington University School of Medicine in St. Louis. The clinical diagnosis of idiopathic PD was based on modified United Kingdom Parkinson's Disease Society Brain Bank clinical diagnostic criteria with clear clinical response to levodopa [Hughes, A. J., et al, "Accuracy of clinical diagnosis of idiopathic Parkinson's disease: a clinico-pathological study of 100 cases," 1992, *J. Neurol. Neurosurg. Psychiatry*, 55:181-184]. Dementia was determined by a movement disorders specialist based on clinical assessment of cognitive dysfunction sufficiently severe to impair activities of daily living, with further evaluation of cognitive impairment using the AD8 and Mini-Mental Status Exam (MMSE) [Galvin, J. E., et al., "The AD8: a brief informant interview to detect dementia," 2005, Neurology 65:559-564; Folstein, M. F., et al., ""Mini-mental state". A practical method for grading the cognitive state of patients for the clinician," 1975, *J. Psychiatr Res*, 12:189-198]. LB stage was assessed at autopsy using a PD staging scale (range: 0, 1-6) [Braak, H., et al., "Stages in the development of Parkinson's disease-related pathology," 2004, *Cell Tissue Res.*, 318:121-134]. PD cases were selected based on a clinical diagnosis of PD plus dementia, Braak LB stage 5-6 pathology, and the absence of significant Aβ or tau pathology determined by immunohistochemistry. Control cases were selected based on the absence of α-synuclein, Aβ and tau pathology. Samples were used from both male and female subjects.

Transgenic mouse lines expressing human A53T α-synuclein (M83 line) or human wild type α-synuclein (M7 line) were obtained from the University of Pennsylvania. Mice used in this study were homozygous for each of the transgenes and were bred on mixed B6C3H and 129Sv backgrounds. M83 mice were observed for the development of neurological impairment and were euthanized after the onset of motor impairment. Brain tissue was removed and

TABLE 9

Comparison of Ki values for certain quinolone, N-substituted phenyl amides, and styryl pyridinyl derivatives in a ThT competition assay using α-synuclein, Aβ$_{1-42}$, and tau fibrils.

| | α-synuclein | | | | Aβ-fibrils | | | | Tau fibrils | | | |
|---|---|---|---|---|---|---|---|---|---|---|---|---|
| Compound No. | Ki (nM) | Ki (avg) | $EC_{50}$ | $EC_{50}$ (avg) | Ki (nM) | Ki (avg) | $EC_{50}$ | $EC_{50}$ (avg) | Ki (nM) | Ki (avg) | $EC_{50}$ | $EC_{50}$ (avg) |
| [$^{18}$F]TZ-36-148 | 17, 19 | 18 | 44.5, 49 | 46.75 | 163, 173 | 168 | 435, 462 | 448.5 | 124, 102 | 113 | 305, 251 | 278 |
| TZ-36-138 | 49 | 49 | 128 | 128 | | | | | | | | |
| TZ-36-142 | 233 | 233 | 609 | 609 | | | | | | | | |
| TZ-36-144 | 42 | 42 | 110 | 110 | | | | | | | | |
| TZ-36-146 | 233, 21 | 127 | 609, 56 | 332.5 | | | | | | | | |
| TZ-36-32 | 34, 26 | 30 | 90, 67 | 78.5 | | | | | | | | |
| TZ-36-36 | 128, 175 | 151.5 | 335, 457 | 396 | | | | | | | | |
| TZ-36-54 | 65, 72 | 68.5 | 169, 188 | 178.5 | | | | | | | | |

The results in Table 9 show, of the compounds tested, compound TZ-36-148 had the lowest Ki value of 18 nM against α-synuclein fibrils.

Example 131: Radioligand Binding Assays and Competitive Binding Assays with Human Postmortem Brain Tissue Preparations Brain tissue samples were selected from an autopsy case series of patients evaluated for parkinsonism by movement disorders specialists at the Movement Disorders Center of midbrain/pons/medulla tissue samples were dissected by first making a midsagittal cut using a brain matrix, which was then followed by an axial cut at the cervicomedullary junction and a second axial cut rostral to the superior colliculus for each hemisphere. Both male and female mice were used in the study.

Preparation of Human Brain Tissue for In Vitro Binding and Competition Studies

Grey matter was isolated from frozen postmortem frontal cortex tissue by dissection with a scalpel. To prepare insoluble fractions, dissected tissue was sequentially homogenized in four buffers (3 ml/g wet weight of tissue) with glass Dounce tissue grinders (Kimble): 1) High salt (HS) buffer: 50 mM Tris-HCl pH 7.5, 750 mM NaCl, 5 mM EDTA; 2) HS buffer with 1% Triton X-100; 3) HS buffer with 1% Triton X-100 and 1 M sucrose; and 4) phosphate buffered saline (PBS). Homogenates were centrifuged at 100,000×g after each homogenization step and the pellet was resuspended and homogenized in the next buffer in the sequence. For comparison in initial binding studies, crude tissue homogenates were also prepared by homogenization of tissue in only PBS.

Extraction of Insoluble α-Synuclein for Western Blot and ELISA

Insoluble α-synuclein was isolated by sequential extraction of frozen postmortem human brain tissue as described previously [Kotzbauer, P. T., et al., "Fibrillization of alpha-synuclein and tau in familial Parkinson's disease caused by the A53T alpha-synuclein mutation," 2004, *Exp Neurol*, 187:279-288]. Grey matter was isolated from frozen postmortem frontal cortex tissue by dissection with a scalpel. To prepare insoluble fractions for Western blot and ELISA analysis, dissected tissue was sequentially extracted in six buffers (3 ml/g wet weight of tissue) with glass Dounce tissue grinders (Kimble) [Kotzbauer, P. T., et al., "Fibrillization of alpha-synuclein and tau in familial Parkinson's disease caused by the A53T alpha-synuclein mutation," 2004, *Exp Neurol*, 187:279-288]: 1, 2) High salt (HS) buffer: 50 mM Tris-HCl pH 7.5, 750 mM NaCl, 5 mM EDTA; 3) HS buffer with 1% Triton X-100; 4) HS buffer with 1% Triton X-100 and 1 M sucrose; and 5, 6) 1× radioimmunoprecipitation assay (RIPA) buffer. Extracts were centrifuged at 100,000×g after each step and the pellet was resuspended and extracted in the next buffer in the sequence. The final pellet was then resuspended in 50 mM Tris-HCl pH 8.0, 2% SDS (1 ml/g wet weight of tissue) and sonicated for 5 sec with 5 sec rest intervals in between for a total sonication time of 30 sec. Sonicated samples were centrifuged at 100,000×g and the supernatant was saved (SDS extract). The pellet was resuspended in 70% formic acid (1 ml/g wet weight of tissue) and sonicated for 5 sec with 5 sec rest intervals in between for a total sonication time of 30 sec. The formic acid was evaporated in a speed vacuum for 2 h. Then 1 volume of 50 mM Tris-HCl pH 8.0, 2% SDS was added to each sample to solubilize the protein. The samples were sonicated for 5 sec with 5 sec rest intervals in between for a total sonication time of 30 sec.

Western Blot

Western Blot was performed as described previously [Engel, L. A., et al., "Catalytic function of PLA2G6 is impaired by mutations associated with infantile neuroaxonal dystrophy but not dystonia-parkinsonism," 2010, PLoS ONE 5: e12897]. Frontal cortex PD and control SDS extracts (8 μl) and anterior cingulate and temporal cortex PD extracts (4 μl) were run on an 18% Tris-glycine gel (Bio-Rad Criterion) and transferred to a nitrocellulose membrane as described previously [18]. The membrane was blocked with 5% nonfat milk in Tris buffered saline (TBS) with 0.1% TWEEN-20 for 1 h at room temperature, followed by incubation overnight at 4° C. with syn1 (BD Biosciences) or syn303 [Giasson, B. I., "Oxidative damage linked to neurodegeneration by selective alpha-synuclein nitration in synucleinopathy lesions," 2000, *Science*, 290:985-989. 8948 [pii]], both mouse monoclonal antibodies against α-synuclein. The blot was then incubated with HRP-conjugated anti-mouse secondary antibody for 1 h at room temperature, followed by washing and detection with Immobilon enhanced chemiluminescence (ECL) reagent (Millipore). The blot was imaged with the G:Box Chemi XT4 (Synpotics) imager and was quantified using Multi-Gauge software (Fujifilm). Western blots included a standard curve of recombinant α-synuclein protein ranging from 2.5 ng to 30 ng. The ECL signal was linear over the range of the standards.

Sandwich ELISA for α-Synuclein

The levels of α-synuclein were measured by sandwich ELISA following the sequential extraction procedure. Mouse monoclonal α-synuclein 211 (Santa Cruz Biotechnology) was used as the capture antibody and biotinylated goat polyclonal anti-human synuclein-α (R&D Systems) was used as the detection antibody. PBS with 0.05% Tween 20, 2% BSA was used to block for 1 h at 37° C. before adding samples. All washes were done in PBS-TWEEN 20. Bound detection antibody was quantified using Streptavidin Poly HRP80 (Fitzgerald) and SuperSlow 3,3',5,5'-Tetramethylbenzidine (TMB) liquid substrate (Sigma-Aldrich). The standard curve was generated by combining bacterial recombinant α-synuclein with extracts prepared from control tissue samples, and ranged from 0 ng/well to 100 ng/well.

Radioligand binding assays with $^{11}$C- and $^{18}$F-labeled compounds were used to further characterize the binding properties. Saturation binding assays or homologous competition assays were used to define direct binding properties of the radioligands. Brian tissue homogenate preparations for either PD, AD, or control cases were used as binding substrates in the assays.

Saturation binding assays combine binding substrate and varying radioligand concentrations, with or without the addition of a high concentration (50-100 times the estimated $K_d$) of a competitor compound to determine nonspecific binding. The assay buffer was 30 mM Tris pH 7.4 with 0.1% BSA. Bound ligand is separated from unbound by vacuum filtration in 96 well filter plates containing glass fiber (GF/B) filters, followed by three washes with cold assay buffer, followed by scintillation counting of the filters. The filtration and washing steps are performed rapidly to minimize nonspecific filter binding and dissociation of bound ligand. The binding reactions were transferred to the filter plate and then washed using a 96-channel pipettor, and the total time to complete this process was approximately 30 sec. Specific binding is determined by subtracting nonspecific binding from total binding. Nonlinear regression is used to determine $K_d$ and $B_{max}$ values. The results are shown in Table 10.

TABLE 10

Comparison of $K_d$ values for certain quinolone, N-substituted phenyl amides, and styryl pyridinyl derivatives analogues in assays with PD and AD tissues.

| | PD Tissue | | AD Tissue | | Control Tissue | |
|---|---|---|---|---|---|---|
| Compound | $K_d$ (nM) | $B_{max}$ (pmol/nmol) | $K_d$ (nM) | $B_{max}$ (pmol/nmol) | $K_d$ (nM) | $B_{max}$ (pmol/nmol) |
| [$^{11}$C]TZ-37-74 | 26 | 1305 | 303 | 18351 | 782 | 37400 |
| [$^{11}$C]TZ-36-28-2T | 55 | 367 | 13 | 4316 | 158 | 1081 |
| [$^{18}$F]TZ-36-148 | 167 | 1510 | 83 | 12945 | 477 | 604 |

The results in Table 10 show compound TZ-37-74 had the lowest $K_d$ value of 26 nM against PD tissue and compound TZ-36-28-2T had the lowest $K_d$ value of 13 nM against AD tissue.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

What is claimed is:
1. A compound having the structure of Formula (III-A):

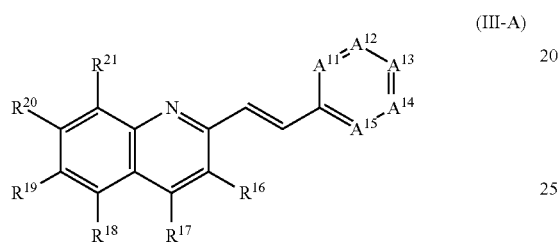

wherein $A^{11}$ is C—$R^{11}$ or nitrogen; $A^{12}$ is C—$R^{12}$ or nitrogen; $A^{13}$ is C—$R^{13}$ or nitrogen; $A^{14}$ is C—$R^{14}$; $A^{15}$ is C—$R^{15}$ or nitrogen and at least one of $A^{11}$, $A^{12}$, $A^{13}$, or $A^{15}$ is nitrogen;

$R^{11}$, $R^{12}$, $R^{13}$, $R^{15}$, $R^{16}$, $R^{17}$, $R^{18}$, $R^{20}$, and $R^{21}$ are independently hydrogen, nitro, halo, hydroxy, carboxyl, substituted or unsubstituted alkyl, substituted or unsubstituted alkoxy, substituted or unsubstituted carboxylate, substituted or unsubstituted amino, or substituted or unsubstituted amido;

$R^{14}$ is nitro, halo, hydroxy, carboxyl, substituted or unsubstituted alkyl, substituted or unsubstituted alkoxy, substituted or unsubstituted carboxylate, substituted or unsubstituted amino, or substituted or unsubstituted amido; and $R^{19}$ is nitro, halo, hydroxy, carboxyl, substituted or unsubstituted alkyl, substituted or unsubstituted alkoxy, substituted or unsubstituted carboxylate, substituted or unsubstituted amino, or substituted or unsubstituted amido, and wherein the compound is radiolabeled with a synthetic radioactive isotope.

2. A compound selected from the group consisting of:

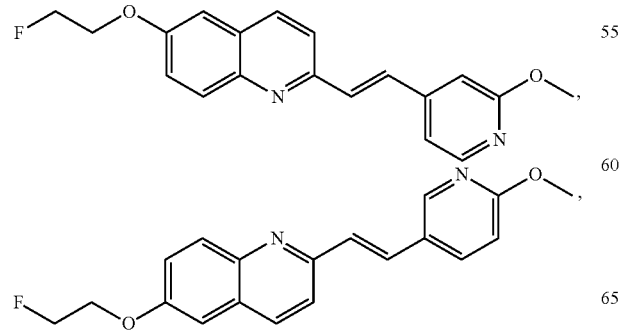

-continued

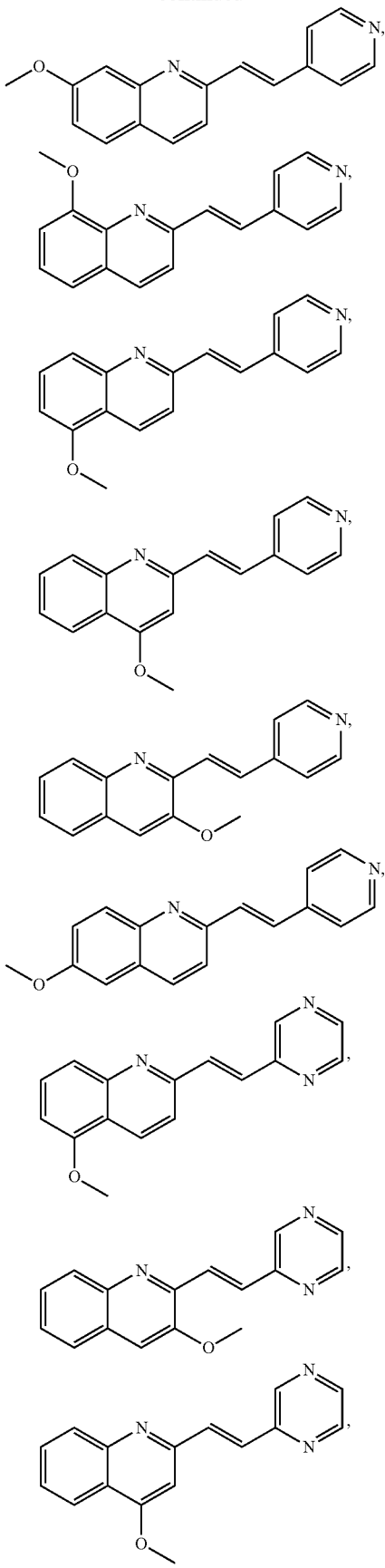

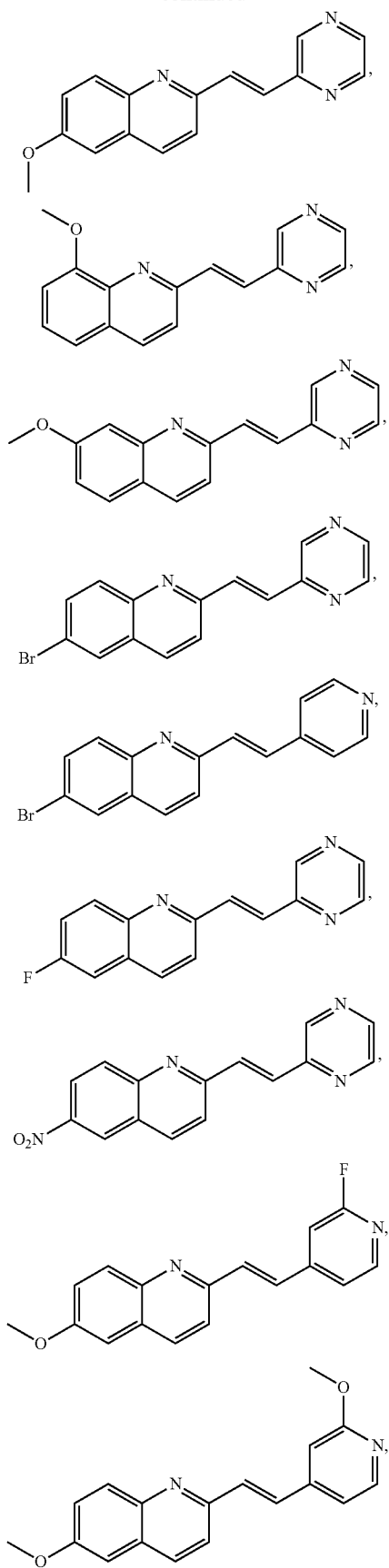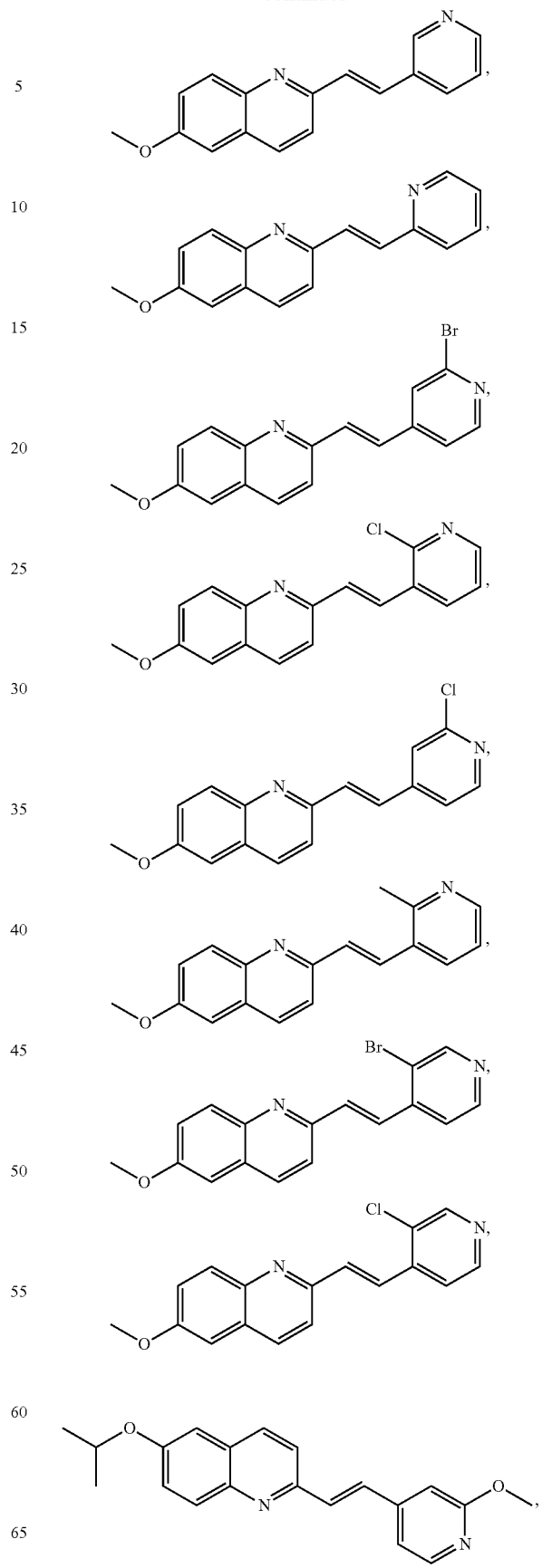

-continued

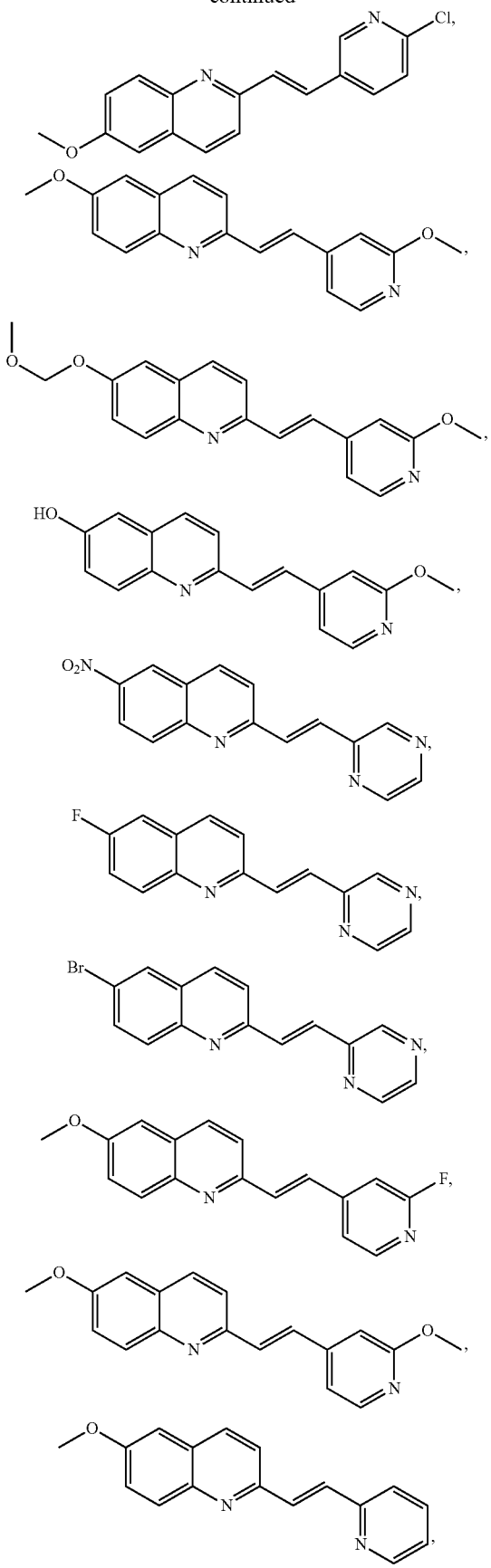

-continued

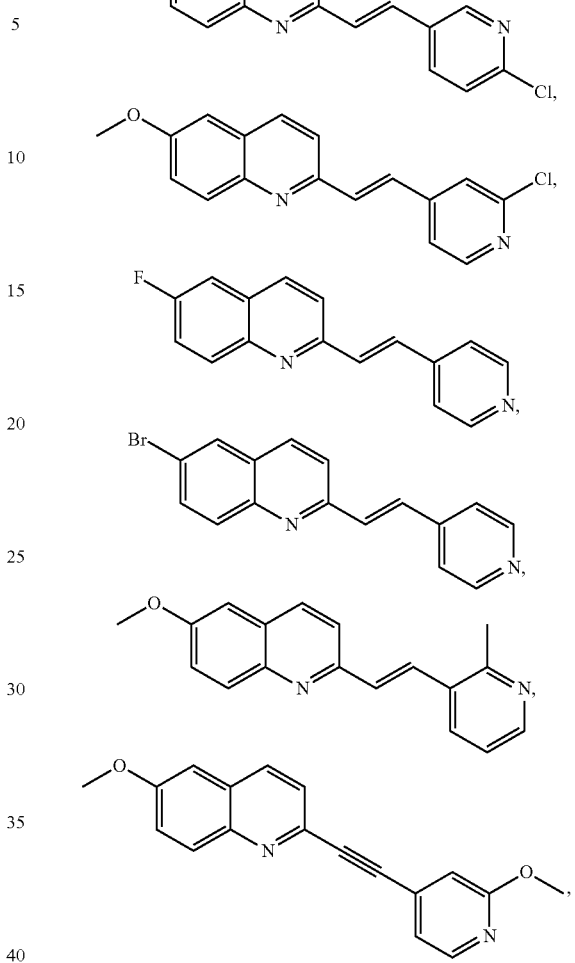

and pharmaceutically acceptable salts thereof.

3. The compound of claim 2 wherein the compound is radiolabeled with a synthetic radioactive isotope.

4. The compound of claim 3 wherein the synthetic radioactive isotope is selected from the group consisting of carbon-11, nitrogen-13, oxygen-15, fluorine-18, bromine-76, iodine-123, and iodine-125.

5. A pharmaceutical composition comprising a radiolabeled compound of claim 1 and at least one excipient.

6. A pharmaceutical composition comprising a compound of claim 1 wherein the composition comprises from about 0.001 mg to about 10 g of the compound and at least about 10 wt. % of the compound in the pharmaceutical composition is radiolabeled.

7. A method of diagnosing or monitoring a synucleinopathy in a human subject comprising administering a pharmaceutical composition comprising a compound of claim 1 to a human subject; and imaging the subject's brain by positron emission tomography.

8. The compound of claim 1 wherein $A^{13}$ is nitrogen.

9. The compound of claim 1 wherein $A^{11}$ is C—$R^{11}$; $A^{12}$ is C—$R^{12}$; and $A^{15}$ is C—$R^{15}$.

10. The compound of claim 8 wherein $A^{11}$ is C—$R^{11}$; $A^{12}$ is C—$R^{12}$; and $A^{15}$ is C—$R^{15}$.

11. The compound of claim 1 wherein $R^{11}$, $R^{12}$, $R^{13}$, $R^{15}$, $R^{16}$, $R^{17}$, $R^{18}$, $R^{20}$, and $R^{21}$ are independently hydrogen, nitro, halo, hydroxy, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, amino, $C_1$ to $C_6$ alkyl-substituted amino, amido, $C_1$ to $C_6$ alkyl-substituted amido, $C_1$ to $C_6$ alkyl-substituted carboxylate, or $C_1$ to $C_6$ haloalkyl-substituted carboxylate.

12. The compound of claim 1 wherein $R^{14}$ and $R^{19}$ are independently nitro, halo, hydroxy, carboxyl, $C_1$ to $C_6$ alkyl, halo-substituted $C_1$ to $C_6$ alkyl, $C_1$ to $C_6$ alkoxy, halo-substituted $C_1$ to $C_6$ alkoxy, amino, $C_1$ to $C_6$ alkyl-substituted amino, amido, $C_1$ to $C_6$ alkyl-substituted amido, $C_1$ to $C_6$ alkyl-substituted carboxylate, or $C_1$ to $C_6$ haloalkyl-substituted carboxylate.

13. The compound of claim 1 wherein $R^{14}$ and $R^{19}$ are independently nitro, halo, hydroxy, carboxyl, $C_1$ to $C_6$ alkyl, halo-substituted $C_1$ to $C_6$ alkyl, $C_1$ to $C_6$ alkoxy, or halo-substituted $C_1$ to $C_6$ alkoxy.

14. The compound of claim 1 wherein $R^{19}$ is halo, $C_1$ to $C_6$ alkyl, halo-substituted $C_1$ to $C_6$ alkyl, $C_1$ to $C_6$ alkoxy, or halo-substituted $C_1$ to $C_6$ alkoxy.

15. The compound of claim 1 wherein $R^{14}$ is $C_1$ to $C_6$ alkyl or $C_1$ to $C_6$ alkoxy.

16. The compound of claim 14 wherein $R^{14}$ is $C_1$ to $C_6$ alkyl or $C_1$ to $C_6$ alkoxy.

17. The compound of claim 1 wherein each of $R^{16}$, $R^{17}$, $R^{18}$, $R^{20}$, and $R^{21}$ is hydrogen.

18. The compound of claim 1 wherein at least two of $A^{11}$, $A^{12}$, $A^{13}$, $A^{15}$ are each nitrogen.

19. The compound of claim 1 wherein the synthetic radioactive isotope is selected from the group consisting of carbon-11, nitrogen-13, oxygen-15, fluorine-18, bromine-76, iodine-123, and iodine-125.

20. A method of diagnosing or monitoring a synucleinopathy in a human subject comprising administering a pharmaceutical composition comprising a compound of claim 3 to a human subject; and imaging the subject's brain by positron emission tomography.

* * * * *